US008716282B2

(12) United States Patent
Pastor-Fernández et al.

(10) Patent No.: US 8,716,282 B2
(45) Date of Patent: May 6, 2014

(54) IMIDAZO[1,2-B]PYRIDAZINE DERIVATIVES AND THEIR USE AS PDE10 INHIBITORS

(75) Inventors: Joaquin Pastor-Fernández, Toledo (ES); José Manuel Bartolomé-Nebreda, Toledo (ES); Gregor James Macdonald, Zoersel (BE); Susana Conde-Ceide, Toledo (ES); Óscar Delgado-González, Valencia (ES); Greta Constantia Peter Vanhoof, Zoersel (BE); Michiel Luc Maria Van Gool, Madrid (ES); María Luz Martín-Martín, Salamanca (ES); Sergio-Alvar Alonso-de Diego, Madrid (ES); Kelly Ann Swinney, Pulle (BE); Carina Leys, Stabroek (BE); Johan Erwin Edmond Weerts, Beerse (BE); Stijn Wuyts, Oostham (BE)

(73) Assignee: Janssen Pharmaceutica NV, Beerse (BE)

( * ) Notice: Subject to any disclaimer, the term of this patent is extended or adjusted under 35 U.S.C. 154(b) by 99 days.

(21) Appl. No.: 13/096,545

(22) Filed: Apr. 28, 2011

(65) Prior Publication Data

US 2011/0269752 A1    Nov. 3, 2011

Related U.S. Application Data

(63) Continuation-in-part of application No. PCT/EP2010/066264, filed on Oct. 27, 2010.

(30) Foreign Application Priority Data

Oct. 30, 2009  (EP) ..................................... 09174711

(51) Int. Cl.
| | |
|---|---|
| *A61K 31/5025* | (2006.01) |
| *A61K 31/5377* | (2006.01) |
| *C07D 413/14* | (2006.01) |
| *C07D 403/14* | (2006.01) |
| *C07D 487/04* | (2006.01) |

(52) U.S. Cl.
CPC ................................... *C07D 487/04* (2013.01)
USPC ......... 514/233.2; 514/248; 544/236; 544/117

(58) Field of Classification Search
None
See application file for complete search history.

(56) References Cited

U.S. PATENT DOCUMENTS

| | | | |
|---|---|---|---|
| 4,242,513 A | 12/1980 | Hoover et al. | |
| 4,713,381 A | 12/1987 | Ao et al. | |
| 5,137,876 A | 8/1992 | MacCoss et al. | |
| 5,317,019 A | 5/1994 | Bender et al. | |
| 5,360,796 A | 11/1994 | Hansen, Jr. et al. | |
| 5,486,525 A | 1/1996 | Summers, Jr. et al. | |
| 5,498,774 A | 3/1996 | Mitsudera et al. | |
| 6,054,587 A | 4/2000 | Reddy et al. | |
| 6,245,769 B1 | 6/2001 | Arvanitis et al. | |
| 6,248,755 B1 | 6/2001 | Chapman et al. | |
| 6,352,990 B1 | 3/2002 | McCarthy | |
| 6,403,588 B1 | 6/2002 | Hayakawa et al. | |
| 6,589,947 B1 | 7/2003 | Hamanaka et al. | |
| 6,777,395 B2 | 8/2004 | Bhat et al. | |
| 6,806,268 B2 | 10/2004 | Gall | |
| 6,844,341 B2 | 1/2005 | Thomas | |
| 6,855,719 B1 | 2/2005 | Thomas et al. | |
| 6,900,217 B2 | 5/2005 | Chen | |
| 6,936,617 B2 | 8/2005 | Hutchison et al. | |
| 6,992,080 B2 | 1/2006 | Dwyer et al. | |
| 6,992,188 B1 | 1/2006 | Chen | |
| 7,074,801 B1 | 7/2006 | Yoshida et al. | |
| 7,078,405 B2 | 7/2006 | Hibi et al. | |
| 7,078,410 B2 | 7/2006 | Berg et al. | |
| 7,105,533 B2 | 9/2006 | Campbell et al. | |
| 7,132,426 B2 | 11/2006 | Jones et al. | |
| 7,148,353 B2 | 12/2006 | Fang et al. | |
| 7,186,714 B2 | 3/2007 | Gudmundsson et al. | |
| 7,186,740 B2 | 3/2007 | Paruch et al. | |
| 7,186,832 B2 | 3/2007 | Sun et al. | |
| 7,189,723 B2 | 3/2007 | Mitchell et al. | |
| 7,196,095 B2 | 3/2007 | Biftu et al. | |

(Continued)

FOREIGN PATENT DOCUMENTS

| | | | |
|---|---|---|---|
| CA | 2398956 A1 | 8/2001 | |
| CA | 2668738 A1 | 7/2008 | |

(Continued)

OTHER PUBLICATIONS

Siuciak, et al., Expert Opin. Drug Discov. 2:1001 (2007).*
Bertelsen, et al., Arch Gen Psychiatry, 65:762 (2008).*
Kehler, et al., Expert Opin. Ther. Pat., "Phospho-diesterase 10A inhibitors: a 2009-20012 patent update", pp. 1-15 (Dec. 5, 2012).*
Hörig et al., J. Translational Med. 2:44 (2004).*
Grant & Hackh's Chemical Dictionary (5th Ed. 1987) at p. 148.*
Belanger, et al. "Discovery of imidazo[1,2-a]pyrazine-based Aurora kinase inhibitors", Bioorganic & Medicinal Chemistry Letters (2010), 20(17), 5170-5174.

(Continued)

*Primary Examiner* — Michael Barker
(74) *Attorney, Agent, or Firm* — Hal B. Woodrow

(57) ABSTRACT

The present invention relates to novel imidazo[1,2-*b*]pyridazine derivatives which are inhibitors of the phosphodiesterase 10 enzyme (PDE10) and which are useful for the treatment or prevention of neurological, psychiatric and metabolic disorders in which the PDE10 enzyme is involved. The invention is also directed to pharmaceutical compositions comprising such compounds, to processes to prepare such compounds and compositions, to the use of such compounds or pharmaceutical compositions for the prevention or treatment of neurological, psychiatric and metabolic disorders and diseases.

18 Claims, 2 Drawing Sheets

(56) References Cited

U.S. PATENT DOCUMENTS

| | | |
|---|---|---|
| 7,244,740 B2 | 7/2007 | Gudmundsson et al. |
| 7,259,164 B2 | 8/2007 | Mitchell et al. |
| 7,306,631 B2 | 12/2007 | Glenn, Jr. et al. |
| 7,312,341 B2 | 12/2007 | DeSimone et al. |
| 7,320,995 B2 | 1/2008 | Bonjouklian et al. |
| 7,348,359 B2 | 3/2008 | Gardinier et al. |
| 7,393,848 B2 | 7/2008 | Currie et al. |
| 7,405,295 B2 | 7/2008 | Currie et al. |
| 7,417,041 B2 | 8/2008 | Blumberg et al. |
| 7,491,716 B2 | 2/2009 | Engler |
| 7,504,404 B2 | 3/2009 | McArthur et al. |
| 7,5110,40 B2 | 3/2009 | Belanger et al. |
| 7,557,103 B2 | 7/2009 | Collins et al. |
| 7,563,797 B2 | 7/2009 | Araldi et al. |
| 7,572,807 B2 | 8/2009 | Li et al. |
| 7,576,085 B2 | 8/2009 | Guzi et al. |
| 7,622,584 B2 | 11/2009 | Kim et al. |
| 7,666,880 B2 | 2/2010 | Lee et al. |
| 7,674,801 B2 | 3/2010 | Basarab et al. |
| 2001/0041673 A1 | 11/2001 | Fossa |
| 2002/0049208 A1 | 4/2002 | Bakthavatchalam et al. |
| 2003/0027820 A1 | 2/2003 | Gall |
| 2004/0014957 A1 | 1/2004 | Eldrup et al. |
| 2004/0058938 A1 | 3/2004 | Cullmann et al. |
| 2005/0031588 A1 | 2/2005 | Sommadossi et al. |
| 2005/0079176 A1 | 4/2005 | Pierson, III et al. |
| 2005/0079387 A1 | 4/2005 | Lee et al. |
| 2005/0165232 A1 | 7/2005 | Beresis et al. |
| 2005/0234029 A1 | 10/2005 | Dodic et al. |
| 2005/0245520 A1 | 11/2005 | Dodic et al. |
| 2005/0288295 A1 | 12/2005 | Currie et al. |
| 2006/0094699 A1 | 5/2006 | Kampen et al. |
| 2006/0100235 A1 | 5/2006 | Andersen et al. |
| 2006/0135517 A1 | 6/2006 | Lee et al. |
| 2006/0154105 A1 | 7/2006 | Yamamoto et al. |
| 2006/0178367 A1 | 8/2006 | Currie et al. |
| 2006/0258722 A1 | 11/2006 | Yasuma et al. |
| 2007/0004736 A1 | 1/2007 | Kubo et al. |
| 2007/0049591 A1 | 3/2007 | Pinkerton et al. |
| 2007/0078136 A1 | 4/2007 | Vaccaro et al. |
| 2007/0099925 A1 | 5/2007 | Calderwood et al. |
| 2007/0105864 A1 | 5/2007 | Guzi et al. |
| 2007/0117804 A1 | 5/2007 | Zhao et al. |
| 2007/0149535 A1 | 6/2007 | Berset et al. |
| 2007/0185063 A1 | 8/2007 | Storer et al. |
| 2007/0197507 A1 | 8/2007 | Morgan et al. |
| 2007/0219205 A1 | 9/2007 | Brenchley et al. |
| 2008/0021217 A1 | 1/2008 | Borchardt et al. |
| 2008/0045536 A1 | 2/2008 | Vaccaro et al. |
| 2008/0070894 A1 | 3/2008 | Kawamura et al. |
| 2008/0102028 A1 | 5/2008 | Morel |
| 2008/0103136 A1 | 5/2008 | Sato et al. |
| 2008/0113978 A1 | 5/2008 | Barbosa et al. |
| 2008/0161341 A1 | 7/2008 | Calderwood et al. |
| 2008/0167314 A1 | 7/2008 | Uchikawa et al. |
| 2008/0207634 A1 | 8/2008 | Gudmundsson |
| 2008/0221092 A1 | 9/2008 | Bluhm et al. |
| 2008/0242862 A1 | 10/2008 | Calderwood et al. |
| 2008/0255358 A1 | 10/2008 | Bamford et al. |
| 2008/0300242 A1 | 12/2008 | Kuntz et al. |
| 2008/0305081 A1 | 12/2008 | Hashihayata et al. |
| 2008/0318975 A1 | 12/2008 | Wagner et al. |
| 2009/0005374 A1 | 1/2009 | Melvin, Jr. et al. |
| 2009/0023737 A1 | 1/2009 | Xu et al. |
| 2009/0054409 A1 | 2/2009 | Andrews et al. |
| 2009/0124625 A1 | 5/2009 | Bessis et al. |
| 2009/0143376 A1 | 6/2009 | Milburn et al. |
| 2009/0153035 A1 | 6/2009 | Shin et al. |
| 2009/0156604 A1 | 6/2009 | Holder et al. |
| 2009/0175852 A1 | 7/2009 | Ciavarri et al. |
| 2009/0176778 A1 | 7/2009 | Schmitz et al. |
| 2009/0203732 A1 | 8/2009 | Dhanak et al. |
| 2009/0209573 A1 | 8/2009 | Wu et al. |
| 2009/0215818 A1 | 8/2009 | Adams et al. |
| 2009/0270436 A1 | 10/2009 | Iino et al. |
| 2009/0317361 A1 | 12/2009 | Cho et al. |
| 2009/0325953 A1 | 12/2009 | Sahoo et al. |
| 2010/0029633 A1 | 2/2010 | Allen et al. |
| 2010/0029638 A1 | 2/2010 | Melvin, Jr. et al. |
| 2010/0063068 A1 | 3/2010 | Pracitto et al. |

FOREIGN PATENT DOCUMENTS

| | | |
|---|---|---|
| CL | 3212-2007 | 6/2008 |
| EP | 0728759 | 8/1996 |
| EP | 1 293 213 A1 | 3/2003 |
| IT | 1374954 B1 | 5/2010 |
| JP | 6247969 A | 9/1994 |
| JP | 2001-006877 | 1/2001 |
| JP | 2001-057292 A | 2/2001 |
| JP | 2003-313126 A | 11/2003 |
| JP | 2004-002826 A | 1/2004 |
| JP | 2005-343889 A | 12/2005 |
| WO | WO 90/15534 A1 | 12/1990 |
| WO | WO 91/19497 A1 | 12/1991 |
| WO | WO 92/10190 A1 | 6/1992 |
| WO | WO 92/10498 A1 | 6/1992 |
| WO | WO 96/34866 A1 | 11/1996 |
| WO | WO 02/34748 A1 | 5/2002 |
| WO | WO 02/066478 A1 | 8/2002 |
| WO | WO 2004/017950 A2 | 3/2004 |
| WO | WO 2004/026877 A1 | 4/2004 |
| WO | WO 2004/035579 A1 | 4/2004 |
| WO | WO 2004/075846 | 9/2004 |
| WO | WO 2004/087710 | 10/2004 |
| WO | WO 2004/089416 A2 | 10/2004 |
| WO | WO 2004/103991 A1 | 12/2004 |
| WO | WO 2005/014599 A1 | 2/2005 |
| WO | WO 2005/020885 A2 | 3/2005 |
| WO | WO 2005/047290 A2 | 5/2005 |
| WO | WO 2006/044509 A2 | 4/2006 |
| WO | WO 2006/102194 | 9/2006 |
| WO | WO 2007/003386 A1 | 1/2007 |
| WO | WO 2007/013673 A1 | 2/2007 |
| WO | WO 2007/048779 | 5/2007 |
| WO | WO 2007/087548 A2 | 8/2007 |
| WO | WO 2007/145921 A1 | 12/2007 |
| WO | WO 2008/003511 A1 | 1/2008 |
| WO | WO 2008/030579 A2 | 3/2008 |
| WO | WO 2008/030795 A2 | 3/2008 |
| WO | WO 2008/057402 A2 | 5/2008 |
| WO | WO 2008/079460 A2 | 7/2008 |
| WO | WO 2008/081910 A1 | 7/2008 |
| WO | WO 2008/121687 A2 | 10/2008 |
| WO | WO 2008/124153 A1 | 10/2008 |
| WO | WO 2008/133192 A1 | 11/2008 |
| WO | WO 2008/134553 A1 | 11/2008 |
| WO | WO 2008/138834 A1 | 11/2008 |
| WO | WO 2008/141079 A1 | 11/2008 |
| WO | WO 2008/156614 A2 | 12/2008 |
| WO | WO 2009/005675 A1 | 1/2009 |
| WO | WO 2009/016286 A2 | 2/2009 |
| WO | WO 2009/016560 A2 | 2/2009 |
| WO | WO 2009/017701 A2 | 2/2009 |
| WO | WO 2009/021990 A1 | 2/2009 |
| WO | WO 2009/023253 A2 | 2/2009 |
| WO | WO 2009/024585 A2 | 2/2009 |
| WO | WO 2009/037394 A2 | 3/2009 |
| WO | WO 2009/060197 A1 | 5/2009 |
| WO | WO 2009/061856 A1 | 5/2009 |
| WO | WO 2009/077334 | 6/2009 |
| WO | WO 2009/081857 A1 | 7/2009 |
| WO | WO 2009/086123 A1 | 7/2009 |
| WO | WO 2009/086130 A1 | 7/2009 |
| WO | WO 2009/097233 A1 | 8/2009 |
| WO | WO 2009/108546 A1 | 9/2009 |
| WO | WO 2009/112679 A1 | 9/2009 |
| WO | WO 2009/117157 A1 | 9/2009 |
| WO | WO 2009/124653 A2 | 10/2009 |
| WO | WO 2009/126691 A1 | 10/2009 |
| WO | WO 2009/143156 A2 | 11/2009 |
| WO | WO 2009/146358 | 12/2009 |
| WO | WO 2009/152072 A1 | 12/2009 |
| WO | WO 2010/002985 A1 | 1/2010 |

(56) References Cited

FOREIGN PATENT DOCUMENTS

| WO | WO 2010/009155 A2 | 1/2010 |
|---|---|---|
| WO | WO 2010/011837 A1 | 1/2010 |
| WO | WO 2010/016005 A1 | 2/2010 |
| WO | WO 2010/018327 A1 | 2/2010 |
| WO | WO 2010/033906 A2 | 3/2010 |
| WO | WO 2010/036407 A2 | 4/2010 |
| WO | WO 2010/047279 A1 | 4/2010 |
| WO | WO 2010/048149 A2 | 4/2010 |
| WO | WO 2010/059836 A1 | 5/2010 |
| WO | WO 2010/059838 A2 | 5/2010 |
| WO | WO 2010/069684 A1 | 6/2010 |
| WO | WO 2010/084425 A1 | 7/2010 |
| WO | WO 2010/084690 A1 | 7/2010 |
| WO | WO 2010/088368 A2 | 8/2010 |
| WO | WO 2010/088518 A2 | 8/2010 |
| WO | WO 2010/098458 A1 | 9/2010 |
| WO | WO 2010/108074 A2 | 9/2010 |
| WO | WO 2010/110277 A1 | 9/2010 |
| WO | WO 2010/119264 A1 | 10/2010 |
| WO | WO 2011/013729 A1 | 2/2011 |
| WO | WO 2011/021520 A1 | 2/2011 |
| WO | WO 2011/059099 A1 | 5/2011 |
| WO | WO 2011/089400 A1 | 7/2011 |
| WO | WO 2011/110545 A1 | 9/2011 |

OTHER PUBLICATIONS

Belanger, et al. "Discovery of orally bioavailable imidazo[1,2-a]pyrazine-based Aurora kinase inhibitors", Bioorganic & Medicinal Chemistry Letters (2010), 20(22), 6739-6743.

Bouloc, et al. "Structure-based design of imidazo[1,2-a]pyrazine derivatives as selective inhibitors of Aurora-A kinase in cells", Bioorganic & Medicinal Chemistry Letters (2010), 20(20), 5988-5993.

Blokland et al., Expert Opin. Ther. Patents (2012) 22(4), pp. 349-354.

Carverley, M.J. Tetrahedron, 1987, 43(20), 4609-19.

Charych et al., The Journal of Neuroscience, Jul. 7, 2010 • 30(27):9027-9037.

Ennanceur, Behav Brain Res 1988, 31, 47-59.

Gaudry et al., Organic Syntheses, 1976, 55, 24-27.

Gehlert, et al. "3-(4-Chloro-2-morpholin-4-yl-thiazol-5-yl)-8-(1-ethylpropyl)-2,6-dimethyl-imidazo[1,2-b]pyridazine: a novel brain-penetrant, orally available corticotropin-releasing factor receptor 1 antagonist with efficacy in animal models of alcoholism", Journal of Neuroscience (2007), 27(10), 2718-2726.

Gennaro et al. Remington's Pharmaceutical Sciences (18$^{th}$ ed., Mack Publishing Company, 1990, see especially Part 8: Pharmaceutical preparations and their Manufacture), pp. 1435-1712 (split/uploaded into 4 separate files due to size).

Gudmundsson, et al. "Imidazo[1,2-a]pyridines with potent activity against herpesviruses", Bioorganic & Medicinal Chemistry Letters (2007), 17(10), 2735-2739.

Gudmundsson, et al. "Synthesis of Novel Imidazo[1,2-a]pyridines with Potent Activity against Herpesviruses", Organic Letters (2003), 5(8), 1369-1372 CODEN: ORLEF7; ISSN: 1523-7060.

Hebb et al., Current Opinion in Pharmacology 2007, 7:86-92.

Il'icheva, et al. "Theoretical Study of the Structure of Adenosine Deaminase Complexes with Adenosine Analogues: I. Aza-, Deaza-, and Isomeric Azadeazaanalogues of Adenosine", Russian Journal of Bioorganic Chemistry (2005), 31(5), 439-452.

Kehler et al., Expert Opin. Ther. Patents (2007) 17(2), pp. 147-158.

Kehler et al. Expert Opin. Ther. Patents (2009) 19(12), pp. 1715-1725.

Kerekes, et al. "Aurora Kinase Inhibitors Based on the Imidazo[1,2-a]pyrazine Core: Fluorine and Deuterium Incorporation Improve Oral Absorption and Exposure" Journal of Medicinal Chemistry (2011), 54(1), 201-210.

Kobe, et al. "Use of distance geometry approach for the in vitro antiviral activity evaluation of N-bridgehead C-nucleosides", European Journal of Medicinal Chemistry (1992), 27(3), 259-66.

Kolar, et al. "Transformations of the pyrido[1,2-a]pyrazine ring system into imidazo[1,2-a]pyridines, imidazo[1,2-a]pyrimidines and 2-oxa-6a,10c-diazaaceanthrylenes", Journal of Heterocyclic Chemistry (1996), 33(3), 639-642.

Lhassani, et al. "Synthesis and antiviral activity of imidazo[1,2-a]pyridines", European Journal of Medicinal Chemistry (1999), 34(3), 271-274.

MacCoss, et al. "Synthesis and biological evaluation of nucleosides containing 8-aminoimidazo[1,2-a]pyrazine as an isosteric replacement for adenine", Journal of Heterocyclic Chemistry (1993), 30(5), 1213-20.

Meng, et al. "Bioisosteric approach to the discovery of imidazo[1,2-a]pyrazines as potent Aurora kinase inhibitors" Bioorganic & Medicinal Chemistry Letters (2011), 21(1), 592-598.

Owen et al., Bioorganic & Medicinal Chemistry Letters, vol. 17, No. 2, pp. 486-490 (2007).

Pan, et al. "Synthesis of novel isoxazolinyl substituted imidazo[1,2-a]pyridine C-nucleoside analogs", Tetrahedron Letters (1998), 39(45), 8191-8194.

Schmidt et al., The Journal of Pharmacology and Experimental Therapeutics, vol. 325, No. 2, pp. 681-690 (2008).

Siuciak, Judith A., CNS Drugs 2008; 22 (12): 983-993.

van den Heuvel, M. et al.; J. Org. Chem., 2004, 250.

Wang, et al. "Synthesis of novel isoxazolinyl substituted imidazo]1,2-a]pyridine C-nucleoside analogs", Hecheng Huaxue (2001), 9(5), 386-389.

Wang, X. et al. Tetrahedron Lett., 2000, 4335-4338.

Yu, Tao et al. "Discovery of a Potent, Injectable Inhibitor of Aurora Kinases Based on the Imidazo-[1,2-a]-Pyrazine Core", ACS Medicinal Chemistry Letters (2010), 1(5), 214-218.

Zarubin, et al. "Theoretical study of adenosine and its isosteric analogs. A possible mechanism of their binding in an active site of mammalian adenosine deaminase", Vestnik Samarskogo Gosudarstvennogo Universiteta, Estestvennonauchnaya Seriya (2003), (Spec.), 152-173.

International Search Report for PCT/EP2010/066264 dated Dec. 8, 2010.

International Search Report for PCT/EP2011/053445 dated Aug. 18, 2011.

\* cited by examiner

IMIDAZO[1,2-B]PYRIDAZINE DERIVATIVES AND THEIR USE AS PDE10 INHIBITORS

CROSS REFERENCE TO RELATED APPLICATIONS

This application is a continuation-in-part of International Patent Application No. PCT/EP2010/066264 filed Oct. 27, 2010, which claims priority from European Patent Application No. 09174711.3, filed Oct. 30, 2009, the entire disclosures of which are hereby incorporated in their entirety.

FIELD OF THE INVENTION

The present invention relates to novel imidazo[1,2-b]pyridazine derivatives which are inhibitors of the phosphodiesterase 10 enzyme (PDE10) and which are useful for the treatment or prevention of neurological, psychiatric and metabolic disorders in which the PDE10 enzyme is involved. The invention is also directed to pharmaceutical compositions comprising such compounds, to processes to prepare such compounds and compositions, to the use of such compounds or pharmaceutical compositions for the prevention or treatment of neurological, psychiatric and metabolic disorders and diseases.

BACKGROUND OF THE INVENTION

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

Scheme A

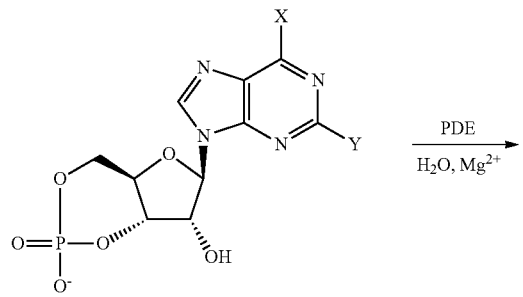

cAMP X = NH$_2$, Y = H
cGMP X = = O, Y = NH$_2$

-continued

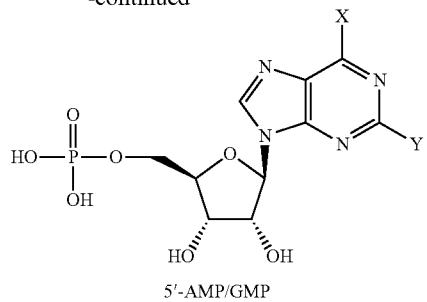

5'-AMP/GMP

On the basis of substrate specificity, the PDE families can be divided into three groups: i) the cAMP-specific PDEs, which include PDE4, 7 and 8; ii) the cGMP-selective enzymes PDE5 and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may play different physiological functions. Compounds that inhibit selectively PDE families or isozymes may display particular therapeutic activity, fewer side effects, or both.

The discovery of phosphodiesterase 10A (PDE10A) was reported in 1999. Of all the 11 known PDE families, PDE10 has the most restricted distribution with high expression only in the brain and testes.

In the brain, PDE10A mRNA and protein are highly expressed in a majority of striatal Medium Spiny Neurons (MSNs). This unique distribution of PDE10A in the brain, together with its increased pharmacological characterization, indicates a potential use of PDE10A inhibitors for treating neurological and psychiatric disorders like schizophrenia.

In the basal ganglia, MSNs constitute the major site for reception and integration of cortical glutamatergic and midbrain dopaminergic input, and form key output pathways that help discriminate and act on relevant and irrelevant cognitive and motor patterns.

MSNs are GABAergic projection neurons evenly distributed between two distinct pathways. Striatonigral MSNs (in the direct pathway) express the D$_1$ dopamine receptor and neuropeptides dynorphin and substance P; striatopallidal MSNs (in the indirect pathway) express the D$_2$ dopamine receptors and neuropeptide enkephalin. D$_1$ dopamine receptors are positively coupled to cAMP production, while D$_2$ dopamine receptors are negatively coupled to cAMP production. These pathways affect the concentration of extracellular dopamine and modulate motor and behavioural responses.

PDE10 Inhibitors and Schizophrenia

Due to the predominant localisation of PDE10 in MSNs, the majority of research on PDE10 inhibitors has focused on preclinical models of psychosis.

On the basis of studies performed on knockout mice, the effects of PDE10 inhibition on striatal gene expression have been compared to the effects induced by a D$_1$ agonist and a D$_2$ antagonist.

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affection, poverty of speech and the inability to experience pleasure. In addition, schizophrenic patients suffer from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered, which proposes that hyperactivity of dopamine transmission is responsible for the positive symptoms observed in schizophrenic patients.

The efficacy of currently marketed antipsychotics correlates their ability to inhibit the $D_2$ dopamine receptors. Acute and chronic administration of antipsychotics such as haloperidol has characteristic effects on striatal gene expression. Inhibition of PDE10A has also been observed to produce alterations in striatal gene expression similar to those exerted by haloperidol.

Atypical antipsychotics, such as clozapine, olanzapine, risperidone and paliperidone display lower profile of extrapyramidal adverse effects and tardive dyskinesia associated with acute and long-term $D_2$ receptor blockade. However there is still a need to develop novel antipsychotics with lower side effects and using approaches beyond dopamine $D_2$ receptor blockade.

In vivo data suggest that PDE10 inhibitors can produce catalepsy, but differently to that observed with current antipsychotics, such as haloperidol, attributed to activation of both direct and indirect pathway neurons in the striatum.

PDE10 inhibitors may possess a pharmacological profile similar to that of the atypical antipsychotics, but lacking the non-target related side effects that are often observed with the currently available antipsychotics. Although EPS-like side effects are observed at relatively low doses, they are relatively mild.

Since PDE10 inhibitors can be used to raise levels of cAMP and/or cGMP within cells that express the PDE10 enzyme, for example neurons that comprise the basal ganglia, PDE10 inhibitors may be useful in treating schizophrenia and additionally, a variety of conditions involving the basal ganglia, such as the conditions described herein, for example, obesity, non-insulin dependent diabetes, bipolar disorder, obsessive compulsive disorder and pain.

WO 2004/087710 (Pharmacia and Upjohn Company) discloses N-(1-ethylpropyl)-7-(6-methoxy-2-methyl-3-pyridinyl)-2,6-dimethyl-pyrrolo[1,2-b]pyridazin-4-amine and 7-(6-methoxy-2-methyl-3-pyridinyl)-2,6-dimethyl-N-(1-methylpropyl)-pyrrolo[1,2-b]pyridazin-4-amine as CRF receptor antagonists, WO 2006/102194 (Eli Lilly and Company) discloses imidazo[1,2-b]pyridazines bearing a 5-membered aromatic ring at the 3 position and a linear alkyl substituent at the 8-position as CRF1 receptor antagonists. The CRF receptor has been validated as a possible target for depression, anxiety, cerebrovascular disorders, irritable bowel syndrome and congestive heart failure, but not for schizophrenia.

There is still a great need for antipsychotic therapies with pharmacological profile similar to that of the atypical antipsychotics, with low extrapyramidal symptom liability.

It is the object of the present invention to provide novel compounds that are PDE10 inhibitors. The present compounds are centrally active, potent compounds which display efficacy in preclinical behavior challenge models in which known clinical useful antipsychotics display similar positive responses, such as in the reversal of apomorphine-induced stereotypy and phencyclidine (PCP)-induced hyperlocomotion in rodents. Additionally, representative compounds reverse the hypolocomotion effects exerted by SCH23390, a D1 receptor antagonist. Thus, the present compounds may act as dopamine modulating agents, inhibiting states of dopaminergic ($D_2$) hyperactivity and reversing states of dopaminergic ($D_2$) hypoactivity.

SUMMARY OF THE INVENTION

The present invention relates to compounds having PDE10 inhibitory activity, said compounds having the Formula (I)

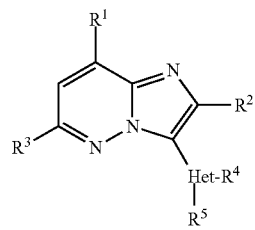

(I)

and the stereoisomeric forms thereof, wherein
$R^1$ is pyridinyl; pyridinyl optionally substituted with halogen, $C_{1-4}$alkyl, trifluoromethyl or $C_{1-4}$alkyloxy; tetrahydropyranyl; or $NR^6R^7$;
$R^2$ is hydrogen, $C_{1-4}$alkyl, trifluoromethyl, $C_{3-8}$cycloalkyl, or $C_{1-4}$alkyloxy;
$R^3$ is hydrogen, chloro, $C_{1-4}$alkyl, trifluoromethyl, or $C_{3-8}$cycloalkyl;
Het is a 5- or 6-membered heterocyclic ring selected from the group consisting of pyridinyl, pyrimidinyl, pyridazinyl, pyrrolyl, oxazolyl, thiazolyl, imidazolyl, pyrazolyl, isothiazolyl, isoxazolyl, oxadiazolyl and triazolyl;
$R^4$ is hydrogen, $C_{1-4}$alkyl, trifluoromethyl$C_{0-4}$alkyl, hydroxy$C_{1-4}$alkyl, difluorocyclopropylmethyl, cyclopropyldifluoroethyl, $C_{3-8}$cycloalkyl, $C_{1-4}$alkyloxy$C_{1-5}$alkyl, $C_{1-4}$alkyloxy, trifluoromethyl$C_{0-4}$alkyloxy, $C_{3-8}$cycloalkyl$C_{1-4}$alkyloxy, $C_{3-8}$cycloalkyl$C_{1-4}$alkyl, $C_{1-6}$alkyloxy$C_{1-4}$alkyloxy, tetrahydropyranyl, pyridinylmethyl, $NR^{6a}R^{7a}C_{1-4}$alkyl or $NR^{6a}R^{7a}$;
$R^5$ is hydrogen or $C_{1-4}$alkyl;
$R^6$, $R^{6a}$, $R^7$ and $R^{7a}$ are each independently hydrogen, or $C_{1-4}$alkyl, or taken together with N can be a radical of Formula (a), (b) or (c)

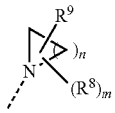

(a)

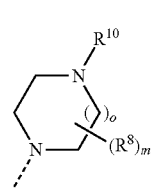

(b)

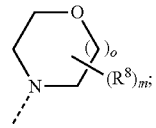

(c)

wherein
each $R^8$, if present, independently of one another is $C_{1-4}$alkyl;
$R^9$ is hydrogen or $C_{1-4}$alkyloxy;

$R^{10}$ is hydrogen or $C_{1-4}$alkyl;

m is 0, 1, 2, 3, 4 or 5;

n is 2, 3, 4, 5 or 6;

o is 1 or 2;

and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament.

The invention also relates to the use of a compound according to Formula (I) or a pharmaceutical composition according to the invention for the manufacture of a medicament for treating or preventing neurological, psychiatric or metabolic disorders and diseases.

Additionally, the invention relates to the use of a compound of Formula (I) in combination with an additional pharmaceutical agent for the manufacture of a medicament for treating or preventing neurological, psychiatric or metabolic disorders and diseases.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a product comprising a compound of Formula (I) and an additional pharmaceutical agent, as a combined preparation for simultaneous, separate or sequential use in the treatment or prevention of neurological, psychiatric or metabolic disorders and diseases.

DETAILED DESCRIPTION OF THE INVENTION

Figure 1A:
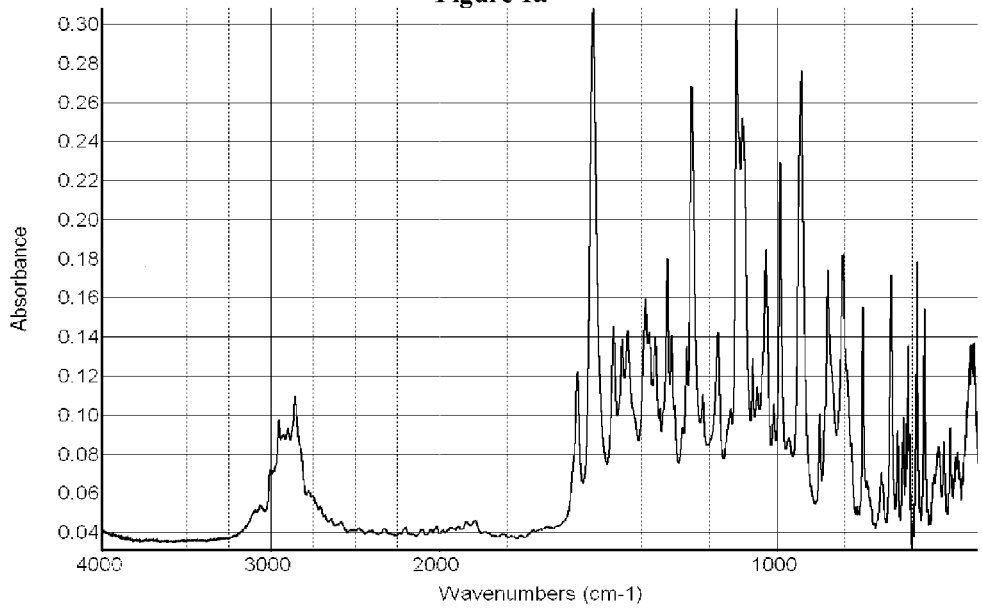
FIG. 1a is an Infrared (IR) spectrum representation of compound 1.

The Chemical names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006). In case of tautomeric forms, the name of the depicted tautomeric form of the structure was generated. However it should be clear that the other non-depicted tautomeric form is also included within the scope of the present invention.

DEFINITIONS

The term "halogen" or "halo" as used herein alone or as part of another group refers to fluoro, chloro, bromo or iodo, with fluoro or chloro being preferred.

The term "$C_{0-4}$alkyl", "$C_{1-4}$alkyl" or "$C_{1-5}$alkyl" as employed herein alone or as part of another group, unless otherwise stated, refers to a saturated straight or branched hydrocarbon radical, having unless otherwise stated, from 0 to 4, 1 to 4 or 1 to 5 carbon atoms, which is attached to the rest of the molecule by a single bond, such as methyl, ethyl, propyl, butyl, 1-pentyl, 1-methylethyl, 1,1-dimethylethyl, 2-methylpropyl, and 3-methylbutyl.

The term "$C_{3-8}$cycloalkyl" as employed herein alone or as part of another group unless otherwise stated, is generic to cyclopropyl, cyclobutyl, cyclopentyl, cyclohexyl, cycloheptyl and cyclooctyl.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation or reversal of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "treatment" is intended to refer to all processes, wherein there may be a slowing, interrupting, arresting or stopping of the progression of a disease, but does not necessarily indicate a total elimination of all symptoms.

Unless otherwise stated, heterocyclic substituents in $R^1$ such as tetrahydropyranyl and pyridinyl may be attached to the remainder of the molecule of formula (I) through any available ring carbon atom. Thus, for example, when Het is pyridinyl, it may be pyridin-2-yl, pyridin-3-yl or pyridin-4-yl, unless otherwise specified.

Substituents covered by the term Het may be attached to the remainder of the molecule of formula (I) through any available ring carbon or heteroatom as appropriate, if not otherwise specified. Het as used herein, is preferably a 5- or 6-aromatic membered heterocyclic ring preferably bound to the imidazo[1,2-b]pyridazine ring system through an available carbon atom of the ring. When Het is pyridine and $R^5$ is methyl, the $R^5$ substituent is placed in Het preferably in meta- or para-position relative to the position of attachment to the imidazo[1,2-b]pyridazine core.

In one embodiment, the invention relates to a compound according to Formula (I) or a stereochemically isomeric form thereof, wherein $R^1$ is selected from pyridinyl; pyridinyl optionally substituted with halogen, $C_{1-4}$alkyl, trifluoromethyl or $C_{1-4}$alkyloxy; tetrahydropyranyl; and $NR^6R^7$; wherein $R^6$ and $R^7$ taken together with the nitrogen can be a radical of Formula (a), (b) or (c) as previously defined;

$R^2$ is selected from hydrogen, methyl, ethyl, cyclopropyl, isopropyl, methoxy and trifluoromethyl;

$R^3$ is selected from hydrogen, chloro, methyl, trifluoromethyl and cyclopropyl;

Het is selected from the group consisting of pyridinyl, pyrimidinyl, pyridazinyl, oxazolyl, thiazolyl, pyrazolyl, isothiazolyl, isoxazolyl, oxadiazolyl and triazolyl and $R^4$-$R^{10}$, m, n and o are as previously defined;

or a pharmaceutically acceptable salt or a solvate thereof.

In a more preferred embodiment, the invention relates to a compound according to Formula (I) or a stereochemically isomeric form thereof, wherein $R^1$ is selected from pyridinyl which may be optionally substituted with halogen, $C_{1-4}$alkyl, trifluoromethyl or $C_{1-4}$alkyloxy; morpholinyl; and $NR^6R^7$; wherein $R^6$ and $R^7$ taken together with the nitrogen can be a radical of Formula (a) or (c) wherein n is 3 and o is 1;

Het is selected from pyridinyl and pyrazolyl;

$R^4$ is hydrogen, $C_{1-4}$alkyl, trifluoromethyl$C_{0-4}$alkyl, hydroxy$C_{1-4}$alkyl, difluorocyclopropylmethyl, cyclopropyldifluoroethyl, $C_{3-8}$cycloalkyl, $C_{1-4}$alkyloxy$C_{1-5}$alkyl, $C_{1-4}$alkyloxy, trifluoromethyl$C_{0-4}$alkyloxy, $C_{3-8}$cycloalkyl$C_{1-4}$alkyloxy, $C_{1-6}$alkyloxy$C_{1-4}$alkyloxy, tetrahydropyranyl, pyridinylmethyl, $NR^{6a}R^{7a}C_{1-4}$alkyl or $NR^{6a}R^{7a}$;

wherein $R^6$, $R^{6a}$, $R^7$ and $R^{7a}$ are each independently hydrogen or $C_{1-4}$alkyl, or taken together with the nitrogen can be a radical of formula (a), (b) or (c), wherein n is 3, $R^9$ is hydrogen or $C_{1-4}$alkyloxy, m is 0, o is 1 and $R^{10}$ is hydrogen;

and the remaining variables $R^2$-$R^5$ are as previously defined;

or a pharmaceutically acceptable salt or a solvate thereof.

In another preferred embodiment, the invention relates to a compound according to Formula (I) or a stereochemically isomeric form thereof, wherein $R^1$ is selected from pyridinyl, morpholinyl and pyrrolidinyl;

$R^4$ is selected from hydrogen; methyl; ethyl; isopropyl; isobutyl; trifluoromethyl; 2,2,2-trifluoroethyl; 2-hydroxy-2-methylpropyl; (2,2-difluorocyclopropyl)methyl; 2,2-difluoro-2-cyclopropylethyl; cyclopropyl; 2-methoxyethyl; 2-methoxypropyl; (2S)-2-methoxypropyl; 2-isopropoxyethyl; 2-ethoxyethyl; ethoxymethyl; 1-ethoxy-1-methylethyl; 1-methoxy-1-methylethyl; 2-methoxy-1,1-dimethylethyl; 3-methoxy-3-methylbutyl; 3-methoxypropyl; 2-methoxy-2-methyl-propyl; isopropoxy; 2,2,2-trifluoroethoxy; cyclopropylmethoxy; 2-methoxyethoxy; 2-methoxy-2-methyl-propoxy; tetrahydro-2H-pyran-4-yl; (pyridin-3-yl)methyl; 2-(pyrrolidin-1-yl)ethyl; isopropylamino; morpholin-4-yl; pyrrolidin-1-yl; piperazin-1-yl; (3R)-3-methoxypyrrolidin-1-yl; and (3S)-3-methoxypyrrolidin-1-yl;

$R^5$ is hydrogen or methyl;

and $R^2$, $R^3$ and Het are as previously defined;

or a pharmaceutically acceptable salt or a solvate thereof.

In yet another preferred embodiment, the invention relates to a compound according to Formula (I) or a stereochemically isomeric form thereof wherein $R^1$ is selected from morpholinyl and pyridinyl;

$R^2$ is selected from hydrogen, methyl, ethyl, methoxy, and cyclopropyl;

$R^3$ is selected from hydrogen, methyl, and cyclopropyl;

Het is pyridinyl or pyrazolyl;

$R^4$ is selected from ethyl; isopropyl; isobutyl; 2,2,2-trifluoroethyl; 2-hydroxy-2-methylpropyl; 2,2-difluoro-2-cyclopropylethyl; cyclopropyl; 2-methoxyethyl; (2S)-2-methoxypropyl; 2-ethoxyethyl; ethoxymethyl; 1-ethoxy-1-methylethyl; 1-methoxy-1-methylethyl; 2-methoxy-1,1-dimethylethyl; 3-methoxy-3-methylbutyl; 3-methoxypropyl; 2-methoxy-2-methyl-propyl; 2-methoxyethoxy; 2-methoxy-2-methyl-propoxy; tetrahydro-2H-pyran-4-yl; morpholin-4-yl; piperazin-1-yl; and (3R)-3-methoxypyrrolidin-1-yl;

and $R^5$ is hydrogen or methyl;

or a pharmaceutically acceptable salt or a solvate thereof.

In yet another preferred embodiment, the invention relates to a compound according to Formula (I) or a stereochemically isomeric form thereof wherein $R^1$ is selected from morpholinyl and pyridinyl;

$R^2$ is selected from hydrogen, methyl, methoxy, and cyclopropyl;

$R^3$ is selected from hydrogen, methyl, and cyclopropyl;

Het is pyridinyl or pyrazolyl;

$R^4$ is selected from ethyl; isopropyl; isobutyl; 2,2,2-trifluoroethyl; 2-hydroxy-2-methylpropyl; 2,2-difluoro-2-cyclopropylethyl; cyclopropyl; 2-methoxyethyl; (2S)-2-methoxypropyl; 2-ethoxyethyl; ethoxymethyl; 1-ethoxy-1-methylethyl; 1-methoxy-1-methylethyl; 2-methoxy-1,1-dimethylethyl; 3-methoxy-3-methylbutyl; 3-methoxypropyl; 2-methoxy-2-methyl-propyl; 2-methoxyethoxy; 2-methoxy-2-methyl-propoxy; tetrahydro-2H-pyran-4-yl; morpholin-4-yl; piperazin-1-yl; and (3R)-3-methoxypyrrolidin-1-yl;

and $R^5$ is hydrogen or methyl;

or a pharmaceutically acceptable salt or a solvate thereof.

In yet another preferred embodiment, the invention relates to a compound according to Formula (I) or a stereochemically isomeric form thereof wherein $R^1$ is selected from morpholinyl and pyridinyl;

$R^2$ is selected from hydrogen, methyl, methoxy, and cyclopropyl;

$R^3$ is selected from hydrogen, methyl, and cyclopropyl;

Het is pyridinyl or pyrazolyl;

$R^4$ is selected from 2-methoxyethyl; 3-methoxypropyl; 2-methoxy-2-methylpropyl; 2-methoxy-1,1-dimethylethyl; 1-ethoxy-1-methylethyl; 1-methoxy-1-methylethyl; 2-methoxyethoxy; ethoxymethyl; 2-methoxy-2-methylpropoxy; morpholin-4-yl; 2-ethoxyethyl; tetrahydro-2H-pyran-4-yl; ethyl; 3-methoxy-3-methylbutyl; piperazin-1-yl; isopropyl; cyclopropyl; (3R)-3-methoxypyrrolidin-1-yl; and isobutyl;

and $R^5$ is hydrogen or methyl;

or a pharmaceutically acceptable salt or a solvate thereof.

More preferably, the invention relates to a compound according to Formula (I) or a stereochemically isomeric form thereof wherein $R^1$ is selected from morpholin-4-yl, pyridin-3-yl and pyridin-4-yl;

Het is selected from pyridin-3-yl, pyridin-4-yl and 1H-pyrazol-4-yl;

and $R^2$-$R^5$ are as previously defined;

or a pharmaceutically acceptable salt or a solvate thereof.

In a yet a more preferred embodiment, the invention relates to a compound according to Formula (I), or a stereochemically isomeric form thereof, wherein $R^1$ is morpholin-4-yl;

Het is pyridin-3-yl or pyridin-4-yl;

and $R^2$-$R^5$ are as previously defined;

or a pharmaceutically acceptable salt or a solvate thereof.

In the most preferred embodiment, the invention relates to a compound according to Formula (I) wherein $R^1$ is morpholin-4-yl;

$R^2$ is methyl;

$R^3$ is hydrogen;

Het is pyridin-3-yl;

$R^4$ is 2-methoxyethyl; and $R^5$ is hydrogen;

or a pharmaceutically acceptable salt or a solvate thereof.

An additional embodiment refers to compounds according to Formula (I), wherein $R^3$ is hydrogen and the rest of variables are as previously defined, and the stereochemically isomeric forms thereof and the pharmaceutically acceptable salts and solvates thereof.

In an additional embodiment, the invention relates to compounds according to formula (I), having the formula (I'-a) or (I'-b)

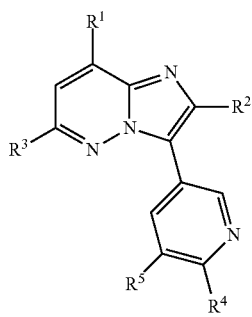
(I'-a)

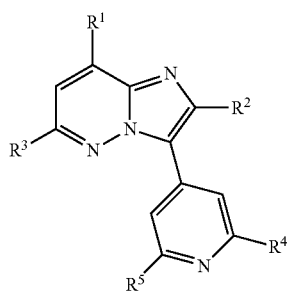
(I'-b)

wherein $R^1$, $R^2$, $R^3$, $R^4$ and $R^5$ are as previously defined.

In an additional embodiment, $R^1$ is morpholin-4-yl.
In an additional embodiment, $R^1$ is pyridin-4-yl.
In an additional embodiment, $R^1$ is pyridin-3-yl.
In an additional embodiment, $R^3$ is hydrogen.
In an additional embodiment, $R^2$ is methyl and $R^3$ is hydrogen.
In an additional embodiment, Het is 3-pyridinyl or 4-pyridinyl.
In an additional embodiment, Het is 1H-pyrazol-4-yl.
In an additional embodiment, $R^4$ is selected from ethyl; isopropyl; isobutyl; 2,2,2-trifluoroethyl; 2-hydroxy-2-methylpropyl; 2,2-difluoro-2-cyclopropylethyl; cyclopropyl; 2-methoxyethyl; (2S)-2-methoxypropyl; 2-ethoxyethyl; ethoxymethyl; 1-ethoxy-1-methylethyl; 1-methoxy-1-methylethyl; 2-methoxy-1,1-dimethylethyl; 3-methoxy-3-methylbutyl; 3-methoxypropyl; 2-methoxy-2-methyl-propyl; 2-methoxyethoxy; 2-methoxy-2-methyl-propoxy; tetrahydro-2H-pyran-4-yl; morpholin-4-yl; piperazin-1-yl; and (3R)-3-methoxypyrrolidin-1-yl.

In an additional embodiment, $R^4$ is selected from ethyl; isopropyl; isobutyl; 2-hydroxy-2-methylpropyl; cyclopropyl; 2-methoxyethyl; 2-ethoxyethyl; ethoxymethyl; 1-ethoxy-1-methylethyl; 1-methoxy-1-methylethyl; 2-methoxy-1,1-dimethylethyl; 3-methoxy-3-methylbutyl; 3-methoxypropyl; 2-methoxy-2-methylpropyl; 2-methoxyethoxy; 2-methoxy-2-methyl-propoxy; tetrahydro-2H-pyran-4-yl; morpholin-4-yl; piperazin-1-yl; and (3R)-3-methoxypyrrolidin-1-yl.

In an additional embodiment, $R^4$ is selected from ethyl; 2-hydroxy-2-methylpropyl; 2-methoxyethyl; 2-methoxy-2-methylpropyl; 2-methoxyethoxy; 2-methoxy-2-methyl-propoxy; and morpholin-4-yl.

In an additional embodiment, the invention relates to a compound according to formula (I'-a) of (I'-b) wherein
$R^1$ is morpholin-4-yl;
$R^2$ is methyl;
$R^3$ is hydrogen;
Het is pyridin-3-yl;
$R^4$ is 2-methoxyethyl; and
$R^5$ is hydrogen.

In an additional embodiment, the invention relates to a compound according to formula (I'-c)

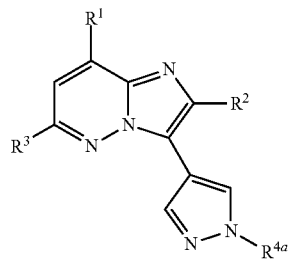
(I'-c)

wherein $R^1$, $R^2$, $R^3$ are as previously defined, $R^{4a}$ is selected from the group consisting of $R^{4a}$ is selected from the group consisting of hydrogen, $C_{1-4}$alkyl, trifluoromethyl$C_{0-4}$alkyl, hydroxy$C_{1-4}$alkyl, difluorocyclopropylmethyl, cyclopropyldifluoroethyl, $C_{3-8}$cycloalkyl, $C_{1-4}$alkyloxy$C_{1-5}$alkyl, tetrahydropyranyl and pyridinylmethyl.

In an additional embodiment, $R^{4a}$ is selected from hydrogen; isobutyl; 2,2,2-trifluoroethyl; (2,2-difluorocyclopropyl)methyl; 2,2-difluoro-2-cyclopropylethyl; 2-methoxyethyl; (2S)-2-methoxypropyl; 2-methoxy-2-methyl-propyl; tetrahydro-2H-pyran-4-yl; and (pyridin-3-yl)methyl.

In another embodiment, $R^{4a}$ is selected from isobutyl; 2,2,2-trifluoroethyl; 2,2-difluoro-2-cyclopropylethyl; 2-methoxyethyl; (2S)-2-methoxypropyl; and 2-methoxy-2-methylpropyl.

Particularly preferred compounds may be selected from the group of:
3-[6-(2-methoxyethyl)-3-pyridinyl]-2-methyl-8-(4-morpholinyl)-imidazo[1,2-b]pyridazine (compound 1),
3-[6-(3-methoxypropyl)-3-pyridinyl]-2-methyl-8-(4-morpholinyl)-imidazo[1,2-b]pyridazine (compound 2),
3-[6-(2-methoxy-2-methylpropyl)-3-pyridinyl]-2-methyl-8-(4-morpholinyl)-imidazo[1,2-b]pyridazine (compound 3),
3-[6-(2-methoxy-1,1-dimethylethyl)-3-pyridinyl]-2-methyl-8-(4-morpholinyl)-imidazo[1,2-b]pyridazine (compound 4),
3-[6-(1-ethoxy-1-methylethyl)-3-pyridinyl]-2-methyl-8-(4-morpholinyl)-imidazo[1,2-b]pyridazine (compound 5),
3-[6-(1-methoxy-1-methylethyl)-3-pyridinyl]-2-methyl-8-(4-morpholinyl)-imidazo[1,2-b]pyridazine (compound 6),
3-[6-(2-methoxy-2-methylpropyl)-3-pyridinyl]-2-methyl-8-(4-pyridinyl)-imidazo[1,2-b]pyridazine (compound 7),
3-[6-(2-methoxyethoxy)-5-methyl-3-pyridinyl]-2-methyl-8-(4-pyridinyl)-imidazo[1,2-b]pyridazine (compound 8),
3-[6-(2-methoxyethoxy)-3-pyridinyl]-2-methyl-8-(3-pyridinyl)-imidazo[1,2-b]pyridazine (compound 9),
2-cyclopropyl-3-[6-(2-methoxyethyl)-3-pyridinyl]-8-(4-pyridinyl)-imidazo[1,2-b]pyridazine (compound 10),
3-[6-(2-methoxyethyl)-3-pyridinyl]-8-(4-morpholinyl)-imidazo[1,2-b]pyridazine (compound 11),
2-methoxy-3-[6-(2-methoxyethyl)-3-pyridinyl]-8-(4-morpholinyl)-imidazo[1,2-b]pyridazine (compound 12),
6-cyclopropyl-3-[6-(2-methoxyethyl)-3-pyridinyl]-2-methyl-8-(4-morpholinyl)-imidazo[1,2-b]pyridazine (compound 13),
6-cyclopropyl-3-[6-(2-methoxyethyl)-3-pyridinyl]-2-methyl-8-(4-pyridinyl)-imidazo[1,2-b]pyridazine (compound 14),
2-cyclopropyl-3-[6-(2-methoxyethyl)-3-pyridinyl]-6-methyl-8-(4-morpholinyl)-imidazo[1,2-b]pyridazine (compound 15), 3-[6-(2-methoxyethoxy)-3-pyridinyl]-2-methyl-8-(4-morpholinyl)-imidazo[1,2-b]pyridazine (compound 16), 3-[6-(ethoxymethyl)-3-pyridinyl]-2-methyl-8-(4-morpholinyl)-imidazo[1,2-b]pyridazine (compound 17), 3-[6-(2-methoxy-2-methylpropoxy)-3-pyridinyl]-2-methyl-8-(4-morpholinyl)-imidazo[1,2-b]pyridazine (compound 18), 2-methyl-8-(4-morpholinyl)-3-[6-(4-morpholinyl)-3-pyridinyl]-imidazo[1,2-b]pyridazine (compound 19), 3-[6-(2-methoxyethyl)-3-pyridinyl]-2-methyl-8-(4-pyridinyl)-imidazo[1,2-b]pyridazine (compound 20), 3-[6-(2-methoxyethoxy)-3-pyridinyl]-2-methyl-8-(4-pyridinyl)-imidazo[1,2-b]pyridazine (compound 21), 2-cyclopropyl-3-[6-(2-methoxyethyl)-3-pyridinyl]-8-(4-morpholinyl)-imidazo[1,2-b]pyridazine (compound 22), 3-[6-(2-methoxyethyl)-3-pyridinyl]-2,6-dimethyl-8-(4-morpholinyl)-imidazo[1,2-b]pyridazine (compound 23), 3-[6-(2-methoxyethyl)-3-pyridinyl]-2,6-dimethyl-8-(4-pyridinyl)-imidazo[1,2-b]pyridazine (compound 24), 3-[6-(2-ethoxyethyl)-3-pyridinyl]-2-methyl-8-(4-morpholinyl)-imidazo[1,2-b]pyridazine (compound 25), 3-[2-(2-methoxyethyl)-4-pyridinyl]-2-methyl-8-(4-morpholinyl)-imidazo[1,2-b]pyridazine (compound 26), 2-methyl-8-(4-morpholinyl)-3-[6-(tetrahydro-2H-pyran-4-yl)-3-pyridinyl]-imidazo[1,2-b]pyridazine (compound 27), 3-(6-ethyl-3-pyridinyl)-2-methyl-8-(4-morpholinyl)-imidazo[1,2-b]pyridazine (compound 28), 3-[6-(3-methoxy-3-methylbutyl)-3-pyridinyl]-2-methyl-8-(4-morpholinyl)-imidazo[1,2-b]pyridazine (compound 29), 2-methyl-8-(4-morpholinyl)-3-[6-(1-piperazinyl)-3-pyridinyl]-imidazo[1,2-b]pyridazine (compound 30), 2-methyl-3-[6-(4-morpholinyl)-3-pyridinyl]-8-(4-pyridinyl)-imidazo[1,2-b]pyridazine (compound 31), 2-methyl-3-[6-(1-methylethyl)-3-pyridinyl]-8-(4-morpholinyl)-imidazo[1,2-b]pyridazine (compound 32), 3-(6-cyclopropyl-3-pyridinyl)-2-methyl-8-(4-morpholinyl)-imidazo[1,2-b]pyridazine (compound 33), 3-[6-[(3R)-3-methoxy-1-pyrrolidinyl]-3-pyridinyl]-2-methyl-8-(4-morpholinyl)-imidazo[1,2-b]pyridazine (compound 34), 2-methyl-3-[1-(2-methylpropyl)-1H-pyrazol-4-yl]-8-(4-morpholinyl)-imidazo[1,2-b]pyridazine (compound 35), 3-[1-(2-methoxyethyl)-1H-pyrazol-4-yl]-2-methyl-8-(4-morpholinyl)-imidazo[1,2-b]pyridazine (compound 36), 3-[1-(2-methoxy-2-methylpropyl)-1H-pyrazol-4-yl]-2-methyl-8-(4-morpholinyl)-imidazo[1,2-b]pyridazine (compound 37), 2-cyclopropyl-3-[1-(2-methoxy-2-methylpropyl)-1H-pyrazol-4-yl]-8-(4-morpholinyl)-imidazo[1,2-b]pyridazine (compound 38), 2-methyl-3-(6-methyl-3-pyridinyl)-8-(4-morpholinyl)-imidazo[1,2-b]pyridazine (compound 39), 6-cyclopropyl-3-[6-(2-methoxy-2-methylpropyl)-3-pyridinyl]-2-methyl-8-(4-pyridinyl)-imidazo[1,2-b]pyridazine (compound 40), 6-cyclopropyl-3-[6-(2-methoxyethoxy)-3-pyridinyl]-2-methyl-8-(4-morpholinyl)-imidazo[1,2-b]pyridazine (compound 41), 6-cyclopropyl-3-[5-(2-methoxyethoxy)-3-pyridinyl]-2-methyl-8-(4-morpholinyl)-imidazo[1,2-b]pyridazine (compound 42), 6-cyclopropyl-3-[6-(2-methoxy-2-methylpropyl)-3-pyridinyl]-2-methyl-8-(4-morpholinyl)-imidazo[1,2-b]pyridazine (compound 43), 2-cyclopropyl-3-[6-(2-methoxyethoxy)-3-pyridinyl]-8-(4-pyridinyl)-imidazo[1,2-b]pyridazine (compound 44), 2-cyclopropyl-3-[6-(2-methoxy-2-methylpropyl)-3-pyridinyl]-8-(4-morpholinyl)-imidazo[1,2-b]pyridazine (compound 45), 2-cyclopropyl-3-[6-(4-morpholinyl)-3-pyridinyl]-8-(4-pyridinyl)-imidazo[1,2-b]pyridazine (compound 46), 3-[6-(2-methoxy-2-methylpropyl)-3-pyridinyl]-2,6-dimethyl-8-(4-morpholinyl)-imidazo[1,2-b]pyridazine (compound 47), 3-[6-(2-methoxy-2-methylpropyl)-3-pyridinyl]-2,6-dimethyl-8-(4-pyridinyl)-imidazo[1,2-b]pyridazine (compound 48), 3-[6-(2-methoxyethoxy)-3-pyridinyl]-2,6-dimethyl-8-(4-pyridinyl)-imidazo[1,2-b]pyridazine (compound 49), 2-cyclopropyl-3-[6-(2-methoxy-2-methylpropyl)-3-pyridinyl]-8-(4-pyridinyl)-imidazo[1,2-b]pyridazine (compound 50), 3-[6-(2-methoxy-2-methylpropyl)-3-pyridinyl]-8-(4-morpholinyl)-imidazo[1,2-b]pyridazine (compound 51), 3-[6-(2-methoxyethoxy)-3-pyridinyl]-8-(4-morpholinyl)-imidazo[1,2-b]pyridazine (compound 52), 2-cyclopropyl-3-[6-(2-methoxy-2-methylpropyl)-3-pyridinyl]-6-methyl-8-(4-morpholinyl)-imidazo[1,2-b]pyridazine (compound 53), 5-[2-cyclopropyl-8-(4-morpholinyl)imidazo[1,2-b]pyridazin-3-yl]-α,α-dimethyl-2-pyridineethanol (compound 54), 2-cyclopropyl-3-[6-(2-methoxy-2-methylpropyl)-3-pyridinyl]-6-methyl-8-(4-pyridinyl)-imidazo[1,2-b]pyridazine (compound 55), 2-cyclopropyl-3-[6-(2-methoxyethyl)-3-pyridinyl]-6-methyl-8-(4-pyridinyl)-imidazo[1,2-b]pyridazine (compound 56), 3-[6-(2-methoxyethyl)-3-pyridinyl]-8-(4-pyridinyl)-imidazo[1,2-b]pyridazine (compound 57), 6-cyclopropyl-2-methyl-3-[6-(4-morpholinyl)-3-pyridinyl]-8-(4-pyridinyl)-imidazo[1,2-b]pyridazine (compound 58), 6-cyclopropyl-3-[6-(2-methoxyethoxy)-3-pyridinyl]-2-methyl-8-(4-pyridinyl)-imidazo[1,2-b]pyridazine (compound 59), 3-[6-(2-methoxy-2-methylpropyl)-3-pyridinyl]-8-(4-pyridinyl)-imidazo[1,2-b]pyridazine (compound 60), 3-[6-(4-morpholinyl)-3-pyridinyl]-8-(4-pyridinyl)-imidazo[1,2-b]pyridazine (compound 61), 2-methyl-8-(4-morpholinyl)-3-[6-(2,2,2-trifluoroethoxy)-3-pyridinyl]-imidazo[1,2-b]pyridazine (compound 62), 2-methyl-8-(4-morpholinyl)-3-[6-(trifluoromethyl)-3-pyridinyl]-imidazo[1,2-b]pyridazine (compound 63), 3-[6-(2-methoxyethyl)-3-pyridinyl]-2-methyl-8-(4-morpholinyl)-6-(trifluoromethyl)-imidazo[1,2-b]pyridazine (compound 64), 3-[6-(cyclopropylmethoxy)-3-pyridinyl]-2-methyl-8-(4-morpholinyl)-imidazo[1,2-b]pyridazine (compound 65), 2-methyl-3-[6-(1-methylethoxy)-3-pyridinyl]-8-(4-morpholinyl)-imidazo[1,2-b]pyridazine (compound 66), 2-methyl-3-[2-(1-methylethoxy)-4-pyridinyl]-8-(4-morpholinyl)-imidazo[1,2-b]pyridazine (compound 67), 2,6-dimethyl-8-(4-morpholinyl)-3-[6-(4-morpholinyl)-3-pyridinyl]-imidazo[1,2-b]pyridazine (compound 68), 3-[6-(2-methoxyethoxy)-3-pyridinyl]-2,6-dimethyl-8-(4-morpholinyl)-imidazo[1,2-b]pyridazine (compound 69), 2,6-dimethyl-3-[6-(4-morpholinyl)-3-pyridinyl]-8-(4-pyridinyl)-imidazo[1,2-b]pyridazine (compound 70), 2-cyclopropyl-6-methyl-3-[6-(4-morpholinyl)-3-pyridinyl]-8-(4-pyridinyl)-imidazo[1,2-b]pyridazine (compound 71), 2-cyclopropyl-3-[6-(2-methoxyethoxy)-3-pyridinyl]-6-methyl-8-(4-pyridinyl)-imidazo[1,2-b]pyridazine (compound 72), 2-cyclopropyl-3-[6-(2-methoxyethoxy)-3-pyridinyl]-8-(4-morpholinyl)-imidazo[1,2-b]pyridazine (compound 73), 2-cyclopropyl-3-[6-(2-methoxyethoxy)-3-pyridinyl]-6-methyl-8-(4-morpholinyl)-imidazo[1,2-b]pyridazine (compound 74), 2-cyclopropyl-6-methyl-8-(4-morpholinyl)-3-[6-(4-morpholinyl)-3-pyridinyl]-imidazo[1,2-b]pyridazine (compound 75), 2-methyl-3-[6-[2-(1-methylethoxy)ethyl]-3-pyridinyl]-8-(4-morpholinyl)-imidazo[1,2-b]pyridazine (compound 76), 2-methyl-8-(4-morpholinyl)-3-[6-[2-(1-pyrrolidinyl)ethyl]-3-pyridinyl]-imidazo[1,2-b]pyridazine (compound 77), 6-cyclopropyl-2-methyl-8-(4-morpholinyl)-3-[6-(tetrahydro-2H-pyran-4-yl)-3-pyridinyl]-imidazo[1,2-b]pyridazine (compound 78), 2-cyclopropyl-6-methyl-8-(4-morpholinyl)-3-[6-(tetrahydro-2H-pyran-4-yl)-3-pyridinyl]-imidazo[1,2-b]pyridazine (compound 79), 2-cyclopropyl-6-methyl-8-(4-pyridinyl)-3-[6-(tetrahydro-2H-pyran-4-yl)-3-pyridinyl]-imidazo[1,2-b]pyridazine (compound 80), 6-cyclopropyl-2-methyl-8-(4-pyridinyl)-3-[6-(tetrahydro-2H-pyran-4-yl)-3-pyridinyl]-imidazo[1,2-b]pyridazine (compound 81), 8-(4-morpholinyl)-3-[6-(tetrahydro-2H-pyran-4-yl)-3-pyridinyl]-imidazo[1,2-b]pyridazine (compound 82), 3-(6-ethyl-3-pyridinyl)-2-methyl-8-(4-pyridinyl)-imidazo[1,2-b]pyridazine (compound 83), 2-cyclopropyl-3-(6-ethyl-3-pyridinyl)-6-methyl-8-(4-morpholinyl)-imidazo[1,2-b]pyridazine (compound 84), 2-cyclopropyl-3-[6-(2-methoxyethyl)-3-pyridinyl]-8-(4-morpholinyl)-6-(trifluoromethyl)-imidazo[1,2-b]pyridazine (compound 85), 6-cyclopropyl-3-(6-ethyl-3-pyridinyl)-2-methyl-8-(4-pyridinyl)-imidazo[1,2-b]pyridazine (compound 86), 2-cyclopropyl-3-(6-ethyl-3-pyridinyl)-8-(4-pyridinyl)-imidazo[1,2-b]pyridazine (compound 87), 3-(6-ethyl-3-pyridinyl)-2,6-dimethyl-8-(4-pyridinyl)-imidazo[1,2-b]pyridazine (compound 88), 2-methyl-8-(4-morpholinyl)-3-[6-(1-pyrrolidinyl)-3-pyridinyl]-imidazo[1,2-b]pyridazine (compound 89), N-(1-methylethyl)-5-[2-methyl-8-(4-morpholinyl)imidazo[1,2-b]pyridazin-3-yl]-2-pyridinamine (compound 90), 2-methyl-8-(4-morpholinyl)-3-[2-(4-morpholinyl)-4-pyridinyl]-imidazo[1,2-b]pyridazine (compound 91), 2-methyl-8-(4-morpholinyl)-3-[2-(1-pyrrolidinyl)-4-pyridinyl]-imidazo[1,2-b]pyridazine (compound 92), N-(1-methylethyl)-4-[2-methyl-8-(4-morpholinyl)imidazo[1,2-b]pyridazin-3-yl]-2-pyridinamine (compound 93), 6-cyclopropyl-2-methyl-8-(4-morpholinyl)-3-[6-(4-morpholinyl)-3-pyridinyl]-imidazo[1,2-b]pyridazine (compound 94), 2-cyclopropyl-8-(4-morpholinyl)-3-[6-(4-morpholinyl)-3-pyridinyl]-imidazo[1,2-b]pyridazine (compound 95), 2,6-dimethyl-3-[6-(1-piperazinyl)-3-pyridinyl]-8-(4-pyridinyl)-imidazo[1,2-b]pyridazine (compound 96), 2-methyl-3-[6-(1-piperazinyl)-3-pyridinyl]-8-(4-pyridinyl)-imidazo[1,2-b]pyridazine (compound 97), 2-cyclopropyl-8-(4-morpholinyl)-3-[6-(1-piperazinyl)-3-pyridinyl]-imidazo[1,2-b]pyridazine (compound 98), 6-cyclopropyl-2-methyl-3-[6-(1-piperazinyl)-3-pyridinyl]-8-(4-pyridinyl)-imidazo[1,2-b]pyridazine (compound 99), 2-cyclopropyl-6-methyl-8-(4-morpholinyl)-3-[6-(1-piperazinyl)-3-pyridinyl]-imidazo[1,2-b]pyridazine (compound 100), 2-cyclopropyl-6-methyl-3-[6-(1-piperazinyl)-3-pyridinyl]-8-(4-pyridinyl)-imidazo[1,2-b]pyridazine (compound 101), 2-cyclopropyl-3-[6-(1-piperazinyl)-3-pyridinyl]-8-(4-pyridinyl)-imidazo[1,2-b]pyridazine (compound 102), 2-methyl-8-(4-morpholinyl)-3-[2-(1-piperazinyl)-4-pyridinyl]-imidazo[1,2-b]pyridazine (compound 103), 2-methyl-3-[6-(2-methylpropyl)-3-pyridinyl]-8-(4-morpholinyl)-imidazo[1,2-b]pyridazine (compound 104), 2-methyl-3-[2-(2-methylpropyl)-4-pyridinyl]-8-(4-morpholinyl)-imidazo[1,2-b]pyridazine (compound 105), 2-cyclopropyl-3-(6-ethyl-3-pyridinyl)-8-(4-morpholinyl)-imidazo[1,2-b]pyridazine (compound 106), 6-cyclopropyl-3-(6-ethyl-3-pyridinyl)-2-methyl-8-(4-morpholinyl)-imidazo[1,2-b]pyridazine (compound 107), 3-(6-ethyl-3-pyridinyl)-2,6-dimethyl-8-(4-morpholinyl)-imidazo[1,2-b]pyridazine (compound 108), 3-(6-ethyl-3-pyridinyl)-8-(4-morpholinyl)-imidazo[1,2-b]pyridazine (compound 109), 3-(6-cyclopropyl-3-pyridinyl)-2,6-dimethyl-8-(4-morpholinyl)-imidazo[1,2-b]pyridazine (compound 110), 3-(6-cyclopropyl-3-pyridinyl)-2-methyl-8-(4-pyridinyl)-imidazo[1,2-b]pyridazine (compound 111), 3-(6-cyclopropyl-3-pyridinyl)-8-(4-morpholinyl)-imidazo[1,2-b]pyridazine (compound 112), 3-[6-[(3S)-3-methoxy-1-pyrrolidinyl]-3-pyridinyl]-2-methyl-8-(4-morpholinyl)-imidazo[1,2-b]pyridazine (compound 113), 3-[1-(2-methoxyethyl)-M-pyrazol-4-yl]-2-methyl-8-(4-pyridinyl)-imidazo[1,2-b]pyridazine (compound 114), 2-methyl-8-(4-morpholinyl)-3-[1-(3-pyridinylmethyl)-1H-pyrazol-4-yl]-imidazo[1,2-b]pyridazine (compound 115), 2-methyl-8-(4-morpholinyl)-3-(1H-pyrazol-4-yl)-imidazo[1,2-b]pyridazine (compound 116), 2-methyl-8-(4-morpholinyl)-3-[1-(tetrahydro-2H-pyran-4-yl)-1H-pyrazol-4-yl]-imidazo[1,2-b]pyridazine (compound 117), 3-{1-[(2,2-difluorocyclopropyl)methyl]-1H-pyrazol-4-yl}-2-methyl-8-morpholin-4-ylimidazo[1,2-b]pyridazine (compound 118), 2-cyclopropyl-3-[1-(2-methoxyethyl)-1H-pyrazol-4-yl]-8-(4-morpholinyl)-imidazo[1,2-b]pyridazine (compound 119), 3-[1-(2-methoxyethyl)-1H-pyrazol-4-yl]-2-(1-methylethyl)-8-(4-morpholinyl)-imidazo[1,2-b]pyridazine (compound 120), 3-[1-(2-methoxyethyl)-1H-pyrazol-4-yl]-2-(1-methylethyl)-8-(4-pyridinyl)-imidazo[1,2-b]pyridazine (compound 121), 3-[1-(2-methoxyethyl)-1H-pyrazol-4-yl]-8-(4-pyridinyl)-2-(trifluoromethyl)-imidazo[1,2-b]pyridazine (compound 122), 3-[1-(2-methoxy-2-methylpropyl)-1H-pyrazol-4-yl]-2-methyl-8-(4-pyridinyl)-imidazo[1,2-b]pyridazine (compound 123), 2-methyl-3-[1-(2-methylpropyl)-1H-pyrazol-4-yl]-8-(4-pyridinyl)-imidazo[1,2-b]pyridazine (compound 124), 6-cyclopropyl-3-[1-(2-methoxyethyl)-1H-pyrazol-4-yl]-2-methyl-8-(4-morpholinyl)-imidazo[1,2-b]pyridazine (compound 125), 6-cyclopropyl-3-[1-(2-methoxyethyl)-1H-pyrazol-4-yl]-2-methyl-8-(4-pyridinyl)-imidazo[1,2-b]pyridazine (compound 126), 2-ethyl-3-[1-(2-methoxyethyl)-1H-pyrazol-4-yl]-8-(4-morpholinyl)-imidazo[1,2-b]pyridazine (compound 127),
3-[1-(2-cyclopropyl-2,2-difluoroethyl)-1H-pyrazol-4-yl]-2-methyl-8-(4-morpholinyl)-imidazo[1,2-b]pyridazine (compound 128),
3-[1-(2-methoxyethyl)-1H-pyrazol-4-yl]-2-methyl-8-(4-pyridinyl)-6-(trifluoromethyl)-imidazo[1,2-b]pyridazine (compound 129),
3-[1-(2-methoxyethyl)-1H-pyrazol-4-yl]-2-methyl-8-(4-morpholinyl)-6-(trifluoromethyl)-imidazo[1,2-b]pyridazine (compound 130),
3-[1-[(2S)-2-methoxypropyl]-1H-pyrazol-4-yl]-2-methyl-8-(4-morpholinyl)-imidazo[1,2-b]pyridazine (compound 131),
2-ethyl-3-[1-(2-methoxyethyl)-1H-pyrazol-4-yl]-8-(4-pyridinyl)-imidazo[1,2-b]pyridazine (compound 132),
3-[1-(2-methoxyethyl)-1H-pyrazol-4-yl]-2,6-dimethyl-8-(4-morpholinyl)-imidazo[1,2-b]pyridazine (compound 133),
3-[1-(2-methoxyethyl)-1H-pyrazol-4-yl]-2,6-dimethyl-8-(4-pyridinyl)-imidazo[1,2-b]pyridazine (compound 134),
2-methyl-8-(4-pyridinyl)-3-[1-(2,2,2-trifluoroethyl)-1H-pyrazol-4-yl]-imidazo[1,2-b]pyridazine (compound 135),
3-[1-(2-methoxyethyl)-1H-pyrazol-4-yl]-2-methyl-8-(1-pyrrolidinyl)-imidazo[1,2-b]pyridazine (compound 136),
2-methyl-8-(4-morpholinyl)-3-[1-(2,2,2-trifluoroethyl)-1H-pyrazol-4-yl]-imidazo[1,2-b]pyridazine (compound 137),
2-cyclopropyl-8-(4-morpholinyl)-3-[1-(2,2,2-trifluoroethyl)-1H-pyrazol-4-yl]-imidazo[1,2-b]pyridazine (compound 138),
3-[1-(2-methoxyethyl)-1H-pyrazol-4-yl]-8-(4-morpholinyl)-2-(trifluoromethyl)-imidazo[1,2-b]pyridazine (compound 139),
2-methoxy-3-[1-(2-methoxyethyl)-1H-pyrazol-4-yl]-8-(4-morpholinyl)-imidazo[1,2-b]pyridazine (compound 140),
2-cyclopropyl-8-(4-pyridinyl)-3-[1-(2,2,2-trifluoroethyl)-1H-pyrazol-4-yl]-imidazo[1,2-b]pyridazine (compound 141),
2-cyclopropyl-3-[1-(2-methoxyethyl)-1H-pyrazol-4-yl]-8-(4-pyridinyl)-imidazo[1,2-b]pyridazine (compound 142),
2-cyclopropyl-3-[1-(2-methoxy-2-methylpropyl)-1H-pyrazol-4-yl]-8-(4-pyridinyl)-imidazo[1,2-b]pyridazine (compound 143),
8-(4-morpholinyl)-3-[6-(4-morpholinyl)-3-pyridinyl]-imidazo[1,2-b]pyridazine (compound 144),
3-[6-(2-methoxyethyl)-3-pyridinyl]-8-(4-morpholinyl)-2-(trifluoromethyl)-imidazo[1,2-b]pyridazine (compound 145),
6-chloro-2-methyl-8-(4-morpholinyl)-3-[1-(2,2,2-trifluoroethyl)-1H-pyrazol-4-yl]-imidazo[1,2-b]pyridazine (compound 146),
6-chloro-3-[1-(2-methoxyethyl)-1H-pyrazol-4-yl]-2-methyl-8-(4-pyridinyl)-imidazo[1,2-b]pyridazine (compound 147),
2-cyclopropyl-3-[1-(2-methylpropyl)-1H-pyrazol-4-yl]-8-(4-pyridinyl)-imidazo[1,2-b]pyridazine (compound 148), and
3-[5-(2-methoxyethoxy)-3-pyridinyl]-2-methyl-8-(4-pyridinyl)-imidazo[1,2-b]pyridazine (compound 149),
and the stereoisomeric forms, the pharmaceutically acceptable salts and the solvates thereof.

More preferred particular compounds are compounds 1 to 38, and pharmaceutically acceptable salts thereof.

Other particularly preferred compounds include
3-[6-(2-methoxyethyl)-3-pyridinyl]-2-methyl-8-(4-morpholinyl)-imidazo[1,2-b]pyridazine hydrochloride (compound 1a),
3-[6-(2-methoxyethyl)-3-pyridinyl]-2-methyl-8-(4-morpholinyl)-imidazo[1,2-b]pyridazine maleate (compound 1b),
3-[6-(2-methoxyethyl)-3-pyridinyl]-2-methyl-8-(4-morpholinyl)-imidazo[1,2-b]pyridazine monohydrate (compound 1c),
3-[6-(2-methoxyethoxy)-3-pyridinyl]-2-methyl-8-(4-pyridinyl)-imidazo[1,2-b]pyridazine hydrochloride (compound 21a),
2-cyclopropyl-3-[6-(2-methoxy-2-methylpropyl)-3-pyridinyl]-8-(4-morpholinyl)-imidazo[1,2-b]pyridazine hydrochloride (compound 45a),
3-[6-(2-methoxy-2-methylpropyl)-3-pyridinyl]-2,6-dimethyl-8-(4-pyridinyl)-imidazo[1,2-b]pyridazine (compound 48),
2-cyclopropyl-3-[6-(2-methoxy-2-methylpropyl)-3-pyridinyl]-8-(4-pyridinyl)-imidazo[1,2-b]pyridazine (compound 50),
5-[2-cyclopropyl-8-(4-morpholinyl)imidazo[1,2-b]pyridazin-3-yl]-α,α-dimethyl-2-pyridineethanol (compound 54),
3-[6-(4-morpholinyl)-3-pyridinyl]-8-(4-pyridinyl)-imidazo[1,2-b]pyridazine (compound 61),
2,6-dimethyl-8-(4-morpholinyl)-3-[6-(4-morpholinyl)-3-pyridinyl]-imidazo[1,2-b]pyridazine (compound 68),
2-cyclopropyl-6-methyl-3-[6-(4-morpholinyl)-3-pyridinyl]-8-(4-pyridinyl)-imidazo[1,2-b]pyridazine (compound 71),
2-cyclopropyl-3-[6-(2-methoxyethoxy)-3-pyridinyl]-6-methyl-8-(4-pyridinyl)-imidazo[1,2-b]pyridazine (compound 72),
2-methyl-8-(4-morpholinyl)-3-[2-(4-morpholinyl)-4-pyridinyl]-imidazo[1,2-b]pyridazine (compound 91),
3-{1-[(2,2-difluorocyclopropyl)methyl]-1H-pyrazol-4-yl}-2-methyl-8-morpholin-4-ylimidazo[1,2-b]pyridazine (compound 118),
2-methyl-3-[1-(2-methylpropyl)-1H-pyrazol-4-yl]-8-(4-pyridinyl)-imidazo[1,2-b]pyridazine (compound 124),
6-cyclopropyl-3-[1-(2-methoxyethyl)-1H-pyrazol-4-yl]-2-methyl-8-(4-morpholinyl)-imidazo[1,2-b]pyridazine (compound 125),
2-ethyl-3-[1-(2-methoxyethyl)-1H-pyrazol-4-yl]-8-(4-morpholinyl)-imidazo[1,2-b]pyridazine (compound 127),
3-[1-[(2S)-2-methoxypropyl]-1H-pyrazol-4-yl]-2-methyl-8-(4-morpholinyl)-imidazo[1,2-b]pyridazine (compound 131),
3-[1-(2-methoxyethyl)-1H-pyrazol-4-yl]-2,6-dimethyl-8-(4-morpholinyl)-imidazo[1,2-b]pyridazine (compound 133),
3-[1-(2-methoxyethyl)-1H-pyrazol-4-yl]-2,6-dimethyl-8-(4-pyridinyl)-imidazo[1,2-b]pyridazine (compound 134),
2-methyl-8-(4-pyridinyl)-3-[1-(2,2,2-trifluoroethyl)-1H-pyrazol-4-yl]-imidazo[1,2-b]pyridazine (compound 135),
2-cyclopropyl-3-[1-(2-methoxyethyl)-1H-pyrazol-4-yl]-8-(4-pyridinyl)-imidazo[1,2-b]pyridazine (compound 142),
2-cyclopropyl-3-[1-(2-methoxy-2-methylpropyl)-1H-pyrazol-4-yl]-8-(4-pyridinyl)-imidazo[1,2-b]pyridazine (compound 143),
6-chloro-3-[1-(2-methoxyethyl)-1H-pyrazol-4-yl]-2-methyl-8-(4-pyridinyl)-imidazo[1,2-b]pyridazine (compound 147), and
2-cyclopropyl-3-[1-(2-methylpropyl)-1H-pyrazol-4-yl]-8-(4-pyridinyl)-imidazo[1,2-b]pyridazine (compound 148),
and the stereoisomeric forms, the pharmaceutically acceptable salts and the solvates thereof.

An additional embodiment is
3-[6-(2-methoxyethyl)-3-pyridinyl]-2-methyl-8-(4-morpholinyl)-imidazo[1,2-b]pyridazine phosphate (compound 1d).

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acids, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely, said salt forms can be converted into the free base form by treatment with an appropriate base.

The compounds according to Formula (I) containing acidic protons may also be converted into their therapeutically active non-toxic base salt forms by treatment with appropriate organic and inorganic bases. Appropriate base salt forms comprise, for example, the ammonium salts, the alkaline and alkaline earth metal salts, in particular lithium, sodium, potassium, magnesium and calcium salts, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline, and isoquinoline, the benzathine, N-methyl-D-glucamine, hydrabamine salts, and salts with amino acids, for example arginine and lysine.

Conversely, said salt forms can be converted into the free acid forms by treatment with an appropriate acid.

The term solvate comprises the solvent addition forms as well as the salts thereof, which the compounds of formula (I) are able to form. Examples of such solvent addition forms are e.g. hydrates, alcoholates and the like.

The term "stereochemically isomeric forms" or "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. The invention also embraces each of the individual isomeric forms of the compounds of Formula (I) and their salts and solvates, substantially free, i.e. associated with less than 10%, preferably less than 5%, in particular less than 2% and most preferably less than 1%, of the other isomers. Thus, when a compound of formula (I) is for instance specified as (R), this means that the compound is substantially free of the (S) isomer. Stereogenic centers may have the R- or S-configuration; substituents on bivalent cyclic (partially) saturated radicals may have either the cis- or trans-configuration.

Following CAS nomenclature conventions, when two stereogenic centers of known absolute configuration are present in a compound, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the compound has an S configuration and the second center is R, the stereo descriptor would be specified as S-[R*,S*].

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{3}$H, $^{11}$C, $^{18}$F, $^{123}$I, $^{125}$I, $^{131}$I, $^{75}$Br, $^{76}$Br, $^{77}$Br and $^{82}$Br. Preferably, the radioactive isotope is selected from the group of $^{3}$H, $^{11}$C and $^{18}$F.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

A. Preparation of the Final Compounds

A compound of Formula (I) wherein $R^1$, $R^2$, $R^4$ and $R^5$ are as defined before, $R^3$ is hydrogen and Het is pyridinyl, can be prepared by reacting a compound of Formula (Ia)

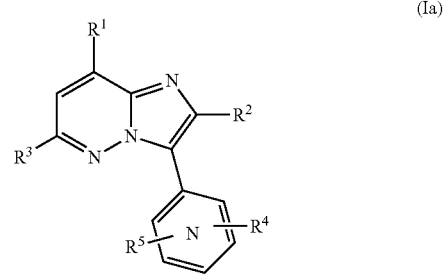

(Ia)

wherein $R^1$, $R^2$, $R^4$ and $R^5$ are as defined before, with hydrogen in the presence of a suitable catalyst, such as 10% palladium on charcoal, in a suitable inert solvent, such as methanol or ethanol, under suitable reaction conditions, such as a convenient temperature, typically ranging between 25° C. and 40° C. or with ammonium formate in the presence of a suitable catalyst such as 10% palladium on charcoal, in a suitable inert solvent, such as methanol, ethanol, ethyl acetate or dichloromethane or mixtures thereof, under suitable reaction conditions, such as heating at a convenient temperature, typically ranging between 40° C. and 100° C.

A compound of Formula (I) wherein $R^1$, $R^2$, $R^4$ and $R^5$ are as defined before, $R^3$ is $C_{1-4}$alkyl or $C_{3-8}$cycloalkyl and Het is pyridinyl can be prepared by reacting a compound of Formula (Ia) wherein $R^1$, $R^2$, $R^4$ and $R^5$ are as defined before, with a boronic acid derivative of Formula $R^3B(OH)_2$ wherein $R^3$ is $C_{1-4}$alkyl or $C_{3-8}$cycloalkyl, in the presence of a suitable catalyst, such as tetrakis(triphenylphosphine)palladium (0) or palladium (II) acetate, in the presence of a suitable phosphine ligand, such as 2-dicyclohexylphosphino-2',6'-dimethoxybiphenyl, in the presence of a suitable base, such as sodium carbonate or potassium phosphate, in a suitable inert solvent, such as a mixture of 1,4-dioxane and water or toluene, under suitable reaction conditions, such as heating at a convenient temperature, either by conventional heating or under microwave irradiation for a period of time to ensure the completion of the reaction.

Alternatively, compounds of Formula (I) wherein $R^1$, $R^2$, $R^3$, $R^4$ and $R^5$ are as defined before and Het is pyridinyl, can also be prepared by reacting an intermediate of Formula (II)

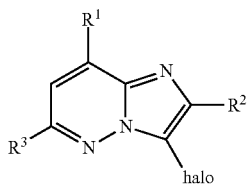
(II)

wherein $R^1$, $R^2$ and $R^3$ are as defined before and halo represents a bromo or iodo, with a boronic acid derivative of Formula (III)

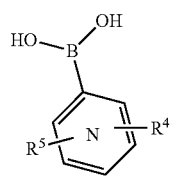
(III)

where $R^4$ and $R^5$ are as defined before, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

Compounds of Formula (I) wherein $R^1$, $R^2$, $R^3$, $R^4$ and $R^5$ are as defined before and Het is pyridinyl, can also be prepared by reacting an intermediate of Formula (II) wherein $R^1$, $R^2$ and $R^3$ are as defined before and halo represents a bromo or iodo, with a boronate derivative of Formula (IV)

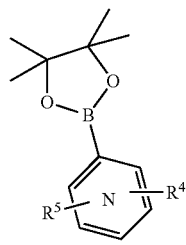
(IV)

where $R^4$ and $R^5$ are as defined before, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

Compounds of Formula (I) wherein $R^1$, $R^2$, $R^3$, $R^4$ and $R^5$ are as defined before and Het is pyridinyl, can also be prepared by reacting an intermediate of Formula (V)

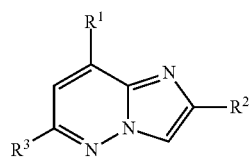
(V)

with a halopyridine of Formula (VI)

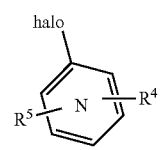
(VI)

where $R^4$ and $R^5$ are as defined before and halo is bromo or iodo, in the presence of a suitable catalyst, such as palladium (II) acetate, in the presence of a suitable phosphine ligand, such as butyldi-1-adamantylphosphine, in the presence of a suitable base, such as potassium phosphate, in a suitable inert solvent, such as N,N-dimethylformamide or N-methylpyrrolidine, under suitable reaction conditions, such as heating at a convenient temperature, either by conventional heating or under microwave irradiation for a period of time to ensure the completion of the reaction.

A compound of Formula (II) wherein $R^1$, $R^2$ and $R^3$ are as defined before, except when simultaneously $R^1$ is $NR^6R^7$, $R^2$ is trifluoromethyl and $R^3$ is chloro, and halo represents a bromo or iodo, can be prepared by reacting a compound of Formula (V) wherein $R^1$, $R^2$ and $R^3$ are as defined before, with N-bromo- or N-iodosuccinimide, in a suitable inert solvent, such as dichloromethane, in the presence of a suitable acid catalyst, such as acetic acid, under suitable reaction conditions, such as a convenient temperature, typically ranging between −10° C. and 40° C.

A compound of Formula (V) wherein $R^1$ and $R^2$ are as defined before and $R^3$ is hydrogen, can also be prepared by reacting a compound of Formula (Va)

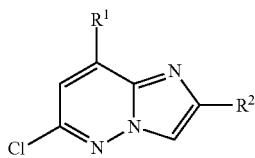

(Va)

wherein R¹ and R² are as defined before, with hydrogen in the presence of a suitable catalyst, such as 10% palladium on charcoal, in the presence of a suitable base, such as triethylamine, in a suitable inert solvent, such as methanol or ethanol, under suitable reaction conditions, such as a convenient temperature, typically ranging between 25° C. and 40° C. or with ammonium formate in the presence of a suitable catalyst such as 10% palladium on charcoal, in a suitable inert solvent, such as methanol, ethanol, ethyl acetate or dichloromethane or mixtures thereof, under suitable reaction conditions, such as heating at a convenient temperature, typically ranging between 40° C. and 100° C.

A compound of Formula (V) wherein R¹ and R² are as defined before, and R³ is $C_{1-4}$alkyl or $C_{3-8}$cycloalkyl can be prepared by reacting a compound of Formula (Va) wherein R¹ and R² are as defined before with a boronic acid derivative of Formula $R^3B(OH)_2$ where R³ is $C_{1-4}$alkyl or $C_{3-8}$cycloalkyl, in the presence of a suitable catalyst, such as tetrakis(triphenylphosphine)palladium (0) or palladium (II) acetate, in the presence of a suitable phosphine ligand, such as 2-dicyclohexylphosphino-2',6'-dimethoxybiphenyl, in the presence of a suitable base, such as sodium carbonate or potassium phosphate, in a suitable inert solvent, such as a mixture of 1,4-dioxane and water or toluene, under suitable reaction conditions, such as heating at a convenient temperature, either by conventional heating or under microwave irradiation for a period of time to ensure the completion of the reaction.

A compound of Formula (V) wherein R¹ is pyridinyl, pyridinyl optionally substituted with halogen, $C_{1-4}$alkyl, trifluoromethyl or $C_{1-4}$alkyloxy, R² is hydrogen, $C_{1-4}$alkyl, trifluoromethyl or $C_{3-8}$cycloalkyl and R³ is chloro or trifluoromethyl, can be prepared by reacting a compound of Formula (VII)

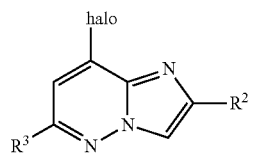

(VII)

where R² is as described before, R³ is chloro or trifluoromethyl and halo represents chloro, bromo or iodo, with a boronic acid derivative of Formula $R^1B(OH)_2$ wherein R¹ is pyridinyl or pyridinyl optionally substituted with halogen, $C_{1-4}$alkyl, trifluoromethyl or $C_{1-4}$alkyloxy, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A compound of Formula (V) wherein R¹ is $NR^6R^7$, R² is as described before, R³ is chloro or trifluoromethyl and R⁶ and R⁷ are as defined before, can be prepared by reacting a compound of Formula (VII) where R² is as described before, R³ is chloro or trifluoromethyl and halo represents chloro, bromo or iodo with a compound of Formula $R^6R^7NH$ wherein R⁶ and R⁷ are as defined before, in a suitable inert solvent, such as acetonitrile, under suitable reaction conditions, such as heating at a convenient temperature, either by conventional heating or under microwave irradiation for a period of time to ensure the completion of the reaction.

Compounds of Formula (V) wherein R¹ is tetrahydropyranyl, R² is as defined before and R³ is chloro or trifluoromethyl, can be prepared by reacting a compound of Formula (VIII)

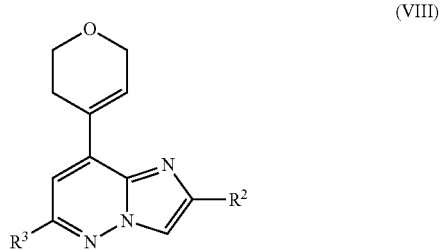

(VIII)

wherein R² is as defined before and R³ is chloro or trifluoromethyl, with hydrogen in the presence of a suitable catalyst, such as 10% palladium on charcoal, in a suitable inert solvent, such as methanol or ethanol, under suitable reaction conditions, such as a convenient temperature, typically ranging between 25° C. and 40° C. or with ammonium formate in the presence of a suitable catalyst such as 10% palladium on charcoal, in a suitable inert solvent, such as methanol, ethanol, ethyl acetate or dichloromethane or mixtures thereof, under suitable reaction conditions, such as heating at a convenient temperature, typically ranging between 40° C. and 100° C.

A compound of Formula (VIII) where R² is as defined before and R³ is chloro or trifluoromethyl, can be prepared by reacting a compound of Formula (VII) where R² is as defined before, R³ is chloro or trifluoromethyl and halo represents chloro, bromo or iodo with 3,6-dihydro-2H-pyran-4-boronic acid pinacol ester, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

3,6-Dihydro-2H-pyran-4-boronic acid pinacol ester can be obtained by procedures similar to those described in, Qiu, Y. et al. WO 2004075846 A2.

A compound of Formula (VIIa)

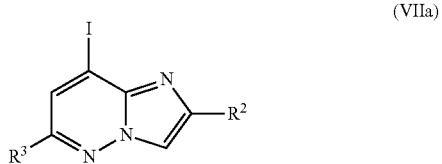

(VIIa)

where R² is hydrogen, $C_{1-4}$alkyl, trifluoromethyl or $C_{3-8}$cycloalkyl and R³ is chloro or trifluoromethyl can be prepared by reacting an intermediate of Formula (VII) wherein R² is hydrogen, $C_{1-4}$alkyl, trifluoromethyl or $C_{3-8}$cycloalkyl, $R^3$ is chloro or trifluoromethyl and halo represents chloro or bromo with sodium iodide, in the presence of a suitable acidic catalyst, such as hydriodic acid, in a suitable inert solvent, such as acetonitrile, under suitable reaction conditions, such as heating at a convenient temperature, either by conventional heating or under microwave irradiation for a period of time to ensure the completion of the reaction.

A compound of Formula (VII) where $R^2$ is hydrogen, $C_{1-4}$alkyl, trifluoromethyl or $C_{3-8}$cycloalkyl, $R^3$ is chloro or trifluoromethyl and halo represents chloro or bromo, can be prepared by reacting a compound of Formula (IX)

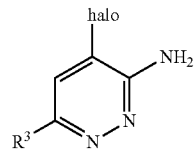
(IX)

wherein $R^3$ is chloro or trifluoromethyl and halo represents chloro or bromo, with a compound of Formula (X)

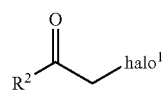
(X)

wherein $R^2$ is hydrogen, $C_{1-4}$alkyl, trifluoromethyl or $C_{3-8}$cycloalkyl and halo$^1$ represents chloro or bromo, either neat or in a suitable inert solvent, such as ethanol, isopropanol or 1,2-dimethoxyethane, under suitable reaction conditions, such as heating at a convenient temperature either by conventional heating or under microwave irradiation for a period of time to ensure the completion of the reaction.

A compound of Formula (IX) where $R^3$ is chloro or trifluoromethyl and halo represents bromo, can be prepared by reacting an aminopyridazine of Formula (XI)

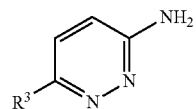
(XI)

with bromine, in the presence of a suitable base, such as sodium hydrogen carbonate, in a suitable inert solvent, such as methanol, under suitable reaction conditions, such as a convenient temperature, typically ranging between −10° C. and 25° C.

A compound of Formula (IX) where $R^3$ is chloro or trifluoromethyl and halo represents chloro, can be obtained from an aminopyridazine of Formula (XI) by procedures similar to those described in Dewdney, N. et al. WO 2009077334 A1.

A compound of Formula (X) wherein $R^2$ is hydrogen, $C_{1-4}$alkyl, trifluoromethyl or $C_{3-8}$cycloalkyl and halo represents chloro or bromo, can be obtained commercially or can be prepared by procedures similar to those described in Gaudry, M.; Marquet, A. Organic Syntheses. 1976, 55.

A compound of Formula (XI) where $R^3$ is chloro can be obtained commercially.

A compound of Formula (XI) where $R^3$ is trifluoromethyl can be obtained by procedures similar to those described in De Bruyn, M. F. L. et al. WO 2007048779 A1.

A compound of Formula (V) wherein $R^1$ is $NR^6R^7$, $R^2$ is $C_{1-4}$alkyloxy and $R^3$ is chloro or trifluoromethyl and $R^6$ and $R^7$ are as defined before, can be prepared by reacting an intermediate of Formula (XII)

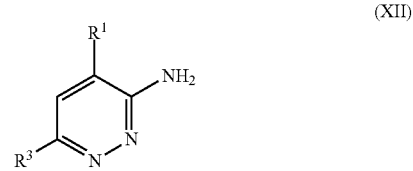
(XII)

wherein $R^1$ is $NR^6R^7$, $R^3$ is chloro or trifluoromethyl and $R^6$ and $R^7$ are as defined before, with a reagent of Formula (X) wherein $R^2$ is $C_{1-4}$alkyloxy and halo$^1$ represents chloro or bromo, in a suitable inert solvent, such as methanol, under suitable reaction conditions, such as heating at a convenient temperature either by conventional heating or under microwave irradiation for a period of time to ensure the completion of the reaction.

Compounds of Formula (XII) wherein $R^1$ is $NR^6R^7$, $R^3$ is chloro or trifluoromethyl and $R^6$ and $R^7$ are as defined before can be prepared by reacting a compound of Formula (IX) where $R^3$ is chloro or trifluoromethyl and halo represents chloro or bromo with a derivative compound of formula $R^6R^7NH$ wherein $R^6$ and $R^7$ are as defined before, in a suitable inert solvent, such as acetonitrile, under suitable reaction conditions, such as heating at a convenient temperature, either by conventional heating or under microwave irradiation for a period of time to ensure the completion of the reaction.

Compounds of Formula (IX) can be obtained as described before.

A compound of Formula (II) wherein $R^1$ is $NR^6R^7$, $R^2$ is trifluoromethyl, $R^3$ is chloro or trifluoromethyl, and halo represents a iodo, can be prepared by reacting a compound of Formula (XIII)

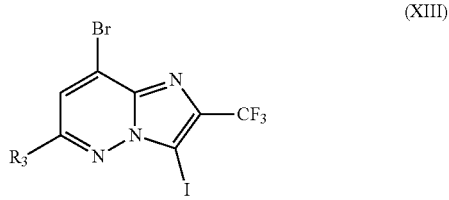
(XIII)

wherein $R^3$ is chloro or trifluoromethyl with a compound of formula $R^6R^7NH$, where $R^6$ and $R^7$ are as defined before in the presence of a suitable base, such as N,N-diisopropylethylamine, in a suitable solvent, such as acetonitrile, under suitable reaction conditions, such as heating at a convenient temperature, either by conventional heating or under microwave irradiation for a period of time to ensure the completion of the reaction.

A compound of Formula (XIII), where $R^3$ is chloro or trifluoromethyl can be prepared by reacting a compound of Formula (VII) where $R^2$ is trifluoromethyl, $R^3$ is chloro or trifluoromethyl and halo represents a bromo, with N-iodosuccinimide, in a suitable inert solvent, such as dichloromethane, in the presence of a suitable acid catalyst, such as trifluoroacetic acid, under suitable reaction conditions, such as a convenient temperature, typically ranging between −10° C. and 60° C.

A compound of Formula (VII) where $R^2$ is trifluoromethyl, $R^3$ is chloro or trifluoromethyl and halo represents a bromo, can be obtained as described before.

A compound of Formula (Ib)

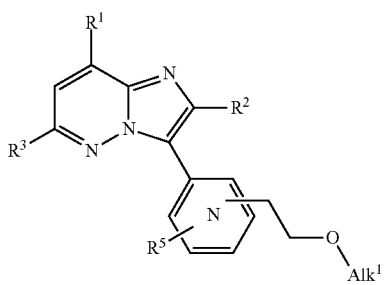

(Ib)

wherein $R^1$, $R^2$, $R^3$ and $R^5$ are as defined before, $R^4$ is $Alk^1$-oxyethyl and $Alk^1$ is $C_{1-4}$alkyl, can be prepared by reacting a compound of Formula (XIV)

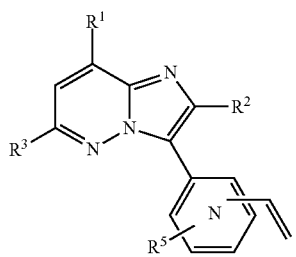

(XIV)

where $R^1$, $R^2$, $R^3$ and $R^5$ are as defined before with an alcohol of Formula $Alk^1$-OH wherein $Alk^1$ is $C_{1-4}$alkyl in the presence of a suitable base, such as the sodium or potassium salt of the corresponding alcohol, in a suitable solvent, such as the corresponding alcohol, under suitable reaction conditions, such as heating at a convenient temperature, either by conventional or under microwave irradiation for a period of time to ensure the completion of the reaction.

Alternatively, a compound of Formula (Ib) wherein $R^1$, $R^2$, $R^3$ and $R^5$ are as defined before, $R^4$ is $Alk^1$-oxyethyl and $Alk^1$ is $C_{1-4}$alkyl, can be prepared by reacting a compound of Formula (XIV), where $R^1$, $R^2$, $R^3$ and $R^5$ are as defined before with an alcohol of Formula $Alk^1$-OH wherein $Alk^1$ is $C_{1-4}$alkyl, in the presence of a suitable acid, such as potassium hydrogensulfate, in a suitable solvent, such as the corresponding alcohol, under suitable reaction conditions, such as heating at a convenient temperature, either by conventional heating or under microwave irradiation for a period of time to ensure the completion of the reaction.

An alcohol of Formula $Alk^1$-OH wherein $Alk^1$ is $C_{1-4}$alkyl can be obtained commercially or alternatively can also be obtained by procedures similar to those described in Morel, P. US 2008102028 A1.

A compound of Formula (XIV) where $R^1$, $R^2$, $R^3$ and $R^5$ are as defined before can be prepared by reacting a compound of Formula (XV)

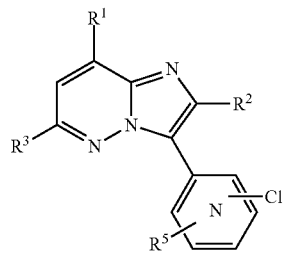

(XV)

wherein $R^1$, $R^2$, $R^3$ and $R^5$ are as defined before, with a compound of Formula (XVI)

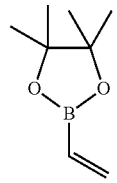

(XVI)

in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

Vinylboronic acid pinacol ester, of Formula (XVI), can be obtained commercially.

A compound of Formula (XV) where $R^1$, $R^2$, $R^3$ and $R^5$ are as defined before, can be prepared by reacting a compound of Formula (II) wherein $R^1$, $R^2$ and $R^3$ are as defined before and halo is bromo or iodo, with a boronic acid derivative of Formula (XVII)

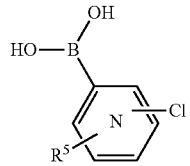

(XVII)

where $R^5$ is as defined before, in the presence of a suitable catalyst, such as tetrakis(triphenylphosphine)palladium (0), in the presence of a suitable base, such as sodium carbonate, in a suitable inert solvent such as a mixture of 1,4-dioxane and water, under suitable reaction conditions, such as heating at a convenient temperature, either by conventional heating or under microwave irradiation for a period of time to ensure the completion of the reaction.

Compounds of Formula (II) can be obtained as described before.

A boronic acid derivative of Formula (XVII) where $R^5$ is as defined before, can be obtained commercially or alternatively can be prepared by reacting a compound of Formula (XVIII)

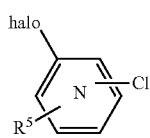

(XVIII)

where R⁵ is as defined before and halo represents a bromo or iodo, with triisopropyl borate, in the presence of a suitable base, such as n-butyllithium in the presence of a suitable diamine such as N,N,N',N'-tetramethylenediamine, in a suitable inert solvent such as diethylether, under suitable reaction conditions, such as a convenient temperature, typically ranging between −78° C. and 25° C.

A halopyridine of Formula (XVIII) where R⁵ is as defined before and halo is bromo or iodo, can be obtained commercially.

Alternatively, a compound of Formula (XV) where R¹, R², R³ and R⁵ are as defined before, can be prepared by reacting a compound of Formula (V) wherein R¹, R² and R³ are as defined before with a halopyridine of Formula (XVIII), where R⁵ is as defined before and halo represents a bromo or iodo, in the presence of a suitable catalyst, such as palladium (II) acetate, in the presence of a suitable phosphine ligand, such as butyldi-1-adamantylphosphine, in the presence of a suitable base, such as potassium phosphate, in a suitable inert solvent, such as N,N-dimethylformamide, under suitable reaction conditions, such as heating at a convenient temperature, either by conventional heating or under microwave irradiation for a period of time to ensure the completion of the reaction.

Compounds of Formula (V) can be obtained as described before.

Compounds of Formula (Ic)

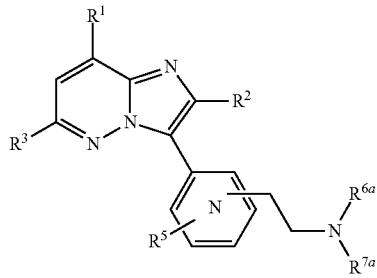

(Ic)

wherein R¹, R², R³ and R⁵ are as defined before, R⁴ is NR⁶ᵃR⁷ᵃ ethyl and R⁶ᵃ and R⁷ᵃ are as defined before, can be prepared by reacting a compound of Formula (XIV) where R¹, R², R³ and R⁵ are as defined before with a reagent of Formula R⁶ᵃR⁷ᵃNH where R⁶ᵃ and R⁷ᵃ are as defined before in the presence of a suitable base, such as sodium tert-butoxide, in a suitable solvent, such as tetrahydrofuran, under suitable reaction conditions, such as heating at a convenient temperature, either by conventional heating or under microwave irradiation for a period of time to ensure the completion of the reaction.

A reagent of Formula R⁶R⁷NH or R⁶ᵃR⁷ᵃNH, wherein R⁶, R⁶ᵃ, R⁷ and R⁷ᵃ are as defined before, can be obtained commercially.

Compounds of Formula (I) where R¹, R², R³ and R⁵ are as defined before, R⁴ is ethyl and Het is pyridinyl, can also be prepared by reacting a compound of Formula (XIV) wherein R¹, R², R³ and R⁵ are as defined before, with hydrogen in the presence of a suitable catalyst, such as 10% palladium on charcoal, in a suitable inert solvent, such as methanol or ethanol, under suitable reaction conditions, such as a convenient temperature, typically ranging between 25° C. and 40° C. or with ammonium formate in the presence of a suitable catalyst such as 10% palladium on charcoal, in a suitable inert solvent, such as methanol, ethanol, ethyl acetate or dichloromethane or mixtures thereof, under suitable reaction conditions, such as heating at a convenient temperature, typically ranging between 40° C. and 100° C.

Compounds of Formula (I) wherein R¹, R², R³ and R⁵ are as defined before, R⁴ is tetrahydropyranyl and Het is pyridinyl, can also be prepared by reacting a compound of Formula (XIX)

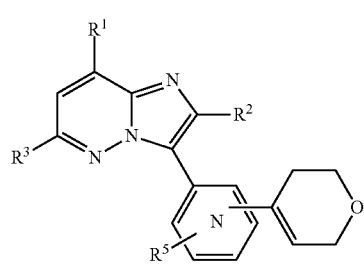

(XIX)

where R¹, R², R³ and R⁵ are as defined before with hydrogen in the presence of a suitable catalyst such as 10% palladium on charcoal, in a suitable inert solvent such as methanol, under suitable reaction conditions, such as a convenient temperature, typically ranging between 25° C. and 40° C. or with ammonium formate in the presence of a suitable catalyst such as 10% palladium on charcoal, in a suitable inert solvent, such as methanol, ethanol, ethyl acetate or dichloromethane or mixtures thereof, under suitable reaction conditions, such as heating at a convenient temperature, typically ranging between 40° C. and 100° C.

A compound of Formula (XIX) wherein R¹, R², R³ and R⁵ are as defined before, can be prepared by reacting a compound of Formula (XV) wherein R¹, R², R³ and R⁵ are as defined before, with 3,6-dihydro-2H-pyran-4-boronic acid pinacol ester, in the presence of a suitable catalyst, such as tetrakis(triphenylphosphine)palladium (0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

3,6-Dihydro-2H-pyran-4-boronic acid pinacol ester can be obtained as described before.

A compound of Formula (Id)

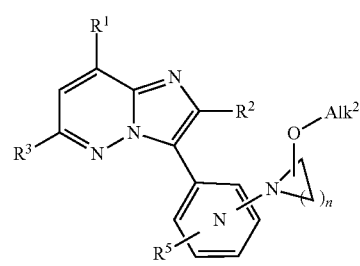

(Id)

wherein R¹, R², R³, R⁵ are as defined before, R⁴ is a radical of Formula (a), n is as defined before and Alk² is C₁₋₄alkyl, can be prepared by reacting a compound of Formula (XX)

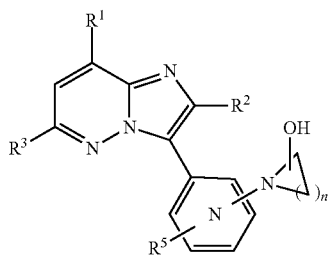

(XX)

where $R^1$, $R^2$, $R^3$, $R^5$ and n are as defined before with a reagent of Formula $Alk^2$-W wherein $Alk^2$ is $C_{1-4}$alkyl and W represents a leaving group, such as halo, e.g. chloro, bromo or iodo, in the presence of a base, such as sodium tert-butoxide, in the presence of a suitable crown ether, such as 18-crown-6, in a suitable solvent, such as tetrahydrofuran and under suitable reaction conditions, such as heating at a convenient temperature, typically ranging from 25° C. to 80° C.

A reagent of Formula $Alk^2$-W where $Alk^2$ is $C_{1-4}$alkyl and W represents a leaving group, such as halo, e.g. chloro, bromo or iodo can be obtained commercially.

Compounds of Formula (I) wherein $R^1$, $R^2$, $R^3$, $R^5$ are as defined before and $R^4$ is $NR^{6a}R^{7a}$ and compounds of formula (XX), as previously defined, can also be prepared by reacting a compound of Formula (XV) wherein $R^1$, $R^2$, $R^3$ and $R^5$ are as defined before and the chlorine atom is ortho to the pyridinyl nitrogen, with a reagent of Formula $R^{6a}R^{7a}$NH, where $R^{6a}$ and $R^{7a}$ are as defined before, either neat or in a suitable inert solvent, such as acetonitrile, under suitable reaction conditions, such as heating at a convenient temperature, either by conventional heating or under microwave irradiation for a period of time to ensure the completion of the reaction.

Alternatively, compounds of Formula (I) wherein $R^1$, $R^2$, $R^3$, $R^5$ are as defined before and $R^4$ is $NR^{6a}R^{7a}$, can also be prepared by reacting a compound of Formula (XV) where $R^1$, $R^2$, $R^3$ and $R^5$ are as defined before with a reagent of Formula $R^{6a}R^{7a}$NH, where $R^{6a}$ and $R^{7a}$ are as defined before, in the presence of a suitable catalyst, such as palladium (II) acetate, in the presence of a suitable phosphine ligand, such as racemic-2,2'-bis(diphenylphosphino)-1,1'-binaphthyl and in the presence of a suitable base, such as cesium carbonate, in a suitable inert solvent, such as toluene, under suitable reaction conditions, such as heating at a convenient temperature, either by conventional heating or under microwave irradiation for a period of time to ensure the completion of the reaction.

A reagent of Formula $R^{6a}R^{7a}$NH, where $R^{6a}$ and $R^{7a}$ are as defined before, can be obtained commercially.

Compounds of Formula (Ie)

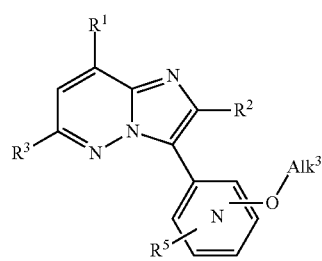

(Ie)

wherein $R^1$, $R^2$, $R^3$ and $R^5$ are as defined before, $R^4$ is $Alk^3$oxy and $Alk^3$ is $C_{1-4}$alkyl, trifluoromethyl$C_{0-4}$alkyl, $C_{3-8}$cycloalkyl$C_{1-4}$alkyl, or $C_{1-4}$alkyloxy$C_{1-5}$alkyl, can be prepared by reacting a compound of Formula (XV) where $R^1$, $R^2$, $R^3$ and $R^5$ are as defined before and the chlorine atom is ortho to the pyridinyl nitrogen, with a reagent of Formula $Alk^3$-OH, where $Alk^3$ is $C_{1-4}$alkyl, trifluoromethyl$C_{0-4}$alkyl, $C_{3-8}$cycloalkyl$C_{1-4}$alkyl, or $C_{1-4}$alkyloxy$C_{1-5}$alkyl in the presence of a suitable base, such as sodium hydride, in a suitable inert solvent such as N,N-dimethylformamide or dimethyl sulfoxide, under suitable reaction conditions, such as heating at a convenient temperature, either by conventional heating or under microwave irradiation for a period of time to ensure the completion of the reaction.

A reagent of Formula $Alk^3$-OH wherein $C_{1-4}$alkyl, trifluoromethyl$C_{0-4}$alkyl, $C_{3-8}$cycloalkyl$C_{1-4}$alkyl or $C_{1-4}$alkyloxy$C_{1-5}$alkyl can be obtained commercially or can be prepared by procedures similar to those described in Morel, P. US 2008102028 A1.

Compounds of Formula (I) wherein $R^1$, $R^2$, $R^3$ and $R^5$ are as defined before, $R^4$ is $C_{1-6}$alkyl and Het is pyridinyl, can also be prepared by reacting a compound of Formula (XV) where $R^1$, $R^2$, $R^3$ and $R^5$ are as defined before and the chlorine atom is ortho to the pyridinyl nitrogen with a Grignard reagent of Formula $R^4$Mghalo, where $R^4$ is $C_{1-6}$alkyl and halo represents a chloro, bromo or iodo, in the presence of a suitable catalyst, such as [1,3-bis(diphenylphosphino)propane]dichloronickel (II) or iron (III) acetylacetonate, in a suitable inert solvent, such as a tetrahydrofuran or N-methylpyrrolidinone, under suitable reaction conditions, such as a convenient temperature, typically ranging between −10° C. and 15° C.

A Grignard reagent of Formula $R^4$Mghalo where $R^4$ is $C_{1-6}$alkyl and halo is chloro, bromo or iodo, can be obtained commercially.

Alternatively, compounds of Formula (I) wherein $R^1$, $R^2$, $R^3$ and $R^5$ are as defined before and $R^4$ is $C_{1-4}$alkyl or $C_{3-8}$cycloalkyl and Het is pyridinyl can also be prepared by reacting a compound of Formula (XV) where $R^1$, $R^2$, $R^3$ and $R^5$ are as defined before with a boronic acid derivative of Formula $R^4B(OH)_2$, where $R^4$ is $C_{1-4}$alkyl or $C_{3-8}$cycloalkyl, in the presence of a suitable catalyst, such as palladium (II) acetate, in the presence of a suitable phosphine ligand, such as 2-dicyclohexylphosphino-2',6'-dimethoxybiphenyl, in the presence of a suitable base, such as potassium phosphate, in a suitable inert solvent, such as toluene, under suitable reaction conditions, such as heating at a convenient temperature, either by conventional heating or under microwave irradiation for a period of time to ensure the completion of the reaction.

A boronic acid derivative of Formula $R^4B(OH)_2$ where $R^4$ is $C_{1-4}$alkyl or $C_{3-8}$cycloalkyl can be obtained commercially.

Compounds of Formula (I) wherein $R^1$, $R^2$, $R^3$ and $R^5$ are as defined before and $R^4$ is $C_{1-4}$alkyl, $C_{1-4}$alkyloxy$C_{1-5}$alkyl or trifluoromethyl$C_{0-4}$alkyl and Het is pyridinyl, can also be prepared by reacting a compound of Formula (XV) where $R^1$, $R^2$, $R^3$ and $R^5$ are as defined before and the chlorine atom is ortho to the pyridinyl nitrogen with an organozinc reagent of Formula $Zn(R^4)_2$ where $R^4$ represents a $C_{1-4}$alkyl, $C_{1-4}$alkyloxy$C_{1-5}$alkyl or trifluoromethyl$C_{0-4}$alkyl, in the presence of a suitable catalyst, such as tetrakis(triphenylphosphine)palladium (0), in a suitable inert solvent, such as tetrahydrofuran, under suitable reaction conditions, such as heating at a convenient temperature, either by conventional heating or under microwave irradiation for a period of time to ensure the completion of the reaction.

A reagent of Formula $Zn(R^4)_2$ wherein $R^4$ represents $C_{1-4}$alkyl, $C_{1-4}$alkyloxy$C_{1-5}$alkyl or trifluoromethyl$C_{0-4}$alkyl can be obtained commercially. Alternatively, a reagent of Formula $Zn(R^4)_2$ wherein $R^4$ represents $C_{1-4}$alkyl, $C_{1-4}$alkyloxy$C_{1-5}$alkyl or trifluoromethyl$C_{0-4}$alkyl, can be prepared by reacting a compound of Formula $R^4$-halo wherein $R^4$ represents $C_{1-4}$alkyl, $C_{1-4}$alkyloxy$C_{1-5}$alkyl or trifluoromethyl$C_{0-4}$alkyl and halo represents iodo, with zinc in the presence of 1,2-dibromoethane and chlorotrimethylsilane, in a suitable inert solvent, such as N,N-dimethylformamide, under suitable reaction conditions such as heating at a convenient temperature, typically ranging between 25° C. and 100° C.

A reagent of $R^4$-halo wherein $R^4$ represents $C_{1-4}$alkyl, $C_{1-4}$alkyloxy$C_{1-5}$alkyl or trifluoromethyl$C_{0-4}$alkyl and halo represents iodo can be obtained commercially or can be prepared by reacting a compound of Formula halo-$R^4$ wherein $R^4$ represents $C_{1-4}$alkyl, $C_{1-4}$alkyloxy$C_{1-5}$alkyl or trifluoromethyl$C_{0-4}$alkyl and halo represents a chloro or bromo with sodium iodide in a suitable inert solvent, such as acetone, under suitable reaction conditions such as a convenient temperature, typically ranging between 25° C. and 40° C.

A compound of Formula halo-$R^4$ wherein $R^4$ represents $C_{1-4}$alkyl, $C_{1-4}$alkyloxy$C_{1-5}$alkyl or trifluoromethyl$C_{0-4}$alkyl and halo represents a chloro or bromo, can be obtained commercially.

A boronic acid of Formula (III) wherein $R^4$ and $R^5$ are as defined before, can be obtained commercially. Alternatively, a boronic acid of Formula (III) wherein $R^4$ and $R^5$ are as defined before, can be prepared by reacting a halopyridine of Formula (VI), wherein $R^4$ and $R^5$ are as defined before and halo is bromo or iodo, with triisopropyl borate, in the presence of a suitable base, such as n-butyllithium, in a suitable inert solvent, such as tetrahydrofuran, under suitable reaction conditions, such as a convenient temperature, typically ranging between −78° C. and −10° C.

A boronic derivative of Formula (IV) wherein $R^4$ and $R^5$ are as defined before, can be obtained commercially. Alternatively, a compound of Formula (IV) wherein $R^4$ and $R^5$ are as defined before, can also be prepared by reacting a halopyridine of Formula (VI), wherein $R^4$ and $R^5$ are as defined before and halo represents a bromo or iodo, with bis(pinacolato)diboron in the presence of a suitable catalyst, such as [1,1′-bis(diphenylphosphino)ferrocene]dichloropalladium (II), in the presence of a suitable base, such as potassium acetate, in a suitable inert solvent, such as N,N-dimethylformamide or dimethyl sulfoxide, under suitable reaction conditions, such as heating at a convenient temperature, either by conventional heating or under microwave irradiation for a period of time to ensure the completion of the reaction.

A halopyridine of Formula (VI) wherein $R^4$ and $R^5$ are as defined before and halo represents a bromo or iodo, can be obtained commercially. Alternatively, a halopyridine of Formula (VI) wherein $R^5$ is as defined before, halo represents a bromo and $R^4$ is $C_{1-6}$alkyl or $C_{3-8}$cycloalkyl can be prepared by reacting a di-halopyridine of Formula (XXI)

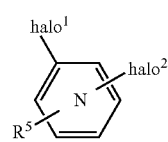

(XXI)

where $R^5$ is as defined before, halo$^1$ represent a bromo and halo$^2$ represent a bromo or iodo ortho to the pyridinyl nitrogen, with a reagent of Formula $R^4B(OH)_2$ where $R^4$ represents a $C_{1-4}$alkyl or $C_{3-8}$cycloalkyl, in the presence of a suitable catalyst, such as tetrakis(triphenylphosphine)palladium (0), in a suitable inert solvent, such as tetrahydrofuran, under suitable reaction conditions, such as heating at a convenient temperature, either by conventional heating or under microwave irradiation for a period of time to ensure the completion of the reaction.

A boronic acid derivative of Formula $R^4B(OH)_2$ where $R^4$ is $C_{1-4}$alkyl or $C_{3-8}$cycloalkyl can be obtained commercially.

Alternatively, a halopyridine of Formula (VI) wherein $R^5$ is as defined before, halo represents a bromo an $R^4$ is $C_{1-4}$alkyl, $C_{1-4}$alkyloxy$C_{1-5}$alkyl or trifluoromethyl$C_{0-4}$alkyl can be prepared by reacting a di-halopyridine of Formula (XXI) where $R^5$ is as defined before and halo$^1$ and halo$^2$ represent independently a bromo or iodo and halo$^2$ is ortho to the pyridinyl nitrogen, with an organozinc reagent of Formula $Zn(R^4)_2$ where $R^4$ represents a $C_{1-4}$alkyl, $C_{1-4}$alkyloxy$C_{1-5}$alkyl or trifluoromethyl$C_{0-4}$alkyl, in the presence of a suitable catalyst, such as tetrakis(triphenylphosphine)palladium (0), in a suitable inert solvent, such as tetrahydrofuran, under suitable reaction conditions, such as heating at a convenient temperature, either by conventional heating or under microwave irradiation for a period of time to ensure the completion of the reaction.

A reagent of Formula $Zn(R^4)_2$ wherein $R^4$ represents $C_{1-4}$alkyl, $C_{1-4}$alkyloxy$C_{1-5}$alkyl or trifluoromethyl$C_{0-4}$alkyl can be obtained as described before.

Compounds of Formula (VIa)

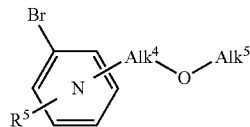

(VIa)

wherein $R^5$ is as defined before, $Alk^4$ represents a $C_{1-4}$alkyl and $Alk^5$ represents a $C_{1-4}$alkyl, can be prepared by reacting a compound of Formula (VIb)

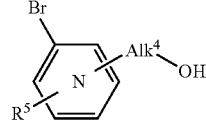

(VIb)

wherein $R^5$ is as defined before and $Alk^4$ represents a $C_{1-4}$alkyl, with a reagent of Formula $Alk^5{}_2SO_4$ where $Alk^5$ represents a $C_{1-4}$alkyl, in the presence of a suitable base, such as sodium hydride, in a suitable inert solvent, such as tetrahydrofuran, under suitable reaction conditions, such as a convenient temperature, typically ranging between −10° C. and 40° C. or with a reagent of Formula $Alk^5$-W wherein $Alk^5$ represents a $C_{1-4}$alkyl and W represents a leaving group, such as halo, e.g. chloro, bromo or iodo, or a sulfonyloxy group, e.g. methylsulfonyloxy, trifluoromethylsulfonyloxy, or methylphenylsulfonyloxy, in the presence of a base, such as sodium hydride or sodium tert-butoxide, in the presence of a suitable crown ether, such as 18-crown-6, in a suitable solvent, such as tetrahydrofuran and under suitable reaction conditions, such as a convenient temperature, typically ranging from 0° C. to 40° C.

Reagents of Formula $Alk^5{}_2SO_4$ and $Alk^5$-W wherein $Alk^5$ represents a $C_{1-4}$alkyl and W represents a leaving group, such as halo, e.g. chloro, bromo or iodo, or a sulfonyloxy group, e.g. methylsulfonyloxy, trifluoromethylsulfonyloxy, or methylphenylsulfonyloxy, can be obtained commercially.

A compound of Formula (VIc)

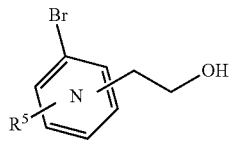

(VIc)

wherein $R^5$ is as defined before, can be prepared by reacting a methylpyridine of Formula (VId)

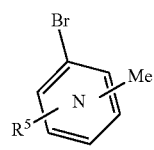

(VId)

wherein $R^5$ is as defined before and the methyl group is ortho to the pyridinyl nitrogen with N,N-dimethylformamide in the presence of a suitable base, such as lithium diisopropylamide, in a suitable inert solvent, such as tetrahydrofuran, under suitable reaction conditions, such as a convenient temperature, typically ranging between –78° C. and –10° C., followed by treatment with sodium borohydride in a suitable solvent, such as methanol, under suitable reaction conditions, such as a convenient temperature, typically ranging between –10° C. and 40° C.

A compound of Formula (VIe)

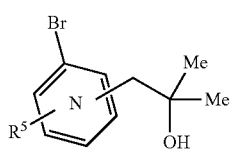

(VIe)

wherein $R^5$ is as defined before, can be prepared by reacting a methylpyridine of Formula (VId), wherein $R^5$ is as defined before and the methyl group is ortho to the pyridinyl nitrogen with acetone in the presence of a suitable base, such as lithium diisopropylamide, in a suitable inert solvent, such as tetrahydrofuran, under suitable reaction conditions, such as a convenient temperature, typically ranging between –78° C. and –10° C.

A methylpyridine of Formula (VId) wherein $R^5$ is as defined before, can be obtained commercially.

A compound of Formula (VIf)

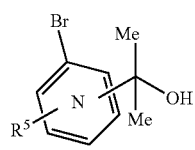

(VIf)

wherein $R^5$ is as defined before, can be prepared by reacting a di-halopyridine of Formula (XXI) where $R^5$ is as defined before, halo$^1$ represents a bromo and halo$^2$ represents a bromo ortho to the pyridinyl nitrogen, with acetone, in the presence of a suitable base, such as n-buthyllithium, in a suitable inert solvent, such as toluene, under suitable reaction conditions, such as a convenient temperature, typically ranging between –78° C. and 25° C.

A di-halopyridine of Formula (XXI) where $R^5$ is as defined before, halo$^1$ is a bromo and halo$^2$ represents bromo can be obtained commercially.

A compound of Formula (VIg)

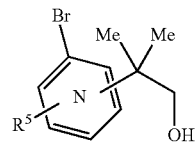

(VIg)

wherein $R^5$ is as defined before, can be prepared by reacting a compound of Formula (XXII)

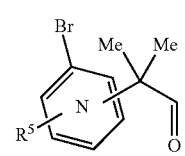

(XXII)

wherein $R^5$ is as defined before, with sodium borohydride, in a suitable inert solvent, such as dichloromethane, under suitable reaction conditions, such as a convenient temperature, typically ranging between –10° C. and 40° C.

A compound of Formula (XXII) wherein $R^5$ is as defined before and halo represents bromo, can be prepared by reacting a compound of Formula (XXIII)

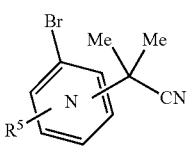

(XXIII)

wherein $R^5$ is as defined before, with diisobutylaluminium hydride, in a suitable inert solvent, such as dichloromethane, under suitable reaction conditions, such as a convenient temperature, typically ranging between –10° C. and 40° C.

A compound of Formula (XXIII) wherein $R^5$ is as defined before, can be prepared by reacting a compound of Formula (XXIV)

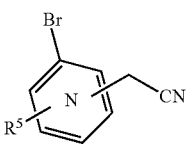

(XXIV)

wherein $R^5$ is as defined before, with a suitable alkylating reagent such as iodomethane, in the presence of a base, such as sodium tert-butoxide, in the presence of a suitable crown ether, such as 18-crown-6, in a suitable solvent, such as tetrahydrofuran and under suitable reaction conditions, such as a convenient temperature, typically ranging between 0° C. and 40° C.

A compound of Formula (XXIV) wherein $R^5$ is as defined before, can be obtained commercially or alternatively, can also be obtained by reacting a compound of Formula (XXV)

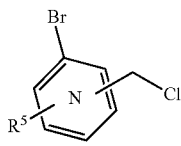
(XXV)

wherein R⁵ is as defined before, with potassium cyanide, in the presence of a suitable inorganic salt, such as potassium iodide, in a suitable solvent, such as a mixture of ethanol and water and under suitable reaction conditions, such as heating at a convenient temperature, typically ranging from 25° C. to 100° C.

A compound of Formula (XXV) wherein R⁵ is as defined before, can be obtained commercially or alternatively, can also be obtained by reacting a compound Formula (XXVI)

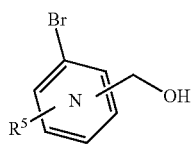
(XXVI)

wherein R⁵ is as defined before, with thionyl chloride, in a suitable solvent, such as dichloromethane and under suitable reaction conditions, such as a convenient temperature, typically ranging from −10° C. to 25° C.

A compound of Formula (XXVI) wherein R⁵ is as defined before can be obtained commercially.

Compounds of Formula (VIh)

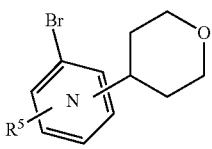
(VIh)

wherein R⁵ is as defined before, can be prepared by reacting an amino pyridine of Formula (XXVII)

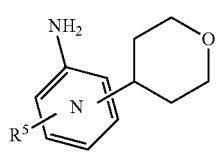
(XXVII)

where R⁵ is as defined before, with sodium nitrite in the presence of a suitable inorganic salt, such as copper (I) bromide and a suitable inorganic acid, such as hydrobromic acid, in a suitable inert solvent, such as water, under suitable reaction conditions, such as a convenient temperature, typically ranging between −10° C. and 25° C.

An aminopyridine of Formula (XXVII) where R⁵ is as defined before, can be prepared by reacting a nitropyridine of Formula (XXVIII)

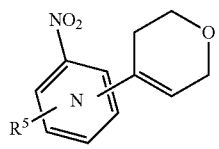
(XXVIII)

where R⁵ is as defined before, with hydrogen in the presence of a suitable catalyst, such as 10% palladium on charcoal, in a suitable inert solvent, such as methanol or ethanol, under suitable reaction conditions, such as heating at a convenient temperature, typically ranging between 25° C. and 40° C.

A nitropyridine of Formula (XXVIII) where R⁵ is as defined before, can be prepared by reacting an halonitropyridine of Formula (XXIX)

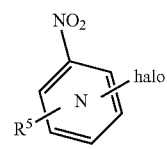
(XXIX)

where R⁵ is as defined before and halo represents a chloro, bromo or iodo, with 3,6-dihydro-2H-pyran-4-boronic acid pinacol ester in the presence of a suitable catalyst, such as tetrakis(triphenylphosphine)palladium(0), in the presence of a suitable base, such as sodium carbonate, in a suitable inert solvent, such as a mixture of 1,4-dioxane and water, under suitable reaction conditions, such as heating at a convenient temperature, either by conventional heating or under microwave irradiation for a period of time to ensure the completion of the reaction.

A halonitropyridine of Formula (XXIX) where R⁵ is as defined before and halo represents a chloro, bromo or iodo can be obtained commercially.

3,6-Dihydro-2H-pyran-4-boronic acid pinacol ester can be obtained as described before.

Compounds of Formula (VIi)

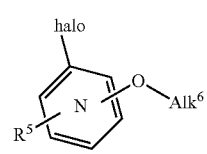
(VIi)

wherein R⁵ is as defined before and Alk⁶ is $C_{1-4}$alkyl, $C_{1-4}$alkyloxy$C_{1-5}$alkyl or $C_{3-8}$cycloalkyl$C_{1-4}$alkyl and halo is a bromo or iodo, can be prepared by reacting a di-halopyridine of Formula (XVIII) where R⁵ is as defined before, halo represents a bromo or iodo and the chlorine atom is ortho to the pyridinyl nitrogen with a reagent of Formula Alk⁶-OH, where Alk⁶ is $C_{1-4}$alkyl, $C_{1-4}$alkyloxy$C_{1-5}$alkyl or $C_{3-8}$cycloalkyl$C_{1-4}$alkyl in the presence of a suitable base, such as sodium hydride, in a suitable inert solvent, such as N,N-dimethylformamide or dimethyl sulfoxide, under suitable reaction conditions, such as heating at a convenient temperature, either by conventional heating or under microwave irradiation for a period of time to ensure the completion of the reaction.

A di-halo pyridine of Formula (XVIII) where $R^5$ is as defined before, halo represents a bromo or iodo, can be obtained commercially.

A reagent of Formula $Alk^6$-OH wherein $Alk^6$ is $C_{1-4}$alkyl, $C_{1-4}$alkyloxy$C_{1-5}$alkyl or $C_{3-8}$cycloalkyl$C_{1-4}$alkyl, can be obtained commercially or alternatively can also be obtained by procedures similar to those described in Morel, P. US 2008102028 A1.

Compounds of Formula (VIj)

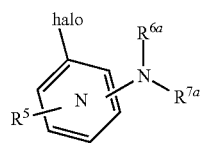

(VIj)

wherein $R^5$, $R^{6a}$ and $R^{7a}$ are as defined before and halo represents bromo or iodo, can also be prepared by reacting a di-halo pyridine of Formula (XVIII) where $R^5$ is as defined before, and halo represents a bromo or iodo and the chlorine atom is ortho to the pyridinyl nitrogen with a compound of formula $R^{6a}R^{7a}$NH, wherein $R^{6a}$ and $R^{7a}$ are as defined before, either neat or in a suitable inert solvent, such as acetonitrile, under suitable reaction conditions, such as heating at a convenient temperature, either by conventional heating or under microwave irradiation for a period of time to ensure the completion of the reaction.

A reagent of Formula $R^{6a}R^{7a}$NH, wherein $R^{6a}$ and $R^{7a}$ are as defined before, can be obtained commercially.

A di-halo pyridine of Formula (XVIII) where $R^5$ is as defined before, halo represents a bromo or iodo, can be obtained commercially.

A compound of Formula (I) wherein $R^1$, $R^2$, $R^4$ and $R^5$ are as defined before, $R^3$ is hydrogen, Het is pyrazolyl and $R^4$ is attached to the nitrogen atom of the pyrazole can be prepared by reacting a compound of Formula (If)

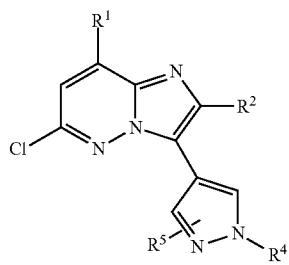

(If)

wherein $R^1$, $R^2$, $R^4$ and $R^5$ are as defined before, with hydrogen in the presence of a suitable catalyst, such as 10% palladium on charcoal, in a suitable inert solvent, such as methanol or ethanol, under suitable reaction conditions, such as a convenient temperature, typically ranging between 25° C. and 40° C. or with ammonium formate in the presence of a suitable catalyst such as 10% palladium on charcoal, in a suitable inert solvent, such as methanol, ethanol, ethyl acetate or dichloromethane or mixtures thereof, under suitable reaction conditions, such as heating at a convenient temperature, typically ranging between 40° C. and 100° C.

Compounds of Formula (I) wherein $R^1$, $R^2$, $R^3$, $R^4$ and $R^5$ are as defined before, Het is pyrazolyl and $R^4$ is attached to the nitrogen atom of the pyrazole can be prepared by reacting a compound of Formula (II) where $R^1$, $R^2$ and $R^3$ are as defined before and halo represents a bromo or iodo, with a boronate of Formula (XXX)

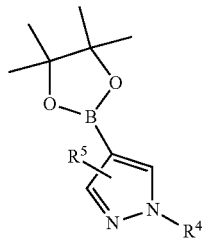

(XXX)

where $R^4$ and $R^5$ are as defined before, in the presence of a suitable catalyst, such as tetrakis(triphenylphosphine)palladium (0), in the presence of a suitable base, such as sodium carbonate, in a suitable inert solvent such as a mixture of 1,4-dioxane and water, under suitable reaction conditions, such as heating at a convenient temperature, either by conventional heating or under microwave irradiation for a period of time to ensure the completion of the reaction.

A compound of Formula (XXX) wherein $R^4$ and $R^5$ are as defined before and $R^4$ is attached to the nitrogen atom of the pyrazole, can be obtained commercially or alternatively, can be prepared by reacting a compound of Formula (XXXI)

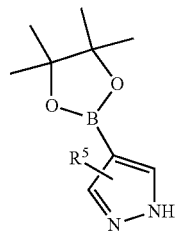

(XXXI)

wherein $R^5$ is as defined before, with a reagent of Formula $R^4$—W wherein $R^4$ is as defined before and W represents a leaving group, such as halo, e.g. chloro, bromo or iodo, or a sulfonyloxy group, e.g. methylsulfonyloxy, trifluoromethylsulfonyloxy, or methylphenylsulfonyloxy in the presence of a base such as cesium carbonate or diisopropylethylamine, in a suitable solvent, such as N,N-dimethylformamide or acetonitrile and under suitable reaction conditions, such as heating at a convenient temperature, either by conventional heating or under microwave irradiation for a period of time to ensure the completion of the reaction.

Compounds of Formula $R^4$—W wherein $R^4$ is as defined before and W represents a leaving group, such as halo, e.g. chloro, bromo or iodo, can be obtained commercially. Compounds of formula $R^4$—W wherein $R^4$ is as defined before and W represents a leaving group, such as a sulfonyloxy group, e.g. methylsulfonyloxy, trifluoromethylsulfonyloxy, or methylphenylsulfonyloxy can be prepared by reacting a compound of Formula $R^4$—OH with a sulfonyl chloride, e.g. methylsulfonyl chloride, trifluoromethylsulfonyl chloride, or methylphenylsulfonyl chloride in the presence of a suitable base, such as pyridine or diisopropylethylamine, in a suitable solvent, such as dichloromethane and under suitable reaction conditions, such as a convenient temperature, typically ranging from −10° C. to 25° C.

Compounds of Formula R⁴—OH wherein R⁴ is as defined before, can be obtained commercially.

Compounds of Formula (XXX) wherein R⁴ and R⁵ are as defined before and R⁴ is attached to the nitrogen atom of the pyrazole, can also be prepared by reacting a compound of Formula (XXXII)

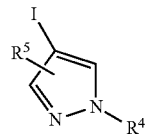

(XXXII)

wherein R⁴ and R⁵ are as defined before, with bis(pinacolato) diboron in the presence of a suitable catalyst, such as [1,1'-bis(diphenylphosphino)ferrocene]dichloropalladium (II), in the presence of a suitable base, such as potassium acetate, in a suitable inert solvent, such as N,N-dimethylformamide or dimethyl sulfoxide, under suitable reaction conditions, such as heating at a convenient temperature, either by conventional heating or under microwave irradiation for a period of time to ensure the completion of the reaction.

Compounds of Formula (XXXII) wherein R⁴ and R⁵ are as defined before and R⁴ is attached to the nitrogen atom of the pyrazole, can be prepared by reacting a 4-iodo-1H-pyrazole of Formula (XXXIII)

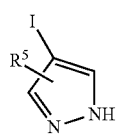

(XXXIII)

wherein R⁵ is as defined before, with a reagent of Formula R⁴—W wherein R⁴ is as defined before and W represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a suitable base, such as cesium carbonate or diisopropylethylamine, in a suitable solvent, such as N,N-dimethylformamide or acetonitrile and under suitable reaction conditions, such as heating at a convenient temperature, either by conventional heating or under microwave irradiation for a period of time to ensure the completion of the reaction.

A 4-iodo-1H-pyrazole of Formula (XXXIII) where R⁵ is as defined before, can be obtained commercially.

Compounds of Formula R⁴—W wherein R⁴ is as defined before and W represents a leaving group such as halo, e.g. chloro, bromo or iodo, can be obtained commercially.

Alternatively, compounds of formula R⁴—W wherein R⁴ is as defined before and W represents a leaving group such as a sulfonyloxy group, e.g. methylsulfonyloxy, trifluoromethylsulfonyloxy, or methylphenylsulfonyloxy can be prepared by reacting a compound of formula R⁴—OH with a sulfonyl chloride, e.g. methylsulfonyl chloride, trifluoromethylsulfonyl chloride, or methylphenylsulfonyl chloride in the presence of a suitable base such, as pyridine or diisopropylethylamine, in a suitable solvent, such as dichloromethane and under suitable reaction conditions, such as a convenient temperature, typically ranging from −10° C. to 25° C.

Compounds of Formula R⁴—OH wherein R⁴ is as defined before, can be obtained commercially.

A compound of Formula (XXXIIa)

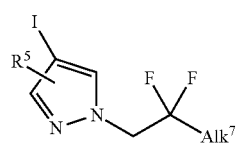

(XXXIIa)

wherein R⁵ is as defined before and Alk⁷ represents $C_{1-4}$alkyl or $C_{3-8}$cycloalkyl groups can be prepared by reacting a compound of Formula (XXXIIb).

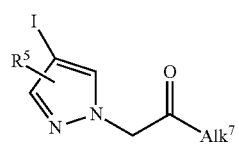

(XXXIIb)

wherein R⁵ is as defined before and Alk⁷ represents $C_{1-4}$alkyl or $C_{3-8}$cycloalkyl groups with (diethylamino)sulphur trifluoride in a suitable inert solvent, such as dichloromethane, and under suitable reaction conditions, such as convenient temperatures, typically ranging from 0° C. to 25° C.

A compound of Formula (XXXIIb), wherein Alk⁷ represents a $C_{1-4}$alkyl or $C_{3-8}$cycloalkyl group can be prepared by reacting a 4-iodo-1H-pyrazole of Formula (XXXIII) with an alpha bromoketone of Formula (XXXV)

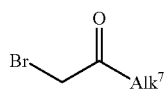

(XXXV)

wherein Alk⁷ represents a $C_{1-4}$alkyl or a $C_{3-8}$cycloalkyl group, in the presence of a suitable base, such as cesium carbonate, in a suitable inert solvent, such as acetonitrile, under suitable reaction conditions, such as heating at a convenient temperature, either by conventional heating or under microwave irradiation for a period of time to ensure the completion of the reaction.

An alpha bromoketone of Formula (XXXV) wherein Alk⁷ is $C_{1-4}$alkyl or $C_{3-8}$cycloalkyl, can be obtained commercially or alternatively can be obtained by procedures similar to those described in Carverley, M. J. Tetrahedron, 1987, 43(20), 4609-19.

A compound of Formula (XXXIIc)

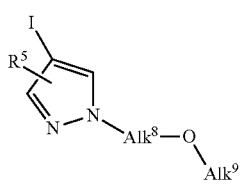

(XXXIIc)

wherein R⁵ is as defined before, Alk⁸ represents $C_{1-4}$alkyl and Alk⁹ represents $C_{1-4}$alkyl, can be prepared by reacting a compound of Formula (XXXVI)

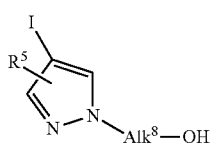

(XXXVI)

where $R^5$ is as defined before and $Alk^8$ represents $C_{1-4}$alkyl with a reagent of Formula $Alk^9$-W wherein $Alk^9$ is $C_{1-4}$alkyl, and W represents a leaving group such as halo, e.g. chloro, bromo or iodo, or a sulfonyloxy group, e.g. methylsulfonyloxy, trifluoromethylsulfonyloxy, or methylphenylsulfonyloxy, in the presence of a suitable base, such as sodium hydride, in a suitable solvent such as tetrahydrofuran and under suitable reaction conditions, such as a convenient temperature, typically ranging from 0° C. to 40° C.

A reagent of Formula $Alk^9$-W wherein $Alk^9$ is $C_{1-4}$alkyl and W represents a leaving group such as halo, e.g. chloro, bromo or iodo, or a sulfonyloxy group, e.g. methylsulfonyloxy, trifluoromethylsulfonyloxy, or methylphenylsulfonyloxy, can be obtained commercially.

A compound of Formula (XXXVI) wherein $R^5$ is as defined before, can be prepared by reacting a 4-iodo-1H-pyrazole of Formula (XXXIII) where $R^5$ is as defined before, with a reagent of Formula W-$Alk^8$-OH, wherein W represents a leaving group such as halo, e.g. chloro, bromo or iodo, or a sulfonyloxy group, e.g. methylsulfonyloxy, trifluoromethylsulfonyloxy, or methylphenylsulfonyloxy and $Alk^8$ represents a $C_{1-4}$alkyl, in the presence of a suitable base, such as cesium carbonate, in a suitable inert solvent, such as N,N-dimethylformamide, under suitable reaction conditions, such as heating at a convenient temperature, either by conventional heating or under microwave irradiation for a period of time to ensure the completion of the reaction.

A reagent of Formula W-$Alk^8$-OH wherein W represents a leaving group such as halo, e.g. chloro, bromo or iodo, or a sulfonyloxy group, e.g. methylsulfonyloxy, trifluoromethylsulfonyloxy, or methylphenylsulfonyloxy and $Alk^8$ represents $C_{1-4}$alkyl or $C_{3-8}$cycloalkyl, can be obtained commercially.

In order to obtain the acid addition salt forms of the compounds according to the invention, for example the HCl salt forms unless otherwise described, several procedures known to those skilled in the art can be used. In a typical procedure, for example, the free base can be dissolved in isopropanol, diisopropylether, diethyl ether and/or dichloromethane and subsequently, 1 to 2 equivalents of the appropriate acid, for example a 6N HCl solution in 2-propanol or a 2N HCl solution in diethyl ether, can be added dropwise. The mixture typically is stirred for 10 min or longer after which the product can be filtered off. The HCl salt is usually dried in vacuo.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

The compounds according to the invention inhibit PDE10 enzyme activity, in particular PDE10A enzyme activity and hence raise the levels of cAMP or cGMP within cells that express PDE10. Accordingly, inhibition of PDE10 enzyme activity may be useful in the treatment of diseases caused by deficient amounts of cAMP or cGMP in cells. PDE10 inhibitors may also be of benefit in cases in which raising the amount of cAMP or cGMP above normal levels results in a therapeutic effect.

Inhibitors of PDE10 may be used to treat disorders of the peripheral and central nervous system, cardiovascular diseases, cancer, gastro-enterological diseases, endocrinological or metabolic diseases and urological diseases.

Hence, the present invention relates to a compound according to the present invention for use as a medicine, as well as to the use of a compound according to the invention or a pharmaceutical composition according to the invention for the manufacture of a medicament. The present invention also relates to a compound according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 10 enzyme. The present invention also relates to the use of a compound according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 10 enzyme.

The present invention also relates to a compound according to the invention, or a pharmaceutical composition according to the invention for use in the treatment, prevention, amelioration, control or reduction of the risk of various neurological, psychiatric and metabolic disorders associated with phosphodiesterase 10 dysfunction in a mammal, including a human, the treatment or prevention of which is affected or facilitated by the inhibition of phosphodiesterase 10.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with phosphodiesterase 10 dysfunction in a mammal, including a human, the treatment or prevention of which is affected or facilitated by the inhibition of phosphodiesterase 10.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the indications that may be treated with PDE10 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; pain and metabolic disorders.

In particular, the psychotic disorders and conditions associated with PDE10 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder and substance-induced mood disorder.

In particular, neurodegenerative disorders include Parkinson's disease; Huntington's disease; dementia such as for example Alzheimer's disease; multi-infarct dementia; AIDS-related dementia or fronto temperal dementia. The neurodegenerative disorder or condition comprises neurodegeneration of striatal medium spiny neurons.

In particular, disorders or conditions comprising as a symptom a deficiency in attention and/or cognition include dementia, such as Alzheimer's disease; multi-infarct dementia; alcoholic dementia or drug-related dementia; dementia associated with intracranial tumours or cerebral trauma; dementia associated with Huntington's disease; dementia associated with Parkinson's disease; AIDS-related dementia; other diseases include delirium; amnestic disorder; post-traumatic stress disorder; mental retardation; a learning disorder; attention-deficit/hyperactivity disorder (ADHD); and age-related cognitive impairment.

In particular, pain includes acute and chronic states, severe pain, intractable pain, neuropathic pain and post-traumatic pain.

In particular, metabolic disorders include diabetes, in particular type 1 or type 2 diabetes, and related disorders such as obesity. Additional related disorders include syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

Additionally, the growth of some cancer cells is inhibited by cAMP and cGMP, the compounds of the invention may be useful in the treatment of cancer, such as renal carcinoma and breast cancer.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by the compounds of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; pain; diabetes and obesity.

Preferably, the disorders treated by the compounds of the present invention are schizophrenia, including positive and negative symptoms thereof, and cognitive deficits, such as impaired attention or memory.

Of the disorders mentioned above, the treatment of anxiety, obsessive-compulsive disorder, schizophrenia, depression, attention-deficit/hyperactivity disorder, Alzheimer's disease and diabetes are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the invention, for use in the treatment of any one of the diseases mentioned hereinbefore.

The invention also relates to a compound according to the invention for use in treating any one of the diseases mentioned hereinbefore.

The invention also relates to a compound according to the invention, for the treatment or prevention, in particular treatment, of any one of the diseases mentioned hereinbefore.

The invention also relates to the use of a compound according to the invention, for the manufacture of a medicament for the treatment or prevention of any one of the disease conditions mentioned hereinbefore.

The invention also relates to the use of a compound according to the invention for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds according to the invention, there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound according to the invention to warm-blooded animals, including humans.

Therefore, the invention also relates to a method for the prevention and/or treatment of any one of the diseases mentioned hereinbefore comprising administering a therapeutically effective amount of compound according to the invention to a patient in need thereof.

The PDE10 inhibitors described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, cannabinoid modulators, and cholinesterase inhibitors (e.g. donepezil, rivastigmine, and galantamine). In such combinations, the compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

One skilled in the art will recognize that a therapeutically effective amount of the PDE10 inhibitors of the present invention is the amount sufficient to inhibit the PDE10 enzyme and that this amount varies inter alia, depending on the type of disease, the concentration of the compound in the therapeutic formulation, and the condition of the patient. Generally, an amount of PDE10 inhibitor to be administered as a therapeutic agent for treating diseases in which inhibition of the PDE10 enzyme is beneficial, such as the disorders described herein, will be determined on a case by case by an attending physician.

Generally, a suitable dose is one that results in a concentration of the PDE10 inhibitor at the treatment site in the range of 0.5 nM to 200 μM, and more usually 5 nM to 50 μM. To obtain these treatment concentrations, a patient in need of treatment likely will be administered between 0.001 mg/kg to 15 mg/kg body weight, in particular from 0.01 mg/kg to 2.50 mg/kg body weight, in particular, from 0.01 to 1.5 mg/kg body weight, in particular from 0.1 mg/kg to 0.50 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Pharmaceutical Compositions

The present invention also provides compositions for preventing or treating diseases in which inhibition of the PDE10 enzyme is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical (for example via a nose spray, eye drops or via a cream, gel, shampoo or the like), rectal or percutaneous administration, by parenteral injection or by inhalation, such as a nose spray. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are employed. For parenteral compositions, the carrier will usually comprise sterile water, at least in large part, though other ingredients, for example, surfactants to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, said additives do not introduce a significant deleterious effect on the skin. Said additives may facilitate the administration to the skin and/or may be helpful for preparing the desired compositions. These compositions may be administered in various ways, e.g., as a transdermal patch, as a spot-on treatment, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility as well. The use of such a composition for the manufacture of a medicament, as well as the use of such a composition for the manufacture of a medicament in the treatment, prevention, control, amelioration or reduction of risk of diseases or conditions for which compounds of Formula (I) or the other drugs may have utility are also contemplated. The present invention also relates to a combination of a compound according to the present invention and an additional pharmaceutical agent. The present invention also relates to such a combination for use as a medicine. The present invention also relates to a product comprising (a) a compound according to the present invention, a pharmaceutically acceptable salt thereof or a solvate thereof, and (b) an additional pharmaceutical agent, as a combined preparation for simultaneous, separate or sequential use in the treatment or prevention of a condition in a mammal, including a human, the treatment or prevention of which is affected or facilitated by the effect of PDE10 inhibitors, in particular PDE10A inhibitors. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

EXAMPLES

Chemistry

Several methods for preparing the compounds of this invention are illustrated in the following Examples. Unless otherwise noted, all starting materials were obtained from commercial suppliers and used without further purification.

Hereinafter, the term "LCMS" means liquid chromatography/mass spectrometry, "HPLC" means high-performance liquid chromatography, "min." means minutes, "h." means hours, "$R_t$" means retention time (in minutes), "$[M+H]^+$" means the protonated mass of the free base of the compound, "m.p." means melting point.

Microwave assisted reactions were performed in a single-mode reactor: Emrys™ Optimizer microwave reactor (Personal Chemistry A.B., currently Biotage).

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from Merck, on irregular silica gel, particle size 15-40 μm (normal phase disposable flash columns) on an SPOT or FLASH system from Armen Instrument.

Reverse phase HPLC was performed on a C18 XBridge 30×100 5 μm column.

¹H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

Melting Point values are peak values, and are obtained with experimental uncertainties that are commonly associated with this analytical method. For a number of compounds, melting points were determined in open capillary tubes either on a Mettler FP62 or on a Mettler FP81HT-FP90 apparatus. Melting points were measured with a temperature gradient of 10° C./minute. Maximum temperature was 300° C. The melting point was read from a digital display.

LCMS Analysis

General Procedure for HP 1100-MS Instruments (TOF, SQD or MSD)

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector was configured with either an electrospray ionization source or an ESCI dual ionization source (electrospray combined with atmospheric pressure chemical ionization). Nitrogen was used as the nebulizer gas. The source temperature was maintained either at 140° C. or 100° C. Data acquisition was performed either with MassLynx-Openlynx software or Chemsation-Agilent Data Browser software.

General Procedure for Acquity-SQD Instrument

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

MS Procedure for LC Method 1:

High-resolution mass spectra (Time of Flight, TOF detector) were acquired only in positive ionization mode or in positive/negative modes by scanning from 100 to 750 umas. The capillary needle voltage was 2.5 kV for positive mode and 2.9 kV for negative ionization mode. The cone voltage was 20 V for both positive and negative ionization modes. Leucine-Enkephaline was the standard substance used for the lock mass calibration.

MS Procedure for LC Methods 2, 4, 5, and 6:

Low-resolution mass spectra (single quadrupole, SQD detector) were acquired only in positive ionization mode or in positive/negative modes by scanning from 100 to 1000 umas. The capillary needle voltage was 3 kV. For positive ionization mode the cone voltage was 20 V, 25 V or 20 V/50 V. For negative ionization mode the cone voltage was 30 V.

MS Procedure for LC Method 3

Low-resolution mass spectra (single quadrupole, MSD detector) were acquired in positive/negative modes by scanning from 100 to 1000 umas. The capillary needle voltage was 1.0 kV and the fragmentor voltage was 70V for both positive and negative ionization modes.

Method 1

In addition to the general procedure: Reversed phase HPLC was carried out on a Sunfire-C18 column (2.5 μm, 2.1×30 mm) from Waters, with a flow rate of 1.0 ml/min, at 60° C. The gradient conditions used are: 95% A (0.5 g/L ammonium acetate solution+5% of acetonitrile), 5% B (acetonitrile or acetonitrile/methanol 1/1), to 100% B and equilibrated to initial conditions up to 7 or 9 minutes run. Injection volume 2 μL.

Method 2

In addition to the general procedure: Reversed phase HPLC was carried out on an Eclipse Plus-C18 column (3.5 μm, 2.1×30 mm) from Agilent, with a flow rate of 1.0 mL/min, at 60° C. The gradient conditions used are: 95% A (0.5 g/L ammonium acetate solution+5% acetonitrile), 5% B (acetonitrile or mixture of acetonitrile/methanol, 1/1), to 100% B and equilibrated to initial conditions up to 7 or 9 minutes run. Injection volume 2 μL.

Method 3

In addition to the general procedure: Reversed phase HPLC was carried out on an Eclipse Plus-C18 column (3.5 μm, 2.1×30 mm) from Agilent, with a flow rate of 1.0 mL/min, at 60° C. The gradient conditions used are: 95% A (0.5 g/L ammonium acetate solution+5% acetonitrile), 5% B (acetonitrile), to 100% B in 5.0 minutes, kept till 5.15 minutes and equilibrated to initial conditions at 5.3 minutes until 7.0 minutes. Injection volume 2 μL.

Method 4

In addition to the general procedure: Reversed phase UPLC was carried out on a BEH-C18 column (1.7 μm, 2.1×50 mm) from Waters, with a flow rate of 0.8 mL/min, at 60° C. The gradient conditions used are: 95% A (0.5 g/L ammonium acetate solution+5% acetonitrile), 5% B (mixture of acetonitrile/methanol, 1/1), to 20% A, 80% B, then to 100% B and equilibrated to initial conditions up to 5 or 7 minutes run. Injection volume 0.5 μL.

Method 5

In addition to the general procedure: Reversed phase UPLC was carried out on a BEH-C18 column (1.7 μm, 2.1×50 mm) from Waters, with a flow rate of 1.0 mL/min, at 50° C. The gradient conditions used are: 95% A (0.5 g/L ammonium acetate solution+5% acetonitrile), 5% B (acetonitrile), to 40% A, 60% B, then to 5% A, 95% B and equilibrated to initial conditions up to 5, 7, or 9 minutes run. Injection volume 0.5 μL.

Method 6

In addition to the general procedure: Reversed phase UPLC was carried out on a BEH-C18 column (1.7 μm, 2.1×50 mm) from Waters, with a flow rate of 0.8 mL/min, at 50° C. The gradient conditions used are: 95% A (formic acid solution, 0.1%), 5% B (methanol), to 40% A, 60% B, then to 5% A, 95% B and equilibrated to initial conditions up to 7.0 minutes run. Injection volume 0.5 μL.

A. Preparation of the Intermediates

Example A1

Preparation of intermediate 1: 4-Bromo-6-chloro-pyridazin-3-ylamine

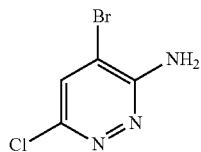

Bromine (7.9 ml, 154.3 mmol) was added to a stirred suspension of 6-chloro-pyridazin-3-ylamine (20 g, 154.3 mmol) and sodium hydrogencarbonate (25.9 g, 308.8 mol) in methanol (500 ml). The mixture was stirred at room temperature for 16 h, then filtered. The filtrate was diluted with ethyl acetate and washed with a saturated solution of sodium thiosulfate, water and a saturated solution of sodium carbonate. The organic layer was separated, dried ($Na_2SO_4$), filtered and the solvents evaporated in vacuo to yield intermediate 1 (24.59 g, 64%) as a brown solid which was used in next step without further purification. LCMS: 208 [M+H]$^+$; $R_t$: 0.59 min (method 5).

Example A2

Preparation of intermediate 2: 6-Chloro-4-morpholin-4-yl-pyridazin-3-ylamine

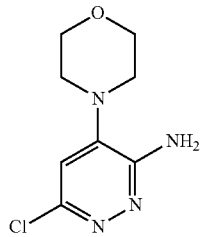 [SMILES: Nc1nnc(Cl)cc1N1CCOCC1]

Morpholine (8.37 ml, 95.9 mmol) was added to a stirred solution of intermediate 1 (2 g, 9.6 mmol) in acetonitrile (5 ml). The mixture was stirred at 80° C. for 16 h., then diluted with dichloromethane and washed with a saturated solution of sodium hydrogen carbonate. The organic layer was separated, dried ($Na_2SO_4$), filtered and the solvents evaporated in vacuo. The crude product was purified by flash column chromatography (silica, methanol in dichloromethane 0/100 to 30/70). The desired fractions were collected and concentrated in vacuo to yield intermediate 2 (1.98 g, 92%) as a pale brown solid. LCMS: 215 [M+H]$^+$; $R_t$: 0.56 min (method 5).

Example A3

Preparation of intermediate 3: Mixture of 6,8-dichloro-2-methyl-imidazo[1,2-b]pyridazine and 8-bromo-6-chloro-2-methyl-imidazo[1,2-b]pyridazine

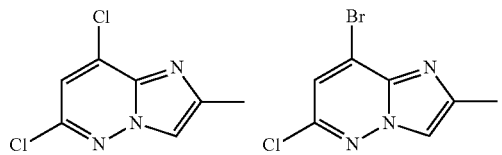

A mixture of intermediate 1 (28.57 g, 137.1 mmol) and chloroacetone (76.4 ml, 959.4 mmol) was stirred at 90° C. for 16 h. in a sealed tube protected from light. After cooling to room temperature, diethylether was added and the solid formed was filtered off and washed with further diethylether. The solid was suspended in a saturated solution of sodium carbonate and extracted with dichloromethane. The organic layer was dried ($Na_2SO_4$), filtered and the solvents evaporated in vacuo. The crude products were purified by open column chromatography (silica; dichloromethane). The desired fractions were collected and concentrated in vacuo to yield intermediate 3 (19.5 g, 66%) as a white solid, in a 70/30 mixture of 6,8-dichloro-2-methyl-imidazo[1,2-b]pyridazine and 8-bromo-6-chloro-2-methyl-imidazo[1,2-b]pyridazine. $C_7H_5Cl_2N_3$ requires 201; Found 202 [M+H]$^+$; $R_t$: 1.25 min and $C_7H_5BrClN_3$ requires 247; Found 248 [M+H]$^+$; $R_t$: 1.33 min (method 5).

Example A4

Preparation of intermediate 4: 8-Bromo-6-cloro-2-cyclopropyl-imidazo[1,2-b]pyridazine

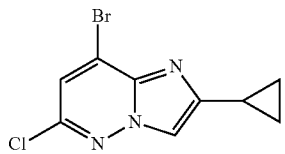 [SMILES: Clc1cc(Br)c2nc(C3CC3)cn2n1]

A mixture of intermediate 1 (5 g, 24 mmol) and 2-bromo-1-cyclopropyl-ethanone (15.25 g, 93.6 mmol) (obtained by a procedure similar to those described in Gaudry, M.; Marquet, A. Organic Syntheses 1976, 55) was stirred at 80° C. for 16 h. The crude product was suspended in dichloromethane and washed with a saturated solution of sodium hydrogen carbonate. The organic layer was separated, dried ($Na_2SO_4$), filtered and the solvents evaporated in vacuo. The crude product was purified by flash column chromatography (silica; dichloromethane in heptane 40/60 to 100/0). The desired fractions were collected and concentrated in vacuo to yield intermediate 4 (4.95 g, 76%) as a black solid. $C_9H_7BrClN_3$ requires 271; Found 272 [M+H]$^+$. $R_t$: 2.05 min (method 5).

Example A5

Preparation of intermediate 5: Mixture of 6,8-dichloro-imidazo[1,2-b]pyridazine and 8-bromo-6-chloro-imidazo[1,2-b]pyridazine

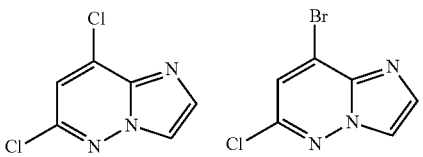

A 50% wt. solution of chloroacetaldehyde in water (5.79 ml, 44.5 mmol) was added dropwise to a solution of intermediate 1 (2.34 g, 11.2 mmol) in ethanol (50 ml). The mixture was stirred at reflux temperature for 2 h. After cooling to room temperature, the mixture was poured onto a mixture of ice/water and ethyl acetate was added. The mixture was basified by addition of a saturated solution of sodium carbonate. The organic layer was separated, washed with brine, dried ($Na_2SO_4$), filtered and the solvents evaporated in vacuo. The crude products were purified by open column chromatography (silica; 7M solution of ammonia in methanol in dichloromethane 2/98). The desired fractions were collected and concentrated in vacuo to yield intermediate 5 (1.5 g, 66%) as a 68/32 mixture of 6,8-dichloro-imidazo[1,2-b]pyridazine and 8-bromo-6-chloro-imidazo[1,2-b]pyridazine.

Example A6

Preparation of intermediate 6: 6-Chloro-8-iodo-2-methyl-imidazo[1,2-b]pyridazine

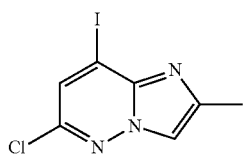

Hydriodic acid (0.1 ml, 0.74 mmol) was added to a solution of intermediate 3 (a 70/30 mixture of 6,8-dichloro-2-methyl-imidazo[1,2-b]pyridazine and 8-bromo-6-chloro-2-methyl-imidazo[1,2-b]pyridazine) (1 g, 4.95 mmol) and sodium iodide (2.23 g, 45.1 mmol) in acetonitrile (10 ml). The mixture was stirred at 160° C. for 30 min. in a sealed tube, under microwave irradiation and then poured onto a 10% w/w solution of sodium carbonate. The mixture was diluted with dichloromethane and washed with a 10% solution of sodium thiosulfite. The organic layer was separated, dried (Na$_2$SO$_4$), filtered and the solvents evaporated in vacuo. The crude product was purified by flash column chromatography (silica; ethyl acetate in heptane 0/100 to 50/50). The desired fractions were collected and concentrated in vacuo to yield intermediate 6 (1.25 g, 86%) as a light brown solid. LCMS: 294 [M+H]$^+$; R$_t$: 1.52 min (method 5).

Example A7

Preparation of intermediate 7: 6-Chloro-2-methyl-8-morpholin-4-yl-imidazo[1,2-b]pyridazine

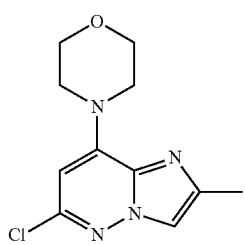 [SMILES: Cc1cn2nc(Cl)cc(N3CCOCC3)c2n1]

Morpholine (6.48 ml, 74.2 mmol) was added to a stirred solution of intermediate 3 (a 70/30 mixture of 6,8-dichloro-2-methyl-imidazo[1,2-b]pyridazine and 8-bromo-6-chloro-2-methyl-imidazo[1,2-b]pyridazine) (12.5 g, 58.0 mmol) and N,N-diisopropylethylamine (16.2 ml, 92.8 mmol) in acetonitrile (40 ml). The mixture was stirred at 80° C. for 16 h. and then diluted with dichloromethane and washed with a saturated solution of ammonium chloride. The organic layer was separated, dried (Na$_2$SO$_4$), filtered and the solvents evaporated in vacuo. The crude product was triturated with diethylether to yield intermediate 7 (15.4 g, 99%) as a pale brown solid. LCMS: 253 [M+H]$^+$; R$_t$: 1.62 min (method 5).

The following intermediates were prepared from the indicated precursors according to a protocol analogous to A7.

Example A8

Preparation of intermediate 8: 6-Chloro-2-cyclopropyl-8-morpholin-4-yl-imidazo[1,2-b]pyridazine

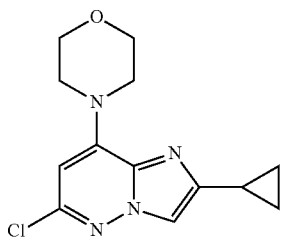 [SMILES: Clc1cc(N2CCOCC2)c2nc(C3CC3)cn2n1]

From intermediate 4. Flash column chromatography (silica; ethyl acetate in heptane 30/70) yielded intermediate 8 as a white solid (81%). LCMS: 279 [M+H]$^+$; R$_t$: 2.60 min (method 4).

Example A9

Preparation of intermediate 9: 6-Chloro-8-morpholin-4-yl-imidazo[1,2-b]pyridazine

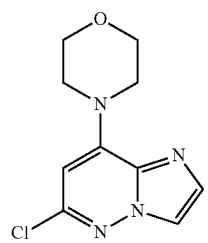 [SMILES: Clc1cc(N2CCOCC2)c2nccn2n1]

From intermediate 5 (a 68/32 mixture of 6,8-dichloro-imidazo[1,2-b]pyridazine and 8-bromo-6-chloro-imidazo[1,2-b]pyridazine). Open column chromatography (silica, dichloromethane) yielded intermediate 9 as a pale yellow solid (66%).

Example A10

Preparation of intermediate 10: 6-Chloro-2-methoxy-8-morpholin-4-yl-imidazo[1,2-b]pyridazine

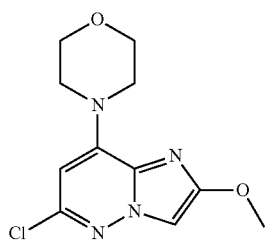 [SMILES: COc1cn2nc(Cl)cc(N3CCOCC3)c2n1]

A mixture of intermediate 2 (0.7 g, 3.26 mmol) and methyl bromoacetate (0.93 ml, 9.78 mmol) in methanol (2.5 ml) was stirred at 130° C. for 15 min under microwave irradiation. The mixture was diluted with water and extracted with dichloromethane. The organic layer was separated, extracted with brine, dried (Na₂SO₄), filtered and the solvents evaporated in vacuo. The crude product was purified by flash column chromatography (silica; 7 M solution of ammonia in methanol in dichloromethane 0/100 to 3/97). The desired fractions were collected and concentrated in vacuo to yield intermediate 10 (0.314 g, 29%).

Example A11

Preparation of intermediate 11: 6-Chloro-2-methyl-8-pyridin-4-yl-imidazo[1,2-b]pyridazine

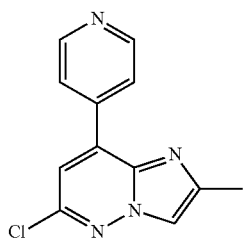 [SMILES: Cc1cn2nc(Cl)cc(-c3ccncc3)c2n1]

Tetrakis(triphenylphosphine)palladium (0) (0.114 g, 0.10 mmol) was added to a stirred solution of intermediate 3 (a mixture 70/30 of 6,8-dichloro-2-methyl-imidazo[1,2-b]pyridazine and 8-bromo-6-chloro-2-methyl-imidazo[1,2-b]pyridazine) (0.4 g, 2.0 mmol) and 4-pyridineboronic acid (0.243 g, 2.0 mmol) in a mixture of 1,4-dioxane (2 ml) and a saturated solution of sodium carbonate (2 ml). The mixture was stirred at 100° C. for 16 h. in a sealed tube under nitrogen and then filtered through a pad of diatomaceous earth. The filtrate was diluted with dichloromethane and extracted with a saturated solution of sodium carbonate. The organic layer was separated, dried (Na₂SO₄), filtered and the solvents evaporated in vacuo. The crude product was purified by column chromatography (silica; ethyl acetate in heptane 0/100 to 50/50). The desired fractions were collected and concentrated in vacuo to yield intermediate 11 (0.26 g, 41%). LCMS: 288 [M+H]⁺; $R_t$: 2.17 min (method 4).

The following intermediates were prepared from the indicated precursors according to a protocol analogous to A11.

Example A12

Preparation of intermediate 12: 6-Chloro-2-cyclopropyl-8-pyridin-4-yl-imidazo[1,2-b]pyridazine

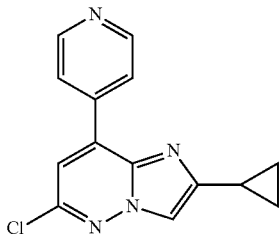 [SMILES: Clc1cc(-c2ccncc2)c2nc(C3CC3)cn2n1]

From intermediate 4. Flash column chromatography (silica; ethyl acetate in dichloromethane 0/100 to 30/70) yielded intermediate 12 as a pale yellow solid (52%). LCMS: 271 [M+H]⁺; $R_t$: 2.11 min (method 5).

Example A13

Preparation of intermediate 13: 6-Chloro-2-methyl-8-pyridin-3-yl-imidazo[1,2-b]pyridazine

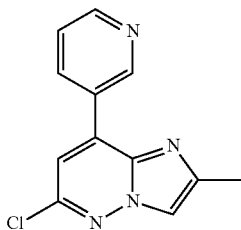 [SMILES: Cc1cn2nc(Cl)cc(-c3cccnc3)c2n1]

From intermediate 6 and 3-pyridineboronic acid. Conditions: 140° C. for 15 min under microwave irradiation. Flash column chromatography (silica; 7 M solution of ammonia in methanol in dichloromethane 0/100 to 4/96) yielded intermediate 13 as a pale brown solid (100%).

Example A14

Preparation of intermediate 14: 2-Methyl-8-morpholin-4-yl-imidazo[1,2-b]pyridazine 10% Palladium on charcoal (0.421 g) was added to a suspension of intermediate 7 (1 g, 3.96 mmol) and ammonium formate (0.75 g, 11.9 mmol) in methanol (25 ml). The mixture was stirred at 80° C. for 4 h. and at room temperature for a further 16 h. The mixture was filtered through a pad of diatomaceous earth and the filtrate was concentrated in vacuo. The crude product was suspended in dichloromethane and washed with a saturated solution of sodium hydrogen carbonate. The organic layer was separated, dried (Na₂SO₄), filtered and the solvents evaporated in vacuo to yield intermediate 14 (0.78 g, 90%) as a white solid. LCMS: 219 [M+H]⁺; $R_t$: 0.98 min (method 5).

The following intermediates were prepared from the indicated precursors according to a protocol analogous to A14.

Example A15

Preparation of intermediate 15: 2-Methoxy-8-morpholin-4-yl-imidazo[1,2-b]pyridazine From intermediate 10. Flash column chromatography (7 M solution of ammonia in methanol in dichloromethane 0/100 to 3/97) yielded intermediate 15 as a pale brown solid (65%).

Example A16

Preparation of intermediate 16: 2-Cyclopropyl-8-morpholin-4-yl-imidazo[1,2-b]pyridazine

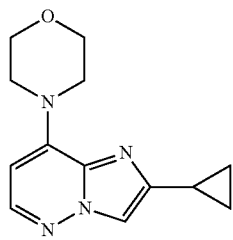 [SMILES: c1cc(N2CCOCC2)c2nc(C3CC3)cn2n1]

10% Palladium on charcoal (0.391 g) was added to a mixture of intermediate 8 (4.1 g, 14.7 mmol) and triethylamine (4.1 ml, 29.4 mmol) in a mixture of methanol (100 ml) and tetrahydrofuran (100 ml). The mixture was hydrogenated (atmospheric pressure) at room temperature for 8 h and then filtered through a pad of diatomaceous earth. The filtrate was concentrated in vacuo to yield intermediate 16 (3.1 g, 94%). LCMS: 219 [M+H]$^+$; R$_t$: 0.98 min (method 5).

The following intermediates were prepared from the indicated precursors according to a protocol analogous to A16.

Example A17

Preparation of intermediate 17: 8-Morpholin-4-yl-imidazo[1,2-b]pyridazine

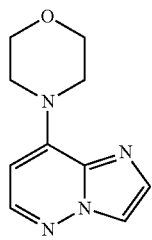 [SMILES: c1cn2nccc(N3CCOCC3)c2n1]

From intermediate 9. Precipitation from diisopropylether yielded intermediate 17 as a pale pink solid (76%).

Example A18

Preparation of intermediate 18: 2-Cyclopropyl-8-pyridin-4-yl-imidazo[1,2-b]pyridazine

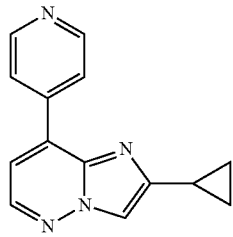 [SMILES: c1cc(-c2ccnn3cc(C4CC4)nc23)ccn1]

From intermediate 12. Flash column chromatography (silica; ethylacetate in heptane 0/100 to 50/50) yielded intermediate 18 as a white solid (50%). LCMS: 237 [M+H]$^+$; R$_t$: 1.83 min (method 5).

Example A19

Preparation of intermediate 19: 2-Methyl-8-pyridin-3-yl-imidazo[1,2-b]pyridazine

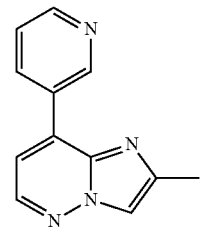 [SMILES: Cc1cn2nccc(-c3cccnc3)c2n1]

From intermediate 13. Flash column chromatography (silica, 7 M solution of ammonia in methanol in dichloromethane 0/100 to 2/98) yielded intermediate 19 as a pale brown solid (43%). LCMS: 211 [M+H]$^+$; R$_t$: 1.14 min (method 5).

Example A20

Preparation of intermediate 20: 2-Methyl-8-pyridin-4-yl-imidazo[1,2-b]pyridazine

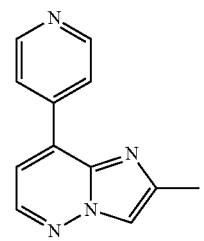 [SMILES: Cc1cn2nccc(-c3ccncc3)c2n1]

10% Palladium on charcoal (1.22 g) was added to a suspension of intermediate 11 (4 g, 16.35 mmol) in a mixture of methanol (400 ml) and dichlorometane (30 ml). The mixture was hydrogenated (40 psi) at 50° C. for 6 h. and then filtered through a pad of diatomaceous earth. The filtrate was concentrated in vacuo to yield intermediate 20 (3 g, 86%) as a yellow solid. LCMS: 211 [M+H]$^+$; R$_t$: 2.11 min (method 1).

Example A21

Preparation of intermediate 21: 2,6-Dimethyl-8-morpholin-4-yl-imidazo[1,2-b]pyridazine

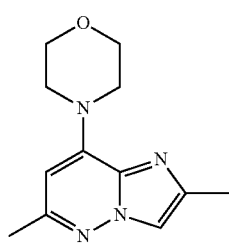

Tetrakis(triphenylphosphine)palladium (0) (0.457 g, 0.396 mmol) was added to a stirred solution of intermediate 7 (1 g, 3.96 mmol) and methylboronic acid (1.18 g, 19.79 mmol) in a mixture of 1,4-dioxane (12 ml) and a saturated solution of sodium carbonate (4 ml). The mixture was stirred at 175° C. for 45 min. in a sealed tube under nitrogen and under microwave irradiation. The mixture was filtered through a pad of diatomaceous earth and the filtrate diluted with ethylacetate and washed with water. The organic layer was separated, dried (Na$_2$SO$_4$), filtered and the solvents evaporated in vacuo. The crude product was purified by column chromatography (silica; ethyl acetate in heptane 20/80 to 50/50). The desired fractions were collected and concentrated in vacuo to yield intermediate 21 (0.364 g, 40%). LCMS: 233 [M+H]$^+$; R$_t$: 1.98 min (method 2).

The following intermediates were prepared from the indicated precursors according to a protocol analogous to A21.

Example A22

Preparation of intermediate 22: 2,6-Dimethyl-8-pyridin-4-yl-imidazo[1,2-b]pyridazine

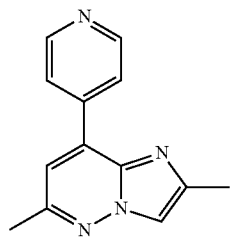

From intermediate 11. Flash column chromatography (silica; 7 M solution of ammonia in methanol in dichloromethane 0/100 to 1.5/98.5) yielded intermediate 22 as a light yellow solid (65%). LCMS: 225 [M+H]$^+$; R$_t$: 2.00 min (method 2).

Example A23

Preparation of intermediate 23: 6-Cyclopropyl-2-methyl-8-morpholin-4-yl-imidazo[1,2-b]pyridazine

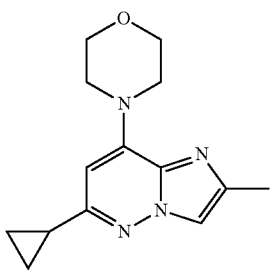 [SMILES: Cc1cn2nc(C3CC3)cc(N3CCOCC3)c2n1]

Palladium (II) acetate (0.066 g, 0.297 mmol) was added to a stirred solution of intermediate 7 (0.5 g, 1.98 mmol), cyclopropylboronic acid (0.255 g, 2.97 mmol), 2-dicyclohexylphosphino-2',6'-dimethoxybiphenyl (0.244 g, 0.594 mmol) and potassium phosphate (0.84 g, 3.96 mmol) in toluene (10 ml). The mixture was stirred at 150° C. for 45 min. in a sealed tube under nitrogen and under microwave irradiation. The mixture was diluted with dichloromethane and washed with water. The organic layer was separated, dried (Na$_2$SO$_4$), filtered and the solvents evaporated in vacuo. The crude product was purified by column chromatography (silica; ethyl acetate in heptane 0/100 to 50/50). The desired fractions were collected and concentrated in vacuo to yield intermediate 23 (0.434 g, 85%). LCMS: 259 [M+H]$^+$; R$_t$: 2.22 min (method 5).

The following intermediates were prepared from the indicated precursors according to a protocol analogous to A23.

Example A24

Preparation of intermediate 24: 6-Cyclopropyl-2-methyl-8-pyridin-4-yl-imidazo[1,2-b]pyridazine

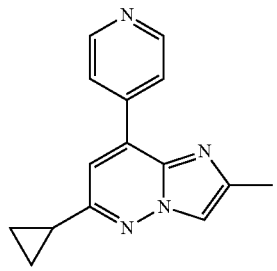 [SMILES: Cc1cn2nc(C3CC3)cc(-c3ccncc3)c2n1]

From intermediate 11. Flash column chromatography (7 M solution of ammonia in methanol in dichloromethane 0/100 to 4/96) yielded intermediate 24 as a light yellow solid (87%). LCMS: 251 [M+H]$^+$; R$_t$: 2.20 min (method 5).

Example A25

Preparation of intermediate 25: 2-Cyclopropyl-6-methyl-8-morpholin-4-yl-imidazo[1,2-b]pyridazine

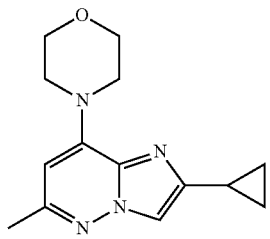 [SMILES: Cc1cc(N2CCOCC2)c2nc(C3CC3)cn2n1]

From intermediate 8 and methylboronic acid. Flash column chromatography (silica; ethyl acetate in dichloromethane 0/100 to 30/70) yielded intermediate 25 as a pale yellow solid (75%).

Example A26

Preparation of intermediate 26: 3-Iodo-2-methyl-8-morpholin-4-yl-imidazo[1,2-b]pyridazine

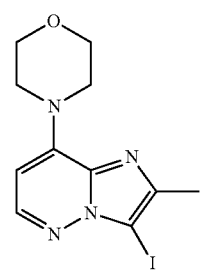 [SMILES: Cc1nc2c(N3CCOCC3)ccnn2c1I]

N-Iodosuccinimide (1.08 g, 4.8 mmol) was added to a stirred solution of intermediate 14 (1 g, 4.58 mmol) in a mixture of dichloromethane (50 ml) and acetic acid (2 ml). The mixture was stirred at 0° C. for 30 min. and then extracted with a saturated solution of sodium carbonate and a 10% solution of sodium thiosulfite. The organic layer was filtered over cotton wool and the solvents evaporated in vacuo. The crude product was purified by flash column chromatography (silica, dichloromethane in heptane 70/30 first, then ethyl acetate in heptane 10/90 to 30/70). The desired fractions were collected and concentrated to yield intermediate 26 (4.68 g, 83%) as a white solid. LCMS: 345 [M+H]$^+$; R$_t$: 2.59 min (method 1).

The following intermediates were prepared from the indicated precursors according to a protocol analogous to A26.

Example A27

Preparation of intermediate 27: 2-Cyclopropyl-3-iodo-8-morpholin-4-yl-imidazo[1,2-b]pyridazine

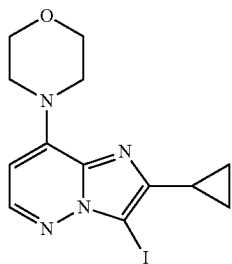 [SMILES: Ic1c(C2CC2)nc2c(N3CCOCC3)ccnn12]

From intermediate 16. Flash column chromatography (silica; ethyl acetate in dichloromethane 0/100 to 20/80) yielded intermediate 27 as a pale brown solid (95%). LCMS: 371 [M+H]$^+$; R$_t$: 3.15 min (method 5).

Example A28

Preparation of intermediate 28: 3-Iodo-2,6-dimethyl-8-morpholin-4-yl-imidazo[1,2-b]pyridazine

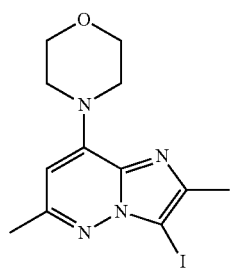

From intermediate 21. Flash column chromatography (silica; 7 M solution of ammonia in methanol in dichloromethane 0/100 to 2/98) yielded intermediate 28 as a white solid (77%). LCMS: 359 [M+H]$^+$; R$_t$: 2.84 min (method 2).

Example A29

Preparation of intermediate 29: 3-Iodo-2-methyl-8-pyridin-4-yl-imidazo[1,2-b]pyridazine

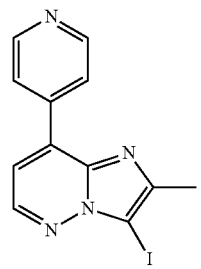 [SMILES: Cc1nc2c(-c3ccncc3)ccnn2c1I]

From intermediate 20. Flash column chromatography (silica; ethyl acetate in dichloromethane 0/100 to 30/70) yielded intermediate 29 as a pale yellow solid (96%). LCMS: 351 [M+H]$^+$; R$_t$: 2.43 min (method 2).

Example A30

Preparation of intermediate 30: 3-Iodo-2,6-dimethyl-8-pyridin-4-yl-imidazo[1,2-b]pyridazine

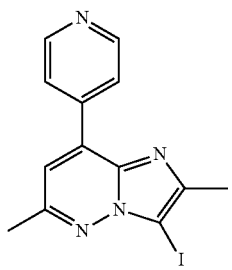

From intermediate 22. Flash column chromatography (silica; ethyl acetate in dichloromethane 30/70 to 70/30) yielded intermediate 30 as a pale yellow solid (72%). LCMS: 351 [M+H]$^+$; R$_t$: 2.71 min (method 2).

Example A31

Preparation of intermediate 31: 6-Chloro-3-iodo-2-methyl-8-morpholin-1-yl-imidazo[1,2-b]pyridazine

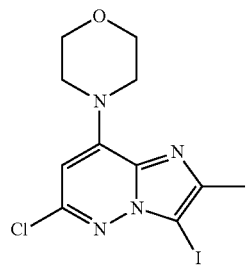 [SMILES: Cc1nc2c(N3CCOCC3)cc(Cl)nn2c1I]

N-Iodosuccinimide (0.95 g, 4.36 mmol) was added to a stirred solution of a mixture 70/30 of intermediate 3 (0.95 g, 3.36 mmol) in a mixture of dichloromethane (9 ml) and acetic acid (1 ml). The mixture was stirred at room temperature for 16 h. and then washed with a saturated solution of sodium carbonate. The organic layer was separated, dried ($Na_2SO_4$), filtered and the solvents evaporated in vacuo to yield 1.33 g of crude product. A portion of this crude product (0.5 g) was dissolved in acetonitrile (8 ml) and morpholine (0.140 ml, 1.6 mmol) and N,N-diisopropylethylamine (0.393 ml, 2.29 mmol) were added. The mixture was stirred at 150° C. for 10 min in a sealed tube, under microwave irradiation. The mixture was diluted with ethyl acetate and washed with a saturated solution of ammonium chloride. The organic layer was separated, dried ($Na_2SO_4$), filtered and the solvents evaporated in vacuo to yield intermediate 31 (0.53 g, 69%).

Example A32

Preparation of intermediate 32: 3-Bromo-2-methyl-8-morpholin-4-yl-imidazo[1,2-b]pyridazine

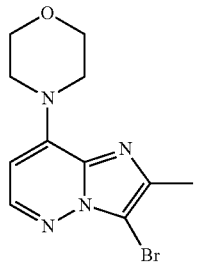 [SMILES: Cc1nc2c(N3CCOCC3)ccnn2c1Br]

N-Bromosuccinimide (0.273 g, 1.53 mmol) was added to a stirred solution of intermediate 14 (0.335 g, 1.53 mmol) in acetonitrile (10 ml). The mixture was stirred at room temperature for 1 h., then diluted with ethyl acetate and washed with a saturated solution of sodium carbonate. The organic layer was separated, dried ($Na_2SO_4$), filtered and the solvents evaporated in vacuo. The crude product was purified by flash column chromatography (silica, 7 M solution of ammonia in methanol in dichloromethane 4/96). The desired fractions were collected and concentrated in vacuo and the crude product purified again by flash column chromatography (silica, ethyl acetate in heptane 0/100 to 100/0). The desired fractions were collected and concentrated in vacuo to yield intermediate 32 (0.1 g, 21.2%).

The following intermediates were prepared from the indicated precursors according to a protocol analogous to A32.

Example A33

Preparation of intermediate 33: 3-Bromo-2-methyl-8-pyridin-4-yl-imidazo[1,2-b]pyridazine

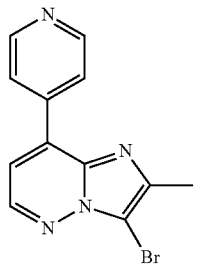 [SMILES: Cc1nc2c(-c3ccncc3)ccnn2c1Br]

From intermediate 20. Flash column chromatography (silica; 7 M solution of ammonia in methanol in dichloromethane 0/100 to 4/96) to yield intermediate 33 as a pale brown solid (73%).

Example A34

Preparation of intermediate 34: 3-Bromo-6-chloro-2-cyclopropyl-8-morpholin-4-yl-imidazo[1,3-b]pyridazine

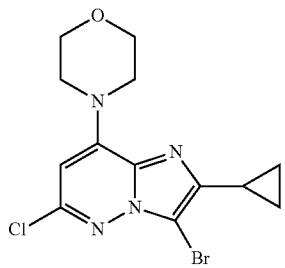 [SMILES: Clc1cc(N2CCOCC2)c2nc(C3CC3)c(Br)n2n1]

From intermediate 8. Flash column chromatography (silica, dichloromethane) yielded intermediate 34 as a white solid (59%). LCMS: 357 $[M+H]^+$; $R_t$: 3.16 min (method 4).

Example A35

Preparation of intermediate 35: 3-(6-Chloro-pyridin-3-yl)-2-methyl-8-morpholin-4-yl-imidazo[1,2-b]pyridazine

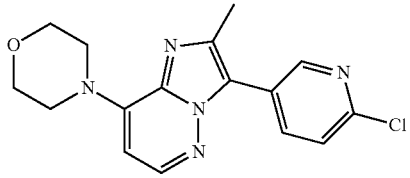 [SMILES: Cc1nc2c(N3CCOCC3)ccnn2c1-c1ccc(Cl)nc1]

Tetrakis(triphenylphosphine)palladium (0) (0.403 g, 0.35 mmol) was added to a stirred solution of intermediate 26 (4 g, 11.6 mmol) and 2-chloropyridine-5-boronic acid (2.01 g, 12.79 mmol) in a mixture of 1,4-dioxane (40 ml) and a saturated solution of sodium carbonate (20 ml). The mixture was stirred at 100° C. for 16 h. in a sealed tube under nitrogen and then diluted with dichloromethane and extracted with water. The organic layer was separated, dried ($Na_2SO_4$), filtered and the solvents evaporated in vacuo. The crude product was precipitated from methanol to yield intermediate 35 (0.364 g, 40%). LCMS: 330 $[M+H]^+$; $R_t$: 1.90 min (method 5).

The following intermediates were prepared from the indicated precursors according to a protocol analogous to A35.

Example A36

Preparation of intermediate 36: 3-(2-Chloro-pyridin-4-yl)-2-methyl-8-morpholin-4-yl-imidazo[1,2-b]pyridazine

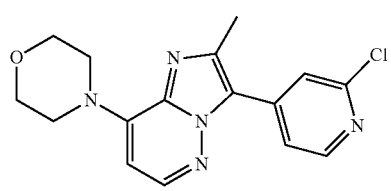 [SMILES: Cc1nc2c(N3CCOCC3)ccnn2c1-c1ccnc(Cl)c1]

From intermediate 26 and 2-chloropyridine-4-boronic acid. Precipitation from methanol yielded intermediate 36 as a pale brown solid (95%).

Example A37

Preparation of intermediate 37: 3-(6-Chloro-pyridin-3-yl)-2-methyl-8-pyridin-4-yl-imidazo[1,2-b]pyridazine

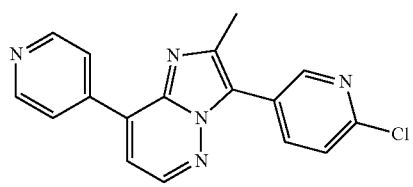 [SMILES: Cc1nc2c(-c3ccncc3)ccnn2c1-c1ccc(Cl)nc1]

From intermediate 29. Conditions: 150° C. for 15 min. under microwave irradiation. Precipitation from methanol yielded intermediate 37 as a pale brown solid (71%).

Example A38

Preparation of intermediate 38: 2-Methyl-8-morpholin-4-yl-3-(6-vinyl-pyridin-3-yl)-imidazo[1,2-b]pyridazine

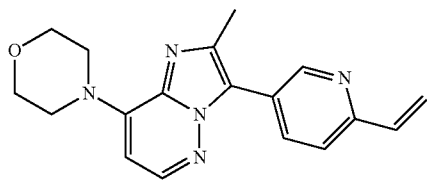 [SMILES: C=Cc1ccc(-c2c(C)nc3c(N4CCOCC4)ccnn23)cn1]

Tetrakis(triphenylphosphine)palladium (0) (0.099 g, 0.086 mmol) was added to a stirred solution of intermediate 35 (0.945 g, 2.86 mmol) and vinylboronic acid pinacol ester (0.58 ml, 3.44 mmol) in a mixture of 1,4-dioxane (20 ml) and a saturated solution of sodium carbonate (4 ml). The mixture was stirred at 90° C. for 16 h. in a sealed tube under nitrogen. The mixture was diluted with dichloromethane and washed with water. The organic layer was separated, filtered over cotton and the solvents evaporated in vacuo. The crude product was purified by flash column chromatography (silica; 7 M solution of ammonia in methanol in dichloromethane 0/100 to 4/96). The desired fractions were collected and concentrated in vacuo to yield intermediate 38 (0.159 g, 74%). LCMS: 322 [M+H]$^+$; R$_t$: 3.66 min (method 6).

The following intermediate was prepared from the indicated precursors according to a protocol analogous to A38.

Example A39

Preparation of intermediate 39: 2-Methyl-8-pyridin-4-yl-3-(6-vinyl-pyridin-3-yl)-imidazo[1,2-b]pyridazine

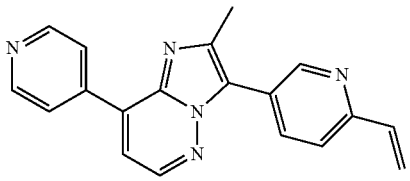 [SMILES: C=Cc1ccc(-c2c(C)nc3c(-c4ccncc4)ccnn23)cn1]

From intermediate 37. Conditions: 150° C. for 15 min. under microwave irradiation. Flash column chromatography (silica; ethyl acetate in dichloromethane 0/100 to 50/50) yielded intermediate 39 as a yellow solid (100%). LCMS: 314 [M+H]$^+$; R$_t$: 1.67 min (method 5).

Example A40

Preparation of intermediate 40: 2-Methyl-8-morpholin-4-yl-3-(2-vinyl-pyridin-4-yl)-imidazo[1,2-b]pyridazine

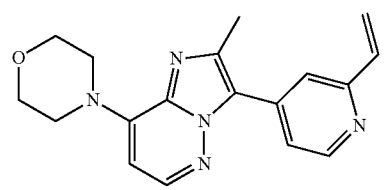 [SMILES: C=Cc1cc(-c2c(C)nc3c(N4CCOCC4)ccnn23)ccn1]

From intermediate 36. Conditions: 150° C. for 15 min. under microwave irradiation. Flash column chromatography (silica; ethyl acetate in heptane 20/80 to 40/60) yielded intermediate 40 as a white solid (90%). LCMS: 322 [M+H]$^+$; R$_t$: 1.83 min (method 5).

Example A41

Preparation of intermediate 41: 3-[6-(3,6-Dihydro-2H-pyran-4-yl)-pyridin-3-yl]-2-methyl-8-morpholin-4-yl-imidazo[1,2-b]pyridazine

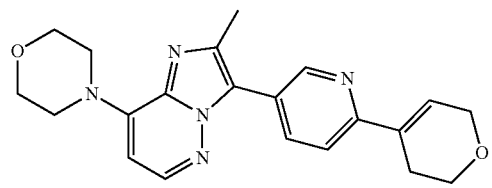 [SMILES: Cc1nc2c(N3CCOCC3)ccnn2c1-c1ccc(C2=CCOCC2)nc1]

Tetrakis(triphenylphosphine)palladium (0) (0.037 g, 0.032 mmol) was added to a stirred solution of intermediate 35 (0.35 g, 1.06 mmol) and 3,6-dihydro-2H-pyran-4-boronic acid pinacol ester (0.267 ml, 1.24 mmol) (obtained by procedures similar to those described in, Qiu, Y. et al. WO 2004/075846-A2 published on 20040910) in a mixture of 1,4- dioxane (5 ml) and a saturated solution of sodium carbonate (2 ml). The mixture was stirred at 85° C. for 5 h. in a sealed tube under nitrogen, then diluted with dichloromethane and washed with water. The organic layer was separated, dried (MgSO$_4$), filtered and the solvents evaporated in vacuo. The crude product was purified by flash column chromatography (silica; ethyl acetate in heptane 20/80 to 0/100). The desired fractions were collected and concentrated in vacuo to yield intermediate 41 (0.159 g, 62%).

Example A42

Preparation of intermediate 42:
1-Bromo-3-methoxy-3-methyl-butane

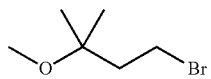

Triphenylphosphine (12.3 g, 47.0 mmol) was added to a stirred solution of 3-methoxy-3-methyl-butan-1-ol (4 ml, 31.3 mmol) and carbon tetrabromide (15.6 g, 47.0 mmol) in dichloromethane (300 ml) at 0° C. The mixture was stirred at room temperature for 18 h. and then a solution of sodium thiosulphate was added. The organic layer was separated, dried (Na$_2$SO$_4$), filtered and the solvents evaporated in vacuo. The crude product was triturated with diethyl ether, filtered off and purified by flash column chromatography (silica; petroleum ether in dichloromethane 0/100 to 50/50). The desired fractions were collected and concentrated in vacuo to yield intermediate 42 (2.1 g, 37%).

Example A43

Preparation of intermediate 43:
1-Iodo-3-methoxy-3-methyl-butane

Sodium iodide (2.9 g, 19.3 mmol) was added to a stirred solution of intermediate 42 (1.4 g, 7.7 mmol) in dry acetone (10 ml). The mixture was stirred at reflux temperature for 3 h. and then filtered. The filtrate was carefully concentrated in vacuo. The crude product was purified by flash column chromatography (silica; dichloromethane). The desired fractions were collected and concentrated in vacuo to yield intermediate 43 (1.7 g, 81%).

The following intermediates were prepared from the indicated precursors according to a protocol analogous to A43.

Example A44

Preparation of intermediate 44:
1-Iodo-3-methoxy-propane

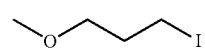

From 1-bromo-3-methoxy-propane. Flash column chromatography (silica; dichloromethane) yielded intermediate 44 as a colourless oil (84%).

Example A45

Preparation of intermediate 45:
5-Bromo-2-(2-methoxy-ethoxy)-3-methyl-pyridine

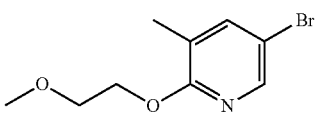

2-Methoxy-ethanol (1.18 ml, 14.95 mmol) was added dropwise to a stirred suspension of a 60% dispersion of sodium hydride in mineral oils (0.558 g, 13.95 mmol) in dimethylsulfoxide (30 ml). The mixture was stirred at room temperature for 30 min. and then 2,5-dibromo-3-methylpyridine (2.5 g, 9.96 mmol) was added. The mixture was stirred at 60° C. for 1 h. and then diluted with heptane and washed with water. The organic layer was separated, dried (Na$_2$SO$_4$), filtered and the solvents evaporated in vacuo. The crude product was purified by flash column chromatography (silica; dichloromethane in heptanes 70/30). The desired fractions were collected and concentrated in vacuo to yield intermediate 45 (2.23 g, 91%).

The following intermediates were prepared from the indicated precursors according to a protocol analogous to A45.

Example A46

Preparation of intermediate 46:
5-Bromo-2-(2-methoxy-2-methyl-propoxy)-pyridine

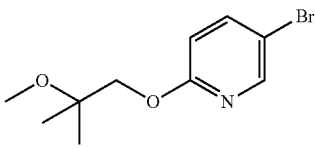

From 2-methoxy-2-methyl-propan-1-ol (obtained by procedures similar to those described in, Morel, P. US 2008102028-A1 published on 20080501) and 5-bromo-2-chloro-pyridine. Flash column chromatography (silica; dichloromethane in heptane 50/50 to 70/30) yielded intermediate 46 as a clear syrup (75%).

Example A47

Preparation of intermediate 47:
5-Bromo-2-(2-methoxy-ethoxy)-pyridine

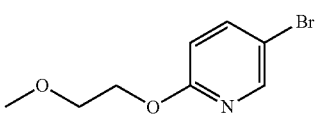

From 2-methoxy-ethanol and 5-bromo-2-chloro-pyridine. Flash column chromatography (silica; dichloromethane in heptane 30/70 to 70/30) yielded intermediate 47 as a colourless oil (75%). LCMS: 232 [M+H]$^+$; R$_f$: 2.50 min (method 1).

Example A48

Preparation of intermediate 48:
5-Bromo-2-(1-ethoxy-1-methyl-ethyl)-pyridine

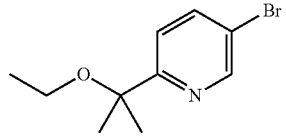

A solution of 2-(5-bromo-pyridin-2-yl)-propan-2-ol (0.80 g, 3.70 mmol) (obtained by procedures similar to those described in, Wang, X. et al. Tetrahedron Lett., 2000, 4335) in tetrahydrofuran (8 ml) was added dropwise to a stirred suspension of a 60% dispersion of sodium hydride in mineral oils (0.440 mg, 11.1 mmol) in tetrahydrofuran (6 ml). The mixture was stirred at 0° C. for 20 min. and then iodoethane (1.27 ml, 15.9 mmol) was added dropwise. The mixture was stirred at room temperature for 4 d., then diluted with dichloromethane and washed with water. The organic layer was separated, dried (Na$_2$SO$_4$), filtered and the solvents evaporated in vacuo. The crude product was purified by flash column chromatography (silica; ethyl acetate in heptane 0/100 to 20/80). The desired fractions were collected and concentrated in vacuo to yield intermediate 48 (0.7 g, 77%). LCMS: 244 [M+H]$^+$; R$_f$: 2.93 min (method 5).

The following intermediate was prepared from the indicated precursors according to a protocol analogous to A48.

Example A49

Preparation of intermediate 49:
5-Bromo-2-(1-methoxy-1-methyl-ethyl)-pyridine

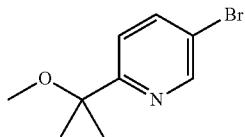

From 2-(5-bromo-pyridin-2-yl)-propan-2-ol (obtained by procedures similar to those described in, Wang, X. et al.; Tetrahedron Lett., 2000, 4335) and dimethylsulfate. Flash column chromatography (silica; dichloromethane in heptane 0/100 to 50/50) yielded intermediate 49 as a colourless oil (69%). LCMS; 230 [M+H]$^+$; R$_f$: 1.81 min (method 5).

Example A50

Preparation of intermediate 50:
(5-Bromo-pyridin-2-yl)-acetonitrile

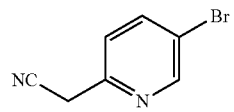

Potassium cyanide (0.489 g, 7.41 mmol) and potassium iodide (0.013 g, 0.079 mmol) were added to a stirred solution of 5-bromo-2-chloromethyl-pyridine (0.9 g, 3.70 mmol) (obtained by procedures similar to those described in, van den Heuvel, M. et al.; J. Org. Chem., 2004, 250) in a mixture of ethanol (6 ml) and water (2 ml). The mixture was stirred at 80° C. for 6 h., then diluted with dichloromethane and washed with a saturated solution of sodium hydrogen carbonate. The organic layer was separated, dried (Na$_2$SO$_4$), filtered and the solvents evaporated in vacuo. The crude product was purified by flash column chromatography (silica; dichloromethane). The desired fractions were collected and concentrated in vacuo to yield intermediate 50 (0.498 g, 68%).

Example A51

Preparation of intermediate 51:
2-(5-Bromo-pyridin-2-yl)-2-methyl-propionitrile

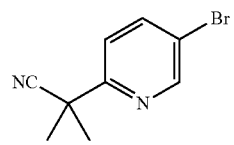

Iodomethane (1.14 ml, 18.27 mmol) was added to a stirred mixture of intermediate 50 (0.45 g, 2.28 mmol), potassium tert-butoxide (0.64 g, 5.71 mmol) and 18-crown-6 (0.091 g, 0.34 mmol) in tetrahydrofuran (10 ml). The mixture was stirred at room temperature for 18 h., then diluted with dichloromethane and washed with water. The organic layer was separated, dried (Na$_2$SO$_4$), filtered and the solvents evaporated in vacuo. The crude product was purified by flash column chromatography (silica; dichloromethane). The desired fractions were collected and concentrated in vacuo to yield intermediate 51 (0.503 g, 98%).

Example A52

Preparation of intermediate 52:
2-(5-Bromo-pyridin-2-yl)-2-methyl-propionaldehyde

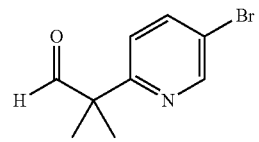

A 1 M solution of diisobutylaluminium hydride in toluene (2.46 ml, 2.46 mmol) was added to a stirred solution of intermediate 51 (0.503 g, 2.23 mmol) in dichloromethane (5 ml) at −78° C. under nitrogen. The mixture was allowed to warm to room temperature and then stirred for 18 h. The mixture was cooled down to −78° C. and a further 1 M solution of diisobutylaluminium hydride in toluene (1 ml, 1.0 mmol) was added. The mixture was stirred at room temperature for 4 h., then a 0.5 M sulphuric acid solution was added at −78° C., after which the reaction was diluted with dichloromethane and filtered through a pad of diatomaceous earth. The organic layer was separated, dried (MgSO$_4$), filtered and the solvents evaporated in vacuo. The crude product was purified by flash column chromatography (silica; dichloromethane in heptane 50/50 to 100/0). The desired fractions were collected and concentrated in vacuo to yield intermediate 52 (0.2 g, 40%).

Example A53

Preparation of intermediate 53: 2-(5-Bromo-pyridin-2-yl)-2-methyl-propan-1-ol

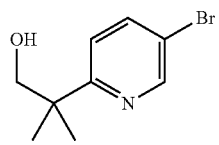

Sodium borohydride (0.043 g, 1.14 mmol) was added to a stirred solution of intermediate 52 (0.2 mg, 0.88 mmol) in dichloromethane (5 ml). The mixture was stirred at room temperature for 2 h. and then a saturated solution of sodium hydrogen carbonate was added. The organic layer was separated, dried (MgSO$_4$), filtered and the solvents evaporated in vacuo. The crude product was purified by flash column chromatography (silica; ethyl acetate). The desired fractions were collected and concentrated in vacuo to yield intermediate 53 (0.2 g, 40%).

Example A54

Preparation of intermediate 54: 5-Bromo-2-(2-methoxy-1,1-dimethyl-ethyl)-pyridine

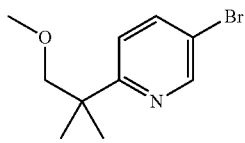

Iodomethane (0.16 ml, 2.61 mmol) was added to a stirred mixture of intermediate 53 (0.20 g, 0.87 mmol), potassium tert-butoxide (0.146 mg, 1.30 mmol) and 18-crown-6 (0.34 mg, 0.13 mmol) in tetrahydrofuran (5 ml). The mixture was stirred at room temperature for 18 h., then diluted with dichloromethane and washed with water. The organic layer was separated, dried (Na$_2$SO$_4$), filtered and the solvents evaporated in vacuo. The crude product was purified by flash column chromatography (silica; dichloromethane). The desired fractions were collected and concentrated in vacuo to yield intermediate 54 (0.088 mg, 41%).

Example A55

Preparation of intermediate 55: 5-Bromo-2-vinyl-pyridine

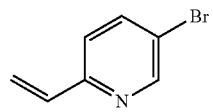

Tetrakis(triphenylphosphine)palladium(0) (1.82 g, 1.53 mmol) was added to a stirred suspension of 2,5-dibromopyridine (15 g, 63.3 mmol) and 4,4,5,5-tetramethyl-2-vinyl-1,3,2-dioxaborolane (11.8 ml, 69.6 mmol) in a mixture of 1,4-dioxane (120 ml) and a saturated solution of sodium carbonate (36 ml). The mixture was stirred at 100° C. for 16 h. in a sealed tube under nitrogen. The mixture was diluted with dichloromethane and washed with water. The organic layer was separated, dried (Na$_2$SO$_4$), filtered and the solvents evaporated in vacuo. The crude product was purified by flash column chromatography (silica; dichloromethane in heptane 20/80 to 80/20). The desired fractions were collected and concentrated in vacuo to yield intermediate 55 (6.23 g, 53%). LCMS: 184 [M+H]$^+$; R$_t$: 2.47 min (method 3).

Example A56

Preparation of intermediate 56: 5-Bromo-2-(2-methoxyethyl)-pyridine

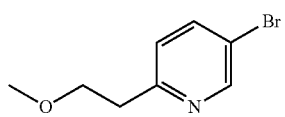

Sodium methoxide (5.48 g, 101.6 mmol) was added to a solution of intermediate 55 (6.23 g, 33.8 mmol) in dry methanol (120 ml). The mixture was stirred at 90° C. for 36 h. and then further sodium methoxide (1.82 g, 33.8 mmol) was added. The mixture was stirred at 90° C. for 7 h. and the solvents evaporated in vacuo. The crude product was dissolved in dichloromethane and washed with water. The organic layer was separated, dried (Na$_2$SO$_4$), filtered and the solvents evaporated in vacuo. The crude product was purified by flash column chromatography (silica; heptane in dichloromethane 70/30 to 0/100). The desired fractions were collected and concentrated in vacuo to yield intermediate 56 (3.78 g, 52%). LCMS: 216 [M+H]$^+$; R$_t$: 1.21 min (method 5).

Example A57

Preparation of intermediate 57: 1-(5-Bromo-pyridin-2-yl)-2-methyl-propan-2-ol

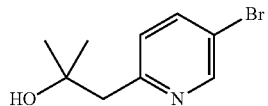

A 2.5 M solution of n-butyllithium in pentane (8.37 ml, 20.9 mmol) was added dropwise to a stirred solution of N,N-diisopropylamine (3.45 ml, 24.4 mmol) in dry tetrahydrofuran (20 ml) at −78° C. The mixture was stirred at 0° C. for 30 min, cooled down to −78° C. and then added dropwise to a solution of 5-bromo-2-picoline (3.0 g, 17.4 mmol) in tetrahydrofuran (20 ml). The mixture was stirred at −78° C. for 15 min. and then acetone (3.85 ml, 52.3 mmol) was added dropwise. The mixture was stirred at −78° C. for 20 min. and then a saturated solution of ammonium chloride was added. The organic layer was separated and the aqueous layer was extracted with dichloromethane. The combined organic extracts were dried (Na$_2$SO$_4$), filtered and the solvents evaporated in vacuo. The crude product was purified by flash column chromatography (silica; ethyl acetate in dichloromethane 0/100 to 20/80). The desired fractions were collected and concentrated in vacuo to yield intermediate 57 (1.75 g, 43%) as a colourless oil.

Example A58

Preparation of intermediate 58: 5-Bromo-2-(2-methoxy-2-methyl-propyl)-pyridine

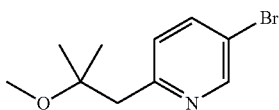

A 60% suspension of sodium hydride in mineral oils (2.36 g, 58.9 mmol) was added portionwise to a stirred solution of intermediate 57 (2.36 g, 58.9 mmol) in tetrahydrofuran (10 ml). The mixture was stirred at 0° C. for 30 min. and then iodomethane (3.67 ml, 58.9 mmol) was added. The mixture was stirred at room temperature for 18 h. and then further 60% suspension of sodium hydride in mineral oils (2.36 g, 58.9 mmol) and iodomethane (3.67 ml, 58.9 mmol) were added. The mixture was stirred at room temperature for 3 h. and then the solvents were evaporated in vacuo. The crude product was diluted with dichloromethane and washed with a saturated solution of ammonium chloride and a saturated solution of sodium hydrogen carbonate. The organic layer was separated, dried (Na$_2$SO$_4$), filtered and the solvents evaporated in vacuo. The crude product was purified by flash column chromatography (silica; ethyl acetate in dichloromethane 0/100 to 10/90). The desired fractions were collected and concentrated in vacuo to yield intermediate 58 (6.90 g, 53%).

Example A59

Preparation of intermediate 59: 5-Bromo-2-(3-methoxy-propyl)-pyridine

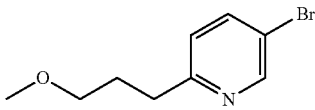

1,2-Dibromoethane (0.237 ml, 2.75 mmol) was added to a stirred suspension of zinc (3.6 g, 55.0 mmol) in dry N,N-dimethylformamide (40 ml). The mixture was stirred at 90° C. for 30 min. under nitrogen and then allowed to warm to room temperature. Chlorotrimethylsilane (0.09 ml, 0.69 mmol) was added and the mixture was stirred at room temperature for 15 min. A solution of intermediate 44 (5.5 g, 27.5 mmol) in tetrahydrofuran (20 ml) was added dropwise and the mixture was stirred at 45° C. for 2.5 h. The excess zinc was allowed to settle for 1 h and the supernatant liquid was transferred via cannula to a mixture of 2,5-dibromopyridine (2.17 g, 9.17 mmol) and bis(triphenylphosphine)palladium dichloride (0.212 g, 0.18 mmol). The mixture was stirred at 55° C. for 4 h. under nitrogen, then the solvents were evaporated in vacuo. The crude product was partitioned between dichloromethane and a saturated solution of sodium hydrogen carbonate. The organic layer was separated, dried (Na$_2$SO$_4$), filtered and the solvents evaporated in vacuo. The crude product was purified by flash column chromatography (silica, ethyl acetate in dichloromethane 0/100 to 20/80). The desired fractions were collected and concentrated in vacuo to yield intermediate 59 (1.4 g, 66%).

Example A60

Preparation of intermediate 60: 5-Bromo-2-ethoxymethyl-pyridine

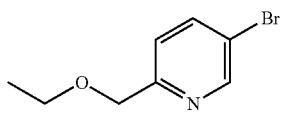

A 60% suspension of sodium hydride in mineral oils (0.073 g, 3.19 mmol) was added to a stirred solution of 5-bromo-2-(hydroxymethyl)pyridine (0.5 g, 2.66 mmol) in tetrahydrofuran (10 ml). The mixture was stirred at 0° C. for 30 min. and then iodoethane (0.498 g, 3.19 mmol) was added. The mixture was stirred at 60° C. for 18 h., then diluted with diethyl ether and washed with a saturated solution of ammonium chloride in water. The organic layer was separated, dried (Na$_2$SO$_4$), filtered and the solvents evaporated in vacuo to yield intermediate 60 (0.520 g, 90%) as a colourless oil.

Example A61

Preparation of intermediate 61: 2-(2-Methoxy-ethyl)-5-(4,4,5,5-tetramethyl-[1,3,2]dioxaborolan-2-yl)-pyridine

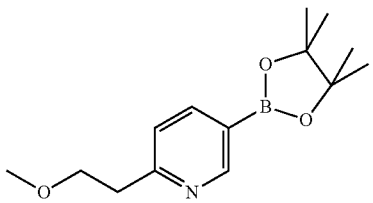

[1,1'-Bis(diphenylphosphino)ferrocene]dichloropalladium (II) (0.061 g, 0.083 mmol) was added to a stirred suspension of intermediate 56 (0.6 g, 2.77 mmol), 4,4,4',4',5,5,5',5'-octamethyl-2,2'-bi-1,3,2-dioxaborolane (0.846 g, 3.33 mmol) and potassium acetate (0.817 g, 8.33 mmol) in a mixture of 1,4-dioxane (9 ml) and N,N-dimethylformamide (1.2 ml). The mixture was stirred at 150° C. for 40 min. in a sealed tube under nitrogen and under microwave irradiation. The mixture was filtered through a pad of diatomaceous earth, and the filtrate diluted with dichloromethane and washed with water. The organic layer was separated, dried (Na$_2$SO$_4$), filtered and the solvents evaporated in vacuo to yield intermediate 61 (1.1 g, 64%, 43% purity) used in next step without further purification. LCMS: 264 [M+H]$^+$; R$_t$: 1.55 min (method 5).

The following intermediates were prepared from the indicated precursors according to a protocol analogous to A61.

Example A62

Preparation of intermediate 62: 2-(2-Methoxy-2-methyl-propoxy)-5-(4,4,5,5-tetramethyl-[1,3,2]dioxaborolan-2-yl)-pyridine

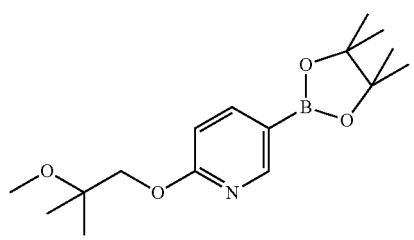

From intermediate 46 in dimethylsulfoxide as solvent, 80° C., 4 h. Extraction with heptane yielded intermediate 62 as a colourless oil (97%).

Example A63

Preparation of intermediate 63: 2-(2-Methoxyethoxy)-5-(4,4,5,5-tetramethyl-[1,3,2]dioxaborolan-2-yl)-pyridine

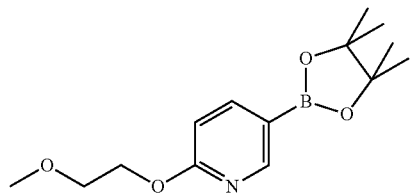

From intermediate 47 in dimethylsulfoxide as solvent, 80° C., 4 h. Extraction with heptane yielded intermediate 63 as a colourless oil (93%).

Example A64

Preparation of intermediate 64: 2-Ethoxymethyl-5-(4,4,5,5-tetramethyl-[1,3,2]dioxaborolan-2-yl)-pyridine

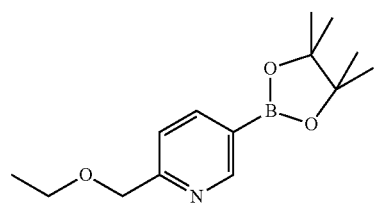 [SMILES: CCOCc1ccc(B2OC(C)(C)C(C)(C)O2)cn1]

From intermediate 60 in dimethylsulfoxide as solvent, 80° C., 4 h. Extraction with heptane yielded intermediate 64 as a colourless oil (84%).

Example A65

Preparation of intermediate 65: 1-(4-Iodo-pyrazol-1-yl)-2-methyl-propan-2-ol

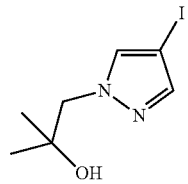

A mixture of 4-iodopyrazole (3 g, 15.47 mmol), 1-chloro-2-methyl-2-propanol and cesium carbonate (8.06 g, 24.75 mmol) in N,N-dimethylformamide (30 ml) was stirred at 160° C. for 40 min in a sealed tube, under microwave irradiation. The mixture was diluted with water and extracted with dichloromethane. The organic layer was separated, dried ($Na_2SO_4$), filtered and the solvents evaporated in vacuo. The crude product was purified by flash column chromatography (silica; ethyl acetate in heptane 20/80 to 40/60). The desired fractions were collected and concentrated in vacuo to yield intermediate 65 (3.98 g, 97%) as a white solid.

Example A66

Preparation of intermediate 66: 4-Iodo-1-(2-methoxy-2-methyl-propyl)-1H-pyrazole A 60% dispersion of sodium hydride in mineral oils (1.85 g, 46.23 mmol) was added portionwise to a stirred solution of intermediate 65 (4.1 g, 15.41 mmol) in tetrahydrofuran (70 ml) at 0° C. The mixture was stirred at room temperature for 15 min and then dimethyl sulfate (3.67 ml, 66.26 mmol) was added. The mixture was stirred at room temperature for a further 18 h. and then partitioned between dichloromethane and a saturated solution of sodium hydrogen carbonate. The organic layer was separated, dried ($Na_2SO_4$), filtered and the solvents evaporated in vacuo. The crude product was purified by flash column chromatography (silica; ethyl acetate in heptane 0/100 to 20/80). Desired fractions were collected and concentrated in vacuo to yield intermediate 66 (3.32 g, 74%) as a colorless oil.

Example A67

Preparation of intermediate 67: 1-(2-Methoxy-2-methyl-propyl)-4-(4,4,5,5-tetramethyl-[1,3,2]dioxaborolan-2-yl)-1H-pyrazole

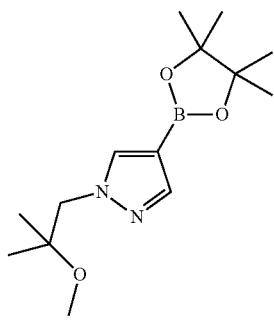 [SMILES: COC(C)(C)Cn1cc(B2OC(C)(C)C(C)(C)O2)cn1]

[1,1'-bis(diphenylphosphino)]dichloropalladium(II) (0.026 g, 0.36 mmol) was added to a stirred solution of intermediate 66 (1.18 g, 4.21 mmol), bis(pinacolato)diboron (1.28 g, 5.06 mmol) and potassium acetate (1.24 g, 12.64 mmol) in dimethylsulfoxide (15 ml). The mixture was stirred at 80° C. for 16 h. in a sealed tube under nitrogen. After cooling to room temperature, the mixture was partitioned between water and heptane and then filtered over cotton to remove the resulting black slurry. The organic layer was separated and the aqueous layer extracted with heptane. The combined organic layers were dried (Na$_2$SO$_4$), filtered and the solvents evaporated in vacuo to yield intermediate 67 (0.96 g, 81%) which was used in the next step without further purification.

Example A68

Preparation of intermediate 68: 1-(2-Methoxy-ethyl)-4-(4,4,5,5-tetramethyl-[1,3,2]dioxaborolan-2-yl)-1H-pyrazole

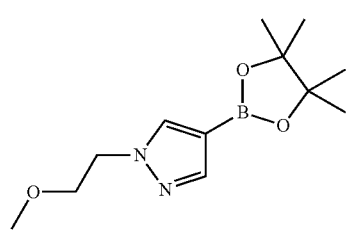

A mixture of 4-(4,4,5,5-tetramethyl-[1,3,2]dioxaborolan-2-yl)-1H-pyrazole (1 g, 5.15 mmol), 2-bromoethyl methyl ether (0.63 ml, 6.7 mmol) and cesium carbonate (2.52 g, 7.73 mmol) in N,N-dimethylformamide (7 ml) was stirred at 150° C. for 30 min. under microwave irradiation. The mixture was partitioned between water and diethyl ether. The organic layer was separated, dried (Na$_2$SO$_4$), filtered and the solvents evaporated in vacuo. The crude product was purified by flash column chromatography (silica; ethyl acetate in heptane 30/70). The desired fractions were collected and concentrated in vacuo to yield intermediate 68 (0.88 g, 68%) as a pale yellow oil.

Example A69

Preparation of intermediate 69: 6-chloro-2-cyclopropyl-3-[1-(2-methoxy-2-methylpropyl)-1H-pyrazol-4-yl]-8-(4-morpholinyl)-imidazo[1,2-b]pyridazine

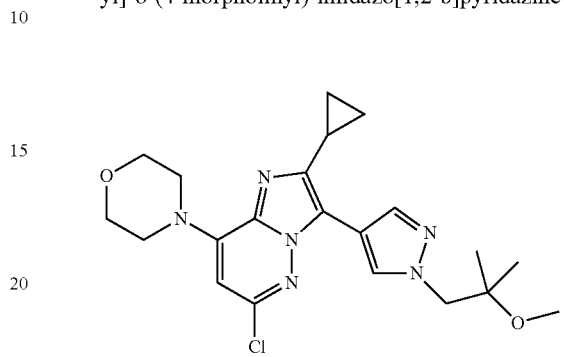

Tetrakis(triphenylphosphine)palladium(0) (0.068 g, 0.059 mmol) was added to a stirred solution of intermediate 34 (0.30 g, 0.84 mmol) and intermediate 67 (0.446 g, 1.59 mmol) in a mixture of 1,4-dioxane (20 ml) and a saturated solution of sodium carbonate (6 ml). The mixture was stirred at 150° C. for 15 min, in a sealed tube under nitrogen and under microwave irradiation. The mixture was diluted with dichloromethane and washed with water. The organic layer was separated, dried (Na$_2$SO$_4$), filtered and the solvents evaporated in vacuo. The crude product was purified by flash column chromatography (silica: 7 M solution of ammonia in methanol in dichloromethane 0/100 to 2/98). The desired fractions were collected and concentrated and the crude product purified again by flash column chromatography (silica; ethyl acetate in heptane 10/90 to 50/50). The desired fractions were collected and concentrated in vacuo to yield intermediate 69 (0.216 g, 59%). LCMS: 431 [M+H]$^+$; R$_t$: 4.30 min (method 1). This compound is also a final compound (compound 150).

B. Preparation of the Final Compounds

Example B1

Preparation of compound 1: 3-[6-(2-methoxyethyl)-3-pyridinyl]-2-methyl-8-(4-morpholinyl)-imidazo[1,2-b]pyridazine

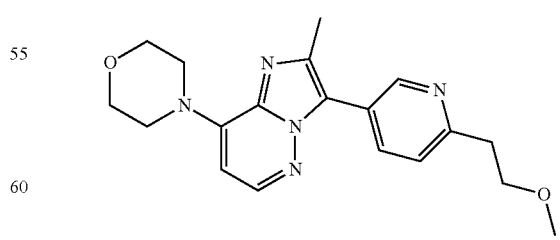

Palladium (II) acetate (0.066 g, 0.294 mmol) was added to a stirred solution of intermediate 14 (1.5 g, 5.89 mmol), intermediate A56 (1.91 g, 8.83 mmol), butyldi-1-adamantylphosphine (0.211 g, 0.59 mmol) and potassium phosphate (3.75 g, 17.7 mmol) in N,N-dimethylformamide (10 ml). The mixture was stirred at room temperature for 15 min. and then at 120° C. for 24 h. in a sealed tube under nitrogen. The mixture was diluted with diethyl ether and washed with a 1% potassium hydroxide solution. The organic layer was separated, dried (MgSO$_4$), filtered and the solvents evaporated in vacuo. The crude product was purified by flash column chromatography (silica; 7 M solution of ammonia in methanol in dichloromethane 0/100 to 40/60). The desired fractions were collected and concentrated in vacuo. The crude product was triturated from diisopropyl ether to yield compound 1 (1.74 g, 84%) as a white solid.

$^1$H NMR (400 MHz, CDCl$_3$) δ ppm 2.54 (s, 3H), 3.13 (t, J=6.7 Hz, 2H), 3.39 (s, 3H), 3.83 (t, J=6.8 Hz, 2H), 3.88-4.04 (m, 8H), 6.10 (d, J=5.5 Hz, 1H), 7.36 (d, J=8.1 Hz, 1H), 7.98 (dd, J=8.1, 2.1 Hz, 1H), 7.99 (d, J=5.5 Hz, 1H), 8.80 (d, J=2.3 Hz, 1H).

For compound 1 (DSC: mp=132.4° C.), the hydrochloride salt (.HCl) (DSC: mp=164.8° C. with decomposition); the maleate salt (C$_4$H$_4$O$_4$) (DSC: mp=113.8° C.), the monohydrate (.H$_2$O) (DSC: dehydration between about 55-90° C. followed by melt at 132.9° C.), and the phosphate salt (.H$_3$PO$_4$) (DSC: mp=165.1° C. with decomposition), were obtained following the procedures described below (the indicated melting points for compound 1 and the different salts and solvate forms thereof were recorded on a TA-Instruments Q1000 MTDSC equipped with a RCS cooling unit using the parameters indicated hereinbelow).

For the formation of the hydrochloride salt (compound 1a):
To a stirred solution of compound 1 (0.5 g, 1.41 mmol) in 2-butanone (7.50 mL) was added hydrogen chloride (1 N, 1.27 mL, 1.27 mmol). The mixture was concentrated in vacuo till dry at 50° C., then 2-butanone (7.50 mL) was added. Formation of a white solid was observed and the suspension was further stirred at room temperature overnight. The solid was filtered off and dried overnight at 50° C. to yield the hydrochloride salt (0.397 g, 72%) as a white solid.

For the formation of the maleate salt (compound 1b):
To a mixture of compound 1 (1.00 g, 2.83 mmol) and (Z)-2-butenedioic acid (344.85 mg, 2.97 mmol), was added 1-methoxy-2-propanol (15.00 mL) and the mixture was heated to 40° C. then cooled down to 0° C. and stirred overnight at 0° C. Precipitation was observed, with formation of very fine solids, giving the reaction mixture an almost milky appearance. A small amount of these solids was set aside and used subsequently as seeding material (see below). The mixture was heated to 50° C. The solvent was partially evaporated to a volume of 10 mL and the reaction mixture was seeded with original solids at 45° C. Stirring was continued at 45° C. for 4 hours, then at 40° C. for 2 hours and continued at 20° C. overnight. The resulting solid was filtered off, washed once with a very small amount of propylene glycol monomethyl ether (PGME) and once with methyl tert-butyl ether (MTBE) and dried overnight at 45° C., to yield the maleate salt (850 mg, 64%) as a white to slightly yellow solid.

For the formation of the hydrate (compound 1c), two different procedures were used:
a) water (2 mL) was added to the solid compound (20 mg) and allowed to slurry at 70° C. for 30 minutes. The heat was turned off and the solution mixture was allowed to continue to slurry at room temperature for 3 days.
b) water (4 mL) was added to the solid compound (200 mg) and allowed to slurry at room temperature for 5 days.

The product was then filtered off and dried to yield the hydrate as a solid.

For the formation of the phosphate salt (compound 1d):
A stirred mixture of compound 1 (1 g, 2.83 mmol), phosphoric acid (0.342 g, aqueous solution 85 wt %) and a small volume of a 50/50 v/v ethanol:1-butanol mixture (2 mL) was heated to reflux. An additional amount of the 50/50 ethanol:1-butanol solvent mixture was added portion-wise (up to a total of 14.65 g of the solvent mixture) to the refluxed reaction mixture, until a clear solution was obtained. The resulting solution was cooled from reflux temperature to room temperature over a period of 30 minutes. Formation of a solid was observed, which was filtered to result in 5 g of a wet material that was dried under vacuum for about 2 hours at 50° C., for 72 hours at room temperature, and for 4 hours at 50° C. to yield compound 1d as a crystalline solid (1 g, 78%).

The following compounds were prepared from the indicated precursors according to a protocol analogous to B1.

Example B2

Preparation of compound 2: 3-[6-(3-methoxypropyl)-3-pyridinyl]-2-methyl-8-(4-morpholinyl)-imidazo[1,2-b]pyridazine

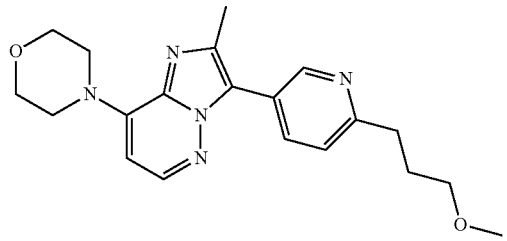 [SMILES: COCCCc1ccc(-c2c(C)nc3c(N4CCOCC4)ccnn23)cn1]

From intermediate 14 and intermediate 59. Flash column chromatography (silica; ethyl acetate in heptane 20/80 to 40/60) and precipitation from methanol yielded compound 2 as a white solid (55%). $^1$H NMR (500 MHz, CDCl$_3$) δ ppm 1.99-2.17 (m, 2H), 2.54 (s, 3H), 2.93 (t, J=7.5 Hz, 2H), 3.37 (s, 3H), 3.48 (t, J=6.4 Hz, 2H), 3.90-4.01 (m, 8H), 6.10 (d, J=5.8 Hz, 1H), 7.31 (d, J=7.8 Hz, 1H), 7.97 (dd, J=8.1, 2.3 Hz, 1H), 7.99 (d, J=5.8 Hz, 1H), 8.78 (d, J=1.7 Hz, 1H).

Example B3

Preparation of compound 3: 3-[6-(2-methoxy-2-methylpropyl)-3-pyridinyl]-2-methyl-8-(4-morpholinyl)-imidazo[1,2-b]pyridazine

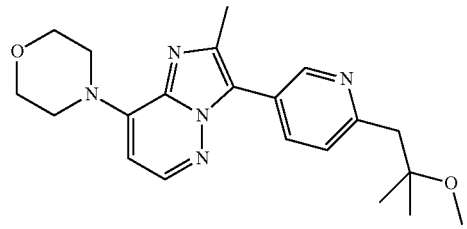 [SMILES: COC(C)(C)Cc1ccc(-c2c(C)nc3c(N4CCOCC4)ccnn23)cn1]

From intermediate 14 and intermediate 58. Flash column chromatography (silica; methanol in dichloromethane 0/100 to 2/98) yielded compound 3 as a white solid (56%). $^1$H NMR (400 MHz, DMSO-d$_6$) δ ppm 1.16 (s, 6H), 2.44 (s, 3H), 2.96 (s, 2H), 3.22 (s, 3H), 3.80 (br t, J=4.9 Hz, 4H), 3.97 (dd, J=4.9, 4.4 Hz, 4H), 6.37 (d, J=5.8 Hz, 1H), 7.40 (d, J=8.1 Hz, 1H), 7.99 (dd, J=8.1, 2.3 Hz, 1H), 8.10 (d, J=5.5 Hz, 1H), 8.74 (d, J=2.1 Hz, 1H).

Example B4

Preparation of compound 4: 3-[6-(2-methoxy-1,1-dimethylethyl)-3-pyridinyl]-2-methyl-8-(4-morpholinyl)-imidazo[1,2-b]pyridazine

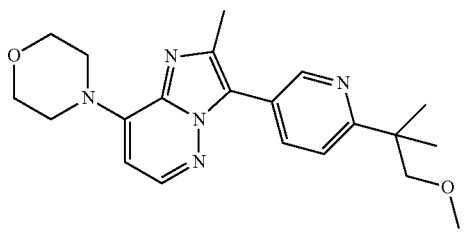 [SMILES: COCC(C)(C)c1ccc(-c2c(C)nc3c(N4CCOCC4)ccnn23)cn1]

From intermediate 14 and intermediate 54. Flash column chromatography (silica; ethyl acetate in dichloromethane 0/100 to 100/0) yielded compound 4 as a white solid (74%). $^1$H NMR (400 MHz, CDCl$_3$) δ ppm 1.41 (s, 6H), 2.55 (s, 3H), 3.34 (s, 3H), 3.62 (s, 2H), 3.85-4.05 (m, 8H), 6.10 (d, J=5.5 Hz, 1H), 7.49 (dd, J=8.3, 0.7 Hz, 1H), 7.99 (d, J=5.5 Hz, 1H), 8.01 (dd, J=8.3, 2.3 Hz, 1H), 8.84 (dd, J=2.1, 0.7 Hz, 1H).

Example B5

Preparation of compound 5: 3-[6-(1-ethoxy-1-methylethyl)-3-pyridinyl]-2-methyl-8-(4-morpholinyl)-imidazo[1,2-b]pyridazine

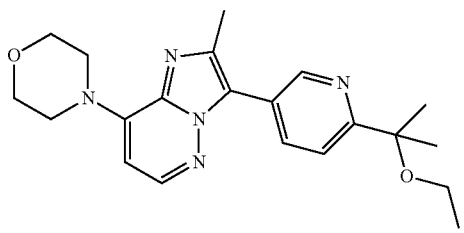 [SMILES: CCOC(C)(C)c1ccc(-c2c(C)nc3c(N4CCOCC4)ccnn23)cn1]

From intermediate 14 and intermediate 48. Flash column chromatography (silica; ethyl acetate in heptane 0/100 to 100/0) and precipitation from diethyl ether yielded compound 5 as a white solid (92%). $^1$H NMR (500 MHz, DMSO-d$_6$) δ ppm 1.16 (t, J=7.1 Hz, 3H), 1.53 (s, 6H), 2.46 (s, 3H), 3.32 (q, J=6.9 Hz, 2H), 3.80 (br. t, J=4.9 Hz, 4H), 3.98 (dd, J=4.9, 4.3 Hz, 4H), 6.38 (d, J=5.8 Hz, 1H), 7.68 (d, J=8.4 Hz, 1H), 8.05-8.17 (m, 2H), 8.79 (d, J=1.7 Hz, 1H).

Example B6

Preparation of compound 6: 3-[6-(1-methoxy-1-methylethyl)-3-pyridinyl]-2-methyl-8-(4-morpholinyl)-imidazo[1,2-b]pyridazine

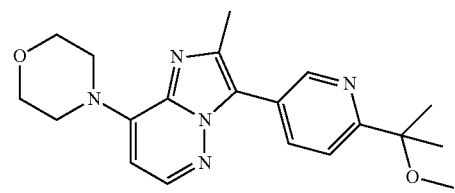 [SMILES: COC(C)(C)c1ccc(-c2c(C)nc3c(N4CCOCC4)ccnn23)cn1]

From intermediate 14 and intermediate 49. Flash column chromatography (silica; ethyl acetate in heptane 0/100 to 100/0) and precipitation from diethyl ether yielded compound 6 as a white solid (92%). $^1$H NMR (500 MHz, DMSO-d$_6$) δ ppm 1.53 (s, 6H), 2.47 (s, 3H), 3.13 (s, 3H), 3.80 (br. t, J=4.9 Hz, 4H), 3.98 (dd, J=4.9, 4.3 Hz, 4H), 6.39 (d, J=5.8 Hz, 1H), 7.67 (d, J=8.1 Hz, 1H), 8.05-8.16 (m, 2H), 8.81 (d, J=1.7 Hz, 1H).

Example B7

Preparation of compound 7: 3-[6-(2-methoxy-2-methylpropyl)-3-pyridinyl]-2-methyl-8-(4-pyridinyl)-imidazo[1,2-b]pyridazine

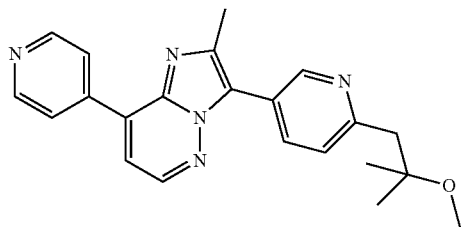 [SMILES: COC(C)(C)Cc1ccc(-c2c(C)nc3c(-c4ccncc4)ccnn23)cn1]

From intermediate 20 and intermediate 58. Flash column chromatography (silica; 7 M solution of ammonia in methanol in dichloromethane 0/100 to 2/98), reverse phase HPLC (0.1% solution of formic acid in acetonitrile 80/20 to 0/100) and precipitation from diethyl ether yielded compound 7 as a white solid (54%). $^1$H NMR (400 MHz, DMSO-d$_6$) δ ppm 1.18 (s, 6H), 2.57 (s, 3H), 2.99 (s, 2H), 3.23 (s, 3H), 7.46 (d, J=8.1 Hz, 1H), 7.71 (d, J=4.9 Hz, 1H), 8.07 (dd, J=8.1, 2.3 Hz, 1H), 8.32 (d, J=6.2 Hz, 2H), 8.65 (d, J=4.9 Hz, 1H), 8.78-8.86 (m, 3H).

Example B8

Preparation of compound 8: 3-[6-(2-methoxyethoxy)-5-methyl-3-pyridinyl]-2-methyl-8-(4-pyridinyl)-imidazo[1,2-b]pyridazine

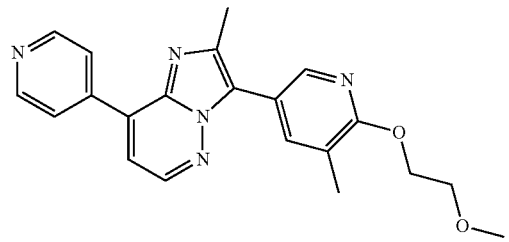 [SMILES: COCCOc1ncc(-c2c(C)nc3c(-c4ccncc4)ccnn23)cc1C]

From intermediate 20 and intermediate 45. Flash column chromatography (silica; 7 M solution of ammonia in methanol in dichloromethane 0/100 to 2/98) and precipitation from diethyl ether yielded compound 8 as a yellow solid (79%). $^1$H NMR (500 MHz, DMSO-d$_6$) δ ppm 2.25 (s, 3H), 2.53 (s, 3H), 3.35 (s, 3H), 3.73 (br. t, J=4.6 Hz, 2H), 4.50 (br. t, J=4.9 Hz, 2H), 7.68 (d, J=4.9 Hz, 1H), 7.88-7.93 (m, 1H), 8.30 (d, J=1.7 Hz, 1H), 8.32 (d, J=6.4 Hz, 2H), 8.63 (d, J=4.9 Hz, 1H), 8.82 (d, J=6.1 Hz, 2H).

Example B9

Preparation of compound 9: 3-[6-(2-methoxyethoxy)-3-pyridinyl]-2-methyl-8-(3-pyridinyl)-imidazo[1,2-b]pyridazine

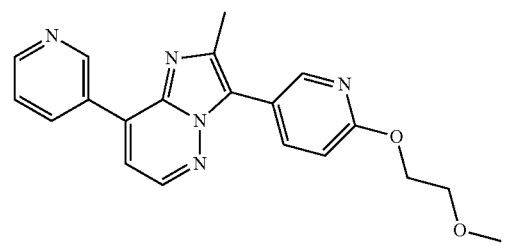 [SMILES: COCCOc1ccc(-c2c(C)nc3c(-c4cccnc4)ccnn23)cn1]

From intermediate 19 and intermediate 47. Flash column chromatography (silica; 7 M solution of ammonia in methanol in dichloromethane 0/100 to 2/98), reverse phase HPLC (0.1% solution of ammonium formate/ammonium hydroxide buffer pH 9 and acetonitrile 20/80 to 0/100) and precipitation from diethyl ether yielded compound 9 as a pale yellow solid (73%). $^1$H NMR (500 MHz, DMSO-$d_6$) δ ppm 2.54 (s, 3H), 3.33 (s, 3H), 3.71 (br. t, J=4.6 Hz, 2H), 4.47 (br. t, J=4.6 Hz, 2H), 7.04 (d, J=8.7 Hz, 1H), 7.64 (d, J=4.9 Hz, 1H), 7.65 (d, J=4.6 Hz, 1H), 8.08 (dd, J=8.5, 2.5 Hz, 1H), 8.49 (d, J=2.6 Hz, 1H), 8.59 (d, J=4.6 Hz, 1H), 8.72 (dt, J=8.0, 1.9 Hz, 1H), 8.74 (dd, J=4.8, 1.6 Hz, 1H), 9.47 (d, J=2.0 Hz, 1H).

Example B10

Preparation of compound 10: 2-cyclopropyl-3-[6-(2-methoxyethyl)-3-pyridinyl]-8-(4-pyridinyl)-imidazo[1,2-b]pyridazine

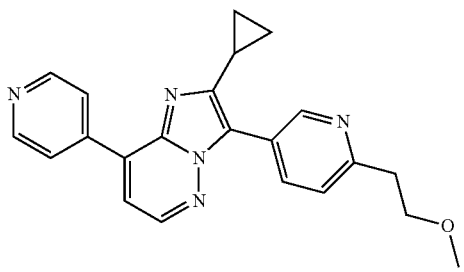 [SMILES: COCCc1ccc(-c2c(C3CC3)nc3c(-c4ccncc4)ccnn23)cn1]

From intermediate 18 and intermediate 56. Flash column chromatography (silica; ethyl acetate in dichloromethane 30/70 to 100/0) and precipitation from diisopropyl ether yielded compound 10 as a pale yellow solid (31%). $^1$H NMR (400 MHz, CDCl$_3$) δ ppm 1.02-1.09 (m, 2H), 1.19-1.28 (m, 2H), 2.14-2.26 (m, 1H), 3.17 (t, J=6.6 Hz, 2H), 3.41 (s, 3H), 3.86 (t, J=6.7 Hz, 2H), 7.26 (d, J=4.6 Hz, 1H), 7.42 (d, J=8.1 Hz, 1H), 8.14 (dd, J=8.1, 2.3 Hz, 1H), 8.14-8.19 (m, J=6.0 Hz, 2H), 8.37 (d, J=4.6 Hz, 1H), 8.81 (d, J=6.0 Hz, 2H), 9.03 (d, J=2.1 Hz, 1H).

Example B11

Preparation of compound 11: 3-[6-(2-methoxyethyl)-3-pyridinyl]-8-(4-morpholinyl)-imidazo[1,2-b]pyridazine

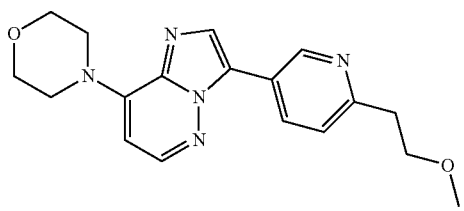 [SMILES: COCCc1ccc(-c2cnc3c(N4CCOCC4)ccnn23)cn1]

From intermediate 17 and intermediate 56. Flash column chromatography (silica; 7 M solution of ammonia in methanol in dichloromethane 0/100 to 3/97) and filtration through an Isolute SCX-2 cartridge followed by elution with a 7 M solution of ammonia in methanol yielded compound 11 as a white solid (83%). $^1$H NMR (500 MHz, DMSO-$d_6$) δ ppm 3.01 (t, J=6.6 Hz, 2H), 3.25 (s, 3H), 3.72 (t, J=6.5 Hz, 2H), 3.79 (br. t, J=4.9 Hz, 4H), 4.00 (dd, J=4.9, 4.3 Hz, 4H), 6.42 (d, J=5.8 Hz, 1H), 7.41 (d, J=8.4 Hz, 1H), 8.06 (s, 1H), 8.24 (d, J=5.8 Hz, 1H), 8.38 (dd, J=8.1, 2.3 Hz, 1H), 9.14 (d, J=1.7 Hz, 1H).

Example B12

Preparation of compound 12: 2-methoxy-3-[6-(2-methoxyethyl)-3-pyridinyl]-8-(4-morpholinyl)-imidazo[1,2-b]pyridazine

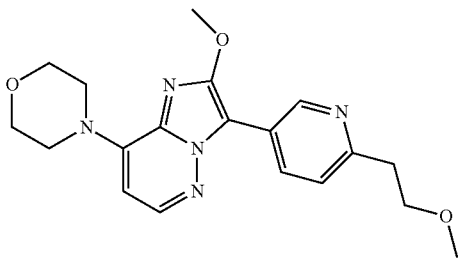 [SMILES: COCCc1ccc(-c2c(OC)nc3c(N4CCOCC4)ccnn23)cn1]

From intermediate 15 and intermediate 56. Flash column chromatography (silica; 7 M solution of ammonia in methanol in dichloromethane 0/100 to 3/97) and precipitation from diisopropyl ether yielded compound 12 as a white solid (83%). $^1$H NMR (400 MHz, DMSO-$d_6$) δ ppm 2.98 (t, J=6.7 Hz, 2H), 3.25 (s, 3H), 3.71 (t, J=6.6 Hz, 2H), 3.80 (dd, J=5.1, 4.4 Hz, 4H), 3.92 (dd, J=5.1, 4.4 Hz, 4H), 4.06 (s, 3H), 6.48 (d, J=6.0 Hz, 1H), 7.38 (d, J=8.3 Hz, 1H), 8.21 (d, J=5.8 Hz, 1H), 8.35 (dd, J=8.3, 2.3 Hz, 1H), 9.15 (d, J=2.3 Hz, 1H).

Example B13

Preparation of compound 13: 6-cyclopropyl-3-[6-(2-methoxyethyl)-3-pyridinyl]-2-methyl-8-(4-morpholinyl)-imidazo[1,2-b]pyridazine

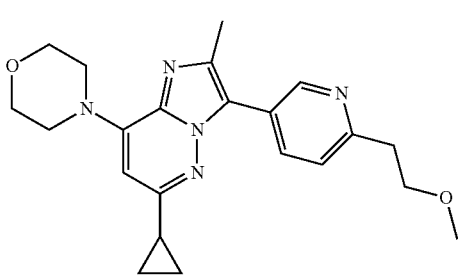 [SMILES: COCCc1ccc(-c2c(C)nc3c(N4CCOCC4)cc(C4CC4)nn23)cn1]

From intermediate 23 and intermediate 56. Flash column chromatography (silica; ethyl acetate in heptane 0/100 to 100/0) yielded compound 13 as a white solid (85%). $^1$H NMR (400 MHz, CDCl$_3$) δ ppm 0.93-0.96 (m, 4H), 1.88-1.97 (m, 1H), 2.53 (s, 3H), 3.13 (t, J=6.7 Hz, 2H), 3.40 (s, 3H), 3.84 (t, J=6.7 Hz, 2H), 3.87-3.92 (m, 4H), 3.92-3.98 (m, 4H), 5.98 (s, 1H), 7.33 (d, J=8.1 Hz, 1H), 7.97 (dd, J=8.1, 2.3 Hz, 1H), 8.85 (d, J=1.6 Hz, 1H).

Example B14

Preparation of compound 14: 6-cyclopropyl-3-[6-(2-methoxyethyl)-3-pyridinyl]-2-methyl-8-(4-pyridinyl)-imidazo[1,2-b]pyridazine

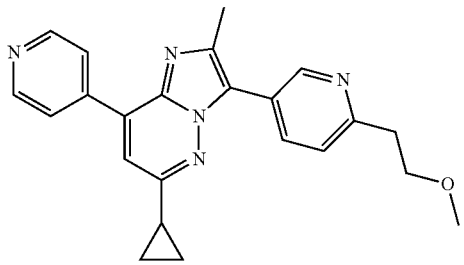 [SMILES: COCCc1ccc(-c2c(C)nc3c(-c4ccncc4)cc(C4CC4)nn23)cn1]

From intermediate 24 and intermediate 56. Flash column chromatography (silica; methanol and ethyl acetate in heptane 0/30/70 to 2/98/0) and precipitation from diisopropyl ether yielded compound 14 as a pale yellow solid (85%). $^1$H NMR (500 MHz, CDCl$_3$) δ ppm 1.03-1.15 (m, 4H), 2.08-2.18 (m, 1H), 2.63 (s, 3H), 3.16 (t, J=6.5 Hz, 2H), 3.41 (s, 3H), 3.87 (t, J=6.6 Hz, 2H), 7.06 (s, 1H), 7.39 (d, J=8.1 Hz, 1H), 8.00 (dd, J=8.1, 2.3 Hz, 1H), 8.05 (d, J=6.1 Hz, 2H), 8.81 (d, J=6.1 Hz, 2H), 8.91 (d, J=1.7 Hz, 1H).

Example B15

Preparation of compound 15: 2-cyclopropyl-3-[6-(2-methoxyethyl)-3-pyridinyl]-6-methyl-8-(4-morpholinyl)-imidazo[1,2-b]pyridazine

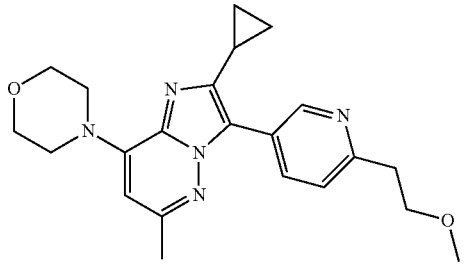 [SMILES: COCCc1ccc(-c2c(C3CC3)nc3c(N4CCOCC4)cc(C)nn23)cn1]

From intermediate 25) and intermediate 56. Flash column chromatography (silica; ethyl acetate in heptane 20/80 to 50/50) yielded compound 15 as a white solid (47%).

$^1$H NMR (400 MHz, CDCl$_3$) δ ppm 0.91-0.98 (m, 2H), 1.03-1.13 (m, 2H), 2.05-2.15 (m, 1H), 2.41 (s, 3H), 3.13 (t, J=6.8 Hz, 2H), 3.40 (s, 3H), 3.84 (t, J=6.7 Hz, 2H), 3.90 (br. s., 8H), 5.96 (s, 1H), 7.35 (d, J=8.1 Hz, 1H), 8.13 (dd, J=8.1, 2.3 Hz, 1H), 9.02 (d, J=2.3 Hz, 1H).

Example B16

Preparation of compound 16: 3-[6-(2-methoxyethoxy)-3-pyridinyl]-2-methyl-8-(4-morpholinyl)-imidazo[1,2-b]pyridazine

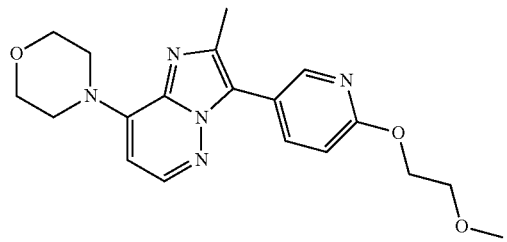 [SMILES: COCCOc1ccc(-c2c(C)nc3c(N4CCOCC4)ccnn23)cn1]

Tetrakis(triphenylphosphine)palladium (0) (0.034 g, 0.009 mmol) was added to a stirred solution of intermediate 26 (0.2 g, 0.58 mmol) and intermediate 63 (0.243 g, 0.87 mmol), in a mixture of 1,4-dioxane (5 ml) and a saturated solution of sodium carbonate (3 ml). The mixture was stirred at 80° C. for 16 h. in a sealed tube under nitrogen and then diluted with dichloromethane and washed with water. The organic layer was separated, filtered over cotton, and the solvents evaporated in vacuo. The crude product was purified by flash column chromatography (silica; ethyl acetate in dichloromethane 0/100 to 50/50). The desired fractions were collected and concentrated in vacuo to yield compound 16 (0.151 g, 70%). $^1$H NMR (400 MHz, CDCl$_3$) δ ppm 2.51 (s, 3H), 3.46 (s, 3H), 3.78 (t, J=4.6 Hz, 2H), 3.86-4.06 (m, 8H), 4.55 (dd, J=4.9, 4.4 Hz, 2H), 6.08 (d, J=5.5 Hz, 1H), 6.96 (d, J=8.8 Hz, 1H), 7.92 (dd, J=8.6, 2.3 Hz, 1H), 7.97 (d, J=5.5 Hz, 1H), 8.37 (d, J=2.3 Hz, 1H).

The following compounds were prepared from the indicated precursors according to a protocol analogous to B16.

Example B17

Preparation of compound 17: 3-[6-(ethoxymethyl)-3-pyridinyl]-2-methyl-8-(4-morpholinyl)-imidazo[1,2-b]pyridazine

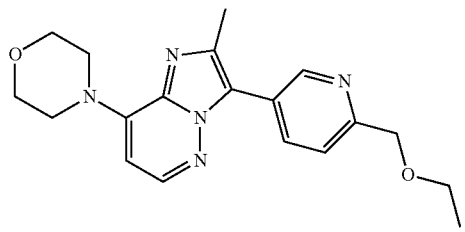

From intermediate 26 and intermediate 64. Conditions: 150° C., 15 min, microwave irradiation. Flash column chromatography (silica; 7 M solution of ammonia in methanol in dichloromethane 0/100 to 2/98) yielded compound 17 as a white solid (75%). $^1$H NMR (400 MHz, DMSO-d$_6$) δ ppm 1.21 (t, J=7.1 Hz, 3H), 2.45 (s, 3H), 3.60 (q, J=7.0 Hz, 2H), 3.79 (dd, J=5.1, 4.4 Hz, 4H), 3.98 (br. t, J=4.6 Hz, 4H), 4.60 (s, 2H), 6.37 (d, J=5.8 Hz, 1H), 7.56 (d, J=8.1 Hz, 1H), 8.10 (dd, J=8.1, 2.1 Hz, 1H), 8.10 (d, J=5.8 Hz, 1H), 8.78 (d, J=2.1 Hz, 1H).

Example B18

Preparation of compound 18: 3-[6-(2-methoxy-2-methylpropoxy)-3-pyridinyl]-2-methyl-8-(4-morpholinyl)-imidazo[1,2-b]pyridazine

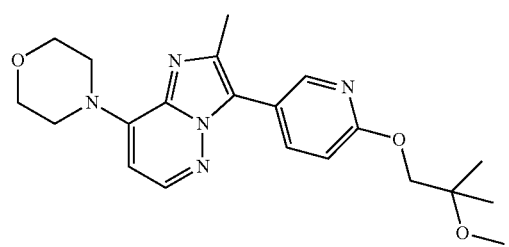 [SMILES: COC(C)(C)COc1ccc(-c2c(C)nc3c(N4CCOCC4)ccnn23)cn1]

From intermediate 26 and intermediate 62. Conditions: 140° C., 20 min, microwave irradiation. Flash column chromatography (silica; ethyl acetate in dichloromethane 0/100 to 50/50) yielded compound 18 as a white solid (82%). ¹H NMR (400 MHz, CDCl₃) δ ppm 1.32 (s, 6H), 2.51 (s, 3H), 3.32 (s, 3H), 3.90-4.01 (m, 8H), 4.30 (s, 2H), 6.08 (d, 1H), 6.98 (dd, J=8.6, 0.5 Hz, 1H), 7.93 (dd, J=8.6, 2.3 Hz, 1H), 7.97 (d, J=5.5 Hz, 1H), 8.37 (d, J=1.8 Hz, 1H).

Example B19

Preparation of compound 19: 2-methyl-8-(4-morpholinyl)-3-[6-(4-morpholinyl)-3-pyridinyl]-imidazo[1,2-b]pyridazine

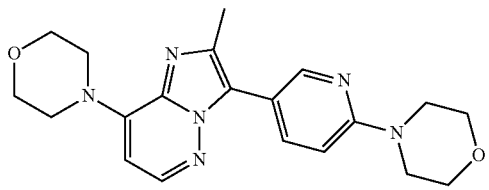

From intermediate 26 and commercially available 1-[5-(4,4,5,5-tetramethyl-[1,3,2]dioxaborolan-2-yl)-pyridin-2-yl]morpholine. Flash column chromatography (silica; ethyl acetate in heptanes 0/100 to 40/60) and flash column chromatography (silica; ethyl acetate and dichloromethane in heptane from 0/0/100 to 20/80/0) yielded compound 19 as a white solid (69%). ¹H NMR (400 MHz, CDCl₃) δ ppm 2.51 (s, 3H), 3.58 (dd, J=5.1, 4.6 Hz, 4H), 3.85 (dd, J=5.1, 4.6 Hz, 4H), 3.95 (br. s., 8H), 6.06 (d, J=5.8 Hz, 1H), 6.78 (d, J=8.8 Hz, 1H), 7.86 (dd, J=8.8, 2.3 Hz, 1H), 7.97 (d, J=5.5 Hz, 1H), 8.43 (d, J=2.3 Hz, 1H).

Example B20

Preparation of compound 20: 3-[6-(2-methoxyethyl)-3-pyridinyl]-2-methyl-8-(4-pyridinyl)-imidazo[1,2-b]pyridazine

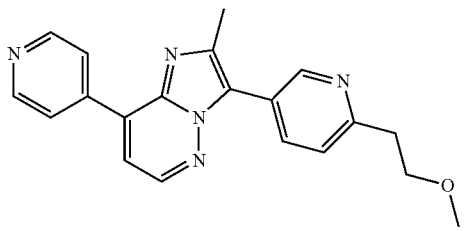 [SMILES: COCCc1ccc(-c2c(C)nc3c(-c4ccncc4)ccnn23)cn1]

From intermediate 33 and intermediate 61. Conditions: 150° C., 5 min, microwave irradiation. Flash column chromatography (silica; 7 M solution of ammonia in methanol in dichloromethane 0/100 to 4/96) and precipitation from diisopropyl ether yielded compound 20 as a white solid (45%). ¹H NMR (400 MHz, CDCl₃) δ ppm 2.66 (s, 3H), 3.16 (t, J=6.6 Hz, 2H), 3.41 (s, 3H), 3.86 (t, J=6.7 Hz, 2H), 7.24 (d, J=4.9 Hz, 1H), 7.41 (d, J=8.1 Hz, 1H), 8.02 (dd, J=8.1, 2.3 Hz, 1H), 8.09 (d, J=6.2 Hz, 2H), 8.40 (d, J=4.9 Hz, 1H), 8.83 (d, J=6.2 Hz, 2H), 8.88 (d, J=2.3 Hz, 1H).

Example B21

Preparation of compound 21: 3-[6-(2-methoxyethoxy)-3-pyridinyl]-2-methyl-8-(4-pyridinyl)-imidazo[1,2-b]pyridazine

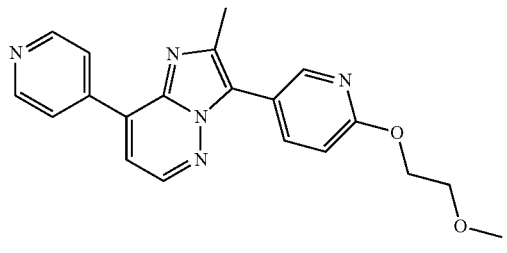 [SMILES: COCCOc1ccc(-c2c(C)nc3c(-c4ccncc4)ccnn23)cn1]

From intermediate 33 and intermediate 63. Conditions: 150° C., 15 min, microwave irradiation. Flash column chromatography (silica; ethyl acetate in heptane 0/100 to 100/0) and precipitation from diethyl ether yielded compound 21 as a white solid (44%). ¹H NMR (500 MHz, DMSO-d₆) δ ppm 2.55 (s, 3H), 3.34 (s, 3H), 3.72 (br t, J=4.6 Hz, 2H), 4.48 (br t, J=4.6 Hz, 2H), 7.05 (d, J=8.7 Hz, 1H), 7.70 (d, J=4.6 Hz, 1H), 8.09 (dd, J=8.7, 2.3 Hz, 1H), 8.33 (dd, J=4.6, 1.7 Hz, 2H), 8.49 (d, J=2.0 Hz, 1H), 8.63 (d, J=4.6 Hz, 1H), 8.82 (dd, J=4.6, 1.7 Hz, 2H).

Example B21a

Preparation of compound 21a: 3-[6-(2-methoxyethoxy)-3-pyridinyl]-2-methyl-8-(4-pyridinyl)-imidazo[1,2-b]pyridazine hydrochloride salt

Hydrochloric acid (38.16 mL, 2M solution in diethyl ether) was added to a solution of compound 21 (19.7 g, 54.51 mmol) in a mixture of diethylether (220 mL) and dichloromethane (600 mL). The mixture was stirred at room temperature for 2.5 h and then concentrated in vacuo. Diethyl ether was then added, and the solid was filtered, washed with diethyl ether and dried overnight in vacuo, to yield compound 21a (20.94 g, 91%) as an orange solid. ¹H NMR (500 MHz, DMSO-d₆) δ ppm 2.57 (s, 3H), 3.33 (s, 3H), 3.67-3.76 (m, 2H), 4.42-4.51 (m, 2H), 7.07 (d, J=8.7 Hz, 1H), 7.94 (d, J=4.6 Hz, 1H), 8.09 (dd, J=8.5, 2.5 Hz, 1H), 8.50 (d, J=2.3 Hz, 1H), 8.77 (d, J=4.9 Hz, 1H), 8.88-8.98 (m, 2H), 9.09-9.17 (m, 2H).

Example B22

Preparation of compound 22: 2-cyclopropyl-3-[6-(2-methoxyethyl)-3-pyridinyl]-8-(4-morpholinyl)-imidazo[1,2-b]pyridazine

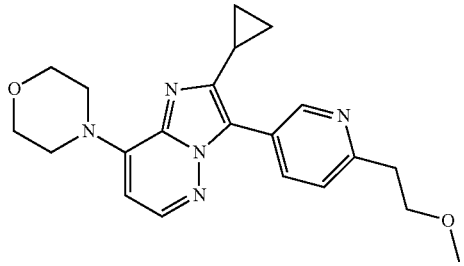 [SMILES: COCCc1ccc(-c2c(C3CC3)nc3c(N4CCOCC4)ccnn23)cn1]

From intermediate 27 and intermediate 61. Conditions: 150° C., 15 min, microwave irradiation. Flash column chromatography (silica; 7 M solution of ammonia in methanol in dichloromethane 0/100 to 7/93) and reverse phase HPLC (0.1% solution of ammonium formate/ammonium hydroxide buffer pH 9 and acetonitrile 80/20 to 0/100) yielded compound 22 as a white solid (14%). ¹H NMR (400 MHz, CDCl₃) δ ppm 0.92-1.01 (m, 2H), 1.06-1.13 (m, 2H), 2.05-2.16 (m, 1H), 3.13 (t, J=6.7 Hz, 2H), 3.39 (s, 3H), 3.83 (t, J=6.7 Hz, 2H), 3.88-4.05 (m, 8H), 6.06 (d, J=5.8 Hz, 1H), 7.37 (d, J=8.1 Hz, 1H), 7.96 (d, J=5.8 Hz, 1H), 8.10 (dd, J=8.0, 2.2 Hz, 1H), 8.96 (d, J=2.3 Hz, 1H).

Example B23

Preparation of compound 23: 3-[6-(2-methoxyethyl)-3-pyridinyl]-2,6-dimethyl-8-(4-morpholinyl)-imidazo[1,2-b]pyridazine

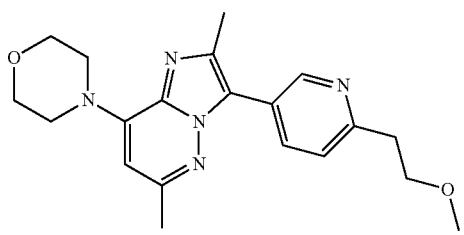 [SMILES: COCCc1ccc(-c2c(C)nc3c(N4CCOCC4)cc(C)nn23)cn1]

From intermediate 28 and intermediate 61. Conditions: 150° C., 15 min, microwave irradiation. Flash column chromatography (silica; 7 M solution of ammonia in methanol in dichloromethane 0/100 to 2/98) and reverse phase HPLC (0.1% solution of ammonium formate/ammonium hydroxide buffer pH 9 and acetonitrile 80/20 to 0/100) yielded compound 23 as a white solid (14%). ¹H NMR (400 MHz, CDCl₃) δ ppm 2.41 (s, 3H), 2.52 (s, 3H), 3.13 (t, J=6.7 Hz, 2H), 3.40 (s, 3H), 3.84 (t, J=6.7 Hz, 2H), 3.88-3.97 (m, 8H), 5.99 (s, 1H), 7.34 (d, J=8.1 Hz, 1H), 7.99 (dd, J=8.1, 2.3 Hz, 1H), 8.86 (d, J=2.3 Hz, 1H).

Example B24

Preparation of compound 24: 3-[6-(2-methoxyethyl)-3-pyridinyl]-2,6-dimethyl-8-(4-pyridinyl)-imidazo[1,2-b]pyridazine

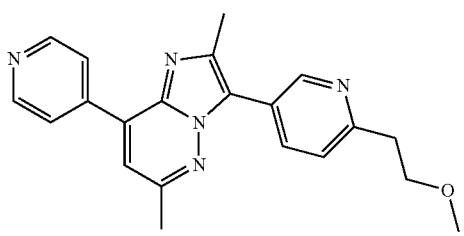 [SMILES: COCCc1ccc(-c2c(C)nc3c(-c4ccncc4)cc(C)nn23)cn1]

From intermediate 30 and intermediate 61. Conditions: 150° C., 15 min, microwave irradiation. Flash column chromatography (silica; 7 M solution of ammonia in methanol in dichloromethane 0/100 to 2/98) and flash column chromatography (silica; 7 M solution of ammonia in methanol in dichloromethane 0/100 to 5/95) and precipitation from diisopropyl ether yielded compound 24 as a yellow solid (29%). ¹H NMR (500 MHz, CDCl₃) δ ppm 2.62 (s, 3H), 2.64 (s, 3H), 3.16 (t, J=6.5 Hz, 2H), 3.41 (s, 3H), 3.87 (t, J=6.6 Hz, 2H), 7.12 (s, 1H), 7.40 (d, J=8.1 Hz, 1H), 8.02 (dd, J=8.1, 2.3 Hz, 1H), 8.06 (d, J=6.1 Hz, 2H), 8.81 (d, J=6.1 Hz, 2H), 8.93 (d, J=1.7 Hz, 1H).

Example B25

Preparation of compound 25: 3-[6-(2-ethoxyethyl)-3-pyridinyl]-2-methyl-8-(4-morpholinyl)-imidazo[1,2-b]pyridazine

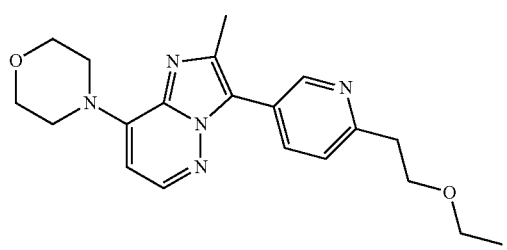 [SMILES: CCOCCc1ccc(-c2c(C)nc3c(N4CCOCC4)ccnn23)cn1]

A 60% dispersion of sodium hydride in mineral oils (0.2 g, 5 mmol) was added portionwise to a stirred solution of intermediate 38 (0.2 g, 0.62 mmol) in ethanol (8 ml). The mixture was stirred at 100° C. for 16 h. in a sealed tube and then poured onto water and extracted with dichloromethane. The organic layer was separated, dried (Na₂SO₄), filtered and the solvents evaporated in vacuo. The crude product was purified by flash column chromatography (silica; 7 M solution of ammonia in methanol in dichloromethane 0/100 to 1/99). The desired fractions were collected and concentrated in vacuo to yield compound 25 (0.042 g, 18%) as a white solid.
¹H NMR (500 MHz, DMSO-d₆) δ ppm 1.10 (t, J=6.9 Hz, 3H), 2.44 (s, 3H), 3.02 (t, J=6.8 Hz, 2H), 3.46 (q, J=6.9 Hz, 2H), 3.72-3.84 (m, 6H), 3.97 (dd, J=4.9, 4.3 Hz, 4H), 6.37 (d, J=5.8 Hz, 1H), 7.44 (d, J=8.1 Hz, 1H), 7.99 (dd, J=8.1, 2.3 Hz, 1H), 8.09 (d, J=5.8 Hz, 1H), 8.74 (d, J=1.7 Hz, 1H).

The following compound was prepared from the indicated precursors according to a protocol analogous to B25.

Example B26

Preparation of compound 26: 3-[2-(2-methoxyethyl)-4-pyridinyl]-2-methyl-8-(4-morpholinyl)-imidazo[1,2-b]pyridazine

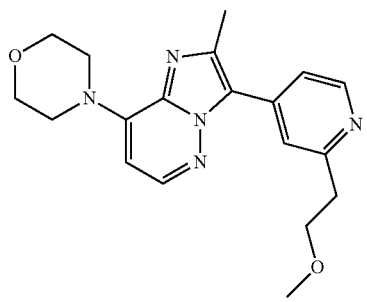 [SMILES: COCCc1cc(-c2c(C)nc3c(N4CCOCC4)ccnn23)ccn1]

From intermediate 40 and sodium methoxide. Flash column chromatography (silica; ethyl acetate in heptane 20/80 to 100/0) yielded compound 26 as a white solid (69%).

$^1$H NMR (500 MHz, CDCl$_3$) δ ppm 2.58 (s, 3H), 3.15 (t, J=6.8 Hz, 2H), 3.38 (s, 3H), 3.83 (t, J=6.8 Hz, 2H), 3.88-4.03 (m, 8H), 6.13 (d, J=5.5 Hz, 1H), 7.54 (dd, J=5.2, 1.7 Hz, 1H), 7.60 (br. s., 1H), 8.03 (d, J=5.8 Hz, 1H), 8.64 (d, J=5.2 Hz, 1H).

Example B27

Preparation of compound 27: 2-methyl-8-(4-morpholinyl)-3-[6-(tetrahydro-2H-pyran-4-yl)-3-pyridinyl]-imidazo[1,2-b]pyridazine

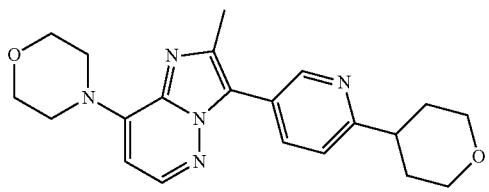 [SMILES: Cc1nc2c(N3CCOCC3)ccnn2c1-c1ccc(C2CCOCC2)nc1]

10% Palladium on charcoal (0.069 g) was added to a suspension of intermediate 41 (0.245 g, 0.65 mmol) and ammonium formate (0.122 g, 1.95 mmol) in methanol (10 ml). The mixture was stirred at 85° C. for 4 h. and then more 10% palladium on charcoal (0.69 g) and ammonium formate (0.122 g, 1.95 mmol) were added. The mixture was stirred at 90° C. for a further 16 h. and then filtered through a pad of diatomaceous earth and the filtrate concentrated in vacuo. The crude product was diluted with dichloromethane and washed with water. The organic layer was separated, dried (Na$_2$SO$_4$), filtered and the solvents evaporated in vacuo. The crude product was purified by flash column chromatography (silica; ethyl acetate in heptane 30/70 to 100/0). The desired fractions were collected and evaporated to yield compound 27 (0.21 g, 86%) as a white solid. $^1$H NMR (400 MHz, CDCl$_3$) δ ppm 1.83-2.06 (m, 4H), 2.54 (s, 3H), 2.94-3.10 (m, 1H), 3.51-3.65 (m, 2H), 3.87-4.03 (m, 8H), 4.07-4.19 (m, 2H), 6.10 (d, J=5.8 Hz, 1H), 7.32 (d, J=8.1 Hz, 1H), 7.99 (d, J=5.5 Hz, 1H), 8.02 (dd, J=8.2, 2.2 Hz, 1H), 8.80 (d, J=2.1 Hz, 1H).

Example B28

Preparation of compound 28: 3-(6-ethyl-3-pyridinyl)-2-methyl-8-(4-morpholinyl)-imidazo[1,2-b]pyridazine

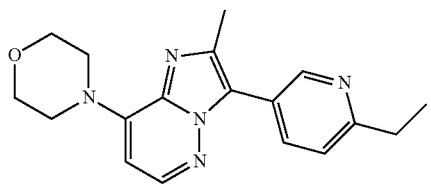 [SMILES: CCc1ccc(-c2c(C)nc3c(N4CCOCC4)ccnn23)cn1]

10% Palladium on charcoal (0.405 g) was added to a suspension of intermediate 38 (2.45 g, 7.62 mmol) in a mixture of methanol (90 ml) and ethyl acetate (90 ml). The mixture was hydrogenated (atmospheric pressure) at room temperature for 16 h. and then filtered through a pad of diatomaceous earth. The filtrate was concentrated in vacuo. The crude product was purified by flash column chromatography (silica; ethyl acetate in dichloromethane 0/100 to 100/0). The desired fractions were collected and concentrated in vacuo. The crude product was precipitated from diethyl ether to yield compound 28 (0.675 g, 27%) as a white solid. $^1$H NMR (500 MHz, DMSO-d$_6$) δ ppm 1.28 (t, J=7.7 Hz, 3H), 2.44 (s, 3H), 2.82 (q, J=7.6 Hz, 2H), 3.79 (br t, J=4.9 Hz, 4H), 3.97 (dd, J=4.9, 4.3 Hz, 4H), 6.36 (d, J=5.8 Hz, 1H), 7.41 (d, J=8.1 Hz, 1H), 7.99 (dd, J=8.1, 2.3 Hz, 1H), 8.09 (d, J=5.8 Hz, 1H), 8.73 (d, J=1.7 Hz, 1H).

Example B29

Preparation of compound 29: 3-[6-(3-methoxy-3-methylbutyl)-3-pyridinyl]-2-methyl-8-(4-morpholinyl)-imidazo[1,2-b]pyridazine

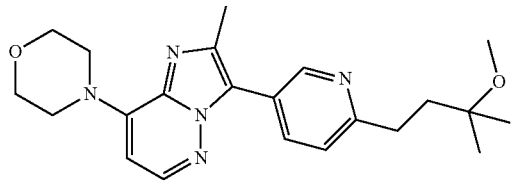 [SMILES: COC(C)(C)CCc1ccc(-c2c(C)nc3c(N4CCOCC4)ccnn23)cn1]

1,2-Dibromoethane (0.016 ml, 0.19 mmol) was added to a stirred suspension of zinc (0.337 g, 5.17 mmol) in dry N,N-dimethylformamide (8 ml). The mixture was stirred at 90° C. for 30 min. under nitrogen and then allowed to cool down to room temperature. Chlorotrimethylsilane (0.006 ml, 0.048 mmol) was added and the mixture was stirred at room temperature for 15 min. A solution of intermediate 43 (0.7 g, 2.58 mmol) in tetrahydrofuran (3 ml) was added dropwise and the mixture was stirred at 50° C. for 1.5 h. The excess zinc was allowed to settle for 1 h and the supernatant liquid was transferred via cannula to a second flask charged with intermediate 35 (0.21 g, 0.64 mmol) and tetrakis(triphenylphosphine)palladium (0) (0.015 g, 0.013 mmol). The mixture was stirred at 55° C. for 16 h. under nitrogen, and then a saturated solution of ammonium chloride was added. The mixture was extracted with ethyl acetate and the organic layer was separated, dried (Na$_2$SO$_4$), filtered and the solvents evaporated in vacuo. The crude product was purified by flash column chromatography (silica; methanol in dichloromethane 0/100 to 2/98). The desired fractions were collected and concentrated to yield compound 29 (0.071 g, 28%). $^1$H NMR (400 MHz, CDCl$_3$) δ ppm 1.26 (s, 6H), 1.86-2.07 (m, 2H), 2.53 (s, 3H), 2.79-2.99 (m, 2H), 3.26 (s, 3H), 3.80-4.11 (m, 8H), 6.09 (d, J=5.5 Hz, 1H), 7.32 (d, J=8.1 Hz, 1H), 7.96 (dd, J=8.1, 1.6 Hz, 1H), 7.98 (d, J=5.5 Hz, 1H), 8.78 (br. s., 1H).

Example B30

Preparation of compound 30: 2-methyl-8-(4-morpholinyl)-3-[6-(1-piperazinyl)-3-pyridinyl]-imidazo[1,2-b]pyridazine

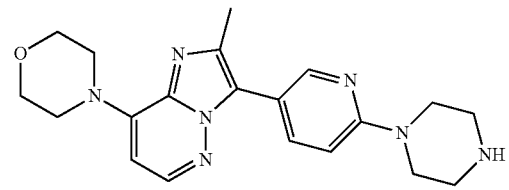 [SMILES: Cc1nc2c(N3CCOCC3)ccnn2c1-c1ccc(N2CCNCC2)nc1]

Piperazine (4.68 g, 54.4 mmol) was added to a stirred solution of intermediate 35 (2.7 g, 6.80 mmol) in acetonitrile (24 ml). The mixture was stirred at 120° C. for 1 d. in a sealed tube and then diluted with dichloromethane and washed with water. The organic layer was separated, dried (Na$_2$SO$_4$), filtered and the solvents evaporated in vacuo. The crude product was purified by column chromatography (silica; 7 M solution of ammonia in methanol in dichloromethane 0/100 to 3/97). The desired fractions were collected and concentrated in vacuo and the crude product was precipitated from diisopropyl ether to yield compound 30 (1.64 g, 39%) as a pale yellow solid. $^1$H NMR (400 MHz, CDCl$_3$) δ ppm 1.75 (s, 1H), 2.51 (s, 3H), 3.01 (br. t, J=5.1 Hz, 4H), 3.59 (dd, J=5.3, 4.9 Hz, 4H), 3.83-4.07 (m, 8H), 6.06 (d, J=5.8 Hz, 1H), 6.78 (d, J=9.0 Hz, 1H), 7.83 (dd, J=8.9, 2.4 Hz, 1H), 7.97 (d, J=5.5 Hz, 1H), 8.41 (d, J=2.3 Hz, 1H).

The following compound was prepared from the indicated precursors according to a protocol analogous to that used of B30.

Example B31

Preparation of compound 31: 2-methyl-3-[6-(4-morpholinyl)-3-pyridinyl]-8-(4-pyridinyl)-imidazo[1,2-b]pyridazine

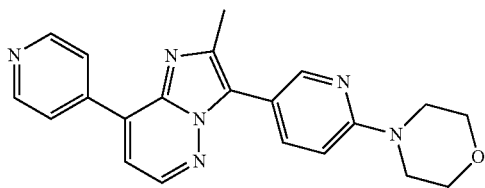 [SMILES: Cc1nc2c(-c3ccncc3)ccnn2c1-c1ccc(N2CCOCC2)nc1]

From intermediate 37 and morpholine. Flash column chromatography (silica; 7 M solution of ammonia in methanol in dichloromethane 0/100 to 2/98) and precipitation from diethyl ether yielded compound 31 as an orange solid (80%). M.p.>300° C. (decomposition). $^1$H NMR (500 MHz, DMSO-d$_6$) δ ppm 2.53 (s, 3H), 3.55 (dd, J=5.2, 4.6 Hz, 4H), 3.74 (br. t, J=4.6 Hz, 4H), 7.02 (d, J=8.7 Hz, 1H), 7.64 (d, J=4.9 Hz, 1H), 7.91 (dd, J=8.8, 2.5 Hz, 1H), 8.32 (d, J=6.1 Hz, 2H), 8.45 (d, J=2.0 Hz, 1H), 8.59 (d, J=4.9 Hz, 1H), 8.81 (d, J=6.4 Hz, 2H).

Example B32

Preparation of compound 32: 2-methyl-3-[6-(1-methylethyl)-3-pyridinyl]-8-(4-morpholinyl)-imidazo[1,2-b]pyridazine

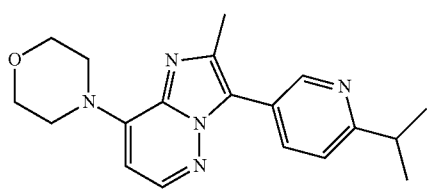 [SMILES: Cc1nc2c(N3CCOCC3)ccnn2c1-c1ccc(C(C)C)nc1]

A 2M solution of isopropylmagnesium chloride in tetrahydrofuran (0.758, 1.52) was added to a stirred solution of intermediate 35 (0.25 g, 0.76 mmol) and [1,3-bis(diphenylphosphino)propane]dichloronickel (II) (0.021 g, 0.038 mmol) in tetrahydrofuran (5 ml) at 0° C. The mixture was allowed to warm to room temperature over 1 h. and then stirred for a further 2 h. A 10% solution of ammonium chloride solution was added and the mixture was extracted with dichloromethane. The organic layer was separated, dried (Na$_2$SO$_4$), filtered and the solvents evaporated in vacuo. The crude product was purified by flash column chromatography (silica; 7 M solution of ammonia in methanol in dichloromethane 0/100 to 2/98). The less pure fractions were evaporated in vacuo and the residue purified again by flash column chromatography (silica, ethyl acetate in heptane 20/80 to 60/40). The desired fractions were combined and concentrated in vacuo to yield compound 32 (0.116 g, 45%). $^1$H NMR (400 MHz, CDCl$_3$) δ ppm 1.36 (d, J=6.9 Hz, 6H), 2.54 (s, 3H), 3.13 (spt, J=6.9 Hz, 1H), 3.85-4.07 (m, 8H), 6.09 (d, J=5.5 Hz, 1H), 7.32 (d, J=8.1 Hz, 1H), 7.98 (dd, J=8.1, 2.1 Hz, 1H), 7.99 (d, J=5.5 Hz, 1H), 8.79 (d, J=2.1 Hz, 1H).

Example B33

Preparation of compound 33: 3-(6-cyclopropyl-3-pyridinyl)-2-methyl-8-(4-morpholinyl)-imidazo[1,2-b]pyridazine

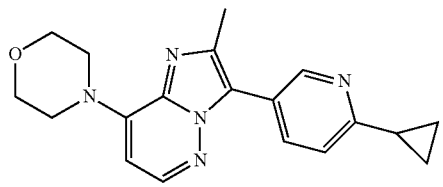 [SMILES: Cc1nc2c(N3CCOCC3)ccnn2c1-c1ccc(C2CC2)nc1]

Palladium (II) acetate (0.031 g, 0.14 mmol) was added to a stirred solution of intermediate 35 (0.3 g, 0.91 mmol), cyclopropylboronic acid (0.117 g, 1.37 mmol), 2-dicyclohexylphosphino-2',6'-dimethoxybiphenyl (0.244 g, 0.594 mmol) and potassium phosphate (0.11 g, 0.27 mmol) in toluene (5 ml). The mixture was stirred at 80° C. for 1 d. in a sealed tube under nitrogen and then diluted with dichloromethane and washed with water. The organic layer was separated, dried (Na$_2$SO$_4$), filtered and the solvents evaporated in vacuo. The crude product was purified by flash column chromatography (silica; ethyl acetate in heptane 20/80 to 100/0). The desired fractions were collected and concentrated in vacuo and the crude product triturated with diisopropyl ether to yield compound 33 (0.091 g, 30%) as a white solid. $^1$H NMR (500 MHz, CDCl$_3$) δ ppm 1.00-1.06 (m, 2H), 1.06-1.12 (m, 2H), 2.06-2.13 (m, 1H), 2.51 (s, 3H), 3.90-4.00 (m, 8H), 6.08 (d, J=5.8 Hz, 1H), 7.26 (d, J=7.5 Hz, 4H), 7.89 (dd, J=8.1, 2.0 Hz, 1H), 7.97 (d, J=5.5 Hz, 1H), 8.69 (d, J=2.3 Hz, 1H).

Example B34

Preparation of compound 34: 3-[6-[(3R)-3-methoxy-1-pyrrolidinyl]-3-pyridinyl]-2-methyl-8-(4-morpholinyl)-imidazo[1,2-b]pyridazine

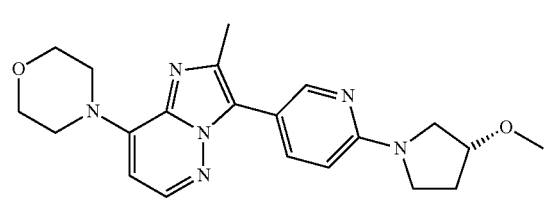

A mixture of intermediate 35 (0.2 g, 0.61 mmol), (R)-(+)-3-pyrrolidinol (0.21 g, 2.43 mmol) and diisopropylethylamine (0.158 ml, 0.91 mmol) was stirred at 120° C. for 3 h. The mixture was diluted with dichloromethane and extracted with a saturated solution of ammonium chloride. The organic layer was separated, dried (MgSO$_4$), filtered and the solvents evaporated in vacuo. The crude product was dissolved in tetrahydrofuran (10 ml) and sodium tert-butoxide (0.34 g, 3.03 mmol), 18-crown-6 (0.024 g, 0.091 mmol) and iodomethane (0.378 ml, 6.06 mmol) were added. The mixture was stirred at room temperature for 18 h., then diluted with dichloromethane and washed with water. The organic layer was separated, dried (MgSO$_4$), filtered and the solvents evaporated in vacuo. The crude product was purified by column chromatography (silica; dichloromethane). The desired fractions were collected and concentrated in vacuo to yield compound 34 (0.091 g, 30%) as a white solid. $^1$H NMR (500 MHz, CDCl$_3$) δ ppm 2.08-2.24 (m, 2H), 2.50 (s, 3H), 3.38 (s, 3H), 3.59 (dd, J=8.5, 5.9 Hz, 2H), 3.64-3.71 (m, 2H), 3.90-3.98 (m, 8H), 4.08-4.14 (m, 1H), 6.04 (d, J=5.5 Hz, 1H), 6.51 (d, J=8.7 Hz, 1H), 7.78 (dd, J=8.7, 2.3 Hz, 1H), 7.95 (d, J=5.5 Hz, 1H), 8.37 (d, J=2.3 Hz, 1H).

Example B35

Preparation of compound 35: 2-methyl-3-[1-(2-methylpropyl)-1H-pyrazol-4-yl]-8-(4-morpholinyl)-imidazo[1,2-b]pyridazine

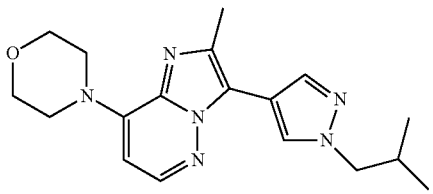 [SMILES: Cc1nc2c(N3CCOCC3)ccnn2c1-c1cnn(CC(C)C)c1]

Tetrakis(triphenylphosphine)palladium(0) (0.017 g, 0.015 mmol) was added to a stirred solution of intermediate 26 (0.2 g, 0.58 mmol) and 1-isobutyl-4-(4,4,5,5-tetramethyl-1,3,2-dioxaborolan-2-yl)-1H-pyrazole (0.18 g, 0.73 mmol) in a mixture of 1,4-dioxane (8 ml) and a saturated solution of sodium carbonate (2 ml). The mixture was stirred at 140° C. for 20 min. in a sealed tube under nitrogen, under microwave irradiation. The mixture was filtered through a pad of diatomaceous earth and the filtrate diluted with dichlorometane and extracted with water. The organic layer was separated, dried (Na$_2$SO$_4$), filtered and the solvents evaporated in vacuo. The crude product was purified by flash column chromatography (silica; ethyl acetate in dichloromethane 0/100 to 40/60). The desired fractions were collected and concentrated in vacuo to yield compound 35 (0.14 mg, 71%) as a white solid. $^1$H NMR (500 MHz, CDCl$_3$) δ ppm 0.97 (d, J=6.6 Hz, 6H), 2.30 (spt, J=6.7 Hz, 1H), 2.61 (s, 3H), 3.89-3.97 (m, 8H), 4.01 (d, J=7.2 Hz, 2H), 6.06 (d, J=5.8 Hz, 1H), 8.01 (s, 1H), 8.05 (d, J=5.5 Hz, 1H), 8.17 (s, 1H).

The following compounds were prepared from the indicated precursors according to a protocol analogous to that of B35.

Example B36

Preparation of compound 36: 3-[1-(2-methoxyethyl)-1H-pyrazol-4-yl]-2-methyl-8-(4-morpholinyl)-imidazo[1,2-b]pyridazine

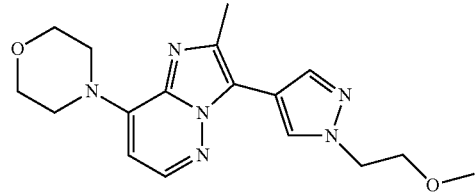 [SMILES: COCCn1cc(-c2c(C)nc3c(N4CCOCC4)ccnn23)cn1]

From intermediate 32 and intermediate 68). Flash column chromatography (silica; 7 M solution of ammonia in methanol in dichloromethane 0/100 to 4/96) and precipitation from diisopropyl ether yielded compound 36 as a white solid (57%). $^1$H NMR (400 MHz, CDCl$_3$) δ ppm 2.61 (s, 3H), 3.36 (s, 3H), 3.82 (t, J=5.4 Hz, 2H), 3.94 (br. s, 8H), 4.39 (t, J=5.4 Hz, 2H), 6.06 (d, J=5.8 Hz, 1H), 8.04 (s, 1H), 8.05 (d, J=5.5 Hz, 1H), 8.24 (s, 1H).

Example B37

Preparation of compound 37: 3-[1-(2-methoxy-2-methylpropyl)-1H-pyrazol-4-yl]-2-methyl-8-(4-morpholinyl)-imidazo[1,2-b]pyridazine

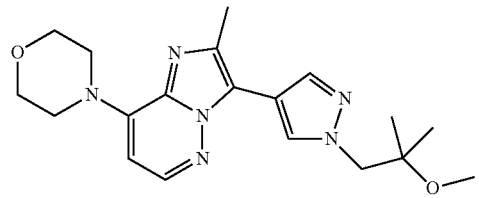 [SMILES: COC(C)(C)Cn1cc(-c2c(C)nc3c(N4CCOCC4)ccnn23)cn1]

From intermediate 26 and intermediate 67. Flash column chromatography (silica; ethyl acetate and dichloromethane in heptane 0/100/0 to 0/0/100 to 80/0/20), filtration through Isolute SCX-2 cartridge and precipitation from diethyl ether yielded compound 37 as a white solid (29%). $^1$H NMR (500 MHz, DMSO-d$_6$) δ ppm 1.12 (s, 6H), 2.50 (s, 3H), 3.20 (s, 3H), 3.78 (br t, J=4.9 Hz, 4H), 3.96 (br t, J=4.9 Hz, 4H), 4.23 (s, 2H), 6.31 (d, J=5.8 Hz, 1H), 8.00 (s, 1H), 8.16 (d, J=5.8 Hz, 1H), 8.26 (s, 1H).

Example B38

Preparation of compound 38: 2-cyclopropyl-3-[1-(2-methoxy-2-methylpropyl)-1H-pyrazol-4-yl]-8-(4-morpholinyl)-imidazo[1,2-b]pyridazine

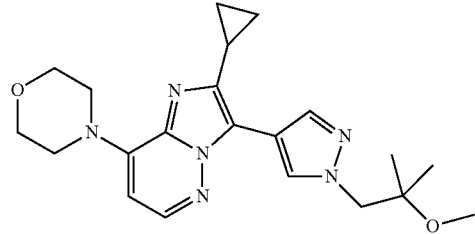 [SMILES: COC(C)(C)Cn1cc(-c2c(C3CC3)nc3c(N4CCOCC4)ccnn23)cn1]

10% Palladium on activated charcoal (0.284 g) was added to a mixture of intermediate 69 (0.125 g, 0.29 mmol) and triethylamine (0.08 ml, 0.58 mmol) in a mixture of methanol (6 ml) and tetrahydrofuran (6 ml). The mixture was hydrogenated (atmospheric pressure) at room temperature for 24 h. and then filtered through a pad of diatomaceous earth and the filtrate was concentrated in vacuo. The crude product was purified by flash column chromatography (silica; ethyl acetate in heptane 30/70 to 100/0). The desired fractions were collected and concentrated in vacuo to yield compound 38 (0.116 g, 99%) as a white solid. $^1$H NMR (500 MHz, DMSO-$d_6$) δ ppm 0.85-0.95 (m, 2H), 0.95-1.02 (m, 2H), 1.12 (s, 6H), 2.15-2.23 (m, 1H), 3.20 (s, 3H), 3.71-3.83 (m, 4H), 3.85-3.98 (m, 4H), 4.23 (s, 2H), 6.30 (d, J=5.8 Hz, 1H), 8.09 (s, 1H), 8.15 (d, J=5.5 Hz, 1H), 8.32 (s, 1H).

Additional compounds were prepared from the corresponding intermediates according to procedures similar to those described for the synthesis of the corresponding Examples previously described. The corresponding intermediates were prepared by procedures similar to those previously described either in the Experimental Part or in the Synthesis section. Compound 1 was isolated as the free base and also converted to the hydrochloride salt (compound 1a), the maleate salt (compound 1b), the monohydrate form (compound 1c), and the phosphate salt (compound 1d). Compound 45 was isolated as the corresponding hydrochloric acid salt (.HCl). The assignment of configuration in compounds 34, 113 and 131 derives from the reagent used in the synthesis of the compounds.

TABLE 1

Compounds and melting points thereof according to formula (I) prepared according to the above methods.

TABLE 1-continued
Compounds and melting points thereof according to formula (I) prepared according to the above methods.
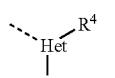
| Co. No. | Ex. No. | R¹ | R² | R³ | Het–R⁴ / R⁵ | M. p. (° C.) |
|---|---|---|---|---|---|---|
| 4 | B4 | 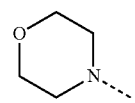 | 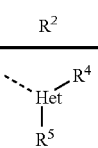 | 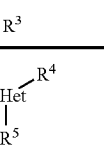 | 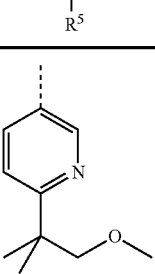 | >300 Dec. |
| 5 | B5 | 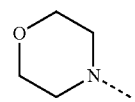 |  |  | 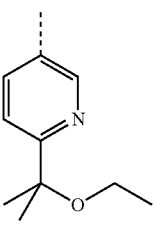 | 135.3 |
| 6 | B6 | 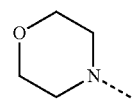 |  |  | 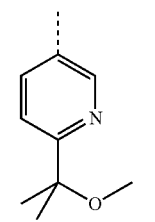 | 132.5 |
| 7 | B7 | 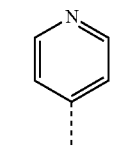 | 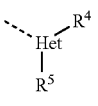 | 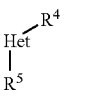 | 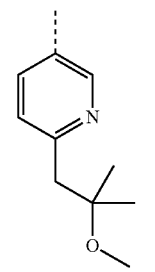 | 126.1 |
| 8 | B8 | 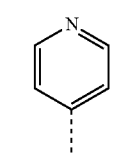 | 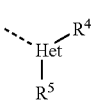 | 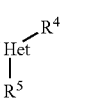 | 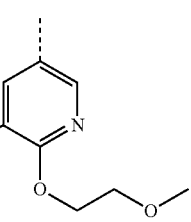 | 159 |

TABLE 1-continued
Compounds and melting points thereof according to formula (I) prepared according to the above methods.
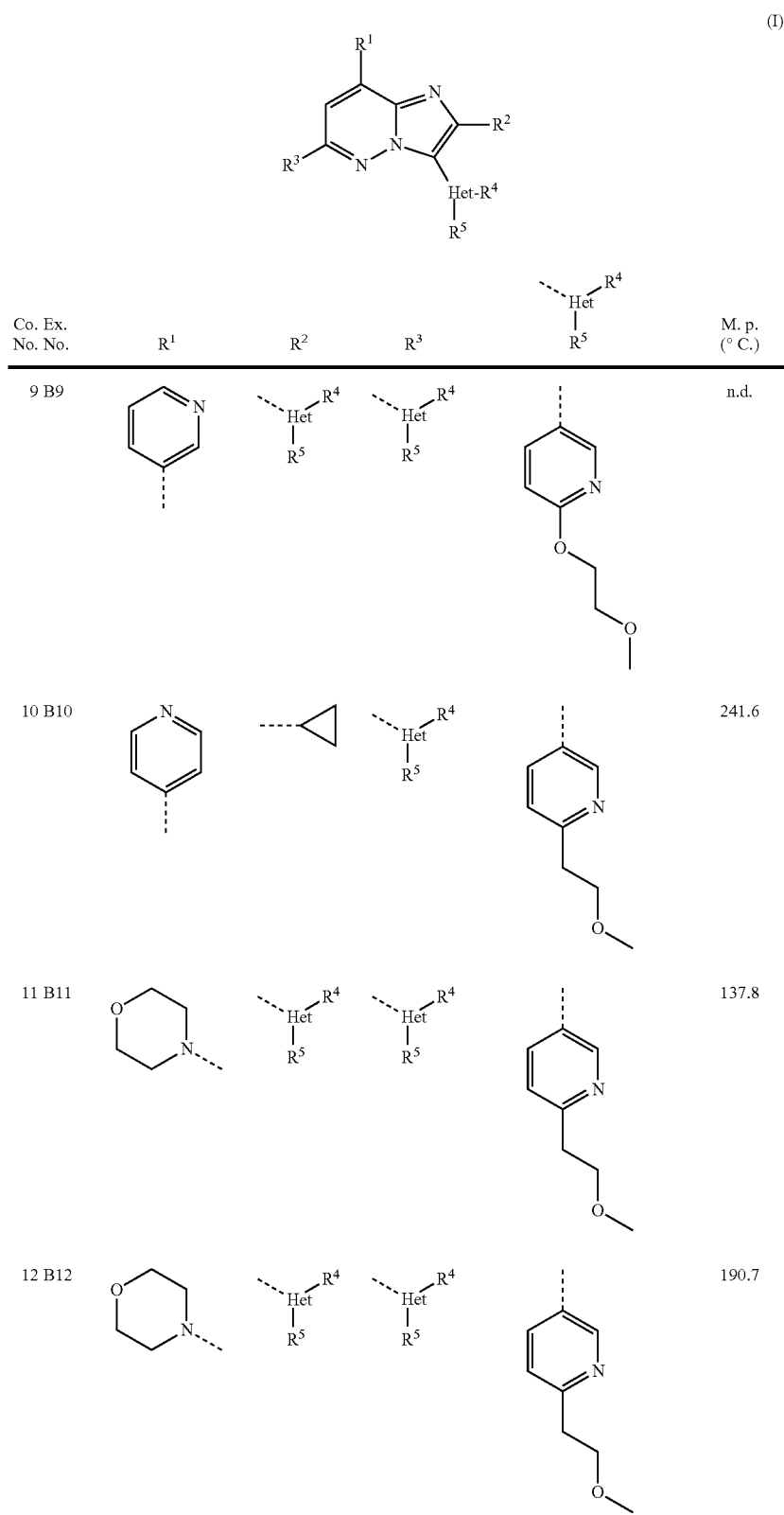

TABLE 1-continued

Compounds and melting points thereof according to formula (I) prepared according to the above methods.

| Co. No. | Ex. No. | R¹ | R² | R³ | Het(R⁴)(R⁵) | M.p. (°C.) |
|---|---|---|---|---|---|---|
| 13 | B13 | morpholinyl | Het-R⁴/R⁵ | cyclopropyl | pyridine with CH₂CH₂OCH₃ | 137.2 |
| 14 | B14 | pyridinyl | Het-R⁴/R⁵ | cyclopropyl | pyridine with CH₂CH₂OCH₃ | >300 Dec. |
| 15 | B15 | morpholinyl | cyclopropyl | Het-R⁴/R⁵ | pyridine with CH₂CH₂OCH₃ | 122.5 |
| 16 | B16 | morpholinyl | Het-R⁴/R⁵ | Het-R⁴/R⁵ | pyridine with OCH₂CH₂OCH₃ | n.d. |

TABLE 1-continued

Compounds and melting points thereof according to formula (I) prepared according to the above methods.

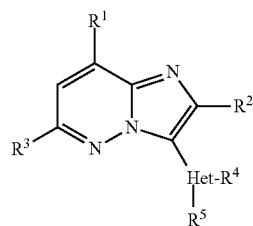

| Co. No. | Ex. No. | R¹ | R² | R³ | ⋯Het⟨R⁴/R⁵ | M. p. (° C.) |
|---|---|---|---|---|---|---|
| 17 | B17 | morpholin-4-yl | ⋯Het⟨R⁴/R⁵ | ⋯Het⟨R⁴/R⁵ | 6-(ethoxymethyl)pyridin-3-yl | >300 Dec. |
| 18 | B18 | morpholin-4-yl | ⋯Het⟨R⁴/R⁵ | ⋯Het⟨R⁴/R⁵ | 6-(2-methoxy-2-methylpropoxy)pyridin-3-yl | >300 Dec. |
| 19 | B19 | morpholin-4-yl | ⋯Het⟨R⁴/R⁵ | ⋯Het⟨R⁴/R⁵ | 6-(morpholin-4-yl)pyridin-3-yl | n.d. |
| 20 | B20 | pyridin-4-yl | ⋯Het⟨R⁴/R⁵ | ⋯Het⟨R⁴/R⁵ | 6-(2-methoxyethyl)pyridin-3-yl | 149.7 |

TABLE 1-continued

Compounds and melting points thereof according to formula (I) prepared according to the above methods.

| Co. Ex. No. | No. | R¹ | R² | R³ | Het-R⁴ / R⁵ | M.p. (°C.) |
|---|---|---|---|---|---|---|
| 21 | B21 | pyridin-4-yl | Het(R⁴)(R⁵) | Het(R⁴)(R⁵) | 6-(2-methoxyethoxy)pyridin-3-yl | 168.7 |
| 22 | B22 | morpholin-4-yl | cyclopropyl | Het(R⁴)(R⁵) | 6-(2-methoxyethyl)pyridin-3-yl | 111.4 |
| 23 | B23 | morpholin-4-yl | Het(R⁴)(R⁵) | Het(R⁴)(R⁵) | 6-(2-methoxyethyl)pyridin-3-yl | 115.4 |
| 24 | B24 | pyridin-4-yl | Het(R⁴)(R⁵) | Het(R⁴)(R⁵) | 6-(2-methoxyethyl)pyridin-3-yl | >300 Dec. |

TABLE 1-continued

Compounds and melting points thereof according to formula (I) prepared according to the above methods.

| Co. No. | Ex. No. | R¹ | R² | R³ | Het / R⁴ / R⁵ | M. p. (° C.) |
|---|---|---|---|---|---|---|
| 25 | B25 | morpholinyl | Het-R⁴/R⁵ | Het-R⁴/R⁵ | 5-(2-ethoxyethyl)pyridin-2-yl | n.d. |
| 26 | B26 | morpholinyl | Het-R⁴/R⁵ | Het-R⁴/R⁵ | 4-(2-methoxyethyl)pyridin-2-yl | n.d. |
| 27 | B27 | morpholinyl | Het-R⁴/R⁵ | Het-R⁴/R⁵ | 2-(tetrahydropyran-4-yl)pyridin-5-yl | 274.4 |
| 28 | B28 | morpholinyl | Het-R⁴/R⁵ | Het-R⁴/R⁵ | 2-ethylpyridin-5-yl | 130.2 |
| 29 | B29 | morpholinyl | Het-R⁴/R⁵ | Het-R⁴/R⁵ | 5-(3-methoxy-3-methylbutyl)pyridin-2-yl | >300 Dec. |

TABLE 1-continued
Compounds and melting points thereof according to formula (I) prepared according to the above methods.
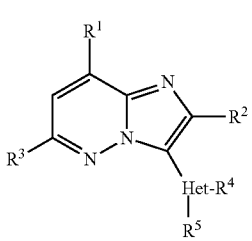
| Co. No. | Ex. No. | R¹ | R² | R³ | Het-R⁴ / R⁵ | M. p. (° C.) |
|---|---|---|---|---|---|---|
| 30 | B30 | 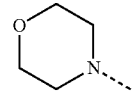 | 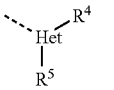 | 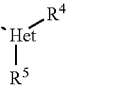 | 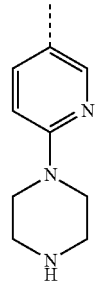 | n.d. |
| 31 | B31 | 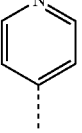 | 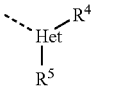 | 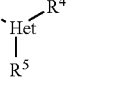 | 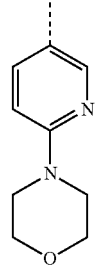 | >300 Dec. |
| 32 | B35 | 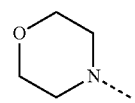 | 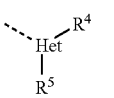 | 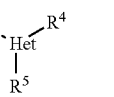 | 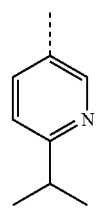 | 129.3 |
| 33 | B33 | 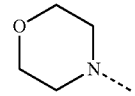 | 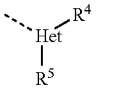 | 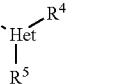 | 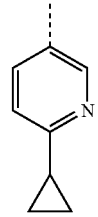 | 142.5 |

TABLE 1-continued

Compounds and melting points thereof according to formula (I) prepared according to the above methods.

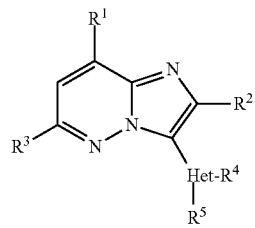

| Co. No. | Ex. No. | R¹ | R² | R³ | Het-R⁴/R⁵ | M. p. (° C.) |
|---|---|---|---|---|---|---|
| 34 | B34 | morpholine | Het-R⁴/R⁵ | Het-R⁴/R⁵ | pyridine-pyrrolidine-OMe | 162 |
| 35 | B35 | morpholine | Het-R⁴/R⁵ | Het-R⁴/R⁵ | pyrazole-isobutyl | n.d. |
| 36 | B36 | morpholine | Het-R⁴/R⁵ | Het-R⁴/R⁵ | pyrazole-CH₂CH₂OMe | 113.7 |
| 37 | B37 | morpholine | Het-R⁴/R⁵ | Het-R⁴/R⁵ | pyrazole-CH₂C(CH₃)₂OMe | 126.1 |
| 38 | B38 | morpholine | cyclopropyl | Het-R⁴/R⁵ | pyrazole-CH₂C(CH₃)₂OMe | n.d. |

TABLE 1-continued
Compounds and melting points thereof according to formula (I) prepared according to the above methods.
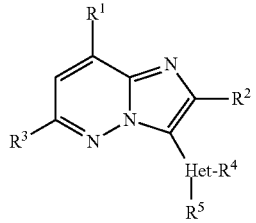
| Co. No. | Ex. No. | R¹ | R² | R³ | Het—R⁴ / R⁵ | M. p. (° C.) |
|---|---|---|---|---|---|---|
| 39 | B1 | 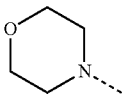 | 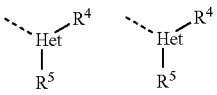 | 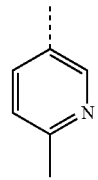 | 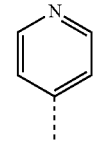 | 176.9 |
| 40 | B1 | 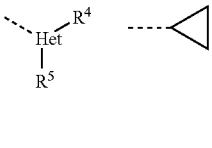 | 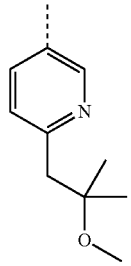 | 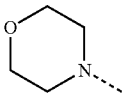 | 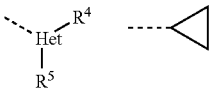 | 133.9 |
| 41 | B1 | 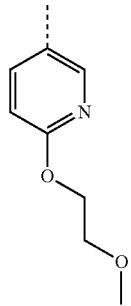 | 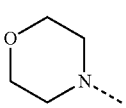 | 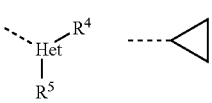 | 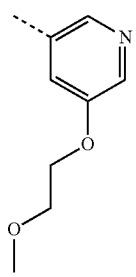 | 106.2 |
| 42 | B1 | | | | | 108.8 |

TABLE 1-continued

Compounds and melting points thereof according to formula (I) prepared according to the above methods.

| Co. Ex. No. No. | R¹ | R² | R³ | Het-R⁴ / R⁵ | M. p. (° C.) |
|---|---|---|---|---|---|
| 43 B1 | morpholin-4-yl | Het-R⁴/R⁵ | cyclopropyl | 5-pyridyl with 2-(2-methoxy-2-methylpropyl) | 128.5 |
| 44 B1 | 4-pyridyl | cyclopropyl | Het-R⁴/R⁵ | 5-pyridyl with 2-(2-methoxyethoxy) | 146.0 |
| 45 B1 | morpholin-4-yl | cyclopropyl | Het-R⁴/R⁵ | 5-pyridyl with 2-(2-methoxy-2-methylpropyl) | n.d. |
| 46 B1 | 4-pyridyl | cyclopropyl | Het-R⁴/R⁵ | 5-pyridyl with 2-(morpholin-4-yl) | >300 Dec. |

TABLE 1-continued

Compounds and melting points thereof according to formula (I) prepared according to the above methods.

(I)

| Co. No. | Ex. No. | R¹ | R² | R³ | ![Het-R⁴/R⁵ structure] | M. p. (° C.) |
|---|---|---|---|---|---|---|
| 47 | B1 | morpholine (N-linked) | Het(R⁴,R⁵) | Het(R⁴,R⁵) | 5-pyridyl-CH₂-C(CH₃)₂-OCH₃ | 123.5 |
| 48 | B1 | 4-pyridyl | Het(R⁴,R⁵) | Het(R⁴,R⁵) | 5-pyridyl-CH₂-C(CH₃)₂-OCH₃ | 159.0 |
| 49 | B1 | 4-pyridyl | Het(R⁴,R⁵) | Het(R⁴,R⁵) | 5-pyridyl-O-CH₂CH₂-OCH₃ | 128.3 |
| 50 | B1 | 4-pyridyl | cyclopropyl | Het(R⁴,R⁵) | 5-pyridyl-CH₂-C(CH₃)₂-OCH₃ | 114.1 |

TABLE 1-continued

Compounds and melting points thereof according to formula (I) prepared according to the above methods.

| Co. No. | Ex. No. | R¹ | R² | R³ | Het-R⁴ / R⁵ | M. p. (° C.) |
|---|---|---|---|---|---|---|
| 51 | B1 | morpholine | Het(R⁴,R⁵) | Het(R⁴,R⁵) | 5-pyridyl-CH₂-C(CH₃)₂-OCH₃ | 143.3 |
| 52 | B1 | morpholine | Het(R⁴,R⁵) | Het(R⁴,R⁵) | 5-pyridyl (2-O-CH₂CH₂-OCH₃) | n.d. |
| 53 | B1 | morpholine | cyclopropyl | Het(R⁴,R⁵) | 5-pyridyl-CH₂-C(CH₃)₂-OCH₃ | 200.9 |
| 54 | B1 | morpholine | cyclopropyl | Het(R⁴,R⁵) | 5-pyridyl-CH₂-C(CH₃)₂-OH | n.d. |

TABLE 1-continued

Compounds and melting points thereof according to formula (I) prepared according to the above methods.

(I)

| Co. No. | Ex. No. | R¹ | R² | R³ | ![Het-R⁴/R⁵] | M. p. (° C.) |
|---|---|---|---|---|---|---|
| 55 | B1 | 4-pyridyl | cyclopropyl | Het-R⁴/R⁵ | 5-(2-methoxy-2-methylpropyl)pyridin-2-yl | >300 Dec. |
| 56 | B1 | 4-pyridyl | cyclopropyl | Het-R⁴/R⁵ | 5-(2-methoxyethyl)pyridin-2-yl | >300 Dec. |
| 57 | B1 | 4-pyridyl | Het-R⁴/R⁵ | Het-R⁴/R⁵ | 5-(2-methoxyethyl)pyridin-2-yl | 142.1 |
| 58 | B1 | 4-pyridyl | Het-R⁴/R⁵ | cyclopropyl | 5-morpholinopyridin-2-yl | 198.1 |

TABLE 1-continued

Compounds and melting points thereof according to formula (I) prepared according to the above methods.

(I)

| Co. No. | Ex. No. | R¹ | R² | R³ | Het-R⁴ / R⁵ | M. p. (° C.) |
|---|---|---|---|---|---|---|
| 59 | B1 | 4-pyridyl | Het-R⁴/R⁵ | cyclopropyl | 5-(2-methoxyethoxy)pyridin-2-yl | 119.3 |
| 60 | B1 | 4-pyridyl | Het-R⁴/R⁵ | Het-R⁴/R⁵ | 5-(2-methoxy-2-methylpropyl)pyridin-2-yl | 152.1 |
| 61 | B1 | 4-pyridyl | Het-R⁴/R⁵ | Het-R⁴/R⁵ | 5-(morpholin-4-yl)pyridin-2-yl | 167.7 |
| 62 | B16 | morpholin-4-yl | Het-R⁴/R⁵ | Het-R⁴/R⁵ | 5-(2,2,2-trifluoroethoxy)pyridin-2-yl | >300 Dec. |

TABLE 1-continued

Compounds and melting points thereof according to formula (I) prepared according to the above methods.

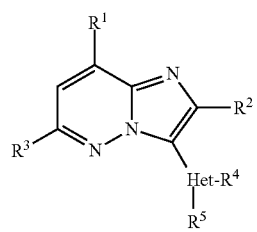

| Co. No. | Ex. No. | R¹ | R² | R³ | Het-R⁴/R⁵ | M. p. (° C.) |
|---|---|---|---|---|---|---|
| 63 | B16 | morpholinyl | Het-R⁴/R⁵ | Het-R⁴/R⁵ | 5-(6-CF₃)pyridinyl | n.d. |
| 64 | B16 | morpholinyl | Het-R⁴/R⁵ | Het-R⁴/R⁵ | 5-(6-(CH₂CH₂OCH₃))pyridinyl | 132.2 |
| 65 | B16 | morpholinyl | Het-R⁴/R⁵ | Het-R⁴/R⁵ | 5-(6-(OCH₂-cyclopropyl))pyridinyl | n.d. |
| 66 | B16 | morpholinyl | Het-R⁴/R⁵ | Het-R⁴/R⁵ | 5-(6-O-iPr)pyridinyl | n.d. |
| 67 | B16 | morpholinyl | Het-R⁴/R⁵ | Het-R⁴/R⁵ | 4-(2-O-iPr)pyridinyl | n.d. |

TABLE 1-continued
Compounds and melting points thereof according to formula (I) prepared according to the above methods.
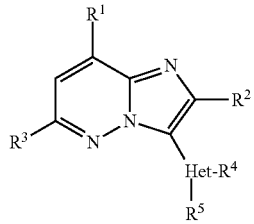
| Co. No. | Ex. No. | R¹ | R² | R³ |  | M. p. (° C.) |
|---|---|---|---|---|---|---|
| 68 | B16 |  | 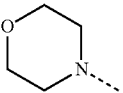 |  |  | 200.5 |
| 69 | B16 | 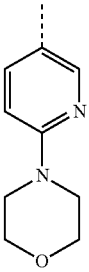 | 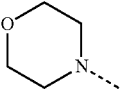 |  |  | 239.4 |
| 70 | B16 | 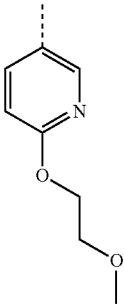 | 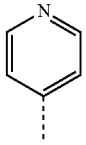 |  |  | n.d. |
| 71 | B16 | 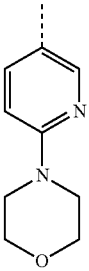 | 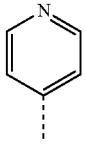 |  |  | >300 Dec. |

TABLE 1-continued

Compounds and melting points thereof according to formula (I) prepared according to the above methods.

| Co. No. | Ex. No. | R¹ | R² | R³ | Het(R⁴)(R⁵) | M. p. (° C.) |
|---|---|---|---|---|---|---|
| 72 | B16 | 4-pyridyl | cyclopropyl | Het-R⁴/R⁵ (cyclopropyl) | 6-(2-methoxyethoxy)pyridin-3-yl | 123.1 |
| 73 | B16 | morpholin-4-yl | cyclopropyl | Het-R⁴/R⁵ (cyclopropyl) | 6-(2-methoxyethoxy)pyridin-3-yl | n.d. |
| 74 | B16 | morpholin-4-yl | cyclopropyl | Het-R⁴/R⁵ (cyclopropyl) | 6-(2-methoxyethoxy)pyridin-3-yl | 99.7 |
| 75 | B16 | morpholin-4-yl | cyclopropyl | Het-R⁴/R⁵ (cyclopropyl) | 6-(morpholin-4-yl)pyridin-3-yl | 183.2 |

TABLE 1-continued

Compounds and melting points thereof according to formula (I) prepared according to the above methods.

| Co. No. | Ex. No. | R¹ | R² | R³ | Het-R⁴ / R⁵ | M. p. (° C.) |
|---|---|---|---|---|---|---|
| 76 | B25 | morpholin-4-yl | Het(R⁴,R⁵) | Het(R⁴,R⁵) | pyridin-3-yl with 2-(2-isopropoxyethyl) substituent | n.d. |
| 77 | B25 | morpholin-4-yl | Het(R⁴,R⁵) | Het(R⁴,R⁵) | pyridin-3-yl with 2-(2-pyrrolidin-1-ylethyl) substituent | >300 Dec. |
| 78 | B28 | morpholin-4-yl | Het(R⁴,R⁵) | cyclopropyl | pyridin-3-yl with 2-(tetrahydropyran-4-yl) substituent | 177.4 |
| 79 | B28 | morpholin-4-yl | cyclopropyl | Het(R⁴,R⁵) | pyridin-3-yl with 2-(tetrahydropyran-4-yl) substituent | 196.2 |

TABLE 1-continued
Compounds and melting points thereof according to formula (I) prepared according to the above methods.
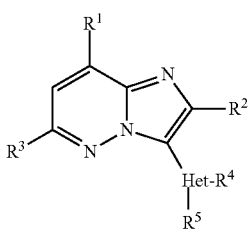
(I)
| Co. No. | Ex. No. | R¹ | R² | R³ | Het–R⁴ / R⁵ | M. p. (° C.) |
|---|---|---|---|---|---|---|
| 80 | B28 | 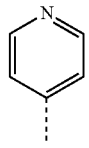 |  | 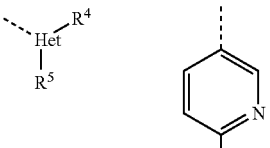 | 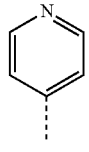 | 195.4 |
| 81 | B28 |  | 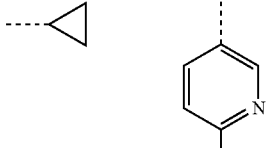 | 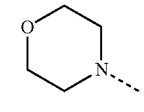 |  | n.d. |
| 82 | B28 | 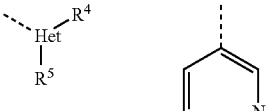 | 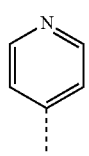 |  | 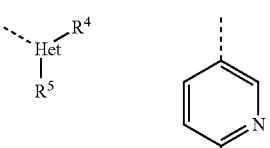 | n.d. |
| 83 | B29 | | | | | 153.7 |

TABLE 1-continued

Compounds and melting points thereof according to formula (I) prepared according to the above methods.

| Co. No. | Ex. No. | R¹ | R² | R³ | R⁴/R⁵ (Het) | M. p. (° C.) |
|---|---|---|---|---|---|---|
| 84 | B29 | morpholin-4-yl | cyclopropyl | Het-R⁴/R⁵ | 6-ethylpyridin-3-yl | 147.2 |
| 85 | B30 | morpholin-4-yl | cyclopropyl | Het-R⁴/R⁵ | 6-(2-methoxyethyl)pyridin-3-yl | n.d. |
| 86 | B30 | pyridin-4-yl | Het-R⁴/R⁵ | cyclopropyl | 6-ethylpyridin-3-yl | >300 Dec. |
| 87 | B30 | pyridin-4-yl | cyclopropyl | Het-R⁴/R⁵ | 6-ethylpyridin-3-yl | 140.3 |
| 88 | B30 | pyridin-4-yl | Het-R⁴/R⁵ | Het-R⁴/R⁵ | 6-ethylpyridin-3-yl | >300 Dec. |

TABLE 1-continued

Compounds and melting points thereof according to formula (I) prepared according to the above methods.

(I)

| Co. Ex. No. | No. | R¹ | R² | R³ | Het–R⁴ / R⁵ | M. p. (° C.) |
|---|---|---|---|---|---|---|
| 89 | B31 | morpholine | Het-R⁴/R⁵ | Het-R⁴/R⁵ | 2-(pyrrolidin-1-yl)pyridin-5-yl | 174.3 |
| 90 | B31 | morpholine | Het-R⁴/R⁵ | Het-R⁴/R⁵ | 2-(isopropylamino)pyridin-4-yl | >300 Dec. |
| 91 | B31 | morpholine | Het-R⁴/R⁵ | Het-R⁴/R⁵ | 2-morpholinopyridin-4-yl | 200.8 |
| 92 | B31 | morpholine | Het-R⁴/R⁵ | Het-R⁴/R⁵ | 2-(pyrrolidin-1-yl)pyridin-4-yl | n.d. |
| 93 | B31 | morpholine | Het-R⁴/R⁵ | Het-R⁴/R⁵ | 2-(isopropylamino)pyridin-4-yl | 201.2 |

TABLE 1-continued

Compounds and melting points thereof according to formula (I) prepared according to the above methods.

| Co. Ex. No. | No. | R¹ | R² | R³ | Het-R⁴ / R⁵ | M. p. (° C.) |
|---|---|---|---|---|---|---|
| 94 | B31 | morpholin-4-yl | Het(R⁴,R⁵) | cyclopropyl | 2-(morpholin-4-yl)pyridin-5-yl | 191.3 |
| 95 | B31 | morpholin-4-yl | cyclopropyl | Het(R⁴,R⁵) | 2-(morpholin-4-yl)pyridin-5-yl | n.d. |
| 96 | B31 | pyridin-4-yl | Het(R⁴,R⁵) | Het(R⁴,R⁵) | 2-(piperazin-1-yl)pyridin-5-yl | 220.2 |
| 97 | B31 | pyridin-4-yl | Het(R⁴,R⁵) | Het(R⁴,R⁵) | 2-(piperazin-1-yl)pyridin-5-yl | >300 Dec. |

TABLE 1-continued

Compounds and melting points thereof according to formula (I) prepared according to the above methods.

| Co. No. | Ex. No. | R¹ | R² | R³ | Het-R⁴ / R⁵ | M. p. (° C.) |
|---|---|---|---|---|---|---|
| 98 | B31 | morpholinyl | cyclopropyl | Het-R⁴/R⁵ | 5-(piperazin-1-yl)pyridin-2-yl | n.d. |
| 99 | B31 | pyridin-4-yl | Het-R⁴/R⁵ | cyclopropyl | 5-(piperazin-1-yl)pyridin-2-yl | >300 Dec. |
| 100 | B31 | morpholinyl | cyclopropyl | Het-R⁴/R⁵ | 5-(piperazin-1-yl)pyridin-2-yl | 200.1 |
| 101 | B31 | pyridin-4-yl | cyclopropyl | Het-R⁴/R⁵ | 5-(piperazin-1-yl)pyridin-2-yl | 223.2 |

TABLE 1-continued

Compounds and melting points thereof according to formula (I) prepared according to the above methods.

(I)

| Co. Ex. No. | No. | R¹ | R² | R³ | R⁵ (Het-R⁴) | M. p. (° C.) |
|---|---|---|---|---|---|---|
| 102 | B31 | 4-pyridyl | cyclopropyl | Het-R⁴/R⁵ (cyclopropyl-triazole) | 5-(2-piperazin-1-yl-pyridyl) | 212.1 |
| 103 | B31 | morpholinyl | Het-R⁴/R⁵ | Het-R⁴/R⁵ | 4-(2-piperazin-1-yl-pyridyl) | n.d. |
| 104 | B33 | morpholinyl | Het-R⁴/R⁵ | Het-R⁴/R⁵ | 5-(2-isobutyl-pyridyl) | 116.1 |
| 105 | B33 | morpholinyl | Het-R⁴/R⁵ | Het-R⁴/R⁵ | 4-(2-isobutyl-pyridyl) | 127.0 |
| 106 | B33 | morpholinyl | cyclopropyl | Het-R⁴/R⁵ | 5-(2-ethyl-pyridyl) | 118.0 |

TABLE 1-continued

Compounds and melting points thereof according to formula (I) prepared according to the above methods.

(I)

[Structure of formula (I): imidazo-pyridazine core with R¹, R², R³, and Het-R⁴/R⁵ substituents]

| Co. No. | Ex. No. | R¹ | R² | R³ | Het(R⁴)(R⁵) | M. p. (° C.) |
|---------|---------|----|----|----|-------------|--------------|
| 107 | B33 | morpholin-4-yl | Het-R⁴/R⁵ | cyclopropyl | 6-ethylpyridin-3-yl | 137.4 |
| 108 | B33 | morpholin-4-yl | Het-R⁴/R⁵ | Het-R⁴/R⁵ | 6-ethylpyridin-3-yl | 164.4 |
| 109 | B33 | morpholin-4-yl | Het-R⁴/R⁵ | Het-R⁴/R⁵ | 6-ethylpyridin-3-yl | n.d. |
| 110 | B34 | morpholin-4-yl | Het-R⁴/R⁵ | Het-R⁴/R⁵ | 6-cyclopropylpyridin-3-yl | 154.6 |
| 111 | B34 | pyridin-4-yl | Het-R⁴/R⁵ | Het-R⁴/R⁵ | 6-cyclopropylpyridin-3-yl | 179.6 |

TABLE 1-continued
Compounds and melting points thereof according to formula (I) prepared according to the above methods.
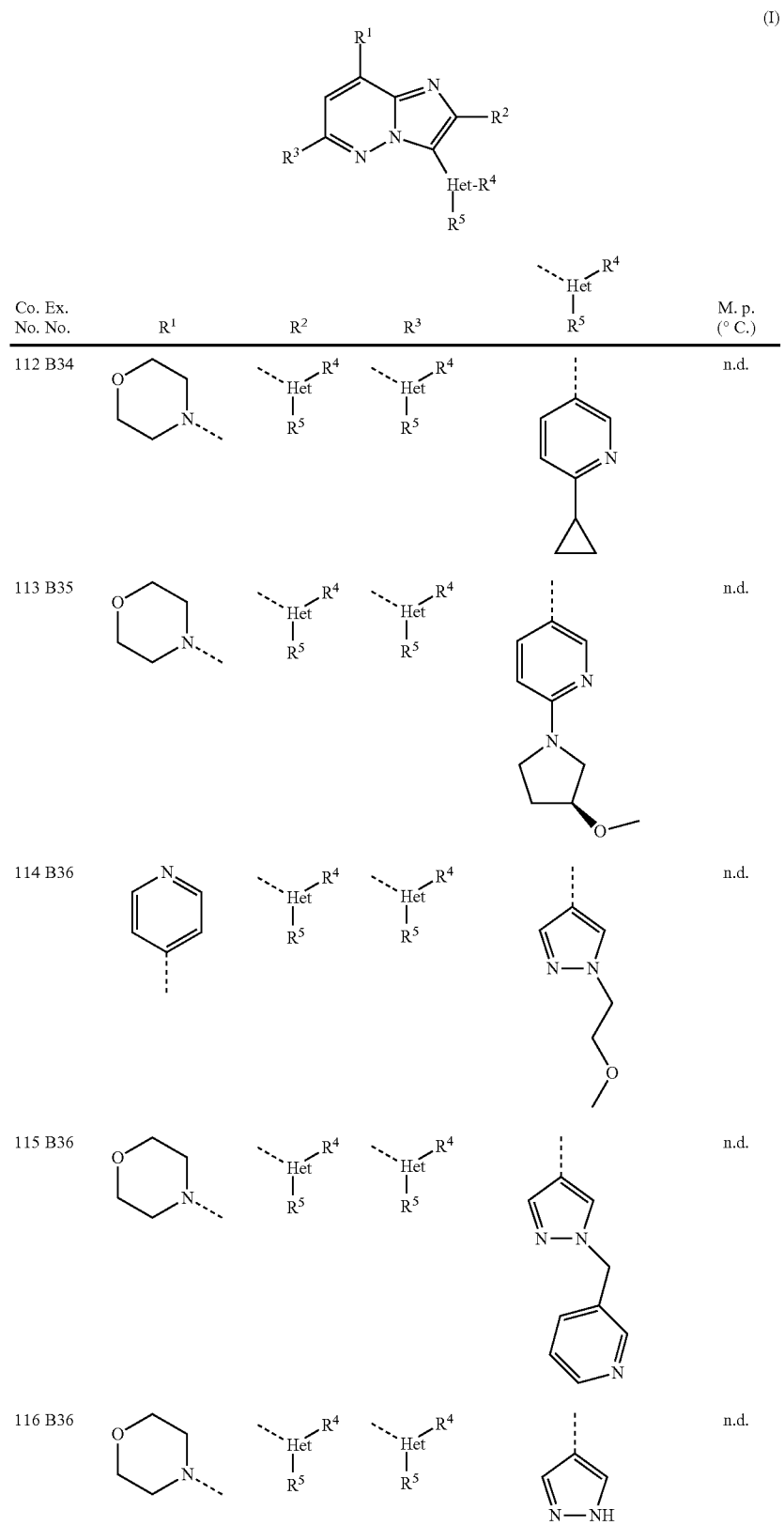

TABLE 1-continued

Compounds and melting points thereof according to formula (I) prepared according to the above methods.

| Co. No. | Ex. No. | R¹ | R² | R³ | Het-R⁴ / R⁵ | M.p. (°C.) |
|---|---|---|---|---|---|---|
| 117 | B36 | morpholinyl | Het(R⁴)(R⁵) | Het(R⁴)(R⁵) | pyrazolyl-tetrahydropyran | n.d. |
| 118 | B36 | morpholinyl | Het(R⁴)(R⁵) | Het(R⁴)(R⁵) | pyrazolyl-CH₂-(difluorocyclopropyl) | n.d. |
| 119 | B36 | morpholinyl | cyclopropyl | Het(R⁴)(R⁵) | pyrazolyl-CH₂CH₂-OCH₃ | n.d. |
| 120 | B36 | morpholinyl | isopropyl | Het(R⁴)(R⁵) | pyrazolyl-CH₂CH₂-OCH₃ | 150.1 |

TABLE 1-continued

Compounds and melting points thereof according to formula (I) prepared according to the above methods.

(I)

| Co. Ex.<br>No. No. | R¹ | R² | R³ | Het—R⁴<br>\|<br>R⁵ | M. p.<br>(° C.) |
|---|---|---|---|---|---|
| 121 B36 | pyridin-4-yl | isopropyl | Het-R⁴/R⁵ | pyrazole with N-CH₂CH₂-O-CH₃ | 129.8 |
| 122 B36 | pyridin-4-yl | Het-R⁴/R⁵ | Het-R⁴/R⁵ | pyrazole with N-CH₂CH₂-O-CH₃ | n.d. |
| 123 B36 | pyridin-4-yl | Het-R⁴/R⁵ | Het-R⁴/R⁵ | pyrazole with N-CH₂-C(CH₃)₂-O-CH₃ | n.d. |
| 124 B36 | pyridin-4-yl | Het-R⁴/R⁵ | Het-R⁴/R⁵ | pyrazole with N-isobutyl | 132.6 |

TABLE 1-continued

Compounds and melting points thereof according to formula (I) prepared according to the above methods.

(I)

[Structure of formula (I): imidazo-pyridazine core with substituents R¹, R², R³, Het-R⁴, R⁵]

| Co. Ex. No. | No. | R¹ | R² | R³ | Het-R⁴ / R⁵ | M. p. (° C.) |
|---|---|---|---|---|---|---|
| 125 | B36 | morpholinyl | Het(R⁴)(R⁵) | cyclopropyl | pyrazole-CH₂CH₂-O-CH₃ | 138.0 |
| 126 | B36 | 4-pyridyl | Het(R⁴)(R⁵) | cyclopropyl | pyrazole-CH₂CH₂-O-CH₃ | 130.6 |
| 127 | B36 | morpholinyl | Het(R⁴)(R⁵) | Het(R⁴)(R⁵) | pyrazole-CH₂CH₂-O-CH₃ | 120.8 |
| 128 | B36 | morpholinyl | Het(R⁴)(R⁵) | Het(R⁴)(R⁵) | pyrazole-CH₂-CF₂-cyclopropyl | n.d. |

TABLE 1-continued
Compounds and melting points thereof according to formula (I) prepared according to the above methods.
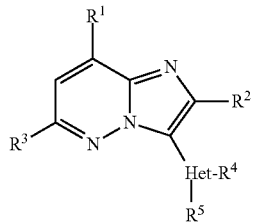
| Co. No. | Ex. No. | R¹ | R² | R³ | Het−R⁴ / R⁵ | M. p. (° C.) |
|---|---|---|---|---|---|---|
| 129 | B36 | 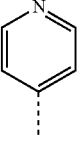 | 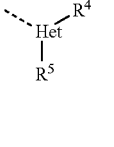 | 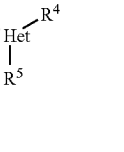 | 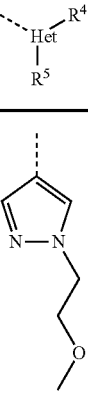 | 165.2 |
| 130 | B36 | 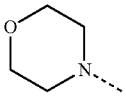 | 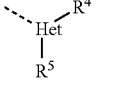 | 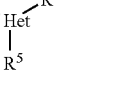 | 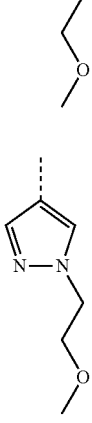 | 173.7 |
| 131 | B36 | 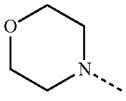 | 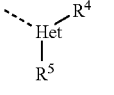 | 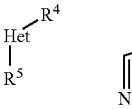 | 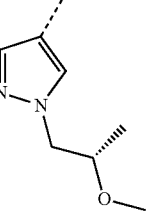 | n.d. |
| 132 | B36 | 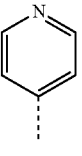 | 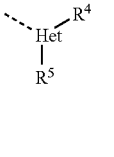 | 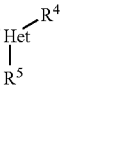 | 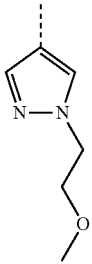 | 174.4 |

TABLE 1-continued

Compounds and melting points thereof according to formula (I) prepared according to the above methods.

| Co. No. | Ex. No. | R¹ | R² | R³ | Het-R⁴ / R⁵ | M. p. (° C.) |
|---|---|---|---|---|---|---|
| 133 | B36 | morpholin-4-yl | Het(R⁴,R⁵) | Het(R⁴,R⁵) | pyrazole-N-CH₂CH₂OCH₃ | 140.3 |
| 134 | B36 | pyridin-4-yl | Het(R⁴,R⁵) | Het(R⁴,R⁵) | pyrazole-N-CH₂CH₂OCH₃ | 138.5 |
| 135 | B36 | pyridin-4-yl | Het(R⁴,R⁵) | Het(R⁴,R⁵) | pyrazole-N-CH₂CF₃ | n.d. |
| 136 | B39 | pyrrolidin-1-yl | Het(R⁴,R⁵) | Het(R⁴,R⁵) | pyrazole-N-CH₂CH₂OCH₃ | n.d. |

TABLE 1-continued

Compounds and melting points thereof according to formula (I) prepared according to the above methods.

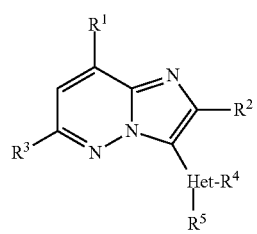

| Co. No. | Ex. No. | R¹ | R² | R³ | Het-R⁴ / R⁵ | M. p. (° C.) |
|---|---|---|---|---|---|---|
| 137 | B39 | morpholin-4-yl | Het(R⁴)(R⁵) | Het(R⁴)(R⁵) | 1-(2,2,2-trifluoroethyl)-1H-pyrazol-4-yl | n.d. |
| 138 | B39 | morpholin-4-yl | cyclopropyl | Het(R⁴)(R⁵) | 1-(2,2,2-trifluoroethyl)-1H-pyrazol-4-yl | 178.0 |
| 139 | B39 | morpholin-4-yl | Het(R⁴)(R⁵) | Het(R⁴)(R⁵) | 1-(2-methoxyethyl)-1H-pyrazol-4-yl | 132.6 |
| 140 | B39 | morpholin-4-yl | Het(R⁴)(R⁵) | Het(R⁴)(R⁵) | 1-(2-methoxyethyl)-1H-pyrazol-4-yl | >300 Dec. |
| 141 | B39 | pyridin-4-yl | cyclopropyl | Het(R⁴)(R⁵) | 1-(2,2,2-trifluoroethyl)-1H-pyrazol-4-yl | n.d. |

TABLE 1-continued

Compounds and melting points thereof according to formula (I) prepared according to the above methods.

| Co. Ex. No. | No. | R¹ | R² | R³ | Het(R⁴)(R⁵) | M.p. (° C.) |
|---|---|---|---|---|---|---|
| 142 | B39 | 4-pyridyl | cyclopropyl | Het-R⁴/R⁵ | 1-(2-methoxyethyl)pyrazol-4-yl | 114.0 |
| 143 | B39 | 4-pyridyl | cyclopropyl | Het-R⁴/R⁵ | 1-(2-methoxy-2-methylpropyl)pyrazol-4-yl | 138.0 |
| 144 | B39 | morpholinyl | Het-R⁴/R⁵ | Het-R⁴/R⁵ | 6-morpholinopyridin-3-yl | 190.7 |
| 145 | B39 | morpholinyl | Het-R⁴/R⁵ | Het-R⁴/R⁵ | 6-(2-methoxyethyl)pyridin-3-yl | n.d. |

TABLE 1-continued
Compounds and melting points thereof according to formula (I) prepared according to the above methods.
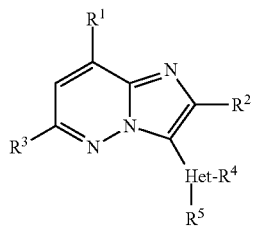
| Co. Ex. No. | No. | R¹ | R² | R³ | 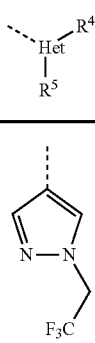 Het−R⁴ / R⁵ | M. p. (° C.) |
|---|---|---|---|---|---|---|
| 146 | A69 | 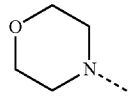 | 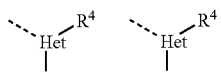 | | | n.d. |
| 147 | A69 | 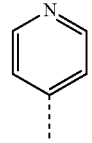 | 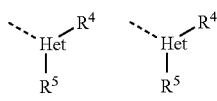 | | 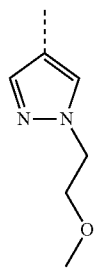 | >300 Dec. |
| 148 | B36 | 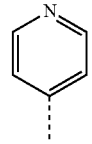 | 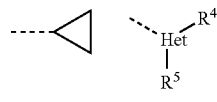 | | 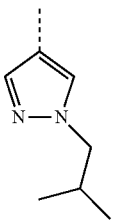 | 191.2 |
| 149 | B1 | 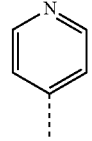 | 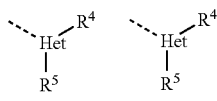 | | 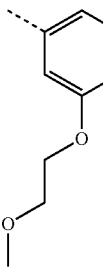 | 167.7 |

TABLE 1-continued
Compounds and melting points thereof according to formula (I) prepared according to the above methods.
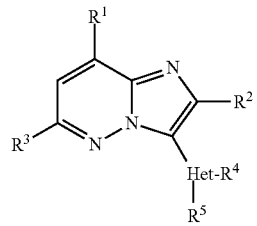
(I)
| Co. No. | Ex. No. | R¹ | R² | R³ | Het R⁴ R⁵ | M. p. (° C.) |
|---|---|---|---|---|---|---|
| 150 | A69 | morpholine | cyclopropyl | Het R⁴ R⁵ | pyrazole with CH₂C(CH₃)₂OCH₃ | n.d. |
(Dec means decomposition)
TABLE 2
Physico-chemical data for some compounds (nd = not determined).
| Co. No. | M. Wt. | [M + H]⁺ | R_t | Method |
|---|---|---|---|---|
| 4 | 381 | 382 | 3.08 | 5 |
| 5 | 381 | 382 | 3.07 | 5 |
| 6 | 367 | 368 | 2.64 | 5 |
| 7 | 373 | 374 | 2.31 | 5 |
| 8 | 376 | 375 | 2.68 | 5 |
| 9 | 361 | 362 | 2.20 | 5 |
| 10 | 371 | 372 | 2.61 | 5 |
| 11 | 339 | 340 | 1.98 | 5 |
| 12 | 369 | 370 | 2.65 | 5 |
| 13 | 393 | 394 | 2.87 | 5 |
| 14 | 385 | 386 | 2.63 | 5 |
| 15 | 393 | 394 | 3.14 | 5 |
| 16 | 369 | 370 | 2.40 | 5 |
| 17 | 353 | 354 | 2.32 | 5 |
| 18 | 397 | 398 | 2.99 | 5 |
| 19 | 380 | 381 | 2.29 | 5 |
| 20 | 345 | 346 | 1.86 | 5 |
| 21 | 361 | 362 | 2.21 | 5 |
| 21a | 361 | 362 | 2.20 | 5 |
| 22 | 379 | 380 | 2.83 | 5 |
| 23 | 367 | 368 | 3.30 | 1 |
| 24 | 359 | 360 | 2.17 | 5 |
| 25 | 367 | 368 | 2.41 | 5 |
| 26 | 353 | 354 | 2.0 | 5 |
| 27 | 379 | 380 | 2.28 | 5 |
| 28 | 323 | 324 | 2.44 | 5 |
| 29 | 395 | 396 | 2.78 | 5 |
| 30 | 379 | 380 | 1.25 | 5 |
| 31 | 372 | 373 | 2.15 | 5 |
| 32 | 337 | 338 | 3.43 | 2 |
| 33 | 335 | 336 | 1.99 | 5 |
| 34 | 394 | 395 | 3.00 | 5 |
| 35 | 340 | 341 | 3.39 | 1 |
| 36 | 342 | 343 | 3.02 | 1 |
| 37 | 370 | 371 | 2.31 | 5 |
| 38 | 396 | 397 | 3.03 | 5 |
| 39 | 309 | 310 | 1.98 | 5 |
| 40 | 413 | 414 | 3.06 | 5 |
| 41 | 409 | 410 | 3.26 | 5 |
| 42 | 409 | 410 | 2.72 | 5 |
| 43 | 421 | 422 | 3.31 | 5 |
| 44 | 387 | 388 | 3.03 | 5 |
| 45 | 407 | 408 | 3.33 | 5 |
| 46 | 398 | 399 | 2.92 | 5 |
| 47 | 395 | 396 | 2.81 | 5 |
| 48 | 387 | 388 | 2.61 | 5 |
| 49 | 375 | 376 | 2.55 | 5 |
| 50 | 399 | 400 | 3.08 | 5 |
| 51 | 367 | 368 | 2.44 | 5 |
| 52 | 355 | 356 | 2.32 | 5 |
| 53 | 421 | 422 | 3.61 | 5 |
| 54 | 393 | 394 | 2.74 | 5 |
| 55 | 413 | 414 | 3.36 | 5 |
| 56 | 385 | 386 | 2.89 | 5 |
| 57 | 331 | 332 | 1.76 | 5 |
| 58 | 412 | 413 | 2.92 | 5 |
| 59 | 401 | 402 | 3.03 | 5 |
| 60 | 359 | 360 | 2.19 | 5 |
| 61 | 358 | 359 | 3.31 | 1 |
| 62 | 393 | 394 | 4.07 | 1 |
| 63 | 380 | 381 | 2.29 | 5 |
| 64 | 421 | 422 | 3.16 | 5 |
| 65 | 365 | 366 | 3.38 | 5 |
| 66 | 353 | 354 | 3.35 | 5 |
| 67 | 353 | 354 | 3.35 | 5 |
| 68 | 394 | 395 | 2.58 | 5 |
| 69 | 383 | 384 | 2.71 | 5 |
| 70 | 386 | 387 | 2.45 | 5 |
| 71 | 412 | 413 | 3.21 | 5 |
| 72 | 401 | 402 | 2.40 | 5 |
| 73 | 395 | 396 | 3.26 | 5 |
| 74 | 409 | 410 | 3.55 | 5 |

TABLE 2-continued

Physico-chemical data for some compounds (nd = not determined).

| Co. No. | M. Wt. | [M + H]+ | $R_t$ | Method |
|---|---|---|---|---|
| 75 | 420 | 421 | 3.41 | 5 |
| 76 | 381 | 382 | 2.74 | 5 |
| 77 | 392 | 393 | 1.34 | 5 |
| 78 | 419 | 420 | 3.08 | 5 |
| 79 | 419 | 420 | 3.36 | 5 |
| 80 | 411 | 412 | 3.11 | 5 |
| 81 | 411 | 412 | 2.78 | 5 |
| 82 | 365 | 366 | 2.18 | 5 |
| 83 | 315 | 316 | 2.23 | 5 |
| 84 | 363 | 364 | 3.61 | 5 |
| 85 | 447 | 448 | 3.88 | 5 |
| 86 | 355 | 356 | 3.07 | 5 |
| 87 | 341 | 342 | 3.03 | 5 |
| 88 | 329 | 330 | 2.56 | 5 |
| 89 | 364 | 365 | 2.84 | 5 |
| 90 | 352 | 353 | 2.56 | 5 |
| 91 | 380 | 381 | 2.28 | 5 |
| 92 | 364 | 365 | 2.72 | 5 |
| 93 | 352 | 353 | 2.51 | 5 |
| 94 | 420 | 421 | 3.16 | 5 |
| 95 | 405 | 406 | 4.34 | 1 |
| 96 | 385 | 386 | 1.26 | 5 |
| 97 | 371 | 372 | 1.08 | 5 |
| 98 | 405 | 406 | 1.86 | 5 |
| 99 | 411 | 412 | 1.68 | 5 |
| 100 | 419 | 420 | 2.07 | 5 |
| 101 | 411 | 412 | 1.89 | 5 |
| 102 | 397 | 398 | 1.68 | 5 |
| 103 | 379 | 380 | 1.33 | 5 |
| 104 | 351 | 352 | 3.20 | 5 |
| 105 | 351 | 352 | 3.07 | 5 |
| 106 | 349 | 350 | 3.28 | 5 |
| 107 | 363 | 364 | 3.33 | 5 |
| 108 | 337 | 338 | 2.78 | 5 |
| 109 | 309 | 310 | 2.35 | 5 |
| 110 | 349 | 350 | 3.10 | 5 |
| 111 | 327 | 328 | 2.54 | 5 |
| 112 | 321 | 322 | 2.61 | 5 |
| 113 | 394 | 395 | 2.42 | 5 |
| 114 | 334 | 335 | 2.03 | 4 |
| 115 | 375 | 376 | 2.57 | 1 |
| 116 | 284 | 285 | 1.98 | 1 |
| 117 | 368 | 369 | 2.68 | 1 |
| 118 | 374 | 375 | 3.12 | 2 |
| 119 | 368 | 369 | 2.48 | 5 |
| 120 | 370 | 371 | 2.70 | 5 |
| 121 | 362 | 363 | 2.45 | 5 |
| 122 | 388 | 389 | 2.31 | 5 |
| 123 | 362 | 363 | 2.87 | 2 |
| 124 | 332 | 333 | 2.56 | 5 |
| 125 | 382 | 383 | 2.58 | 5 |
| 126 | 374 | 375 | 2.39 | 5 |
| 127 | 356 | 357 | 2.18 | 5 |
| 128 | 388 | 389 | 2.75 | 5 |
| 129 | 402 | 403 | 2.59 | 5 |
| 130 | 410 | 411 | 2.94 | 5 |
| 131 | 356 | 357 | 2.81 | 1 |
| 132 | 348 | 349 | 2.69 | 2 |
| 133 | 356 | 357 | 2.75 | 2 |
| 134 | 348 | 349 | 2.64 | 2 |
| 135 | 358 | 359 | 2.84 | 2 |
| 136 | 326 | 327 | 2.91 | 4 |
| 137 | 366 | 367 | 2.69 | 4 |
| 138 | 392 | 393 | 3.11 | 5 |
| 139 | 396 | 397 | 2.63 | 5 |
| 140 | 358 | 359 | 2.30 | 5 |
| 141 | 384 | 385 | 3.08 | 1 |
| 142 | 360 | 361 | 2.95 | 2 |
| 143 | 388 | 389 | 2.84 | 5 |
| 144 | 366 | 367 | 2.16 | 5 |
| 145 | 407 | 408 | 2.88 | 5 |
| 146 | 400 | 401 | 2.7 | 4 |
| 147 | 368 | 369 | 2.67 | 4 |
| 148 | 358 | 359 | 4.11 | 5 |
| 149 | 361 | 362 | 2.11 | 5 |

LCMS data: [M + H]+ means the protonated mass of the free base of the compound, $R_t$ means retention time (in minutes), method refers to the method used for LCMS.

Characterization of Compound 1 (Free Base Form) and the Phosphate Salt of Compound 1 (Compound 1d)

The results of the characterization by infrared spectrometry (IR), powder X-ray diffraction (XRD), differential scanning calorimetry (DSC), thermogravimetric analysis (TGA) and dynamic vapor sorption (DVS) characteristics for compound 1 (free base form) and the phosphate salt of compound 1 (compound 1d) are described below.

Micro Attenuated Total Reflectance (microATR)

Each sample was analyzed using a suitable microATR accessory as described below.

| | |
|---|---|
| number of scans: | 32 |
| resolution: | 1 cm−1 |
| wavelength range: | 4000 to 400 cm−1 |
| apparatus: | Thermo Nexus 670 FTIR spectrometer |
| detector: | DTGS with KBr windows |
| beamsplitter: | Ge on KBr |
| micro ATR accessory: | Harrick Split Pea with Si crystal |

The IR spectrum of compound 1 (free base form), is as substantially depicted in FIG. 1a, and reflects the vibrational modes of the molecular structure of the compound. Compound 1 is characterized by an FTIR spectrum with typical absorption bands at 1591, 1545, 1483, 1458, 1443, 1389, 1377, 1361, 1325, 1311, 1268, 1254, 1175, 1119, 1102, 1071, 1033, 990, 928, 849, 804, 745, 661, 585 and 563 cm$^{-1}$±2 cm$^{-1}$.

Figure 1B:
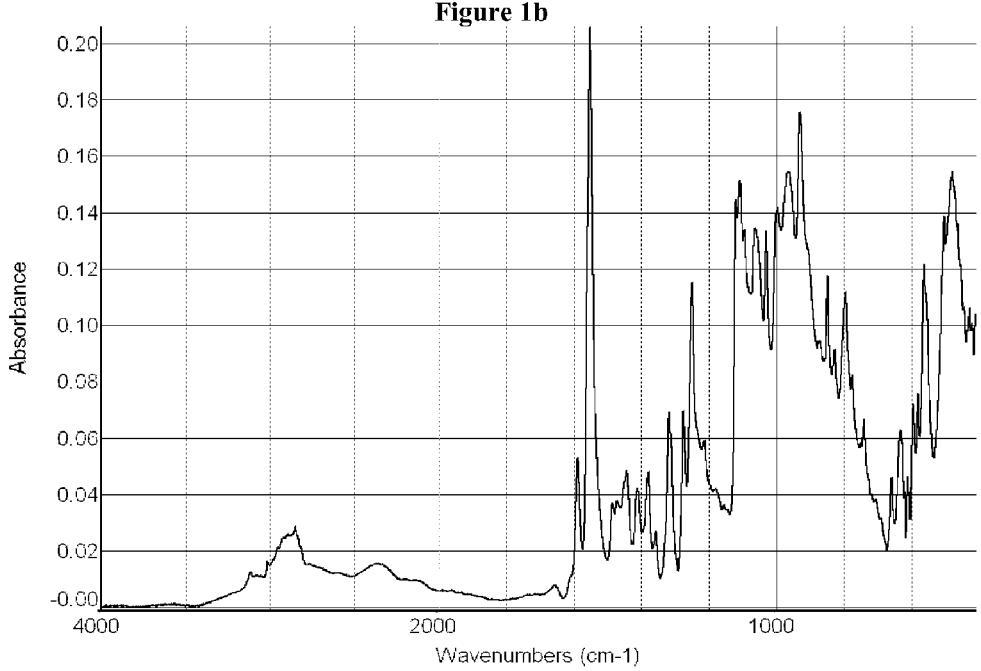
FIG. 1b is an Infrared (IR) spectrum representation of compound 1d.

The IR spectrum of compound 1d (the phosphate salt of compound 1) is as substantially depicted in FIG. 1b, and contains no bands corresponding to the free base. The spectrum reflects the vibrational modes of the molecular structure of the compound and shows the presence of characteristic bands for phosphate salt. Compound 1d is characterized by an FTIR spectrum with typical absorption bands at about 1589, 1552, 1318, 1275, 1250, 1120, 1108, 1095, 1064, 1031, 996, 964, 931, 849, 827, 795, 740, 595, 581, 563, 502 and 478 cm$^{-1}$±2 cm$^{-1}$.

Powder XRD

X-ray powder diffraction (XRPD) analysis was carried out on a Philips X'PertPRO MPD diffractometer PW3050/60 with generator PW3040. The instrument was equipped with a Cu LFF X-ray tube PW3373/10. The compound was spread on a zero background sample holder.

Instrument Parameters

| | |
|---|---|
| generator voltage: | 45 kV |
| generator amperage: | 40 mA |
| geometry: | Bragg-Brentano |
| stage: | spinner stage |

Measurement Conditions

| Incident beam path | | Diffracted beam path | |
|---|---|---|---|
| program, divergence slit: | 15 mm | long anti scatter shield: | + |
| Soller slit: | 0.04 rad | Soller slit: | 0.04 rad |
| beam mask: | 15 mm | Ni filter: | + |
| anti scatter slit: | 1° | detector: | X'Celerator |
| beam knife: | + | | |

| scan mode: | continuous |
|---|---|
| scan range: | 3 to 50° 2θ |
| step size: | 0.0167°/step |
| counting time: | 29.845 sec/step |
| spinner revolution time: | 1 sec |
| radiation type: | CuKα |

Figure 2A:
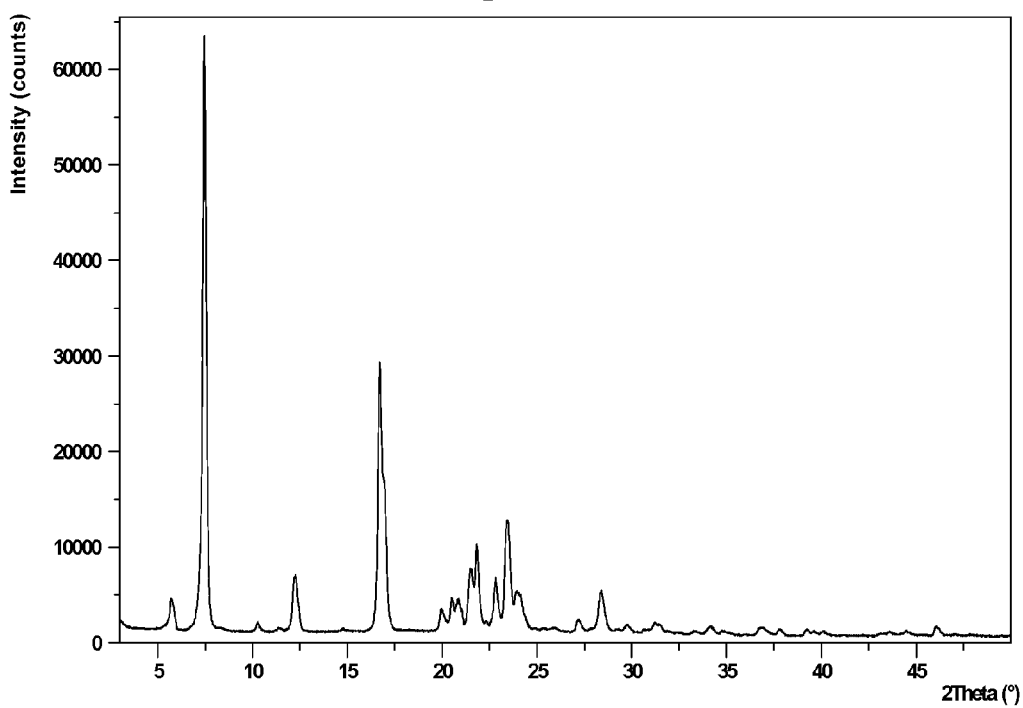
FIG. 2a is a powder X-Ray Diffraction (XRD) pattern representation of compound 1.

The X-ray powder diffraction pattern of compound 1 is as substantially depicted in FIG. 2a and shows diffraction peaks without the presence of a halo, indicating that this compound is present as a crystalline product.

Figure 2B:
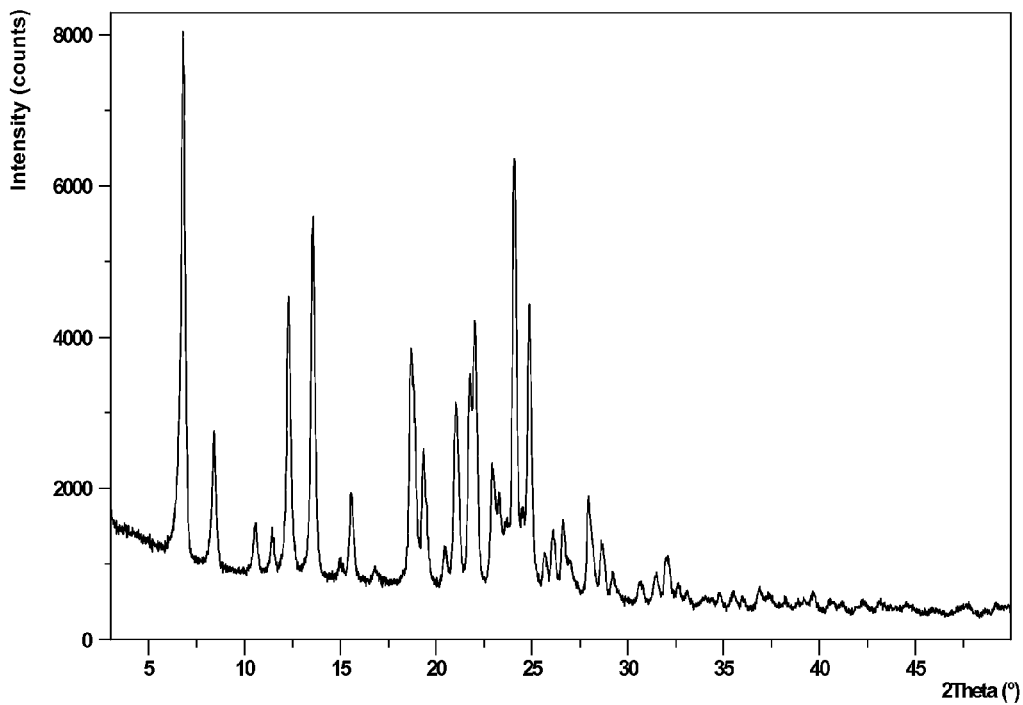
FIG. 2b is a powder X-Ray Diffraction (XRD) pattern representation of compound 1d.

The X-ray powder diffraction pattern of compound 1d (the phosphate salt of compound 1) is as substantially depicted in FIG. 2b and shows diffraction peaks without the presence of a halo, indicating that this compound is present as a crystalline product, containing no free base.

Differential Scanning Calorimetry (DSC)

A sample of about 3 mg of the compound was transferred into a standard aluminum TA-Instrument sample pan. The sample pan was closed with the appropriate cover and the DSC curve was recorded on a TA-Instruments Q1000 MTDSC equipped with a RCS cooling unit using the following parameters:

| initial temperature: | 25° C. |
|---|---|
| heating rate: | 10° C./min |
| final temperature: | 300° C. |
| nitrogen flow: | 50 ml/min |

It was found that compound 1 melts at 132.4° C. with a heat of fusion is 96 J/g and that compound 1d (the phosphate salt of compound 1) melts with decomposition at about 165.1° C.

Thermogravimetry (TGA)

A sample of the compound was transferred into an aluminum sample pan. The TG curve was recorded on a TA Instruments Q500 thermogravimeter using the following parameters:

| initial temperature: | room temperature |
|---|---|
| heating rate: | 20° C./min |
| resolution factor: | 4 |
| final condition: | 300° C. or <80[(w/w)%] |

For compound 1, a weight loss of 0.17% in the temperature region from room temperature up to 125° C. and of 0.16% between 125 and 190° C. were recorded. Additional weight loss was observed above 190° C.

For compound 1d (the phosphate salt of compound 1), a weight loss of 0.29% in the temperature region from room temperature up to 150° C. and a weight loss of 7.5% between 150 and 200° C. were observed.

Adsorption-Desorption

A sample of compound (about 7 mg of compound 1 and about 12 mg in the case of compound 1d (the phosphate salt of compound 1)) was transferred into a SMS dynamic vapor sorption model DVS-Advantage and the weight change with respect to the atmospheric humidity at 25° C. was recorded using the following parameters (RH means relative humidity):

| drying: | 60 min. under dry nitrogen at 25° C. |
|---|---|
| equilibrium: | ≤0.01%/min. for min: 15 min and max: 60 min. |
| RH (%) measurement points: | |
| first set: | 5, 10, 20, 30, 40, 50, 60, 70, 80, 90, 95, 90, 80, 70, 60, 50, 40, 30, 20, 10, 5 |
| second set: | 5, 10, 20, 30, 40, 50, 60, 70, 80, 90, 95, 90, 80, 70, 60, 50, 40, 30, 20, 10, 5, 0 |

During the initial drying step, a weight loss of 0.06% was registered for compound 1. The product showed no hygroscopic behavior and remained the same physical form during the test.

During the initial drying step, a weight loss of 0.3% was registered for compound 1d (the phosphate salt of compound 1). The product shows no hygroscopic behavior and remains crystalline during the test. No dissociation of the salt was observed.

Solubility of Crystalline Form of Compound 1 (Anhydrous Free Base) and the Phosphate Salt of Compound 1 (Compound 1d):

An excess of compound 1 (anhydrous free base) or of compound 1d (phosphate salt of compound 1), respectively was equilibrated with the solvent at 20° C. for at least 24 hours. After removing the undissolved compound (0.45 μm Millex LCR filter), the concentration in the solution was determined using UV spectrometry. The pH of the solution was measured. The results are shown in tables 2a and 2b below.

TABLE 2a

Solubility as a function of pH at 20° C. of compound 1 (anhydrous free base)

| Solvent | Solubility (mg/mL) of compound 1 | pH of solution |
|---|---|---|
| water | 0.009 | 8.7 |
| 0.1N HCl | 2.5 | 2.5 |
| 0.01N HCl | 0.32 | 3.0 |
| citrate-NaOH—HCl buffer pH 2 | 0.61 | 2.9 |
| citrate-NaOH buffer pH 5 | 0.012 | 5.0 |
| phosphate buffer pH 7 | 0.008 | 7.0 |
| borate-KCl—NaOH buffer pH 9 | 0.009 | 8.9 |
| phosphate-NaOH buffer pH 12 | 0.008 | 11.9 |
| 0.1N NaOH | 0.008 | 12.9 |

TABLE 2b

Solubility as a function of pH at 20° C. of compound 1d (phosphate salt of compound 1)

| Solvent | Solubility (mg/mL) of compound 1d | pH of solution |
|---|---|---|
| water | 9.7 | 2.6 |
| 0.1N HCl | 46.0 | 2.1 |
| 0.01N HCl | 11.9 | 2.5 |
| citrate-NaOH—HCl buffer pH 2 | 20.2 | 2.5 |
| citrate-NaOH buffer pH 5 | 0.14 | 4.9 |
| phosphate buffer pH 7 | 0.09 | 6.8 |
| borate-KCl—NaOH buffer pH 9 | 0.10 | 7.4 |
| phosphate-NaOH buffer pH 12 | 0.10 | 11.2 |
| 0.1N NaOH | 0.10 | 12.5 |

Intrinsic Dissolution Rate (IDR) of Compound 1 (Anhydrous Free Base), Compound 1d (Phosphate Salt of Compound 1) and Compound 1c (Monohydrate Form of Compound 1) Pressed as Miniaturized Pellets Dissolution rate measurements were performed using ±5 mg of compound 1 (anhydrous free base), compound 1d (phosphate salt) or compound 1c (monohydrate form), respectively pressed as pellets (of 0.0754 cm² area) made in a Mini-IDR™ compression system (from pION) with a compression of 40 bar for 1 min. The intrinsic dissolution rate was measured using a DISS Profiler™ system consisting in both a mini-bath and UV fiber optic (5 mm pathlength) probes connected to a photodiode array (PDA) spectrophotometer (from pION Inc). Each pellet prepared were positioned in individual vessels. The intrinsic dissolution test was performed using 0.01 M HCl (20 mL) maintained at 37.0±0.5° C. with a stirring rate of 100 rpm. The concentration measurements were performed using UV detection at 326 nm. The intrinsic dissolution rate (IDR) was calculated by dividing the dissolution rate by the exposure area of pellet (0.0754 cm²). The results are shown in table 2c below.

TABLE 2c

Average (IDR) for compound 1 (free base), compound 1d (phosphate salt) and compound 1c (monohydrate form) in 0.01M HCl at 100 rpm (wherein n represents the number of vessels).

| Compound | n | IDR (mg · min$^{-1}$ · cm$^{-2}$) |
|---|---|---|
| 1 (free base) | 2 | 0.8170 |
| 1d (phosphate salt) | 3 | 2.5172 |
| 1c (monohydrate form) | 2 | 1.1011 |

Compound 1d (phosphate salt) showed a fast intrinsic dissolution rate in 0.01 M HCl compared to compounds 1 and 1c (free base and hydrated forms, respectively). The absorbance values measured for the phosphate form after 5 min dissolution were over the UV detector limit. The pellets of compound 1d (phosphate salt) were totally dissolved within 10 min. The pellets of compounds 1 and 1c (free base and hydrated forms, respectively) showed similar intrinsic dissolution profile rates. The tablets started to break after 20 minutes dissolution.

Compound 1d (phosphate salt) showed the highest IDR value (e.i. 2.52 mg·min$^{-1}$·cm$^{-2}$). The free base (compound 1) and hydrated (compound 1c) forms presented lower IDR with similar values (e.i. 0.82 and 1.10 mg·min$^{-1}$·cm$^{-2}$).

Based on the above in vitro results, compound 1d, i.e. the phosphate salt of compound 1, constitutes an advantageous salt form of compound 1, having a much higher solubility compared to that of the anhydrous free base form (compound 1), and a higher intrinsic dissolution rate compared to that of both, compounds 1 and 1c (the anhydrous free base and the monohydrate form, respectively). Additionally, compound 1d constitutes a solid form of robust scalable manufacturability, allowing reproducible stoichiometry control in the salt formation, while the formation of compounds 1a and 1c (hydrochloride salt (.HCl) and the hydrate form (.H$_2$O) of compound 1, respectively) does not allow reproducible stoichiometric control when scaled up. Finally, the melting point measured for compound 1d (DSC, mp=165.1° C.) is higher than that measured for compound 1b, i.e. the maleate salt form of compound 1, (DSC, mp=113.8° C.) which may provide higher resistance to potential salt dissociation phenomena upon mechanical manipulation and formulation during production and/or upon storage of the formulated product.

D. Pharmacological Examples

The compounds provided in the present invention are inhibitors of PDE10, particularly, of PDE10A. The behaviour of the PDE10 inhibitors according to Formula (I) in vitro and using an apomorphine induced stereotypy model in vivo is shown in Table 3. The in vitro selectivity towards PDE10A, occupancy, and results using PCP-induced hyperlocomotion, conditioned avoidance response models, SCH-23390-induced hypolocomotion in mice and object recognition test in rats of selected compounds are shown in tables 4 to 7.

In Vitro Assay PDE10A

Rat recombinant PDE10A (rPDE10A2) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 µA) were added in 384 well plates to 20 µl of incubation buffer (50 mM Tris pH 7.8, 8.3 mM MgCl$_2$, 1.7 mM EGTA). 10 µl of rPDE10A enzyme in incubation buffer was added and the reaction was started by addition of 10 µl substrate to a final concentration of 60 nM cAMP and 0.008 µCi $^3$H-cAMP. The reaction was incubated for 60 minutes at room temperature. After incubation, the reaction was stopped with 20 µl of stop solution consisting of 17.8 mg/ml PDE SPA (scintillation proximity assay) beads. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. The same assay principle is applied for the measurement of the affinity of the compound for other members of the PDE family with appropriate modifications in incubation buffer, substrate concentration, incubation time and stop solution. An overview of the different protocols is presented in table A. A best fit curve is fitted by a minimum sum of squares method to the plot of % of control value substracted with blanc value versus compound concentration and the half maximal inhibitory concentration (IC$_{50}$) value is derived from this curve.

TABLE A

Assay conditions for the Measurement of Phosphodiesterase activity by SPA

| Enzyme | Incubation Buffer | Final Concentration Substrate | $^3$H Substrate µCi/well | Stop Solution | Incubation Time (min) |
|---|---|---|---|---|---|
| hPDE1B1 | B* | 1 µM cAMP | 0.016 | 1* | 30 |
| hPDE2A | A* | 10 µM cGMP | 0.01 | 2* | 40 |
| hPDE3A | A* | 0.1 µM cAMP | 0.024 | 2* | 60 |
| hPDE4D3 | A* | 1 µM cAMP | 0.008 | 1* | 60 |
| hPDE5A3 | A* | 1 µM cGMP | 0.01 | 2* | 60 |
| hPDE6AB | A* | 0.1 µM cGMP | 0.01 | 2* | 120 |
| hPDE7A1 | A* | 60 nM cAMP | 0.008 | 1* | 60 |
| hPDE8A1 | A* | 0.3 µM cAMP | 0.01 | 1* | 60 |
| hPDE9A | C* | 60 nM cGMP | 0.008 | 2* | 60 |
| rPDE10A2 | A* | 60 nM cAMP | 0.008 | 1* | 60 |
| hPDE11A4 | A* | 0.3 µM cGMP | 0.01 | 1* | 30 |

A* 50 mM Tris pH 7.8, 1.7 mM EGTA, 8.3 mM MgCl$_2$
B* 50 mM Tris pH 7.8, 8.3 mM MgCl$_2$
C* 50 mM Tris pH7.8, 5 mM MnCl$_2$
1* 17.8 mg/ml PDE beads
2* 17.8 mg/ml PDE beads + 200 mM ZnCl$_2$ The compounds of the invention are generally selective for PDE10 compared to other PDEs and there are a few that also have affinity for PDE1B1, 4D3 and 5A3. Table 4 provides data of some compounds according to the invention.

Apomorphine-Induced Stereotypy in Rats (APO)

Apomorphine (1.0 mg/kg, i.v.)-induced stereotypy (compulsive sniffing, licking, chewing) was scored every 5 min over the first hour after injection of apomorphine, following a 1 hour interval pre-treatment with the test compound. The score system was: (3) pronounced, (2) moderate, (1) slight, and (0) absent. Criteria for drug-induced inhibition of stereotypy: fewer than 6 scores of 3 (0.16% false positives), fewer than 6 scores of ≥2 (0.0% false positives), or fewer than 7 scores of ≥1 (0.81% false positives).

PDE10 Occupancy

Dose-response or single dose experiments were performed to measure PDE10 occupancy 1 hour after subcutaneous (s.c.) or oral (p.o.) administration. Male Wistar rats (200 g) were treated by s.c. or p.o. administration of various PDE10 inhibitors. The PDE10 radioligand [$^3$H]-MP-10 (10 µCi/animal) was injected intravenously (i.v.) 30 minutes before sacrifice. Brains were immediately removed from the skull and rapidly frozen. Twenty µm-thick brain sections were cut using a cryostat-microtome, thaw-mounted on microscope slides and loaded in a β-imager to quantify PDE10 occupancy in the striatum.

PCP-Induced Hyperlocomotion in Rats

Apparatus

Motor activity [horizontal activity (locomotion) and vertical activity (rearing)] was recorded in male Wiga rats (body weight: 175-275 g; housed overnight in groups of 7 rats) using microprocessor-based activity monitors (MED Associates; length×width×height: 43.2×43.2×41.5 cm) over a period of 30 min. The resolution of the system was set at 100 msec. Total distance was defined as the distance traveled, measured by changes in the number or location of interrupted xy-beams (located in two arrays of 32 infrared light beams (1.25 cm apart) perpendicular to each other in a horizontal plane 2.0 cm above the floor). Vertical activity was defined as the number of periods of continuous breaks reported by an infrared array of 32 light beams in a horizontal plane 13 cm above the floor. The intensity of the light within the activity meters (measured in the centre at floor level) ranged between 110 and 130 LUX.

PCP-Induced Hyperlocomotion in Rats

Male Wiga rats (200 to 260 g) were pretreated with test compound or solvent (10 ml/kg, s.c.) and placed in individual cages. At a predefined interval thereafter (60 min.), the rats were challenged with PCP (1.25 mg/kg, i.v.) and motor activity was measured over a period of 30 min starting immediately after the PCP challenge. The following all-or-none criteria were adopted for drug-induced effects: (1) inhibition (<11000 counts; 2.9% false positives in 102 control rats), (2) blockade (<500 counts; 0.0% false positives). The results of this test are shown in table 5 below.

Conditioned Avoidance Response (CAR) Test

Apparatus

The apparatus consisted of an inner box surrounded by an outer box. The inner box was composed of four walls of transparent, synthetic material (length×width×height: 30×30×30 cm), an open top, and a grid floor made of 15 pairs of iron bars (2 mm diameter; 6 mm inter-bar distance). Odd and even bars were connected with a source of alternative current (1.0 mA; Coulbourn Instruments Solid State Shocker/Distributor), which could be interrupted by a switch. The outer box was composed of the same material (length×width×height: 40×40×36 cm), also with an open top, with a distance of 5 cm between the inner and outer box on all sides. To decrease the amount of environmental stimuli, three walls of the outer box were made non-transparent. The front wall was left transparent to allow the necessary inspection of the animal during the test. The upper edge of the outer and inner box served as a target for the rats on which to jump with fore- and hind-paws, respectively.

Avoidance Conditioning and Selection of Animals

From their arrival in the laboratory on the experimental day, male Wiga Wistar rats (230±30 g) were housed in individual cages provided with bedding material. The rats received 5 training sessions at 15-min time intervals over a 1-h period during which, the rats were conditioned to avoid an electric shock: the rat was placed on the non-electrified grid floor and the grid was electrified 10 s later for not more than 30 s, if the rat did not jump out of the box. Only rats that showed correct avoidance responses in all the last 3 training sessions were included for further experiments, and received the test compound or solvent immediately after the last training session.

Experimental Sessions

The rats were tested 3 times, i.e. at 60, 90 and 120 min after the injection of test compound or solvent. Latency to avoidance was recorded. The median avoidance response obtained over the three experimental sessions for each rat were used for further calculations. A median avoidance latency>8 s was selected as an all-or-none criterion for drug-induced inhibition of avoidance (occurring in only 1.5% of solvent-pretreated control rats; n=66). The results of this test are shown in table 5 below.

SCH-23390-Induced Hypolocomotion in Mice

SCH-23390 (0.08 mg/kg, i.v.)-induced hypolocomotion was evaluated over a 30-min period starting immediately after the SCH-23390 challenge in male NMRI mice pretreated 0.5 h earlier with test compound or solvent. Averaged activity in solvent-treated control mice was 1540±559 counts (mean±SD; n=103). Criterion for drug-induced reversal of the SCH-23390-induced hypolocomotion: total distance: >2500 counts (2.9% false positives in controls).

Object Recognition Test

Methods

Animals 60 female hooded-Lister rats (Charles River, UK) were used as subjects for these studies and weighed 248 g±20 g.

Rats were allowed at least a 7-day acclimatization period to the animal unit prior to commencement of experimentation. Rats were housed in groups of 5 under standard laboratory conditions under a 12 h light:dark cycle, lights on at 0700 h. All testing was carried out in the light phase. Food and water were freely provided. All experiments were conducted in accordance with the Animals Scientific Procedures Act, U.K. 1986 and were approved by the University of Bradford ethical review panel.

Treatment 40 mg of test compound was dissolved in 5 ml of 40% hydroxypropyl β-cyclodextrin (HPBC) solution. The solution was sonicated until completely dissolved. 2 ml of sterile water was added and the pH measured and adjusted with NaOH solution (0.1N) to obtain pH ~4. Finally, sterile water was added to a final volume of 10 ml. This stock solution was then diluted in 20% HPBC to obtain the final concentrations.

100 mg of PQ10 was dissolved in a 40% HPBC solution and 8 mg of tartaric acid. The solution was sonicated until completely dissolved. 5 ml of sterile water was added and the pH measured and adjusted with NaOH solution (0.1N) to obtain pH ~4. Finally sterile water was added to a final volume of 10 ml.

Test compound was administered at doses of 0.3 and 1.0 mg/kg via the oral route 30 min prior to testing.

PQ10 was administered at a dose of 1.0 mg/kg via the oral route 30 min prior to testing.

Object Recognition Memory

Certain pre-clinical tests allow the observation of relatively subtle cognitive deficits in the rat that resemble cognitive symptoms in subjects with schizophrenia. The cognitive deficits observed are seen in behaviours such as episodic memory, which can be measured by recognition tasks such as the novel object recognition (NOR) paradigm. A recognition memory task allows the comparison between presented stimuli and previously stored information. Ennaceur, A Delacour, J (1988) A new one-trial test for neurobiological studies of memory in rats Behav Brain Res 31: 47-59 described the NOR test in rats which was based on the differential exploration of familiar and new objects. The NOR test is a non-rewarded, ethologically relevant paradigm based on the spontaneous exploratory behaviour of rats that measures episodic memory. Each session consists of two trials. In the first trial, the rats are exposed to two identical objects in an open field. During the second trial, rats are exposed to two dissimilar objects, one familiar object from the first trial and one new object. Object recognition in rats can be measured as the difference in time spent exploring the familiar and the new object. Rats have been shown to spend more time exploring the new object. It was found that rats are able to discriminate between the familiar and the novel object when the inter-trial interval is between 3 minutes and 1-3 hours, but not when it is greater than 24 hours, although this effect may be sex dependent in the rat. The duration of each trial is also important as a preference for the novel object only lasts during the first 1 or 2 minutes, after which time preference diminishes as both objects become familiar and are explored equally.

Procedure

Allocation of Treatment Groups

Rats were randomly assigned to the 8 treatment groups

Habituation

Rats were allowed to habituate to the empty test box and the behavioural test room environment for 1 h on day 1. Prior to behavioural testing on day 2 rats were given a further 3 min habituation.

Behavioural Testing

Following the 3 min habituation period, the rats were given two 3 min trials (T1 and T2) which were separated by a 1 min inter-trial interval in the home cage during which the objects were changed.

T1=Trial 1, the Acquisition Trial

In this trial, the animals were allowed to explore two identical objects (A1 and A2) for 3 min.

T2=Trial 2, the Retention Trial

In this trial, the animals explored a familiar object (A) from T1 and a novel object (B) for 3 min. The familiar object presented during T2 was a duplicate of the object presented in T1 in order to avoid any olfactory trails.

Object Exploration

The object exploration was defined by animals licking, sniffing or touching the object with the forepaws whilst sniffing, but not leaning against, turning around, standing or sitting on the object. The exploration time (s) of each object (A1, A2, A and B) in each trial were recorded using two stopwatches and the following factors were calculated.

Total exploration time of both objects in the acquisition trial (s).

Total exploration time of both objects in the retention trial (s).

Habituation of exploratory activity. The locomotor activity (LMA) included the exploration time, as measured by the number of lines crossed, for both the trials.

Discrimination index (DI), which was calculated as shown below:

$$\frac{\text{time spent exploring novel object} - \text{time spent exploring familiar object}}{\text{total time spent in exploring the objects}}$$

Behaviour in all trials was recorded on video for subsequent blind scoring.

Exclusion Criteria

If an animal failed to explore one or both of the objects in the acquisition trial, that animal was not included in the final analysis, ie if exploration time was 0 seconds at either object in acquisition that animal was excluded.

Statistical Analysis

All data are expressed as mean±SEM, (n=3 to 10 per group) and were analysed by a two way ANOVA (factors are: drug and exploration time of the two objects) or one way ANOVA (LMA and DI) with further analysis by a post-hoc student's t-test (time spent exploring objects in acquisition and retention trials) or Dunnett's t-test (LMA and DI). When student's t-test was used to analyse time spent exploring objects, significance was based upon the difference in time spent exploring the novel or familiar object, not in comparison to vehicle. For the discrimination index Dunnett's t-tests were used to compare values against PCP/Veh treated group, and against the Veh/Veh group, as appropriate. Results showed that sub-chronic PCP (2 mg/kg ip twice daily for 7 days followed by 7 days drug-free period) produced a selective cognitive deficit in the retention phase of the NOR task in female rats.

The effects of acute treatment with compound 1 (0.3-1.0 mg/kg) or the comparator PQ10, were selective for the retention phase of the NOR task.

TABLE 3

Pharmacological data for compounds according to the invention.

| Co. No. | PDE10A2 pIC$_{50}$ | APO ED$_{50}$ (mg/kg) | Co. No. | PDE10A2 pIC$_{50}$ | APO ED$_{50}$ (mg/kg) | Co. No. | PDE10A2 pIC$_{50}$ | APO ED$_{50}$ (mg/kg) | Co. No. | PDE10A2 pIC$_{50}$ | APO ED$_{50}$ (mg/kg) |
|---|---|---|---|---|---|---|---|---|---|---|---|
| 141 | 8.00 | n.d.* | 138 | 7.40 | n.d.*(a) | 133 | 7.02 | 3.1 | 65 | 6.79 | n.d.(a) |
| 10 | 7.94 | 1.2 | 4 | 7.39 | n.d. | 73 | 7.01 | n.d. | 18 | 6.77 | 5 |
| 50 | 7.84 | 0.8 | 29 | 7.36 | ≥2.5 | 111 | 7.01 | n.d. | 140 | 6.76 | n.d.(a) |
| 142 | 7.84 | 5 | 80 | 7.35 | n.d. | 117 | 7.01 | n.t. | 66 | 6.75 | n.d.(a) |
| 46 | 7.76 | n.d. | 102 | 7.35 | n.d. | 21 | 6.99 | 1.5 | 101 | 6.75 | n.d. |
| 143 | 7.76 | 1.2 | 44 | 7.34 | n.d. | 51 | 6.98 | n.d. | 58 | 6.73 | n.d. |
| 135 | 7.74 | 3.1* | 91 | 7.33 | 1.2 | 134 | 6.98 | 5 | 96 | 6.73 | n.d. |
| 5 | 7.72 | n.d. | 2 | 7.33 | n.d. | 19 | 6.97 | 5 | 43 | 6.72 | n.d. |
| 54 | 7.68 | 1.2 | 37 | 7.30 | 1.5 | 98 | 6.96 | n.d. | 60 | 6.72 | n.d. |
| 87 | 7.66 | n.d. | 45 | 7.30 | n.d. | 9 | 6.95 | n.d. | 11 | 6.71 | n.d. |
| 124 | 7.65 | 1.2 | 76 | 7.30 | n.d. | 23 | 6.95 | n.d. | 13 | 6.71 | n.d. |
| 6 | 7.63 | n.d. | 118 | 7.30 | ≤10* | 127 | 6.95 | 2.0 | 81 | 6.71 | n.d. |
| 93 | 7.60 | n.d. | 126 | 7.30 | n.d. | 48 | 6.94 | ≥2.5 | 49 | 6.68 | n.d. |
| 105 | 7.60 | n.d. | 128 | 7.30 | n.d.(a) | 88 | 6.94 | n.d. | 53 | 6.67 | n.d. |
| 148 | 7.60 | 5 | 56 | 7.29 | n.d. | 34 | 6.93 | n.d. | 130 | 6.66 | n.d.*(a) |
| 7 | 7.59 | 0.3 | 83 | 7.29 | n.d. | 40 | 6.93 | n.d. | 12 | 6.65 | n.d. |
| 137 | 7.59 | n.d. | 114 | 7.28 | n.d. | 14 | 6.92 | n.d. | 59 | 6.63 | n.d. |
| 3 | 7.58 | 0.8 | 146 | 7.28 | n.t. | 16 | 6.92 | 3.1 | 121 | 6.63 | n.d.(a) |
| 20 | 7.56 | n.d. | 104 | 7.27 | n.d. | 30 | 6.91 | 7.1 | 109 | 6.60 | n.d. |
| 123 | 7.56 | n.d. | 17 | 7.26 | n.d.* | 72 | 6.91 | ≥2.5* | 62 | 6.59 | n.d.* |
| 38 | 7.54 | n.d. | 95 | 7.26 | n.d.* | 103 | 6.59 | n.d. | 57 | 6.37 | n.t. |
| 122 | 7.52 | n.d. | 22 | 7.25 | 0.5 | 79 | 6.58 | n.d. | 112 | 6.37 | n.t. |
| 26 | 7.51 | n.d. | 36 | 7.25 | 5 | 86 | 6.58 | n.d. | 75 | 6.35 | n.t. |
| 27 | 7.5 | n.d. | 1 | 7.24 | 1.3 | 107 | 6.57 | n.d. | 52 | 6.33 | n.d. |
| 25 | 7.47 | n.d.* | 92 | 7.24 | n.d. | 15 | 6.52 | n.d.* | 64 | 6.32 | n.d.* |
| 131 | 7.46 | 3.1 | 145 | 7.23 | n.d. | 99 | 6.52 | n.d. | 136 | 6.28 | n.t. |
| 115 | 7.45 | n.d.*(a) | 31 | 7.22 | n.d. | 69 | 6.49 | n.d. | 74 | 6.23 | n.t. |
| 35 | 7.42 | 5 | 119 | 7.21 | n.d.*(a) | 144 | 6.49 | n.t. | 85 | 6.18 | n.t. |
| 55 | 7.42 | n.d. | 106 | 7.18 | n.d. | 110 | 6.48 | n.t. | 120 | 6.16 | n.d.(a) |
| 90 | 7.17 | n.d. | 78 | 6.91 | n.d. | 61 | 6.47 | 1.2 | 100 | 6.14 | n.t. |
| 147 | 7.17 | 5 | 70 | 6.90 | n.d. | 84 | 6.43 | n.t. | 129 | 5.58 | n.t. |
| 139 | 7.16 | n.d.* | 77 | 6.89 | n.d. | 94 | 6.42 | n.t. | 150 | n.t. | n.t. |
| 39 | 7.15 | n.d. | 89 | 6.88 | n.d.* | 41 | 6.39 | n.d. | | | |
| 132 | 7.15 | n.d.(a) | 116 | 6.88 | n.d.*(a) | | | | | | |
| 32 | 7.11 | 5 | 63 | 6.87 | n.d.(a) | | | | | | |
| 33 | 7.11 | ≥2.5* | 97 | 6.85 | n.d. | | | | | | |
| 24 | 7.10 | n.d. | 82 | 6.84 | n.d. | | | | | | |
| 28 | 7.08 | 1.2 | 149 | 6.82 | n.d. | | | | | | |
| 71 | 7.08 | ≥2.5* | 21a | 6.82 | n.t. | | | | | | |
| 125 | 7.08 | ≥2.5 | 108 | 6.81 | n.d. | | | | | | |
| 67 | 7.06 | n.d.(a) | 68 | 6.80 | ≥2.5* | | | | | | |
| 47 | 7.04 | n.d. | 113 | 6.80 | n.d. | | | | | | |
| 42 | 7.03 | n.d. | 8 | 6.79 | n.d. | | | | | | | pIC$_{50}$ corresponds to the −log IC$_{50}$ expressed in mol/L.
ED$_{50}$ is the dose at which 50% of the tested animals show the effect.
n.t. means not tested.
n.d. means the compound was found not active at 2.5 or at 10 mg/kg (the latter being indicated as (a)), taken as threshold value, and was not further tested.
*means the compound was not soluble and was tested orally as a suspension.
≤ means that the compound was found active in 60% of the animals at the indicated dose level; ≥ means that in 30% of the animals the compound was found active at the indicated dose level.

TABLE 4

In vitro selectivity of compounds according to the invention (expressed as pIC$_{50}$).

| Co. No. | PDE 10A2 | PDE 11A4 | PDE 1B1 | PDE 2A | PDE 3A | PDE 4D3 | PDE 5A3 | PDE 6AB | PDE 7A | PDE 8A1 | PDE 9A |
|---|---|---|---|---|---|---|---|---|---|---|---|
| 10 | 7.94 | 5.85 | n.t. | 5.18 | <5 | 5.9 | 5.89 | n.t. | <5 | n.t. | <5 |
| 50 | 7.84 | n.t. | n.t. | 5.16 | n.t. | n.t. | n.t. | n.t. | n.t. | n.t. | n.t. |
| 142 | 7.84 | 5.74 | n.t. | 5.26 | 5.29 | 5.55 | 5.94 | n.t. | 5.3 | n.t. | <5 |
| 143 | 7.76 | 5.71 | n.t. | 5.4 | 5.84 | 5.29 | 6.19 | n.t. | 5.23 | n.t. | <5 |
| 135 | 7.74 | 5.23 | n.t. | <5 | 5.13 | <5 | 5.59 | n.t. | <5 | n.t. | <5 |
| 54 | 7.68 | n.t. | n.t. | <5 | n.t. | n.t. | n.t. | n.t. | n.t. | n.t. | n.t. |
| 124 | 7.65 | 5.27 | n.t. | 5.06 | 5.16 | 5.13 | 5.71 | n.t. | 5.27 | n.t. | <5 |
| 148 | 7.6 | 5.72 | n.t. | 5.36 | 5.5 | 5.59 | 5.91 | n.t. | 5.54 | n.t. | <5 |
| 7 | 7.59 | n.t. | n.t. | <5 | n.t. | n.t. | n.t. | n.t. | n.t. | n.t. | n.t. |
| 3 | 7.58 | <5 | n.t. | <5 | <5 | <5 | 5.1 | n.t. | <5 | n.t. | <5 |
| 131 | 7.46 | <5 | n.t. | <5 | <5 | <5 | 5.07 | n.t. | <5 | n.t. | <5 |
| 35 | 7.42 | <5 | n.t. | <5 | 5.13 | <5 | <5 | n.t. | <5 | n.t. | <5 |
| 29 | 7.36 | <5 | n.t. | 5.92 | <5 | <5 | 5.35 | n.t. | <5 | n.t. | <5 |
| 91 | 7.33 | <5 | n.t. | <5 | <5 | <5 | 5.07 | n.t. | <5 | n.t. | <5 |
| 37 | 7.3 | 4.4 | n.t. | 4.27 | 4.96 | 4.51 | 5.22 | n.t. | 4.34 | n.t. | <4 |
| 118 | 7.3 | <5 | n.t. | <5 | <5 | <5 | 5 | n.t. | <5 | n.t. | <5 |
| 146 | 7.28 | <5 | n.t. | <5 | <5 | <5 | 5.72 | n.t. | 5.07 | n.t. | <5 |
| 1 | 7.24 | 4.13 | 5.28 | 4.4 | 4.01 | 4.51 | 4.77 | 4.07 | 4.16 | 4.11 | <4 |
| 22 | 7.25 | 5.17 | n.t. | 5.23 | <4.3 | 5.56 | 5.46 | n.t. | 4.55 | n.t. | <4.3 |
| 36 | 7.25 | <5 | n.t. | <5 | <5 | <5 | <5 | <5 | <5 | <5 | <5 |
| 147 | 7.17 | 5.42 | n.t. | <5 | <5 | 5.42 | 5.93 | n.t. | 5.45 | n.t. | <5 |
| 32 | 7.11 | <5 | n.t. | <5 | <5 | <5 | <5 | n.t. | <5 | n.t. | <5 |

TABLE 4-continued

In vitro selectivity of compounds according to the invention (expressed as $pIC_{50}$).

| Co. No. | PDE 10A2 | PDE 11A4 | PDE 1B1 | PDE 2A | PDE 3A | PDE 4D3 | PDE 5A3 | PDE 6AB | PDE 7A | PDE 8A1 | PDE 9A |
|---|---|---|---|---|---|---|---|---|---|---|---|
| 33 | 7.11 | <5 | n.t. | <5 | <5 | <5 | <5 | n.t. | <5 | n.t. | <5 |
| 28 | 7.08 | 4.52 | n.t. | 4.57 | 4.52 | 4.88 | 4.86 | n.t. | 4.59 | n.t. | <4 |
| 71 | 7.08 | n.t. | n.t. | 5.64 | n.t. | n.t. | n.t. | n.t. | n.t. | n.t. | n.t. |
| 125 | 7.08 | 5.35 | n.t. | 5.07 | <5 | 5.68 | 5.9 | n.t. | <5 | n.t. | <5 |
| 133 | 7.02 | <5 | n.t. | <5 | <5 | <5 | 5.62 | n.t. | <5 | n.t. | <5 |
| 117 | 7.01 | 5 | n.t. | <5 | <5 | <5 | <5 | n.t. | <5 | n.t. | <5 |
| 21 | 6.99 | <4.3 | n.t. | 4.32 | <4.3 | 4.55 | 4.72 | n.t. | <4.3 | n.t. | <4.3 |
| 30 | 6.91 | <5 | n.t. | <5 | <5 | <5 | <5 | n.t. | <5 | n.t. | <5 |
| 134 | 6.98 | 5.27 | n.t. | 5.09 | <5 | 5.26 | 6.23 | n.t. | 5.31 | n.t. | <5 |
| 19 | 6.97 | <5 | n.t. | <5 | <5 | <5 | <5 | n.t. | <5 | n.t. | <5 |
| 127 | 6.95 | <5 | n.t. | <5 | <5 | <5 | 5.33 | n.t. | <5 | n.t. | <5 |
| 48 | 6.94 | n.t. | n.t. | <5 | n.t. | n.t. | n.t. | n.t. | n.t. | n.t. | n.t. |
| 16 | 6.92 | <5 | n.t. | <5 | <5 | <5 | <5 | n.t. | <5 | n.t. | <5 |
| 72 | 6.91 | n.t. | n.t. | 5.98 | n.t. | n.t. | n.t. | n.t. | n.t. | n.t. | n.t. |
| 68 | 6.8 | n.t. | n.t. | <5 | n.t. | n.t. | n.t. | n.t. | n.t. | n.t. | n.t. |
| 18 | 6.77 | <5 | n.t. | <5 | <5 | <5 | 5 | n.t. | <5 | n.t. | <5 |
| 144 | 6.49 | n.t. | n.t. | <5 | n.t. | n.t. | n.t. | n.t. | n.t. | n.t. | n.t. |
| 110 | 6.48 | n.t. | n.t. | <5 | n.t. | n.t. | n.t. | n.t. | n.t. | n.t. | n.t. |
| 61 | 6.47 | <5 | <5 | 5.1 | <5 | <5 | 5.57 | n.t. | <5 | n.t. | <5 |
| 84 | 6.43 | n.t. | n.t. | <5 | n.t. | n.t. | n.t. | n.t. | n.t. | n.t. | n.t. |
| 94 | 6.42 | n.t. | n.t. | <5 | n.t. | n.t. | n.t. | n.t. | n.t. | n.t. | n.t. |
| 57 | 6.37 | n.t. | n.t. | <5 | n.t. | n.t. | n.t. | n.t. | n.t. | n.t. | n.t. |
| 112 | 6.37 | n.t. | n.t. | 5.09 | n.t. | n.t. | n.t. | n.t. | n.t. | n.t. | n.t. |
| 75 | 6.35 | n.t. | n.t. | <5 | n.t. | n.t. | n.t. | n.t. | n.t. | n.t. | n.t. |
| 136 | 6.28 | n.t. | n.t. | <5 | n.t. | n.t. | n.t. | n.t. | n.t. | n.t. | n.t. |
| 74 | 6.23 | n.t. | n.t. | <5 | n.t. | n.t. | n.t. | n.t. | n.t. | n.t. | n.t. |
| 85 | 6.18 | n.t. | n.t. | <5 | n.t. | n.t. | n.t. | n.t. | n.t. | n.t. | n.t. |
| 100 | 6.14 | n.t. | n.t. | <5 | n.t. | n.t. | n.t. | n.t. | n.t. | n.t. | n.t. |
| 129 | 5.58 | n.t. | n.t. | <5 | n.t. | n.t. | n.t. | n.t. | n.t. | n.t. | n.t. |

TABLE 5

Pharmacological data for compounds according to the invention in the occupancy test.

| Co. No. | PDE10 in vivo Occ. | $ED_{50}$ sc (mg/kg) | $ED_{50}$ po (mg/kg) | SD sc % occupancy at 10 mg/kg | SD po % occupancy at 10 mg/kg |
|---|---|---|---|---|---|
| 1 | DR sc and po | 0.48 | 1.4 | 76% | n.t. |
| 3 | DR sc | 2.0 | n.t. | n.t. | n.t. |
| 7 | DR sc | 1.6 | n.t. | n.t. | n.t. |
| 16 | SD sc | n.t. | n.t. | 52% | n.t. |
| 18 | SD sc | n.t. | n.t. | 46% | n.t. |
| 19 | SD sc | n.t. | n.t. | 57% | n.t. |
| 21 | DR sc and po | 2.6 | 14 | 61% | n.t. |
| 22 | DR sc | 0.94 | n.t. | n.t. | n.t. |
| 28 | DR sc | 1.1 | n.t. | n.t. | n.t. |
| 30 | DR sc | >10 (6%)* | n.t. | n.t. | n.t. |
| 35 | SD sc | n.t. | n.t. | 67% | n.t. |
| 37 | DR sc | 2.2 | n.t. | 67% | n.t. |
| 48 | DR po | n.t. | 4.3 | n.t. | n.t. |
| 62 | SD po | n.t. | n.t. | n.t. | 38% |
| 65 | SD sc | n.t. | n.t. | 17% | n.t. |
| 66 | SD sc | n.t. | n.t. | 29% | n.t. |
| 67 | SD sc | n.t. | n.t. | 1% | n.t. |
| 114 | SD sc | n.t. | n.t. | 72% | n.t. |
| 118 | SD po | n.t. | n.t. | n.t. | 4% |
| 121 | SD sc | n.t. | n.t. | 0% | n.t. |
| 124 | DR sc | 3.0 | n.t. | n.t. | n.t. |
| 125 | DR sc | >10 (42%)* | n.t. | n.t. | n.t. |
| 127 | SD sc | n.t. | n.t. | 4% | n.t. |
| 128 | SD sc | n.t. | n.t. | 40% | n.t. |
| 130 | SD po | n.t. | n.t. | n.t. | 6% |
| 131 | SD sc | n.t. | n.t. | 59% | n.t. |
| 132 | SD sc | n.t. | n.t. | 44% | n.t. |
| 137 | SD po | n.t. | n.t. | n.t. | 12% |
| 138 | SD po | n.t. | n.t. | n.t. | 11% |
| 140 | SD po | n.t. | n.t. | n.t. | 0% |
| 142 | SD sc | n.t. | n.t. | 78% | n.t. |
| 147 | SD sc | n.t. | n.t. | 22% | n.t. |
| 148 | SD sc | n.t. | n.t. | 66% | n.t. |
| 21a | DR sc and po | 2.6 | 14 | 61% | n.t. |

Occ. means occupancy; $ED_{50}$ means effective dose; SD means single dose; DR means dose response; sc means subcutaneous administration; po means per os, oral administration;
*the data between brackets means the % occupancy at the highest dose tested.

TABLE 6

Pharmacological data for compounds according to the invention in the PCP, CAR and SCH-23390 tests.

| Co. No. | PCP $ED_{50}$ (mg/kg) | CAR $ED_{50}$ (mg/kg) | SCH-23390 $ED_{50}$ (mg/kg) |
|---|---|---|---|
| 1 | 2.0 | 4.7 | 7.1 |
| 21 | 6.1 | 5.4 | 5 |

TABLE 7

Effects of compound 1 on short-term memory.

|  | Vehicle + 20% HPBCD | PCP + 20% HPBCD | PCP + co. no. 1 (0.3 mg/kg) | PCP + co. no. 1 (1.0 mg/kg) | PCP + PQ10 (1 mg/kg) |
|---|---|---|---|---|---|
| T2(A) (seconds) | 7.5 (±1.4395) | 17.5 (±2.1042) | 11.8 (±2.6709) | 10.7 (±1.8622) | 7.9 (±1.6017) |
| T2(B) (seconds) | 19.9 (±3.6346)** | 17.4 (±2.2716) | 17.6 (±2.7899)* | 22.3 (±3.2251)** | 19.9 (±3.247)** |
| DI | 0.3748 (±0.1695) | −0.005 (±0.0357) | 0.3014 (±0.1405) | 0.3335 (±0.0804) | 0.4193 (±0.0772) |
| LMA (no. of lines crossed) | 62.8 (±4.567518) | 69.5 (±5.647517) | 56.5 (±6.107503) | 56.4 (±7.212951) | 65.5 (±5.518152) |

Day 1: The ability of acute treatment with compound 1 (0.3-1.0 mg/kg, p.o) or PQ10 (1 mg/kg, p.o) to reverse the effect of sub-chronic PCP (2 mg/kg, i.p twice daily for seven days) on the exploration time (s) during the retention trial (T2) of a familiar object and a novel object in the 3 min retention trial in female rats.
Data are expressed as the mean ± s.e.m (n = 3-10 per group) and were analysed by ANOVA and post-hoc student's t-test.
*P<0.05-**P<0.01; significant difference between time spent exploring the familiar (A) and novel (B) object. The difference in time exploring the novel and familiar object is analysed by student's t-test.

E. Prophetic Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

|  |  |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

|  |  |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

We claim:

1. A compound of formula (I)

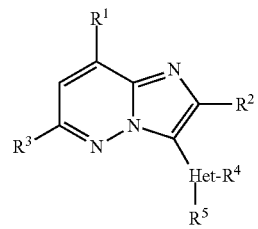

(I)

or a stereoisomeric form thereof, wherein
$R^1$ is pyridinyl; pyridinyl optionally substituted with halogen, $C_{1-4}$alkyl, trifluoromethyl or $C_{1-4}$alkyloxy; tetrahydropyranyl; or $NR^6R^7$;
$R^2$ is hydrogen, $C_{1-4}$alkyl, trifluoromethyl, $C_{3-8}$cycloalkyl, or $C_{1-4}$alkyloxy;
$R^3$ is hydrogen, chloro, $C_{1-4}$alkyl, trifluoromethyl, or $C_{3-8}$cycloalkyl;
Het is a 5- or 6-membered heterocyclic ring selected from the group consisting of pyridinyl, pyrimidinyl, pyridazinyl, pyrrolyl, oxazolyl, thiazolyl, imidazolyl, pyrazolyl, isothiazolyl, isoxazolyl, oxadiazolyl and triazolyl;
$R^4$ is hydrogen, $C_{1-4}$alkyl, trifluoromethyl$C_{0-4}$alkyl, hydroxy$C_{1-4}$alkyl, difluorocyclopropylmethyl, cyclopropyldifluoroethyl, $C_{3-8}$cycloalkyl, $C_{1-4}$alkyloxy$C_{1-5}$alkyl, $C_{1-4}$alkyloxy, trifluoromethyl$C_{0-4}$alkyloxy, $C_{3-8}$cycloalkyl$C_{1-4}$alkyloxy, $C_{3-8}$cycloalkyl$C_{1-4}$alkyl, $C_{1-6}$alkyloxy$C_{1-4}$alkyloxy, tetrahydropyranyl, pyridinylmethyl, $NR^{6a}R^{7a}C_{1-4}$alkyl or $NR^{6a}R^{7a}$;
$R^5$ is hydrogen or $C_{1-4}$alkyl;
$R^6$, $R^{6a}$, $R^{7a}$ are each independently hydrogen or $C_{1-4}$alkyl, or taken together with N can be a radical of Formula (a), (b) or (c)

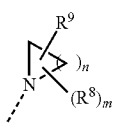

(a)

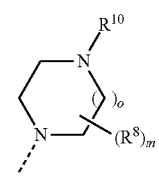

(b)

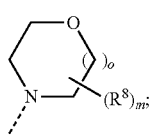

wherein
each $R^8$, if present, independently of one another is $C_{1-4}$alkyl;
$R^9$ is hydrogen or $C_{1-4}$alkyloxy;
$R^{10}$ is hydrogen or $C_{1-4}$alkyl;
m is 0, 1, 2, 3, 4 or 5;
n is 2, 3, 4, 5 or 6;
o is 1 or 2;
or a pharmaceutically acceptable salt thereof.

2. The compound according to claim 1 or a stereoisomeric form thereof, wherein
$R^1$ is selected from pyridinyl; pyridinyl optionally substituted with halogen, $C_{1-4}$alkyl, trifluoromethyl or $C_{1-4}$alkyloxy; tetrahydropyranyl; and $NR^6R^7$; wherein $R^6$ and $R^7$ taken together with the nitrogen can be a radical of Formula (a), (b) or (c) as defined in claim 1;
$R^2$ is selected from hydrogen, methyl, ethyl, cyclopropyl, isopropyl, methoxy and trifluoromethyl;
$R^3$ is selected from hydrogen, chloro, methyl, trifluoromethyl and cyclopropyl; and
Het is selected from the group consisting of pyridinyl, pyrimidinyl, pyridazinyl, oxazolyl, thiazolyl, pyrazolyl, isothiazolyl, isoxazolyl, oxadiazolyl and triazolyl;
or a pharmaceutically acceptable salt thereof.

3. The compound according to claim 1 or a stereoisomeric form thereof, wherein
$R^1$ is selected from pyridinyl which may be optionally substituted with halogen, $C_{1-4}$alkyl, trifluoromethyl or $C_{1-4}$alkyloxy; morpholinyl; and $NR^6R^7$; wherein $R^6$ and $R^7$ taken together with the nitrogen can be a radical of Formula (a) or (c) wherein n is 3 and o is 1;
Het is selected from pyridinyl and pyrazolyl;
$R^4$ is hydrogen, $C_{1-4}$alkyl, trifluoromethyl$C_{0-4}$alkyl, hydroxy$C_{1-4}$alkyl, difluorocyclopropylmethyl, cyclopropyldifluoroethyl, $C_{3-8}$cycloalkyl, $C_{1-4}$-alkyloxy$C_{1-5}$alkyl, $C_{1-4}$-alkyloxy, trifluoromethyl$C_{0-4}$alkyloxy, $C_{3-8}$cycloalkyl$C_{1-4}$alkyloxy, $C_{1-6}$alkyloxy$C_{1-4}$alkyloxy, tetrahydropyranyl, pyridinylmethyl, $NR^{6a}R^{7a}C_{1-4}$alkyl or $NR^{6a}R^{7a}$;
wherein $R^6$, $R^{6a}$, $R^7$ and $R^{7a}$ are each independently hydrogen or $C_{1-4}$alkyl, or taken together with the nitrogen can be a radical of formula (a), (b) or (c), wherein n is 3, $R^9$ is hydrogen or $C_{1-4}$alkyloxy, m is 0, o is 1 and $R^{10}$ is hydrogen;
or a pharmaceutically acceptable salt thereof.

4. The compound according to claim 1 or a stereoisomeric form thereof, wherein
$R^1$ is selected from morpholinyl and pyridinyl;
$R^2$ is selected from hydrogen, methyl, ethyl, methoxy, and cyclopropyl;
$R^3$ is selected from hydrogen, methyl, and cyclopropyl;
Het is pyridinyl or pyrazolyl;
$R^4$ is selected from ethyl; isopropyl; isobutyl; 2,2,2-trifluoroethyl; 2-hydroxy-2-methylpropyl; 2,2-difluoro-2-cyclopropylethyl; cyclopropyl; 2-methoxyethyl; (2S)-2-methoxypropyl; 2-ethoxyethyl; ethoxymethyl; 1-ethoxy-1-methylethyl; 1-methoxy-1-methylethyl; 2-methoxy-1,1-dimethylethyl; 3-methoxy-3-methylbutyl; 3-methoxypropyl; 2-methoxy-2-methyl-propyl; 2-methoxyethoxy; 2-methoxy-2-methyl-propoxy; tetrahydro-2H-pyran-4-yl; morpholin-4-yl; piperazin-1-yl; and (3R)-3-methoxypyrrolidin-1-yl; and $R^5$ is hydrogen or methyl;
or a pharmaceutically acceptable salt thereof.

5. The compound according to claim 1 or a stereoisomeric form thereof, wherein
$R^1$ is selected from morpholin-4-yl, pyridin-3-yl and pyridin-4-yl; and
Het is selected from pyridin-3-yl, pyridin-4-yl and 1H-pyrazol-4-yl;
or a pharmaceutically acceptable salt thereof.

6. The compound according to claim 1 or a stereoisomeric form thereof, wherein
$R^1$ is selected from morpholin-4-yl; and
Het is pyridin-3-yl or pyridin-4-yl;
or a pharmaceutically acceptable salt thereof.

7. The compound according to claim 1, or a stereoisomeric form thereof, wherein
$R^1$ is morpholin-4-yl;
$R^2$ is methyl;
$R^3$ is hydrogen;
Het is pyridin-3-yl;
$R^4$ is 2-methoxyethyl; and
$R^5$ is hydrogen;
or a pharmaceutically acceptable salt thereof.

8. The compound of formula (I) according to claim 1 selected from the group consisting of
3-[6-(2-methoxyethyl)-3-pyridinyl]-2-methyl-8-(4-morpholinyl)-imidazo[1,2-b]pyridazine,
3-[6-(2-methoxyethyl)-3-pyridinyl]-2-methyl-8-(4-morpholinyl)-imidazo[1,2-b]pyridazine hydrochloride,
3-[6-(2-methoxyethyl)-3-pyridinyl]-2-methyl-8-(4-morpholinyl)-imidazo[1,2-b]pyridazine maleate,
3-[6-(3-methoxypropyl)-3-pyridinyl]-2-methyl-8-(4-morpholinyl)-imidazo[1,2-b]pyridazine,
3-[6-(2-methoxy-2-dimethylpropyl)-3-pyridinyl]-2-methyl-8-(4-morpholinyl)-imidazo[1,2-b]pyridazine,
3-[6-(2-methoxy-1,1-dimethylethyl)-3-pyridinyl]-2-methyl-8-(4-morpholinyl)-imidazo[1,2-b]pyridazine,
3-[6-(1-ethoxy-1-methylethyl)-3-pyridinyl]-2-methyl-8-(4-morpholinyl)-imidazo[1,2-b]pyridazine,
3-[6-(1-methoxy-1-methylethyl)-3-pyridinyl]-2-methyl-8-(4-morpholinyl)-imidazo[1,2-b]pyridazine,
3-[6-(2-methoxy-2-methylpropyl)-3-pyridinyl]-2-methyl-8-(4-pyridinyl)-imidazo[1,2-b]pyridazine,
3-[6-(2-methoxyethoxy)-5-methyl-3-pyridinyl]-2-methyl-8-(4-pyridinyl)-imidazo[1,2-b]pyridazine,
3-[6-(2-methoxyethoxy)-3-pyridinyl]-2-methyl-8-(3-pyridinyl)-imidazo[1,2-b]pyridazine,
2-cyclopropyl-3-[6-(2-methoxyethyl)-3-pyridinyl]-8-(4-pyridinyl)-imidazo[1,2-b]pyridazine,
3-[6-(2-methoxyethyl)-3-pyridinyl]-8-(4-morpholinyl)-imidazo[1,2-b]pyridazine,
2-methoxy-3-[6-(2-methoxyethyl)-3-pyridinyl]-8-(4-morpholinyl)-imidazo[1,2-b]pyridazine,
6-cyclopropyl-3-[6-(2-methoxyethyl)-3-pyridinyl]-2-methyl-8-(4-morpholinyl)-imidazo[1,2-b]pyridazine,
6-cyclopropyl-3-[6-(2-methoxyethyl)-3-pyridinyl]-2-methyl-8-(4-pyridinyl)-imidazo[1,2-b]pyridazine,
2-cyclopropyl-3-[6-(2-methoxyethyl)-3-pyridinyl]-6-methyl-8-(4-morpholinyl)-imidazo[1,2-b]pyridazine,
3-[6-(2-methoxyethoxy)-3-pyridinyl]-2-methyl-8-(4-morpholinyl)-imidazo[1,2-b]pyridazine,
3-[6-(ethoxymethyl)-3-pyridinyl]-2-methyl-8-(4-morpholinyl)-imidazo[1,2-b]pyridazine, 3-[6-(2-methoxy-2-methylpropoxy)-3-pyridinyl]-2-methyl-8-(4-morpholinyl)-imidazo[1,2-b]pyridazine,
2-methyl-8-(4-morpholinyl)-3-[6-(4-morpholinyl)-3-pyridinyl]-imidazo[1,2-b]pyridazine,
3-[6-(2-methoxyethyl)-3-pyridinyl]-2-methyl-8-(4-pyridinyl)-imidazo[1,2-b]pyridazine,
3-[(6-(2-methoxyethoxy)-3-pyridinyl]-2-methyl-8-(4-pyridinyl)-imidazo[1,2-b]pyridazine,
3-[6-(2-methoxyethoxy)-3-pyridinyl]-2-methyl-8-(4-pyridinyl)-imidazo[1,2-b]pyridazine hydrochloride,
2-cyclopropyl-3-[6-(2-methoxyethyl)-3-pyridinyl]-8-(4-morpholinyl)-imidazo[1,2-b]pyridazine,
3-[6-(2-methoxyethyl)-3-pyridinyl]-2,6-dimethyl-8-(4-morpholinyl)-imidazo[1,2-b]pyridazine,
3-[6-(2-methoxyethyl)-3-pyridinyl]-2,6-dimethyl-8-(4-pyridinyl)-imidazo[1,2-b]pyridazine,
3-[6-(2-ethoxyethyl)-3-pyridinyl]-2-methyl-8-(4-morpholinyl)-imidazo[1,2-b]pyridazine,
3-[2-(2-methoxyethyl)-4-pyridinyl]-2-methyl-8-(4-morpholinyl)-imidazo[1,2-b]pyridazine,
2-methyl-8-(4-morpholinyl)-3-[6-(tetrahydro-2H-pyran-4-yl)-3-pyridinyl]-imidazo[1,2-b]pyridazine,
3-(6-ethyl-3-pyridinyl)-2-methyl-8-(4-morpholinyl)-imidazo[1,2-b]pyridazine,
3-[6-(3-methoxy-3-methylbutyl)-3-pyridinyl]-2-methyl-8-(4-morpholinyl)-imidazo[1,2-b]pyridazine,
2-methyl-8-(4-morpholinyl)-3-[6-(1-piperazinyl)-3-pyridinyl]-imidazo[1,2-b]pyridazine,
2-methyl-3-[6-(4-morpholinyl)-3-pyridinyl]-8-(4-pyridinyl)-imidazo[1,2-b]pyridazine,
2-methyl-3-[6-(1-methylethyl)-3-pyridinyl]-8-(4-morpholinyl)-imidazo[1,2-b]pyridazine,
3-(6-cyclopropyl-3-pyridinyl)-2-methyl-8-(4-morpholinyl)-imidazo[1,2-b]pyridazine,
3-[6-[(3R)-3-methoxy-1-pyrrolidinyl]-3-pyridinyl]-2-methyl-8-(4-morpholinyl)-imidazo[1,2-b]pyridazine,
2-methyl-3-[1-(2-methylpropyl)-1H-pyrazol-4-yl]-8-(4-morpholinyl)-imidazo[1,2-b]pyridazine,
3-[1-(2-methoxyethyl)-1H-pyrazol-4-yl]-2-methyl-8-(4-morpholinyl)-imidazo[1,2-b]pyridazine,
3-[1-(2-methoxy-2-methylpropyl)-1H-pyrazol-4-yl]-2-methyl-8-(4-morpholinyl)-imidazo[1,2-b]pyridazine,
2-cyclopropyl-3-[1-(2-methoxy-2-methylpropyl)-1H-pyrazol-4-yl]-8-(4-morpholinyl)-imidazo[1,2-b]pyridazine,
2-cyclopropyl-3-[6-(2-methoxy-2-methylpropyl)-3-pyridinyl]-8-(4-morpholinyl)-imidazo[1,2-b]pyridazine hydrochloride,
2-cyclopropyl-3-[(6-(2-methoxy-2-methylpropyl)-3-pyridinyl]-8-(4-morpholinyl)-imidazo[1,2-b]pyridazine,
3-[6-(2-methoxy-2-methylpropyl)-3-pyridinyl]-2,6-dimethyl-8-(4-pyridinyl)-imidazo[1,2-b]pyridazine,
2-cyclopropyl-3-[6-(2-methoxy-2-methylpropyl)-3-pyridinyl]-8-(4-pyridinyl)-imidazo[1,2-b]pyridazine,
5µ-cyclopropyl-8-(4-morpholinyl)imidazo[1,2-b]pyridazin-3-yl]-α,α-dimethyl-2-pyridineethanol,
3-[6-(4-morpholinyl)-3-pyridinyl]-8-(4-pyridinyl)-imidazo[1,2-b]pyridazine,
2,6-dimethyl-8-(4-morpholinyl)-3-[6-(4-morpholinyl)-3-pyridinyl]-imidazo[1,2-b]pyridazine,
2-cyclopropyl-6-methyl-3-[6-(4-morpholinyl)-3-pyridinyl]-8-(4-pyridinyl)-imidazo[1,2-b]pyridazine,
2-cyclopropyl-3-[6-(2-methoxyethoxy)-3-pyridinyl]-6-methyl-8-(4-pyridinyl)-imidazo[1,2-b]pyridazine,
2-methyl-8-(4-morpholinyl)-3-[2-(4-morpholinyl)-4-pyridinyl]-imidazo[1,2-b]pyridazine,
3-(1-[(2,2-difluorocyclopropyl)methyl]-1H-pyrazol-4-yl)-2-methyl-8-morpholin-4-ylimidazo[1,2-b]pyridazine,
2-methyl-3-[1-(2-methylpropyl)-1H-pyrazol-4-yl]-8-(4-pyridinyl)-imidazo[1,2-b]pyridazine,
6-cyclopropyl-3-[1-(2-methoxyethyl)-1H-pyrazol-4-yl]-2-methyl-8-(4-morpholinyl)-imidazo[1,2-b]pyridazine,
2-ethyl-3-[1-(2-methoxyethyl)-1H-pyrazol-4-yl]-8-(4-morpholinyl)-imidazo[1,2-b]pyridazine,
3-[1-[(2S)-2-methoxypropyl]-1H-pyrazol-4-yl]-2-methyl-8-(4-morpholinyl)-imidazo[1,2-b]pyridazine,
3-[1-(2-methoxyethyl)-1H-pyrazol-4-yl]-2,6-dimethyl-8-(4-morpholinyl)-imidazo[1,2-b]pyridazine,
3-[1-(2-methoxyethyl)-1H-pyrazol-4-yl]-2,6-dimethyl-8-(4-pyridinyl)-imidazo[1,2-b]pyridazine,
2-methyl-8-(4-pyridinyl)-3-[1-(2,2,2-trifluoroethyl)-1H-pyrazol-4-yl]-imidazo[1,2-b]pyridazine,
2-cyclopropyl-3-[1-(2-methoxyethyl)-1H-pyrazol-4-yl]-8-(4-pyridinyl)-imidazo(1,2-b)pyridazine,
2-cyclopropyl-3-[1-(2-methoxy-2-methylpropyl)-1H-pyrazol-4-yl]-8-(4-pyridinyl)-imidazo[1,2-b]pyridazine,
6-chloro-3-[1-(2-methoxyethyl)-1H-pyrazol-4-yl]-2-methyl-8-(4-pyridinyl)-imidazo[1,2-b]pyridazine, and
2-cyclopropyl-3-[1-(2-methylpropyl)-1H-pyrazol-4-yl]-8-(4-pyridinyl)-imidazo[1,2-b]pyridazine, and the stereoisomeric forms, and the pharmaceutically acceptable salts thereof.

9. A pharmaceutical composition comprising a therapeutically effective amount of a compound according to claim 1 and a pharmaceutically acceptable carrier or excipient.

10. A pharmaceutical composition comprising a therapeutically effective amount of a compound according to claim 8 and a pharmaceutically acceptable carrier or excipient.

11. A compound according to claim 1 for use in the treatment of a central nervous system disorder selected from the group of psychotic disorders; drug induced psychosis; movement disorders; neurodegenerative disorders; disorders or conditions comprising as a symptom a deficiency in attention and/or cognition; drug addiction disorders; pain and metabolic disorders.

12. The compound according to claim 11, wherein the psychotic disorder is selected from the group consisting of schizophrenia, delusional disorder, schizoaffective disorder, schizophreniform disorder and substance-induced psychotic disorder.

13. A compound according to claim 1 in combination with an additional pharmaceutical agent for use in the treatment of a central nervous system disorder selected from the group of psychotic disorders; drug induced psychosis; movement disorders; neurodegenerative disorders; disorders or conditions comprising as a symptom a deficiency in attention and/or cognition; drug addiction disorders; pain and metabolic disorders.

14. A process for preparing a pharmaceutical composition comprising intimately mixing a pharmaceutically acceptable carrier with a therapeutically effective amount of a compound as defined in claim 1.

15. A product comprising
(a) a compound as defined in claim 1; and
(b) an additional pharmaceutical agent,
as a combined preparation for simultaneous, separate or sequential use in the treatment of a central nervous system disorder selected from the group of psychotic disorders; drug induced psychosis; movement disorders; neurodegenerative disorders; disorders or conditions comprising as a symptom a deficiency in attention and/or cognition; drug addiction disorders; pain and metabolic disorders.

16. A compound wherein the compound is 3-[6-(2-methoxyethyl)-3-pyridinyl]-2-methyl-8-(4-morpholinyl)-imidazo[1,2-b]pyridazine.

17. The compound of claim 16 wherein the compound is a monohydrate thereof.

18. A compound of claim 8 wherein the compound is the phosphate salt of 3-[6-(2-methoxyethyl)-3-pyridinyl]-2-methyl-8-(4-morpholinyl)-imidazo[1,2-b]pyridazine phosphate.

* * * * *